(12) United States Patent
Shimoharada et al.

(10) Patent No.: US 8,466,088 B2
(45) Date of Patent: Jun. 18, 2013

(54) HERBICIDAL COMPOSITIONS CONTAINING BENZOYLPYRAZOLE COMPOUNDS

(75) Inventors: Hiroshi Shimoharada, Kusatsu (JP); Masamitsu Tsukamoto, Kusatsu (JP); Masahiko Ikeguchi, Osaka (JP); Hiroshi Kikugawa, Kusatsu (JP); Souichiro Nagayama, Kusatsu (JP); Makiko Sano, Kusatsu (JP); Yoshinori Kitahara, Chiba (JP); Hidemasa Kominami, Kusatsu (JP); Tatsuya Okita, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 491 days.

(21) Appl. No.: 12/525,554

(22) PCT Filed: Feb. 1, 2008

(86) PCT No.: PCT/JP2008/051663
§ 371 (c)(1),
(2), (4) Date: Aug. 3, 2009

(87) PCT Pub. No.: WO2008/093840
PCT Pub. Date: Aug. 7, 2008

(65) Prior Publication Data
US 2010/0099563 A1    Apr. 22, 2010

(30) Foreign Application Priority Data

Feb. 2, 2007  (JP) .................................. 2007-024866
Jun. 8, 2007  (JP) .................................. 2007-152676

(51) Int. Cl.
*A01N 63/00*  (2006.01)

(52) U.S. Cl.
USPC ........................................................ 504/118

(58) Field of Classification Search
None
See application file for complete search history.

(56) References Cited

U.S. PATENT DOCUMENTS

| | | | |
|---|---|---|---|
| 4,885,022 A | 12/1989 | Baba et al. | |
| 5,807,806 A | 9/1998 | Tanaka et al. | |
| 6,534,444 B1 | 3/2003 | Sievernich et al. | |
| 6,831,039 B1 | 12/2004 | Neidlein et al. | |
| 7,012,040 B2 * | 3/2006 | Hacker et al. | 504/127 |

FOREIGN PATENT DOCUMENTS

| | | | |
|---|---|---|---|
| EP | 0 352 543 | | 7/1989 |
| EP | 352543 | * | 1/1990 |
| JP | 62 63503 | | 3/1987 |
| JP | 64 52759 | | 2/1989 |
| JP | 2 173 | | 1/1990 |
| JP | 4 257503 | | 9/1992 |
| JP | 04257503 | * | 9/1992 |
| JP | 2002 518303 | | 6/2002 |
| JP | 2002 531562 | | 9/2002 |
| JP | 2005 509656 | | 4/2005 |
| WO | 98 56766 | | 12/1998 |
| WO | 01 28341 | | 4/2001 |
| WO | 2007 069771 | | 6/2007 |

OTHER PUBLICATIONS

Soltani et al. (HortScience, 2007, 42 No. 1, 110-112), Matsumoto (ACS Symposium Series, 2005, 892, New Discoveries in Agrochemicals, 161-171).*
Matsumoto (ACS Symposium Series, 2005, 892, New Discoveries in Agrochemicals, 161-171).*
Benko et al. (The synthesis and activity of 1-alkyl-4-3-azacyclobenzoyl-5-hydroxypyrazole herbicides, Chimia, 2003, 57 No. 11, 720-724).*
Siddall et al., Synthesis and herbicidal activity of phenyl-substituted benzoylpyrazoles, Pest Management Science, 2002, 58 No. 12, 1175-1186).*
Matsui et al. (Structure-activity relationship of herbicidal pyrazole derivatives, Pestic. Chem.: Hum. Welfare Environ., Proc. Int. Congr. Pestic. Chem., 5th, 1983, Meeting Date 1982).*
U.S. Appl. No. 13/133,993, filed Jun. 10, 2011, Kikugawa, et al.
U.S. Appl. No. 12/993,760, filed Nov. 19, 2010, Tsukamoto, et al.
U.S. Appl. No. 12/521,649, filed Jun. 29, 2009, Shimoharada, et al.
U.S. Appl. No. 12/094,734, filed May 22, 2008, Shimoharada, et al.

* cited by examiner

*Primary Examiner* — Alton Pryor
(74) *Attorney, Agent, or Firm* — Oblon, Spivak, McClelland, Maier & Neustadt, L.L.P.

(57) ABSTRACT

Provided is an herbicidal composition which can be applied at a low dose as compared with individual application, and thus is effective to reduce the environmental load on a place where the composition is applied or a periphery thereof, of which the herbicidal spectrum is enlarged, and of which the herbicidal effects last over a long period of time. The herbicidal composition has as active ingredients (a) a herbicidal benzoylpyrazole compound represented by the formula (I) or its salt:

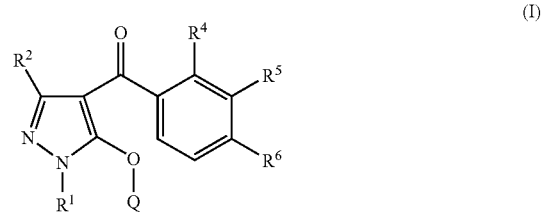

wherein Q is $-C(O)SR^3$ or a hydrogen atom, $R^1$ is alkyl or cycloalkyl, $R^2$ is a hydrogen atom or alkyl, $R^3$ is alkyl, cycloalkyl or the like, $R^4$ is alkyl, haloalkyl or the like, $R^5$ is a hydrogen atom, alkyl or the like, $R^6$ is haloalkyl, halogen or the like, and (b) a further herbicidal compound.

32 Claims, No Drawings

HERBICIDAL COMPOSITIONS CONTAINING BENZOYLPYRAZOLE COMPOUNDS

CROSS REFERENCE TO RELATED APPLICATIONS

The present application is the national stage of international application PCT/JP2008/051663, filed on Feb. 1, 2008, and claims the benefit of the filing dates of Japanese Applications No. 2007-024866, filed on Feb. 2, 2007, and 2007-152676, filed on Jun. 8, 2007.

TECHNICAL FIELD

The present invention relates to herbicidal compositions containing as essential components (a) a herbicidal benzoylpyrazole compound or its salt and (b) other herbicidal compound.

BACKGROUND ART

Patent Document 1 discloses mixed use of some hydroxyphenylpyruvate dioxygenase inhibition type herbicides and some other herbicides. Patent Document 2 discloses mixed use of some pyrazole compounds with atrazine, cyanazine, alachloror metolachlor. Patent Document 3 discloses that some pyrazole compounds are useful as a herbicide, and discloses some of other herbicides which can be used as mixed with the compounds as examples.

However, Patent Documents 1 to 3 failed to specifically disclose a herbicidal composition comprising as active ingredients a herbicidal benzoylpyrazole compound represented by the following formula (I) and other herbicidal compound.

Patent Document 1: WO01/28341
Patent Document 2: JP-A-62-63503
Patent Document 3: EP 0352543A

DISCLOSURE OF THE INVENTION

Object to be Accomplished by the Invention

At present, many herbicidal compositions have been developed and used, but there are a variety of types of weeds to be controlled, and their development lasts for a long period of time. Thus, a high activity and long lasting herbicidal composition having a wider herbicidal spectrum has been desired. Further, in recent years, a technique to reduce the dose of the active ingredient has been desired so as to reduce the environmental load to a place where the herbicide is applied or a periphery thereof.

Means to Accomplish the Object

The present inventors have conducted extensive studies to accomplish the above object and as a result, found a highly useful herbicidal composition.

That is, the present invention relates to a herbicidal composition which comprises as active ingredients (a) a herbicidal benzoylpyrazole compound represented by the formula (I) or its salt (hereinafter referred to as compound A):

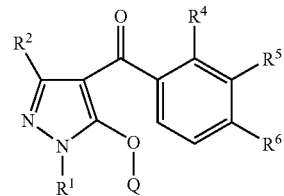

wherein Q is $-C(O)SR^3$ or a hydrogen atom, $R^1$ is alkyl or cycloalkyl, $R^2$ is a hydrogen atom or alkyl, $R^3$ is alkyl; cycloalkyl; haloalkyl; alkoxyalkyl; alkoxycarbonylalkyl; alkenyl; or arylalkyl which may be substituted by $R^8$, $R^4$ is alkyl; haloalkyl; alkoxy; halogen; nitro; cyano; alkylthio; alkylsulfinyl; or alkylsulfonyl, $R^5$ is a hydrogen atom; alkyl; alkenyl; alkynyl; halogen; cyano; cyanoalkyl; cyanoalkenyl; haloalkyl; alkoxyalkyl; haloalkoxyalkyl; amino(thiocarbonyl)alkyl which may be substituted by at least one substituent selected from alkyl, cyano, cyanoalkyl, (alkylthio)carbonylalkyl, alkyl(thiocarbonyl)alkyl, $-C(O)OR^7$ and $-C(O)SR^7$; thiocyanatoalkyl; alkoxy; alkenyloxy; alkynyloxy; haloalkoxy; alkoxyalkoxy; haloalkoxyalkoxy; alkoxyhaloalkoxy; haloalkoxyhaloalkoxy; alkoxyalkoxyalkyl; alkylthio; alkoxyalkylthio; haloalkoxyalkylthio; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; alkylsulfonyl; alkylsulfonylalkyl; alkoxycarbonylalkyl; alkoxycarbonylalkoxy; heterocyclylalkyl; heterocyclyloxy; heterocyclylalkoxy; heterocyclylalkoxyalkyl; heterocyclyloxyalkyl; cycloalkyloxy; $-OC(O)SR^7$; $-OC(O)OR^7$; $-C(O)OR^7$; $-C(O)SR^7$; $-C(S)OR^7$; $-C(S)SR^7$; aminoalkyl which may be substituted by at least one substituent selected from alkyl, cyano, cyanoalkyl, (alkylthio)carbonylalkyl, alkyl(thiocarbonyl)alkyl, $-C(O)OR^7$ and $-C(O)SR^7$; or 4,5-dihydroisoxazol-3-yl which may be substituted by $R^9$, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, and (b) other herbicidal compound. Further, the present invention relates to a method for controlling undesired plants, which comprises applying a herbicidally effective amount of the above herbicidal composition to the undesired plants or to a place where they grow. Further, the present invention relates to a method for controlling undesired plants, which comprises applying a herbicidally effective amount of the compound A and a herbicidally effective amount of other herbicidal compound to the undesired plants or to a place where they grow.

Effects of the Invention

The herbicidal composition of the present invention, i.e. the herbicidal composition comprising as active ingredients the compound A and other herbicidal compound, is capable of controlling a wide range of undesired plants emerging in agricultural fields or non-agricultural fields. It surprisingly presents a synergistic herbicidal effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on a place where the composition is applied or a periphery thereof. Further, the herbicidal spectrum will be enlarged, and further the herbicidal effects will last over a long period of time.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=\alpha+\beta-(\alpha\times\beta+100)$$

where

α: growth inhibition rate when treated with x (g/ha) of herbicide X,

β: growth inhibition rate when treated with y (g/ha) of herbicide Y,

E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

BEST MODE FOR CARRYING OUT THE INVENTION $R^1, R^2, R^3, R^4, R^5, R^6, R^7, R^8, R^9$ and $R^{10}$ in the formula (I) will be described in detail below.

The alkyl or alkyl moiety in each of $R^1, R^2, R^3, R^4, R^5, R^6, R^7, R^8, R^9$ and $R^{10}$ may be linear or branched, and specific examples thereof include $C_{1-9}$ alkyl such as methyl, ethyl, n-propyl, iso-propyl, n-butyl, iso-butyl, sec-butyl, tert-butyl, n-pentyl, iso-pentyl, neopentyl, tert-pentyl, n-hexyl, iso-hexyl, n-heptyl, n-octyl and n-nonyl.

Examples of the cycloalkyl or cycloalkyl moiety in each of $R^1, R^3$ and $R^5$ include $C_{3-6}$ cycloalkyl such as cyclopropyl, cyclobutyl, cyclopentyl and cyclohexyl.

The alkenyl or alkenyl moiety in each of $R^3, R^5$ and $R^7$ may be linear or branched, and specific examples thereof include $C_{2-9}$ alkenyl such as vinyl, 1-propenyl, 2-propenyl, iso-propenyl, allyl, 1-butenyl, 2-butenyl, 3-butenyl, 1,3-butadienyl, 2-pentenyl, 4-pentenyl, 2-hexenyl, 4-hexenyl, 2-heptenyl, 4-heptenyl, 2-octenyl, 6-octenyl and 2-nonenyl.

The alkynyl or alkynyl moiety in each of $R^5$ and $R^7$ may be linear or branched, and specific examples thereof include $C_{2-9}$ alkynyl such as ethynyl, propargyl, 1-propynyl, 1-pentynyl, 3-pentynyl, 1-heptynyl and 1-nonynyl.

Examples of halogen or halogen as the substituent in each of $R^3, R^4, R^5, R^6, R^7, R^8, R^9$ and $R^{10}$ include atoms of fluorine, chlorine, bromine and iodine.

The number of halogens as substituents in each of $R^3, R^4, R^5, R^6$ and $R^7$ may be 1 or more, and if more, they may be the same or different. Further, the positions for substitution of such halogens may be any positions.

The number of alkoxy or alkoxy moieties as substituents in each of $R^3, R^5$ and $R^7$ may be 1 or more, and if more, they may be the same or different. Further, the positions for substitution may be any positions.

Examples of the aryl or aryl moiety as the substituent in each of $R^3$ and $R^7$ include phenyl and naphthyl. The number of aryl or aryl moieties as substituents may be 1 or more, and if more, they may be the same or different. Further, the positions for substitution may be any positions.

The number of $R^8$ as substituents which substitute the arylalkyl in $R^3$ may be 1 or more, and if more, they may be the same or different. Further, the positions for substitution of such substituents may be any positions.

The number of $R^{10}$ as substituents which substitute the arylalkyl in $R^7$ may be 1 or more, and if more, they may be the same or different. Further, the positions for substitution of such substituents may be any positions.

The number of $R^9$ as substituents which substitute the 4,5-dihydroisoxazol-3-yl in $R^5$ may be 1 or more, and if more, they may be the same or different. Further, the positions for substitution of such substituents may be any positions.

The alkoxyalkoxy in $R^5$ is meant for an alkoxy group having the same or different alkoxy moiety bonded thereto. The position for substitution of the alkoxy moiety which substitutes the alkoxy group may be any position. The same applies to haloalkoxyalkoxy, alkoxyhaloalkoxy, alkoxyalkoxyalkyl, alkylthioalkylthio, alkylsulfonylalkyl, alkoxycarbonylalkyl, etc.

The heterocyclyl moiety in $R^5$ may, for example, be a saturated or unsaturated 5-membered or 6-membered ring containing 1 to 4 one or more types of hetero atoms optionally selected from O, S and N, and specific examples thereof include oxolanyl, 1,3-dioxolanyl, tetrahydrofuranyl and tetrahydro-2H-pyranyl. Further, the number of heterocyclyl moieties as substituents may be 1 or more, and if more, they may be the same or different. The positions for substitution of the heterocyclyl moieties may be any positions.

The salt of the herbicidal benzoylpyrazole compound of the formula (I) includes all kinds of salts so long as they are agriculturally acceptable. Examples thereof include alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate.

The compound A can be produced by the following reactions [A] to [AG] and in accordance with a usual method for producing a salt.

Among the compounds of the above formula (I), a compound wherein Q is —C(O)SR³ is novel, which can be produced in accordance with the following reaction [A].

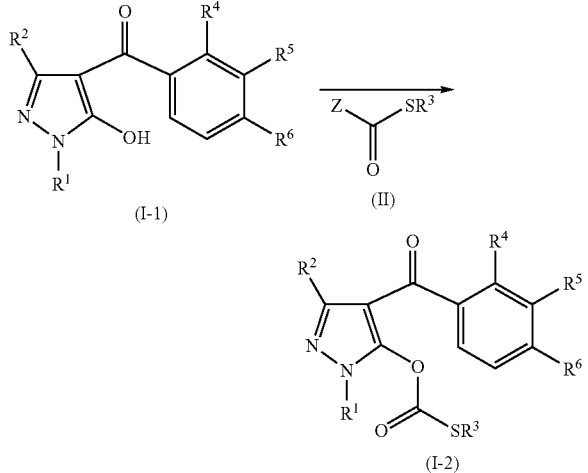

wherein $R^1$, $R^2$, $R^3$, $R^4$, $R^5$ and $R^6$ are as defined above, and Z is a leaving group such as halogen.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

The above reaction may also be carried out in the two-phase system in water and a solvent insoluble in water among the above solvents in the presence of a phase transfer catalyst such as a quaternary ammonium salt.

Herbicidal benzoylpyrazole compounds represented by the formula (III), which are included in the above formula (I-1) or their salts are novel.

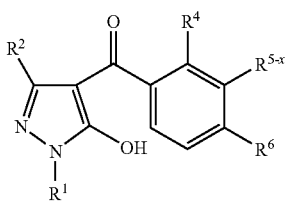

(III)

wherein $R^1$ is alkyl or cycloalkyl, $R^2$ is a hydrogen atom or alkyl, $R^4$ is alkyl; haloalkyl; alkoxy; halogen; nitro; cyano; alkylthio; alkylsulfinyl; or alkylsulfonyl, $R^{5-x}$ is alkyl substituted by at least 2 alkoxy; alkyl substituted by at least 2 haloalkoxy; amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; thiocyanatoalkyl; alkoxy substituted by at least 2 alkoxy, alkoxy substituted by at least 2 haloalkoxy; alkoxyhaloalkoxy; haloalkoxyhaloalkoxy; alkoxyalkyl substituted by at least 2 alkoxy; alkylthio substituted by at least 2 alkoxy; alkylthio substituted by at least 2 haloalkoxy; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; alkyl substituted by at least 2 alkylsulfonyl; alkyl substituted by at least 2 alkoxycarbonyl; alkoxy substituted by at least 2 alkoxycarbonyl; alkyl substituted by at least 2 heterocyclyl; alkoxy substituted by at least 2 heterocyclyl; alkyl substituted by at least 2 heterocyclylalkoxy; —OC(O)SR$^7$; or aminoalkyl which may be substituted by at least one substituent selected from cyano, cyanoalkyl, (alkylthio)carbonylalkyl, alkyl(thiocarbonyl)alkyl, —C(O)OR$^7$ and —C(O)SR$^7$, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and $R^{10}$ is halogen; alkyl; or alkoxy.

Among the compounds of the above formula (I), a compound wherein Q is —C(O)SR$^3$, and $R^3$ is $R^{3-a}$ can be produced in accordance with the following reaction [B-1].

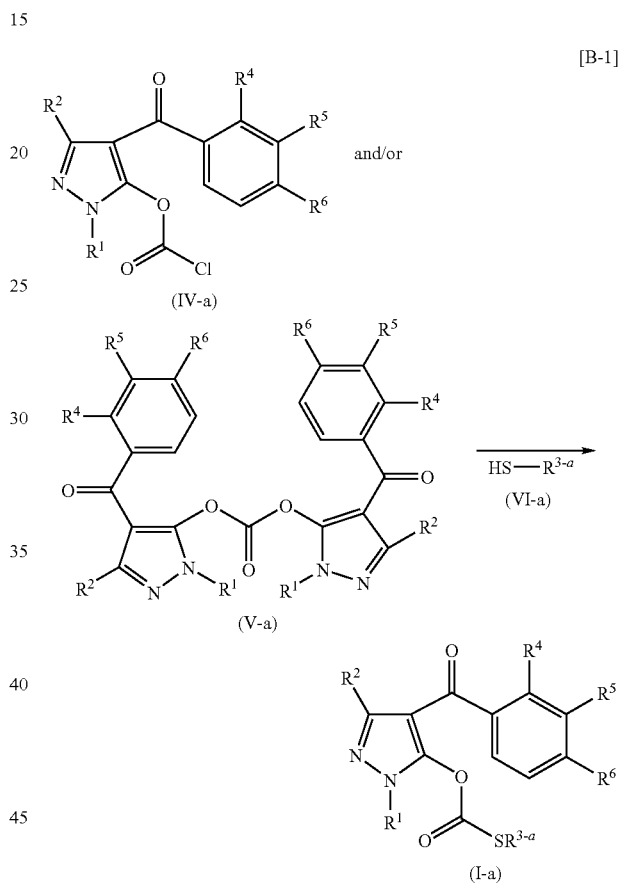

wherein $R^1$, $R^2$, $R^4$, $R^5$ and $R^6$ are as defined above, $R^{3-a}$ is alkyl; cycloalkyl; haloalkyl; alkoxyalkyl; alkoxycarbonylalkyl; alkenyl; or arylalkyl which may be substituted by $R^8$, and $R^8$ is as defined above.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

Among the compounds of the above formula (I), a compound wherein Q is —C(O)SR$^3$, and R$^3$ is R$^{3-b}$ can be produced in accordance with the following reaction [B-2].

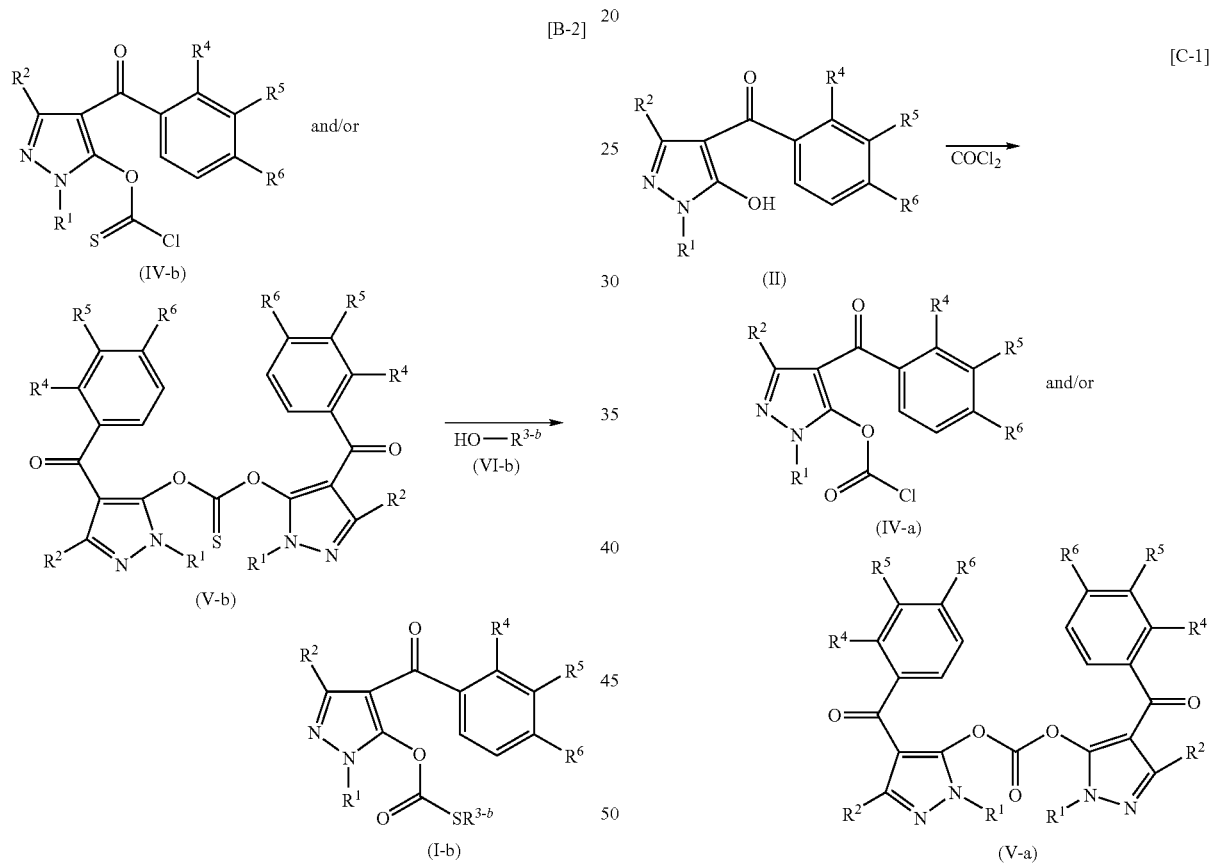

wherein R$^1$, R$^2$, R$^4$, R$^5$ and R$^6$ are as defined above, and R$^{3-b}$ is alkenyl.

The above reaction can be carried out in the presence of a solvent, as the case requires. Examples of the solvent include halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from 0° C. to 150° C. for a reaction time of usually from 1 minute to 48 hours.

The above compound represented by the formula (IV-a) or the formula (V-a) or a mixture thereof can be produced in accordance with the following reaction [C-1].

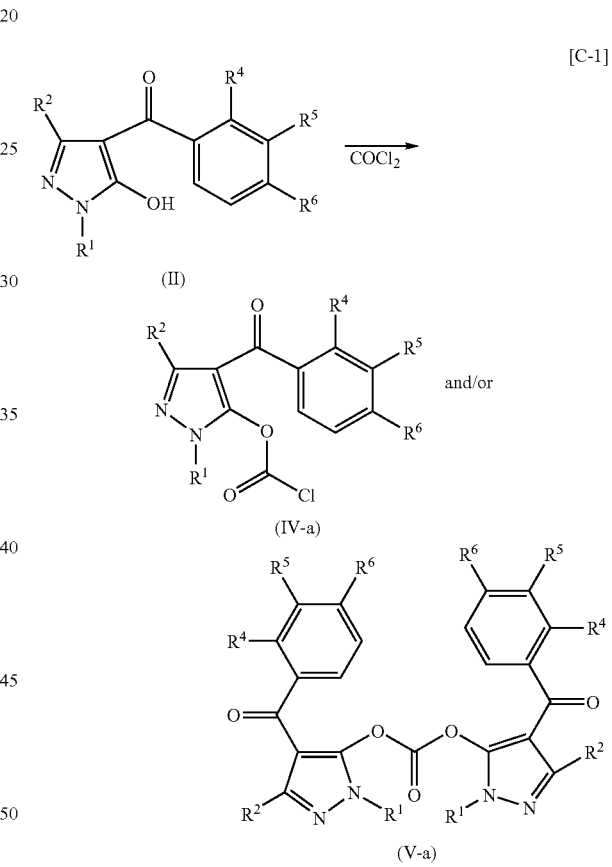

wherein R$^1$, R$^2$, R$^4$, R$^5$ and R$^6$ are as defined above.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from −10° C. to 150° C. for a reaction time of usually from 1 minute to 48 hours.

The above compound represented by the formula (IV-b) or the formula (V-b) or a mixture thereof can be produced in accordance with the following reaction [C-2].

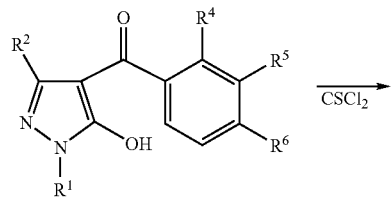

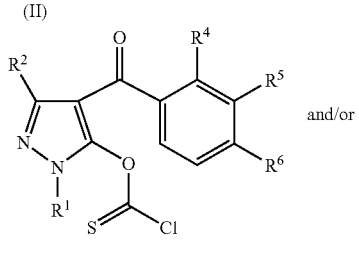

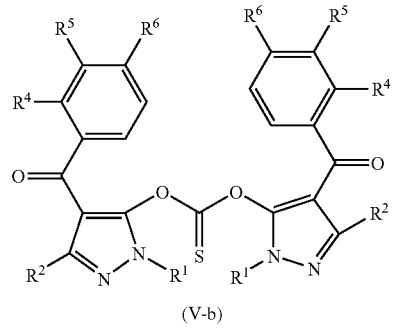

wherein $R^1$, $R^2$, $R^4$, $R^5$ and $R^6$ are as defined above.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkaline earth metal hydroxides such as calcium hydroxide; and alkaline earth metal carbonates such as calcium carbonate. Examples of the organic base include tertiary amines such as triethylamine and diisopropylethylamine; pyridine, 4-(dimethylamino)pyridine and 2,6-lutidine. As the base, one or more types may suitably be selected and mixed.

The above reaction can be carried out at a reaction temperature of usually from −10° C. to 150° C. for a reaction time of usually from 1 minute to 48 hours.

Among the compounds of the above formula (I), compounds wherein Q is a hydrogen atom include a novel compound, which can be produced in accordance with the following reaction [D].

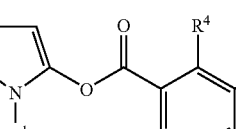

wherein $R^1$, $R^2$, $R^4$, $R^5$ and $R^6$ are as defined above.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either organic base or inorganic base. Examples of the organic base include tertiary amines such as triethylamine and diisopropylethylamine; pyridine, 4-(dimethylamino)pyridine and 2,6-lutidine. Examples of the inorganic base include alkali metal carbonates such as sodium carbonate and potassium carbonate, alkali metal hydroxides such as sodium hydroxide and potassium hydroxide; and alkali metal cyanides such as sodium cyanide and potassium cyanide. As the base, one or more types may suitably be selected and mixed in an amount of from 0.01 to 100 equivalent amounts based on the compound of the formula (VII).

Further, for the above reaction, a catalyst may be added as the case requires. As the catalyst, acetone cyanohydrin can be used in an amount of from 0.01 to 10 equivalent amounts based on the compound of the formula (VII).

The above reaction can be carried out at a reaction temperature of usually from 0° C. to 150° C. for a reaction time of usually from 1 minute to 48 hours.

The compound represented by the above formula (VII) can be produced in accordance with the following reaction [E].

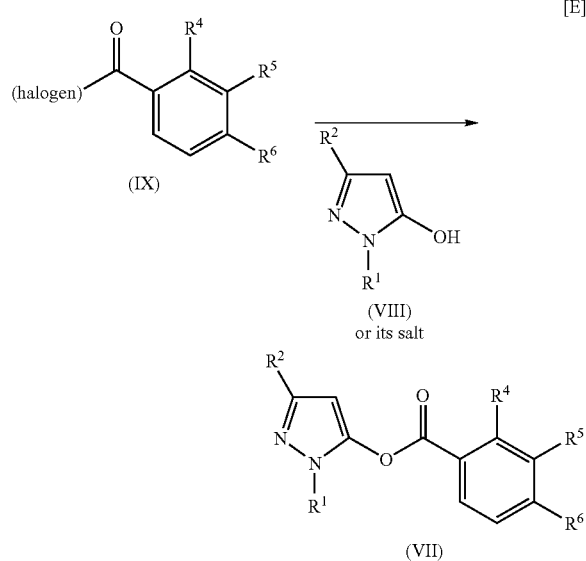

wherein $R^1$, $R^2$, $R^4$, $R^5$ and $R^6$ are as defined above. The salt of the compound of the above formula (VIII) may, for example, be a hydrochloride, a sulfate, a nitrate, etc.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the organic base include tertiary amines such as triethylamine and diisopropylethylamine; pyridine, 4-(dimethylamino)pyridine and 2,6-lutidine. Examples of the inorganic base include alkali metal carbonates such as sodium carbonate and potassium carbonate; alkaline earth metal carbonates such as calcium carbonate and magnesium carbonate; alkali metal hydrogencarbonates such as sodium hydrogencarbonate and potassium hydrogencarbonate; and alkali metal hydroxides such as sodium hydroxide and potassium hydroxide. As the base, one or more types may suitably be selected and mixed in an amount of from 1 to 100 equivalent amounts based on the compound of the formula (IX).

The above reaction can be carried out at a reaction temperature of usually from 0° C. to 150° C. for a reaction time of usually from 1 minute to 48 hours.

The compound represented by the above formula (IX) can be produced in accordance with the following reaction [F].

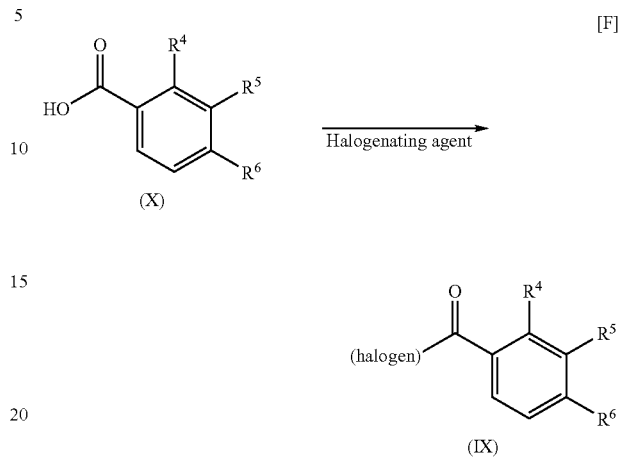

wherein $R^4$, $R^5$ and $R^6$ are as defined above.

In the above reaction, the halogenating agent may, for example, be thionyl chloride, oxalyl chloride, etc. The halogenating agent may be reacted in an amount of from 1 to 100 equivalent amounts based on the compound represented by the formula (X).

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

For the above reaction, a catalyst can be used, as the case requires. The catalyst may, for example, be DMF.

The above reaction can be carried out at a reaction temperature of usually from 0° C. to 150° C. for a reaction time of usually from 1 minute to 48 hours.

In addition to the above processes, the compound represented by the formula (VII) can be produced in accordance with the following reaction [G].

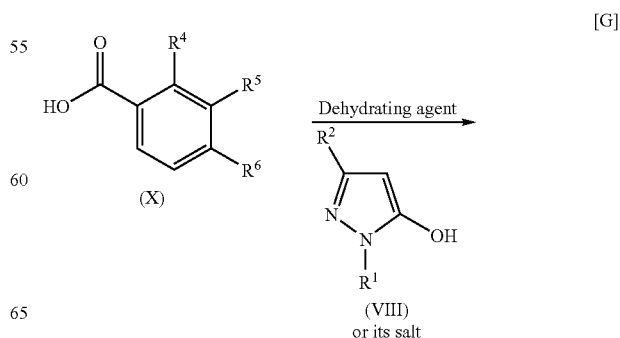

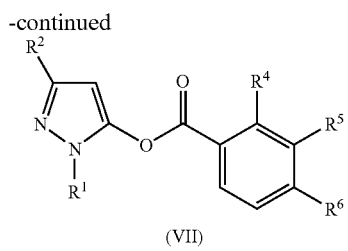

(VII)

wherein $R^1$, $R^2$, $R^4$, $R^5$ and $R^6$ are as defined above. The salt of the above formula (VIII) may, for example, be a hydrochloride, a sulfate, a nitrate, etc.

The dehydrating agent to be used for the above reaction may, for example, be DCC (dicyclohexylcarbodiimide) or 1-ethyl-3-(3-dimethylaminopropyl)-carbodiimide hydrochloride.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. Examples of the base include tertiary amines such as triethylamine and diisopropylethylamine; pyridine, 4-(dimethylamino)pyridine and 2,6-lutidine. As the base, one or more types may suitably be selected and mixed in an amount of from 1 to 100 equivalent amounts based on the compound represented by the formula (X).

The above reaction can be carried out at a reaction temperature of usually from 0° C. to 150° C. for a reaction time of usually from 1 minute to 48 hours.

The compound represented by the above formula (X) can be produced in accordance with the following reaction [H].

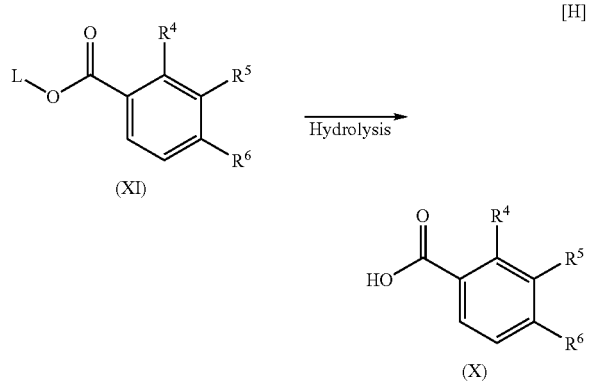

wherein $R^4$, $R^5$ and $R^6$ are as defined above, and L is a protective group such as alkyl.

The above reaction can be carried out in the presence of a solvent, as the case requires. Examples include aromatic hydrocarbons such as benzene, toluene and xylene; aprotic polar solvents such as acetonitrile, N,N-dimethylformamide, dimethylsulfoxide, sulfolane and dimethoxyethane; ethers such as diethyl ether, dioxane and tetrahydrofuran; alcohols such as methanol and ethanol; and water. As the solvent, one or more types may suitably be selected.

The above reaction can be carried out in the presence of a base or an acid, as the case requires. The base may be either inorganic base or organic base. Examples of the inorganic base include alkali metal hydroxides such as lithium hydroxide and sodium hydroxide; alkali metal carbonates such as potassium carbonate and sodium carbonate; and alkaline earth metal carbonates such as calcium carbonate and barium carbonate. Examples of the organic base include tertiary amines such as triethylamine and diisopropylethylamine. Examples of the acid include hydrochloric acid, sulfuric acid and perchloric acid. As the base or acid, one or more types may suitably be selected and mixed in an amount of from 1 to 100 equivalent amounts based on the compound represented by the formula (XI).

The above reaction can be carried out at a reaction temperature of usually from 0° C. to 150° C. for a reaction time of usually from 1 minute to 48 hours.

Among the compounds represented by the above formula (XI), a compound represented by the formula (XI-a-1) wherein $R^5$ is $R^{5-a-1}$ can be produced in accordance with the following reaction [I].

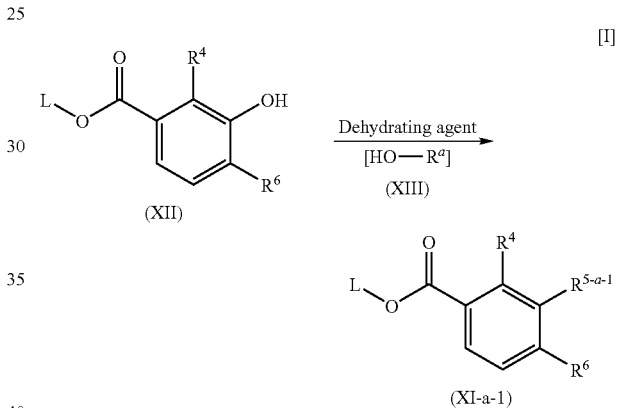

wherein $R^4$, $R^6$ and L are as defined above, $R^{5-a-1}$ is alkoxy, haloalkoxy, alkoxyalkoxy, haloalkoxyalkoxy, alkoxyhaloalkoxy, haloalkoxyhaloalkoxy, heterocyclyloxy, heterocyclylalkoxy, cycloalkyloxy, —OC(O)SR$^7$, —OC(O)OR$^7$, alkylthioalkoxy, alkoxycarbonylalkoxy, alkenyloxy or alkynyloxy and $R^\alpha$ is alkyl, haloalkyl, alkoxyalkyl, haloalkoxyalkyl, alkoxyhaloalkyl, haloalkoxyhaloalkyl, heterocyclyl, heterocyclylalkyl, cycloalkyl, —C(O)SR$^7$, —C(O)OR$^7$, alkylthioalkyl, alkoxycarbonylalkyl, alkenyl or alkynyl.

The dehydrating agent to be used in the above reaction may, for example, be DCC (dicyclohexylcarbodiimide), 1-ethyl-3-(3-dimethylaminopropyl)-carbodiimide hydrochloride or diethylazodicarboxylate.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. Examples of the base include tertiary amines such as triethylamine and diisopropylethylamine; pyridine, 4-(dimethylamino)pyridine and 2,6-lutidine. As the base, one or more types may suitably be selected and mixed in an amount of from 1 to 100 equivalent amounts based on the compound represented by the formula (XII).

The above reaction can be carried out at a reaction temperature of usually from 0° C. to 150° C. for a reaction time of usually from 1 minute to 48 hours.

In addition to the above processes, the compound represented by the formula (XI-a-1) can also be produced in accordance with the following reaction [J].

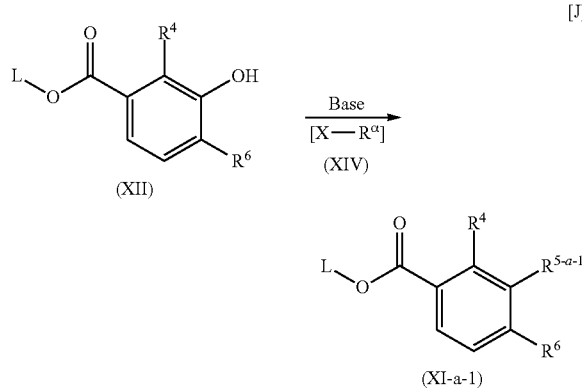

wherein $R^4$, $R^{5-a-1}$, $R^6$, $R^\alpha$ and L are as defined above, and X is a leaving group such as halogen or a methanesulfonyloxy group.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The base to be used in the above reaction may be either inorganic base or organic base. Examples of the organic base include triethylamine, diisopropylethylamine, pyridine, 4-(dimethylamino)pyridine and 2,6-lutidine. Examples of the inorganic base include alkali metal carbonates such as sodium carbonate and potassium carbonate; alkali metal hydroxides such as sodium hydroxide and potassium hydroxide; and alkali metal hydrides such as sodium hydride and potassium hydride. As the base, one or more may suitably be selected and mixed in an amount of from 0.5 to 100 equivalent amounts based on the compound of the formula (XII).

The above reaction can be carried out in the presence of a catalyst, as the case requires. The catalyst may, for example, be potassium iodide or tetra-n-butylammonium iodide.

The above reaction can be carried out at a reaction temperature of usually from 0° C. to 150° C. for a reaction time of usually from 1 minute to 48 hours.

The compound represented by the above formula (XII) can be produced in accordance with the following reaction [K].

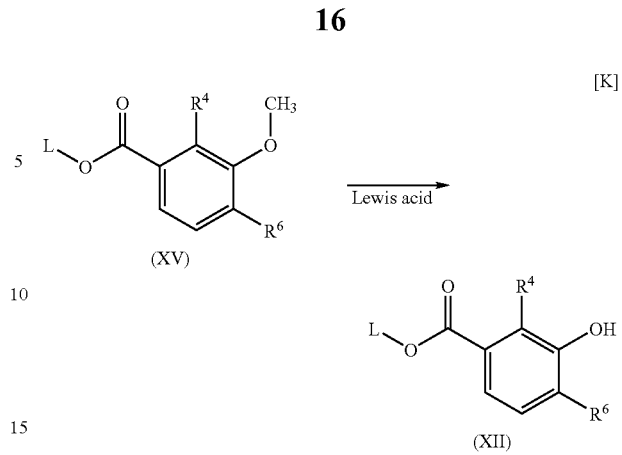

wherein $R^4$, $R^6$ and L are as defined above.

The Lewis acid to be used in the above reaction may, for example, be $BBr_3$, etc.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, and esters such as methyl acetate, ethyl acetate and propyl acetate. As the solvent, one or more types may suitably be selected.

The above reaction can be carried out at a reaction temperature of usually from 0° C. to 150° C. for a reaction time of usually from 1 minute to 48 hours.

The compound represented by the above formula (XV) can be produced in accordance with the following reaction [L].

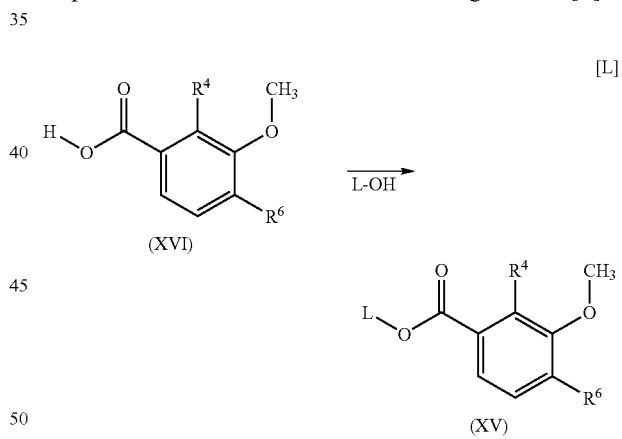

wherein $R^4$, $R^6$ and L are as defined above.

The above reaction can be carried out in the presence of a solvent, as the case requires. Examples of the solvent include alcohols such as methanol and ethanol; aromatic hydrocarbons such as benzene, toluene and xylene; esters such as methyl acetate, ethyl acetate and propyl acetate; halogenated hydrocarbons such as methylene chloride, chloroform, dichloroethane and trichloroethane; and aprotic polar solvents such as acetonitrile, N,N-dimethylformamide, dimethylsulfoxide, sulfolane and dimethoxyethane. As the solvent, one or more may suitably be selected.

The above reaction can be carried out in the presence of an acid, as the case requires. Examples of the acid to be used for the above reaction include hydrochloric acid and sulfuric acid.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-2}$ can be produced in accordance with the following reaction [M].

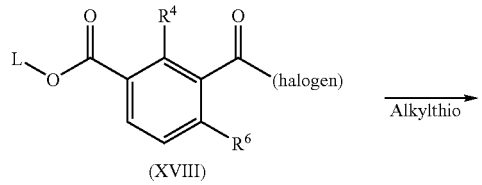

(XVIII)

[M]

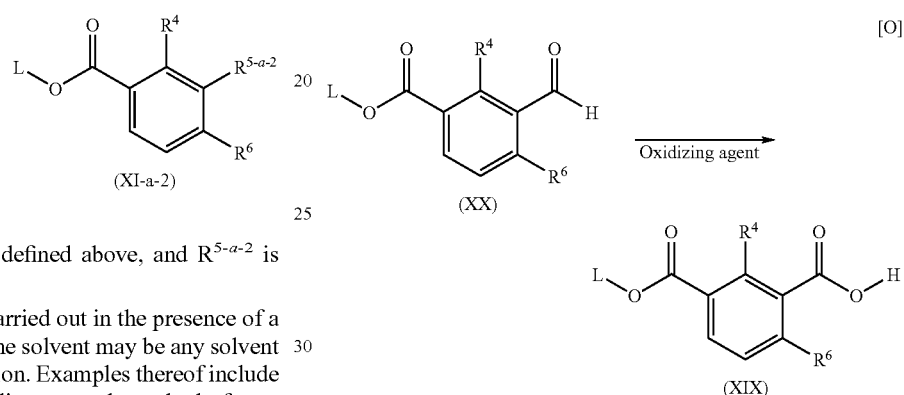

(XI-a-2)

wherein $R^4$, $R^6$ and L are as defined above, and $R^{5-a-2}$ is alkylthiocarbonyl.

The above reaction can be carried out in the presence of a solvent, as the case requires. The solvent may be any solvent so long as it is inert to the reaction. Examples thereof include ethers such as diethyl ether, dioxane and tetrahydrofuran; aromatic hydrocarbons such as benzene, toluene and xylene; esters such as methyl acetate, ethyl acetate and propyl acetate; and halogenated hydrocarbons such as methylene chloride, chloroform, dichloroethane and trichloroethane. As the solvent, one or more types may suitably be selected.

The above reaction can be carried out in the presence of a base, as the case requires. The base may be either inorganic base or organic base. Examples of the organic base include triethylamine, diisopropylethylamine, pyridine, 4-(dimethylamino)pyridine and 2,6-lutidine. Examples of the inorganic base include alkali metal carbonates such as potassium carbonate and sodium carbonate; alkali metal hydroxides such as sodium hydroxide and potassium hydroxide; and alkali metal hydrides such as sodium hydride and potassium hydride. As the base, one or more types may suitably be selected and mixed.

The above reaction can be carried out at a reaction temperature of usually from 0° C. to 150° C. for a reaction time of usually from 1 minute to 48 hours.

The compound represented by the above formula (XVIII) can be produced in accordance with the following reaction [N].

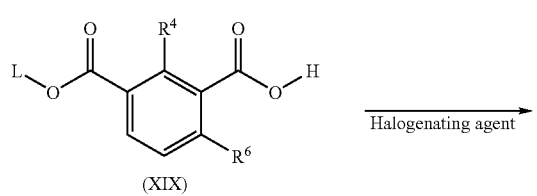

(XIX)

[N]

-continued

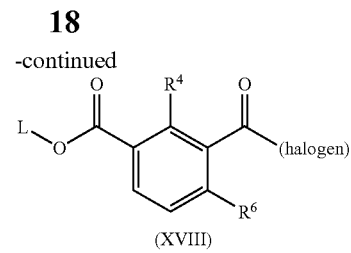

(XVIII)

wherein $R^4$, $R^6$ and L are as defined above.

This reaction can be carried out in the same manner as the above-described reaction [F].

The compound represented by the above formula (XIX) can be produced in accordance with the following reaction [O].

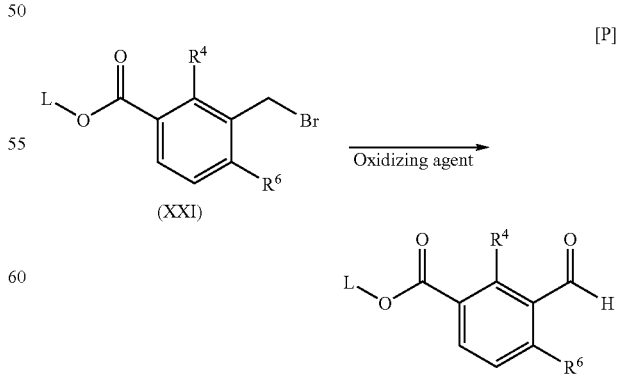

wherein $R^4$, $R^6$ and L are as defined above.

The oxidizing agent in the above reaction may, for example, be potassium permanganate or chromium trioxide.

The above reaction can be carried out in the presence of a solvent, as the case requires. The solvent may be any solvent so long as it is inert to the reaction. Examples thereof include ketones such as acetone and methyl ethyl ketone; esters such as methyl acetate, ethyl acetate and propyl acetate; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

The compound represented by the above formula (XX) can be produced in accordance with the following reaction [P].

wherein $R^4$, $R^6$ and L are as defined above.

The oxidizing agent to be used for the above reaction may, for example, be N-methylmorpholine oxide.

The solvent to be used for the above reaction may be any solvent so long as it is inert to the reaction. Examples thereof include aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-3}$ can be produced in accordance with the following reaction [Q].

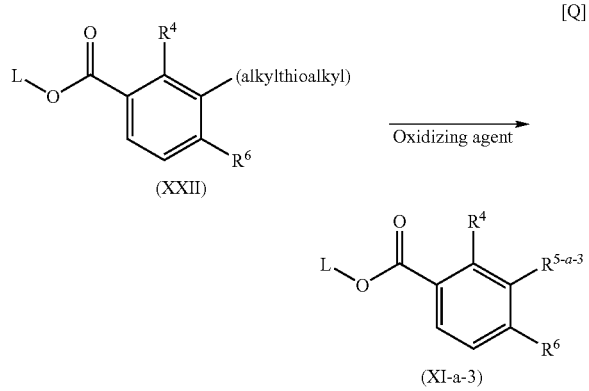

wherein $R^4$, $R^6$ and L are as defined above, and $R^{5-a-3}$ is alkylsulfonylalkyl.

The oxidizing agent to be used for the above reaction may, for example, be hydrogen peroxide, peracetic acid or m-chloroperbenzoic acid.

The solvent to be used for the above reaction may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; and acetic acid. As the solvent, one or more types may suitably be selected.

The above reaction can be carried out at a reaction temperature of usually from 0° C. to 150° C. for a reaction time of usually from 1 minute to 48 hours.

The compound represented by the above formula (XXII) can be produced in accordance with the following reaction [R].

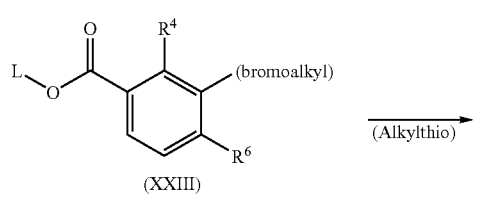

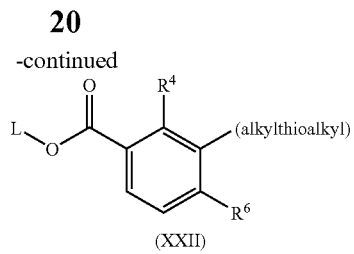

wherein $R^4$, $R^6$ and L are as defined above.

The solvent to be used for the above reaction may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; acetic acid; water; and N,N-dimethylformamide, dimethylsulfoxide, sulfolane and dimethoxyethane. As the solvent, one or more types may suitably be selected.

The above reaction can be carried out in the presence of a base, as the case requires. The base may be either inorganic base or organic base. Examples of the organic base include triethylamine, diisopropylethylamine, pyridine, 4-(dimethylamino)pyridine and 2,6-lutidine. Examples of the inorganic base include alkali metal carbonates such as sodium carbonate and potassium carbonate; alkali metal hydrogencarbonates such as sodium hydrogencarbonate and potassium hydrogencarbonate; alkaline earth metal carbonates such as calcium carbonate and magnesium carbonate; alkali metal hydroxides such as sodium hydroxide; and alkali metal hydrides such as sodium hydride and potassium hydride. As the base, one or more types may suitably be selected and mixed.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-4}$ can be produced in accordance with the following reaction [S].

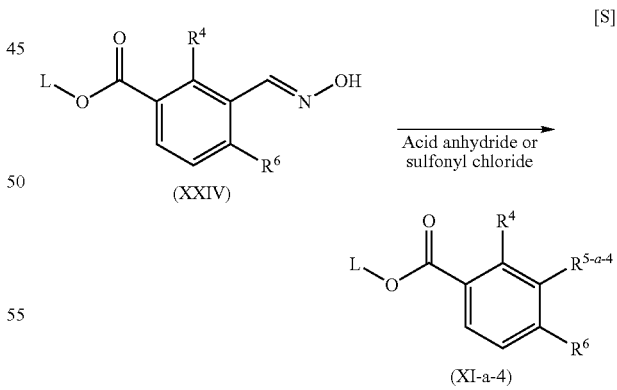

wherein $R^4$, $R^6$ and L are as defined above, and $R^{5-a-4}$ is cyano.

The above reaction can be carried out in the presence of a solvent, as the case requires. The solvent may be any solvent so long as it is inert to the reaction. Examples thereof include halogenated hydrocarbons such as methylene chloride, chloroform, dichloroethane and trichloroethane; ketones such as acetone and dimethyl ethyl ketone; ethers such as diethyl ether, dioxane and tetrahydrofuran; and pyridine. As the solvent, one or more types may suitably be selected.

The above reaction can be carried out in the presence of a base, as the case requires. Examples of the base include triethylamine, N,N-dimethylaminopyridine and diisopropylaminopyridine. As the base, one or more types may suitably be selected and mixed.

The above reaction can be carried out at a reaction temperature of usually from 0 to 150° C. for a reaction time of usually from 1 minute to 48 hours.

The compound represented by the above formula (XXIV) can be produced in accordance with the following reaction [T].

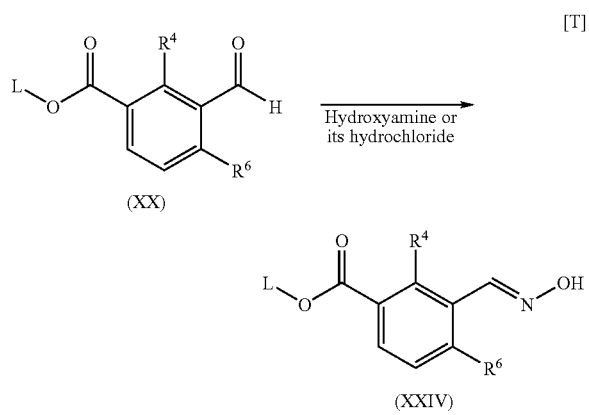

wherein $R^4$, $R^6$ and L are as defined above.

The solvent to be used for the above reaction may be any solvent so long as it is inert to the reaction. Examples thereof include alcohols such as methanol and ethanol; halogenated hydrocarbons such as methylene chloride, chloroform, dichloroethane and trichloroethane; ketones such as acetone and dimethyl ethyl ketone; and ethers such as diethyl ether, dioxane and tetrahydrofuran. As the solvent, one or more types may suitably be selected.

The above reaction can be carried out in the presence of an acid or a base, as the case requires. Examples of the acid include p-toluenesulfonic acid. Examples of the base include sodium acetate.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-5}$ can be produced in accordance with the following reaction [U].

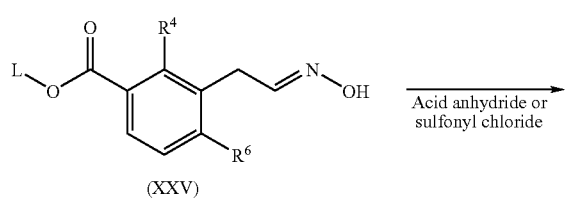

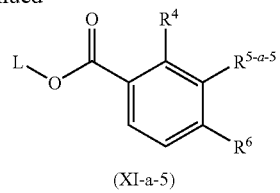

wherein $R^4$, $R^6$ and L are as defined above, and $R^{5-a-5}$ is cyanoalkyl.

This reaction can be carried out in the same manner as the above-described reaction [S].

The compound represented by the above formula (XXV) can be produced in accordance with the following reaction [V].

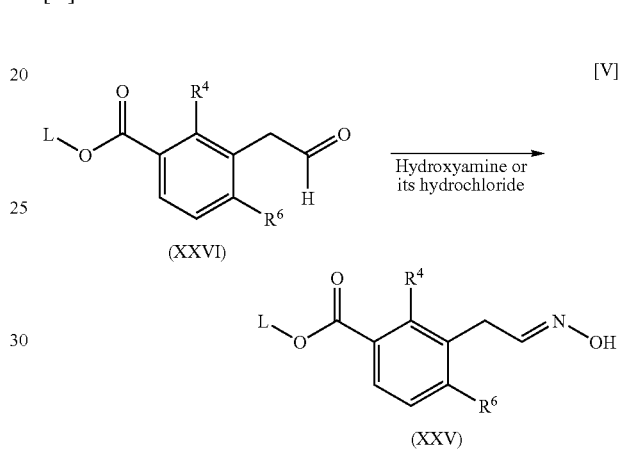

wherein $R^4$, $R^6$ and L are as defined above.

This reaction can be carried out in the same manner as the above-described reaction [T].

The compound represented by the above formula (XXVI) can be produced in accordance with the following reaction [W].

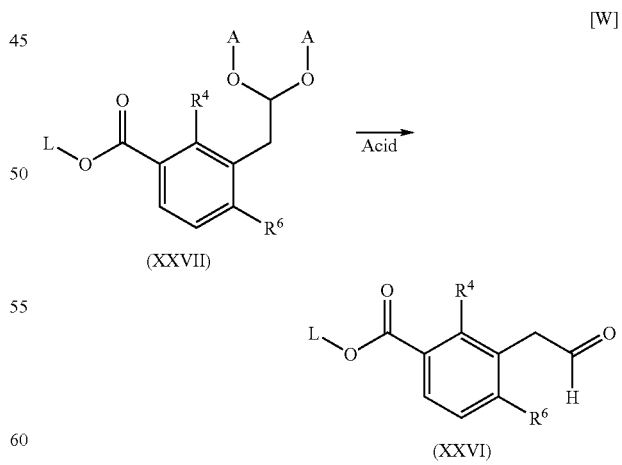

wherein $R^4$, $R^6$ and L are as defined above, and A is alkyl.

The above reaction can be carried out in the presence of a solvent, as the case requires. The solvent may be any solvent so long as it is inert to the reaction. Examples thereof include water; alcohols such a methanol and ethanol; and ethers such as diethyl ether, dioxane and tetrahydrofuran. As the solvent, one or more types may suitably be selected.

The above reaction can be carried out at a reaction temperature of usually from 0° C. to 150° C. for a reaction time of usually from 1 minute to 48 hours.

The compound represented by the above formula (XXVII) can be produced in accordance with the following reaction [X].

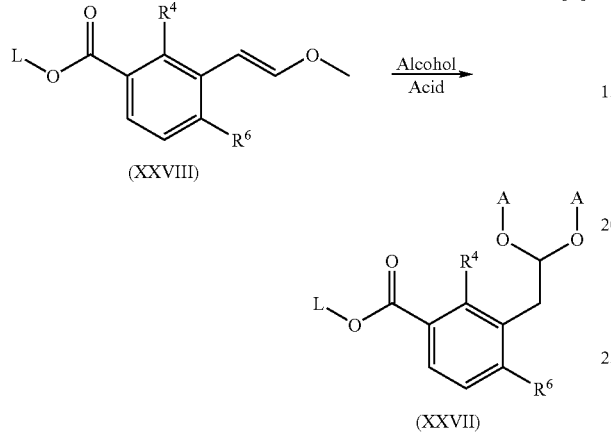

wherein $R^4$, $R^6$, L and A are as defined above.

The alcohol to be used for the above reaction may, for example, be methanol or ethanol. Further, the acid may, for example, be hydrochloric acid or toluenesulfonic acid.

The above reaction can be carried out at a reaction temperature of usually from 0° C. to 150° C. for a reaction time of usually from 1 minute to 48 hours.

The compound represented by the above formula (XXVIII) can be produced in accordance with the following reaction [Y].

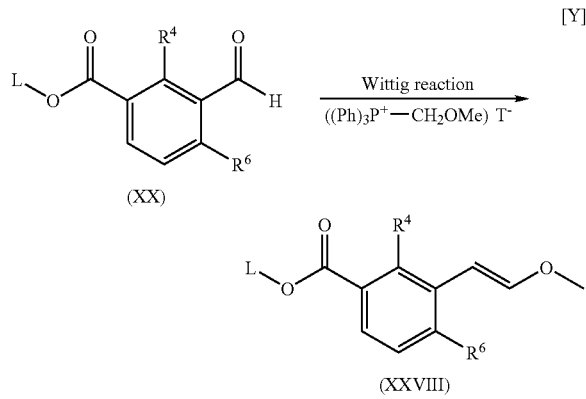

wherein $R^4$, $R^6$ and L are as defined above, T is halogen, Ph is phenyl, and Me is methyl.

The solvent to be used for the above reaction may be any solvent so long as it is inert to the reaction. Examples thereof include ethers such as diethyl ether, dioxane and tetrahydrofuran; aromatic hydrocarbons such as benzene, toluene and xylene; and aprotic polar solvents such as acetonitrile, N,N-dimethylformamide, dimethylsulfoxide, sulfolane and dimethoxyethane.

The above reaction can be carried out in the presence of a base, as the case requires. Examples of the base include sodium hydride (NaH); alkali lithium agents such as n-butyllithium; and metal amides such as sodium amide ($NaNH_2$).

The above reaction can be carried out at a reaction temperature of usually from −80° C. to 150° C. for a reaction time of usually from 1 minute to 48 hours.

Among the compounds represented by the above formula (XI), a compound wherein $R^5$ is $R^{5-a-6}$ can be produced in accordance with the following reaction [Z].

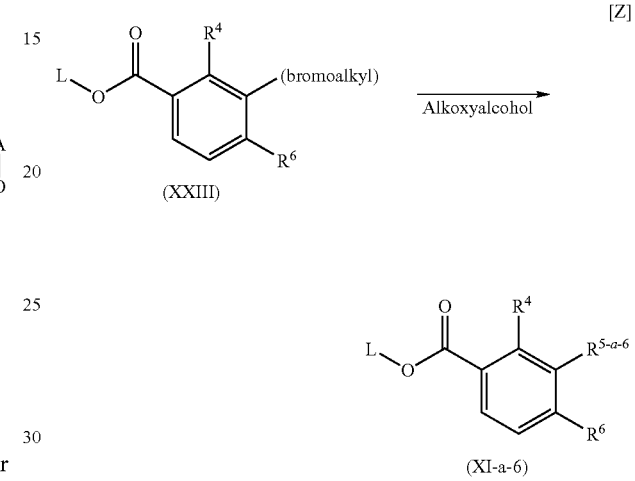

wherein $R^4$, $R^6$ and L are as defined above, and $R^{5-a-6}$ is alkoxyalkoxyalkyl.

The above reaction can be carried out in the presence of a solvent, as the case requires. The solvent may be any solvent so long as it is inert to the reaction, and examples thereof include alcohols such as methanol and ethanol; esters such as methyl acetate, ethyl acetate and propyl acetate; ethers such as diethyl ether, dioxane and tetrahydrofuran; and aprotic polar solvents such as acetonitrile, N,N-dimethylformamide, dimethylsulfoxide, sulfolane and dimethoxyethane. As the solvent, one or more may suitably be selected.

The above reaction can be carried out in the presence of a base, as the case requires. Examples of the base include alkali metal hydrides such as sodium hydride and potassium hydride.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-7}$ can be prepared in accordance with the following reaction [AA].

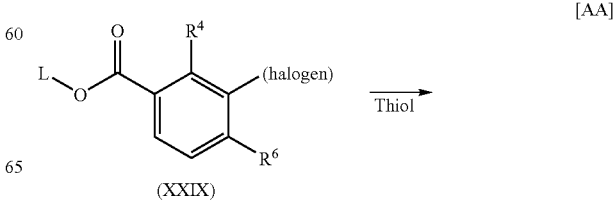

-continued

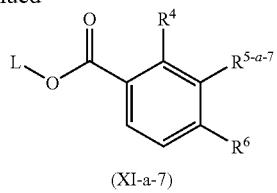

(XI-a-7)

wherein $R^4$, $R^6$ and L are as defined above, and $R^{5-a-7}$ is alkylthio, alkoxyalkylthio, haloalkoxyalkylthio, alkoxyhaloalkylthio, haloalkoxyhaloalkylthio, alkylthioalkylthio, haloalkylthioalkylthio, alkylthiohaloalkylthio or haloalkylthiohaloalkylthio.

The above reaction can be carried out in the presence of a solvent, as the case requires. The solvent may be any solvent so long as it is inert to the reaction, and examples thereof include alcohols such as methanol and ethanol; ethers such as diethyl ether, dioxane and tetrahydrofuran; aprotic polar solvents such as acetonitrile, N,N-dimethylformamide, dimethylsulfoxide, sulfolane and dimethoxyethane; and water. As the solvent, one or more types may suitably be selected.

The above reaction can be carried out in the presence of a base, as the case requires. Examples of the base include alkali metal hydrides such as sodium hydride and potassium hydride; alkali metal hydroxides such as sodium hydroxide and potassium hydroxide; and alkaline earth metal hydroxides such as calcium hydroxide.

The above reaction can be carried out at a reaction temperature of usually from 0° C. to 250° C. for a reaction time of usually from 1 minute to 48 hours.

Among the compounds represented by the above formula (XI), a compound wherein $R^5$ is $R^{5-a-8}$ can be prepared in accordance with following reaction [AB].

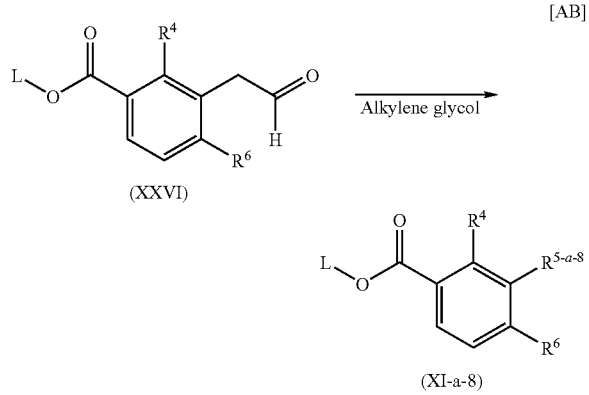

wherein $R^4$, $R^6$ and L are as defined above, and $R^{5-a-8}$ is a heterocyclylalkyl containing two oxygen atoms.

The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The acid catalyst to be used for the above reaction may, for example, be p-toluenesulfonic acid or pyridium p-toluenesulfonate.

In the above reaction, it is preferred to remove moisture generated by the reaction by azeotropy with the solvent or by using a drying agent.

The above reaction can be carried out at a reaction temperature of usually from 0° C. to 150° C. for a reaction time of usually from 1 minute to 48 hours.

Among the compounds represented by the above formula (I), a compound wherein Q is a hydrogen atom, and $R^5$ is $R^{5-a-9}$ can be prepared in accordance with the following reaction [AC].

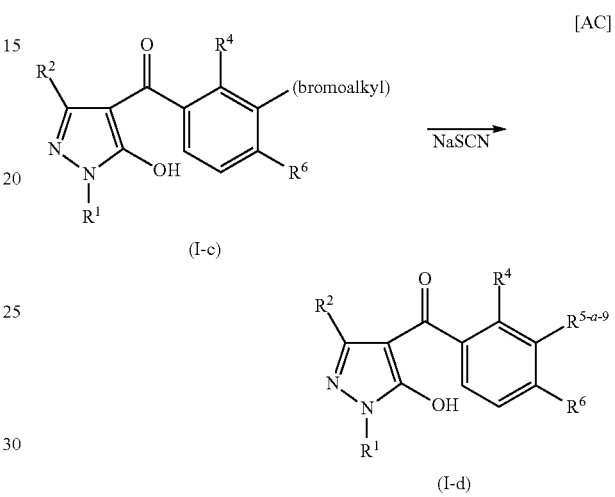

wherein $R^1$, $R^2$, $R^4$ and $R^6$ are as defined above, and $R^{5-a-9}$ is thiocyanatoalkyl.

The above reaction can be carried out in the presence of a solvent, as the case requires. The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; ethers such as diethyl ether, dioxane and tetrahydrofuran; and alcohols such as methanol, ethanol and propanol. As the solvent, one or more types may suitably be selected.

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-10}$ can be prepared in accordance with the following reaction [AD].

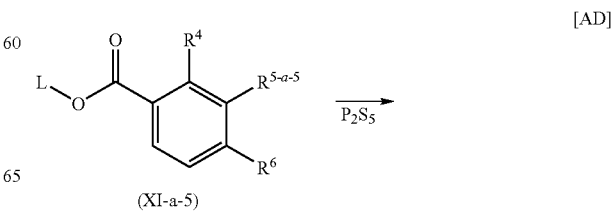

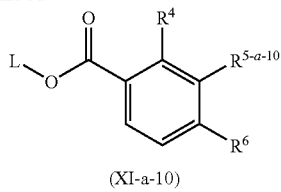

(XI-a-10)

wherein $R^4$, $R^{5-a-5}$, $R^6$ and L are as defined above, and $R^{5-a-10}$ is amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)$OR^7$ and —C(O)$SR^7$.

The solvent to be used for the above reaction may be any solvent so long as it is inert to the reaction, and examples thereof include alcohols such as methanol, ethanol and propanol; halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out at a reaction temperature of usually from 0° C. to 250° C. for a reaction time of usually from 1 minute to 48 hours.

Among the compounds represented by the above formula (XI), a compound wherein $R^5$ is $R^{5-a-11}$ can be prepared in accordance with the following reaction [AE].

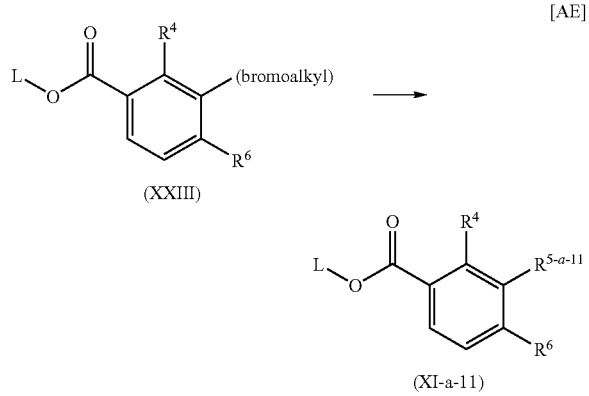

[AE]

wherein $R^4$, $R^6$ and L are as defined above, and $R^{5-a-11}$ is aminoalkyl which may be substituted by at least one substituent selected from alkyl, cyano, cyanoalkyl, (alkylthio)carbonylalkyl, alkyl(thiocarbonyl)alkyl, —C(O)$OR^7$ and —C(O)$SR^7$.

Namely, the compound represented by the formula (XI-a-11) can be produced by reacting ammonia or an amine which may be substituted by at least one substituent selected from alkyl, cyano, cyanoalkyl, (alkylthio)carbonylalkyl, alkyl(thiocarbonyl)alkyl, —C(O)$OR^7$ and —C(O)$SR^7$, with a compound represented by the formula (XXIII).

The above reaction can be carried out in the presence of a solvent, as the case requires. The solvent to be used for the above reaction may be any solvent so long as it is inert to the reaction. Examples thereof include halogenated hydrocarbons such as methylene chloride, chloroform, dichloroethane and trichloroethane; aromatic hydrocarbons such as benzene, toluene and xylene, esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal carbonates such as sodium carbonate and potassium carbonate; alkali metal hydrogencarbonates such as sodium hydrogencarbonate and potassium hydrogencarbonate; alkaline earth metal carbonates such as calcium carbonate and magnesium carbonate; sodium hydride (NaH); alkali lithium reagents such as n-butyllithium; and metal amides such as sodium amide ($NaNH_2$). Examples of the organic base include amines such as triethylamine, N,N-dimethylaminopyridine, diisopropylaminopyridine and DBU (diazabicycloundecene).

The above reaction can be carried out in the presence of a catalyst, as the case requires. The catalyst may, for example, be TBAI (tert-butylammonium iodide).

The above reaction can be carried out at a reaction temperature of usually from 0° C. to 150° C. for a reaction time of usually from 1 minute to 48 hours.

Among the compounds represented by the above formula (XI), a compound wherein $R^5$ is $R^{5-a-12}$ can be prepared in accordance with the following reaction [AF-1].

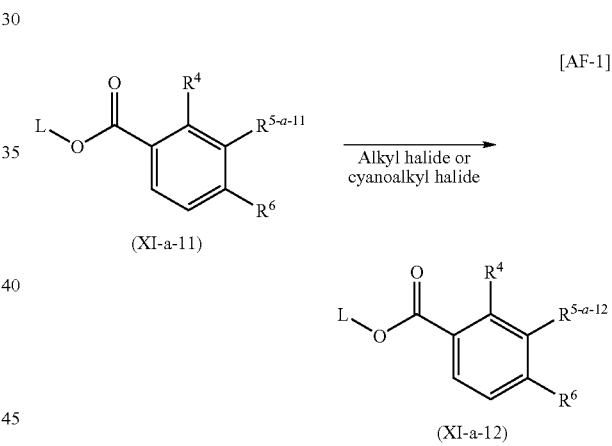

[AF-1]

wherein $R^4$, $R^6$, $R^{5-a-11}$ and L are as defined above, and $R^{5-a-12}$ is one having the amino moiety of $R^{5-a-11}$ substituted by alkyl or cyanoalkyl.

The above reaction can be carried out in the presence of a solvent, as the case requires. The solvent may be any solvent so long as it is inert to the reaction, and examples thereof include alcohols such as methanol, ethanol and propanol; halogenated hydrocarbons such as methylene chloride, chloroform, dichloroethane and trichloroethane; aromatic hydrocarbons such as benzene, toluene and xylene; esters such as methyl acetate, ethyl acetate and propyl acetate; aprotic polar solvents such as acetonitrile, N,N-dimethylformamide, dimethylsulfoxide, sulfolane and dimethoxyethane; and ethers such as diethyl ether, dioxane and tetrahydrofuran. As the solvent, one or more types may suitably be selected.

The above reaction can be carried out in the presence of a base, as the case requires. The base may be either inorganic base or organic base. Examples of the inorganic base include alkali metal carbonates such as sodium carbonate and potassium carbonate; alkali metal hydrogencarbonates such as sodium hydrogencarbonate and potassium hydrogencarbonate; and alkaline earth metal carbonates such as calcium carbonate and magnesium carbonate. Examples of the organic base include amines such as triethylamine, N,N-dimethylaminopyridine, diisopropylaminopyridine and DBU (diazabicycloundecene).

The above reaction can be carried out at a reaction temperature of usually from 0° C. to 150° C. for a reaction time of usually from 1 minute to 48 hours.

Among the compounds represented by the above formula (I), a compound wherein Q is —C(O)SR$^3$, and R$^5$ is R$^{5-a-13}$ can be prepared in accordance with the following reaction [AF-2].

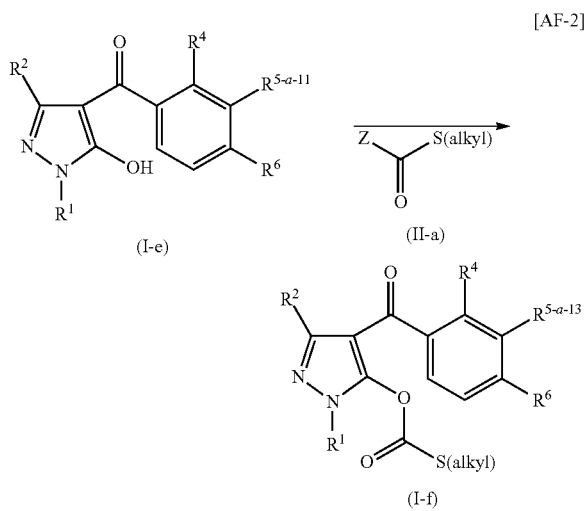

wherein R$^1$, R$^2$, R$^4$, R$^6$, R$^{5-a-11}$ and Z are as defined above, and R$^{5-a-13}$ is one having the amino moiety of R$^{5-a-11}$ substituted by (alkylthio)carbonyl.

This reaction can be carried out in the same manner as the above-described reaction [A].

Among the compounds represented by the above formula (XI), a compound wherein R$^5$ is R$^{5-a-14}$ can be prepared in accordance with the following reaction [AG].

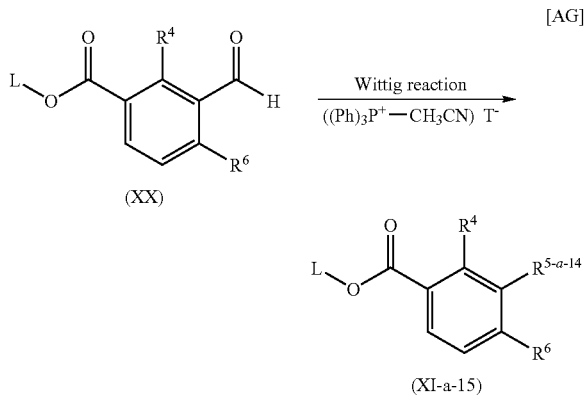

wherein R$^4$, R$^6$, L, T and Ph are as defined above, and R$^{5-a-14}$ is cyanoalkenyl.

This reaction can be carried out in the same manner as the above-described reaction [Y].

Other herbicidal compound in the present invention includes, for example, the following compounds (by common names including ones under application for approval by ISO, or test codes), and one or more may suitably be selected. Even when not specifically mentioned here, in a case where such compounds have alkyl esters, hydrates, different crystal forms, various constitutional isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, triaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone (BAS-670H) or pyrasulfotole; and others such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, TH-547 or a compound disclosed in WO2005092104; a triazolopyrimidinesulfonamide type such as flumetsulam, metosulam, diclosulam, cloransulam-methyl, florasulam or penoxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan (KUH-021); a sulfonylaminocarbonyltriazolinone type such as flucarbazone, flucarbazone-sodium, propoxycarbazone-sodium or propoxycarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochior or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone (KIH-485), dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, HOK-201, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras.*

The herbicidal composition of the present invention has excellent herbicidal effects. The application range extends to agricultural fields such as paddy fields, crop plant fields, orchards and mulberry fields and non-agricultural fields such as forest land, farm roads, play grounds and factory sites. The application method may suitably be selected from soil application, foliar application, water application, etc.

The herbicidal composition of the present invention is capable of controlling a wide range of undesired weeds, such as gramineae such as barnyardgrass (*Echinochloa crus-qalli* L., *Echinochloa oryzicola* vasing.), crabgrass (*Diqitaria sanquinalis* L., *Diqitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.), and cholorado bluestem (*Agropyron tsukushiense* (Honda) Ohwi); cyperaceae such as rice flatsedge (*Cyperus* iria L.), purple nutsedge (*Cyperus rotundus* L.), yellow nutsedge (*Cyperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindernia pyxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly sida (*Sida spinosa* L.); compositae such as common cocklebur (*Xanthium strumarium* L.), common ragweed (*Ambrosia elatior* L.), and thistle (*Breea setosa* (BIEB.) KITAM; solanaceae such as black nightshade (*Solanum nigrum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), and ladysthumb (*Polygonum persicaria* L.); cruciferae such as flexuous bittercress (Cardamine flexuosa WITH.), and shepherd's-purse (*Capsella bursa-pastoris* Medik.); convolvulaceae such as tall morningglory (*Ipomoea purpurea* L.), field bindweed (*Calystegia arvensis* L.), and ivyleaf morningglory (*Ipomoea hederacea* Jacq.); Chenopodiaceae such as common lambsquarters (*Chenopodium album* L.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalypha australis* L.); and Commelinaceae such as common dayflower (*Commelina communis* L.).

Therefore, they can be effectively used for selectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica stend*), peanut (*Arachis hypogaea* L.), flax (*Linum usitatissimum* L.), tobacco (*Nicotiana tabacum* L.), and coffee (*Coffea* spp.). Particularly, the herbicidal composition of the present invention is effectively used for selectively controlling noxious weeds in cultivation of corn, soybean, cotton, wheat, rice, rape, sunflower, sugar beet, sugar cane, Japanese lawngrass, peanut, flax, tobacco, coffee, and the like, and among these, especially corn, wheat, rice and the like. And the herbicidal composition of the present invention can be effectively used for nonselectively controlling noxious weeds.

The herbicidal composition of the present invention is effectively used to selectively control noxious weeds in cultivation of various transformed plants. Examples of the transformed plants include pest-resistant transformed plants, phytopathogen-resistant transformed plants, transformed plants regarding plant components, transformed plants resistant to the compound A, and transformed plants resistant to other herbicidal compound.

Examples of a site where the herbicidal composition of the present invention is applied include a corn field, a wheat, a barley or a rye field, a rice field and a non-agricultural field. One or more of other herbicidal compounds may suitably be selected and used depending upon the application site, and examples thereof include the following.

In a case where undesired plants are selectively controlled in a corn field, for example, said other herbicidal compound is at least one compound selected from the group consisting of a phenoxy compound, an aromatic carboxylic acid compound, a urea compound, a trizaine compound, a hydroxybenzonitrile compound, a diphenylether compound, a cyclic imide compound, a pyrazole compound, a sulfonylurea compound, a triazolopyrimidinesulfonamide compound, an imidazolinone compound, a dinitroaniline compound, a chloroacetamide compound, a thiocarbamate compound, benazolin, benazolin-ethyl, diflufenzopyr, diflufenzopyr-sodium, fluoroxypyr, fluoroxypyr-2-butoxy-1-methylethyl, fluoroxypyr-meptyl, pyridate, bentazone, bentazone-sodium, amicarbazone, carfentrazone-ethyl, saflufenacil, flufenpyr-ethyl, bencarbazone, fluridone, clomazone, sulcotrione, mesotrione, tembotrione, isoxaflutole, difenzoquat, difenzoquat-metilsulfate, isoxachlortole, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, flufenacet, tridiphane, benfuresate, pyroxasulfone, dalapon, dalapon-sodium, dinoterb, dinoterb-ammonium, dinoterb-diolamine, dinoterb-acetate and DNOC.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as dicamba, dicamba-butotyl, dicamba-diglycolamine, dicamba-dimethylammonium, dicamba-diolamine, dicamba-isopropylammonium, dicamba-potassium, dicamba-sodium, clopyralid, clopyralid-olamine, clopyralid-potassium or clopyralid-triisopropanolammonium; a urea compound such as diuron, linuron, metobenzuron, methabenzthiazuron or monolinuron; a triazine compound such as simazine, atrazine, metribuzin, terbuthylazine, cyanazine, ametryn, terbutryn or propazine; a hydroxybenzonitrile compound such as bromoxynil, bromoxynil-octanoate or bromoxynil-heptanoate; a diphenylether compound such as bifenox, oxyfluorfen or aclonifen; a cyclic imide compound such as flumiclorac-pentyl, cinidon-ethyl or fluthiacet-methyl; a pyrazole compound such as topramezone; a sulfonylurea compound such as primisulfuron-methyl, primisulfuron, rimsulfuron, nicosulfuron, prosulfuron, flupyrsulfuron-methyl-sodium, flupyrsulfuron, halosulfuron-methyl, halosulfuron, thifensulfuron-methyl, thifensulfuron, iodosulfuron, iodosulfuron-methyl-sodium, tritosulfuron or foramsulfuron; a triazolopyrimidinesulfonamide compound such as flumetsulam, metosulam or florasulam: an imidazolinone compound such as imazamox or imazamox-ammonium; a dinitroaniline compound such as pendimethalin, ethalfluralin or prodiamine; a chloroacetamide compound such as alachlor, metazachlor, metolachlor, S-metolachlor, pethoxamid, acetochlor, propachlor, dimethenamid or dimethenamid-P; a thiocarbamate compound such as EPTC, butyrate, triallate or orbencarb; benazolin; benazolin-ethyl; diflufenzopyr, diflufenzopyr-sodium; fluoroxypyr; fluoroxypyr-2-butoxy-1-methylethyl; fluoroxypyr-meptyl; pyridate; bentazone; bentazone-sodium; amicarbazone; carfentrazone-ethyl; saflufenacil; flufenpyr-ethyl; bencarbazone; fluridone; clomazone; sulcotrione; mesotrione; tembotrione; isoxaflutole; difenzoquat; difenzoquat-metilsulfate; isoxachlortosinate-ammonium; flufenacet; tridiphane; benfuresate; pyroxasulfone; dalapon, dalapon-sodium; dinoterb; dinoterb-ammonium; dinoterb-diolamine, dinoterb-acetate; or DNOC may, for example, be used.

In a case where undesired plants are selectively controlled in a wheat, a barley or a rye field, for example, said other herbicidal compound is at least one compound selected from the group consisting of a phenoxy compound, an aromatic carboxylic acid compound, a urea compound, a triazine compound, an anilide compound, a hydroxybenzonitrile compound, a diphenylether compound, a cyclic imide compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, a phenyl carbamate compound, a chloroacetamide compound, a thiocarbamate compound, benazolin, benazolin-ethyl, quinclorac, quinmerac, fluoroxypyr, fluoroxypyr-2-butoxy-1-methylethyl, fluoroxypyr-meptyl, pyridate, bentazone, bentazone-sodium, carfentrazone-ethyl, thidiazimin, pyraflufen-ethyl, saflufenacil, flupoxam, fluazolate, bencarbazone, flurtamone, diflufenican, sulcotrione, difenzoquat, difenzoquat-metilsulfate, picolinafen, beflubutamid, flamprop-M-methyl, flamprop-M, flamprop-M-isopropyl, flufenacet, indanofan, pinoxaden, dinoterb, dinoterb-ammonium, dinoterb-diolamine, dinoterb-acetate, DNOC and isoxaben.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, clopyralid, clopyralid-olamine, clopyralid-potassium, clopyralid-triisopropanolammonium or aminopyralid; a urea compound such as chlorotoluron, diuron, linuron, isoproturon, dimefuron, methabenzthiazuron, metoxuron or neburon; a triazine compound such as prometryn, metribuzin, cyanazine or terbutryn; an anilide compound such as propanil or cypromid, a hydroxybenzonitrile compound such as bromoxynil, bromoxynil-octanoate, bromoxynil-heptanoate, ioxynil, ioxynil-octanoate, ioxynil-potassium or ioxynil-sodium; a diphenylether compound such as bifenox, oxyfluorfen, aclonifen, ethoxyfen-ethyl, fluoroglycofen-ethyl or fluoroglycofen; a cyclic imide compound such as cinidon-ethyl, a pyrazole compound such as pyrasulfotole; an aryloxyphenoxypropionic acid compound such as diclofop-methyl, diclofop, fenoxaprop-ethyl, fenoxaprop-P, fenoxaprop-P-ethyl, clodinafop-propargyl or clodinafop; a cyclohexanedione compound such as tralkoxydim or butroxydim; a sulfonylurea compound such as chlorsulfuron, metsulfuron-methyl, metsulfuron, cyclosulfamuron, prosulfuron, flupyrsulfuron-methyl-sodium, flupyrsulfuron, halosulfuron-methyl, halosulfuron, thifensulfuron-methyl, thifensulfuron, ethoxysulfuron, iodosulfuron-methyl-sodium, iodosulfuron, sulfosulfuron, triasulfuron, tribenuron-methyl, tribenuron, tritosulfuron, mesosulfuron-methyl, mesosulfuron, flucetosulfuron or amidosulfuron; a triazolopyrimidinesulfonamide compound such as flumetsulam, metosulam or florasulam; an imidazolinone compound such as imazamox, imazamox-ammonium, imazamethabenz or imazamethabenz-methyl; a pyrimidinylsalicylic acid compound such as pyribenzoxim; a sulfonylaminocarbonyltriazolinone compound such as flucarbazone, flucarbazone-sodium, propoxycarbazone or propoxycarbazone-sodium; a dinitroaniline compound such as pendimethalin or butralin; a phenyl carbamate compound such as barban; a chloroacetamide compound such as butachlor; a thiocarbamate compound such as prosulfocarb, triallate or orbencarb; benazolin, benazolin-ethyl, quinclorac, quinmerac, fluoroxypyr, fluoroxypyr-2-butoxy-1-methylethyl, fluoroxypyr-meptyl, pyridate, bentazone, bentazone-sodium, carfentrazone-ethyl, thidiazimin, pyraflufen-ethyl, saflufenacil, flupoxam, fluazolate, bencarbazone, flurtamone, diflufenican, sulcotrione, difenzoquat, difenzoquat-metilsulfate, picolinafen, beflubutamid, flamprop-M-methyl, flamprop-M, flamprop-M-isopropyl, flufenacet, indanofan, pinoxaden, dinoterb, dinoterb-ammonium, dinoterb-diolamine, dinoterb-acetate, DNOC; or isoxaben may, for example, be used.

In a case where undesired plants are selectively controlled in a rice field, for example, said other herbicidal compound is at least one compound selected from the group consisting of a phenoxy compound, an aromatic carboxylic acid compound, a urea compound, a triazine compound, an anilide compound, a carbamate compound, a diphenylether compound, a pyrazole compound, an aryloxyphenoxypropionic acid compound, a cyclohexanedione compound, a sulfonylurea compound, a triazolopyrimidinesulfonamide compound, a pyrimidinylsalicylic acid compound, a dinitroaniline compound, an organic phosphorus compound, a cumylamine compound, a chloroacetamide compound, a thiocarbamate compound, those which are believed to exhibit herbicidal effects by being parasitic on plants, quinclorac, quinmerac, pyridate, bentazone, bentazone-sodium, oxadiargyl, oxadiazon, carfentrazone-ethyl, pentoxazone, pyraclonil, fluridone, diflufenican, methoxyphenone, clomazone, mesotrione, tefuryltrione, benzobicyclon, cinmethylin, dithiopyr, etobenzanide, mefenacet, flufenacet, cafenstrole, fentrazamide, oxaziclomefone, indanofan, benfuresate, TCA-sodium, trichloroacetic acid, HOK-201 and quinoclamine.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid compound such as picloram, picloram-dimethylammonium, picloram-isoctyl, picloram-potassium, picloram-triisopropanolammonium, picloram-triisopropylammonium, picloram-trolamine, triclopyr, triclopyr-butotyl or triclopyr-triethylammonium; a urea compound such as linuron; a triazine compound such simetryn, prometryn, dimethametryn or triaziflam; an anilide compound such as propanil; a carbamate compound such as swep; a diphenylether compound such as nitrofen, chlomethoxyfen, bifenox, acifluorfen, acifluorfen-sodium, oxyfluorfen, fluoroglycofen-ethyl or fluoroglycofen; a pyrazole compound such as pyrazolynate, pyrazoxyfen or benzofenap; an aryloxyphenoxypropionic acid compound such as cyhalofop-butyl, metamifop-propyl or metamifop; a cyclohexanedione compound such as profoxydim; a sulfonylurea compound such as bensulfuron-methyl, bensulfuron, metsulfuron-methyl, metsulfuron, cinosulfuron, pyrazosulfuron-ethyl, pyrazosulfuron, azimsulfuron, imazosulfuron, cyclosulfamuron, halosulfuron-methyl, halosulfuron, ethoxysulfuron, orthosulfamuron, flucetosulfuron or TH-547; a triazolopyrimidinesulfonamide compound such as penoxsulam; a pyrimidinylsalicylic acid compound such as bispyribac-sodium, pyriminobac-methyl, pyribenzoxim, pyriftalid or pyrimisulfan; a dinitroaniline compound such as oryzalin, pendimethalin or butralin; an organic phosphorus compound such as butamifos, anilofos or piperophos; a cumylamine compound such as daimuron, cumyluron or bromobutide; a chloroacetamide compound such as butachlor, pretilachlor thenylchlor; a thiocarbamate compound such as molinate, dimepiperate, pyributicarb, esprocarb or thiobencarb; quinclorac; quinmerac; pyridate; bentazone; bentazone-sodium; oxadiargyl; oxadiazon; carfentrazone-ethyl; pentoxazone; pyraclonil, fluridone; diflufenican; methoxyphenone; clomazone; mesotrione; tefuryltrione; benzobicyclon; cinmethylin; dithiopyr; etobenzanide; mefenacet; flufenacet; cafenstrole; fentrazamide; oxaziclomefone; indanofan; benfuresate; TCA-sodium; trichloroacetic acid; HOK-201; or quinoclamine may, for example, be used.

In a case where undesired plants are nonselectively controlled, for example, said other herbicidal compound is at least one compound selected from the group consisting of a phenoxy compound, an aromatic carboxylic acid compound, a urea compound, a triazine compound, a uracil compound, a hydroxybenzonitrile compound, a quaternary ammonium salt compound, a sulfonylurea compound, an imidazolinone compound, a pyrimidinylsalicylic acid compound, a dinitroaniline compound, benazolin, benazolin-ethyl, diflufenzopyr, diflufenzopyr-sodium, chlorflurenol, chlorflurenol-methyl, pentanochlor, butafenacil, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, asulam, asulam-sodium, dalapon, dalapon-sodium, TCA-sodium, trichloroacetic acid, CMA, fosamine, fosamine-ammonium, ammonium sulfamate, borax, chloroacetic acid, sodium chloroacete, methylarsonic acid, dimethylarsinic acid, sodium dimethylarsinate, flupropanate, flupropanate-sodium, isoxaben, mefluidide, mefluidide-diolamine, pentachlorophenol, pentachlorophenol-sodium and pentachlorophenol-laurate.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; a urea compound such as diuron, tebuthiuron, isouron, karbutilate, monolinuron or neburon; a triazine compound such as atrazine, hexazinone, terbuthylazine, cyanazine, ametryn, propazine or prometon; a uracil compound such as bromacil or bromacyl-lithium; a hydroxybenzonitrile compound such as bromoxynil, bromoxynil-octanoate or bromoxynil-heptanoate; a quaternary ammonium salt compound such as paraquat or diquat; a sulfonylurea compound such as sulfometuron-methyl, sulfometuron, chlorsulfuron, flazasulfuron or sulfosulfuron; an imidazolinone compound such as imazapyr, imazapyr-isopropylammonium or imazapic; a pyrimidinylsalicylic acid compound such as bispyribac-sodium; a dinitroaniline compound such as oryzalin or prodiamine; benazolin; benazolin-ethyl; diflufenzopyr; diflufenzopyr-sodium; chlorflurenol; chlorflurenol-methyl; pentanochlor; butafenacil; glyphosate; glyphosate-sodium; glyphosate-potassium; glyphosate-ammonium; glyphosate-diammonium; glyphosate-isopropylammonium; glyphosate-trimesium; glyphosate-sesquisodium; glufosinate; glufosinate-ammonium; bilanafos; bilanafos-sodium; asulam; asulam-sodium; dalapon; dalapon-sodium; TCA-sodium; trichloroacetic acid; CMA; fosamine; fosamine-ammonium; ammonium sulfamate; borax; chloroacetic acid; sodium chloroacete; methylarsonic acid; dimethylarsinic acid; sodium dimethylarsinate; flupropanate; flupropanate-sodium; isoxaben; mefluidide; mefluidide-diolamine; pentachlorophenol; sodium pentachlorophenoxide or pentachlorophenol laurate may, for example, be used.

In the present invention, the mixing ratio of the compound A to said other herbicidal compound can not generally be defined, as it varies depending upon various conditions such as the type of the compound, the type of the formulation, the weather conditions, and the type and the growth state of the plants to be controlled, but it is usually from 1:1,000 to 1,000:1, preferably from 1:800 to 100:1, more preferably from 1:600 to 20:1 by the weight ratio.

Said other herbicidal compound in the present invention is not particularly limited to a specific compound, and the mixing ratio with the compound A is not limited to a specific range, but as one embodiment of the present invention, mixing ratios of the compound A to some compounds are exemplified. However, the ratio may also vary depending upon various conditions such as the type of the compound, the type of formulation, the weather conditions, and the type and the growth state of the plants to be controlled as described above.

In a case where said other herbicidal compound is a phenoxy compound, the mixing ratio of (a) the compound A to (b) the phenoxy compound is usually from 1:1 to 1:500, preferably from 1:1 to 1:100, more preferably from 1:5 to 1:50 by the weight ratio.

In a case where said other herbicidal compound is an aromatic carboxylic acid compound, the mixing ratio of (a) the compound A to (b) the aromatic carboxylic acid compound is usually from 1:1 to 1:500, preferably from 1:1 to 1:100, more preferably from 1:5 to 1:50 by the weight ratio.

In a case where said other herbicidal compound is fluoroxypyr, the mixing ratio of (a) the compound A to (b) fluoroxypyr is usually from 1:1: to 1:500, preferably from 1:1 to 1:100, more preferably from 1:5 to 1:50 by the weight ratio.

In a case where said other herbicidal compound is a triazine compound, the mixing ratio of (a) the compound A to (b) the triazine compound is usually from 1:1,000 to 1,000:1, preferably from 1:800 to 10:1, more preferably from 1:600 to 5:1 by the weight ratio.

In a case where said other herbicidal compound is a urea compound, the mixing ratio of (a) the compound A to (b) the urea compound is usually from 1:1 to 1:500, preferably from 1:5 to 1:200, more preferably from 1:10 to 1:80 by the weight ratio.

In a case where said other herbicidal compound is a hydroxybenzonitrile compound, the mixing ratio of (a) the compound A to (b) the hydroxybenzonitrile compound is usually from 1:1 to 1:500, preferably from 1:1 to 1:100, more preferably from 1:3 to 1:30 by the weight ratio.

In a case where said other herbicidal compound is bentazone or its salt (such as bentazone-sodium), the mixing ratio of (a) the compound A to (b) bentazone or its salt is usually from 1:1 to 1:500, preferably from 1:1 to 1:100, more preferably from 1:1 to 1:30 by the weight ratio.

In a case where said other herbicidal compound is a diphenylether compound, the mixing ratio of (a) the compound A to (b) the diphenylether compound is usually from 1:1 to 1:500, preferably from 1:1 to 1:100, more preferably from 1:5 to 1:30 by the weight ratio.

In a case where said other herbicidal compound is a cyclic imide compound, the mixing ratio of (a) the compound A to (b) the cyclic imide compound is usually from 1:50 to 100:1, preferably from 1:50 to 50:1, more preferably from 1:10 to 20:1 by the weight ratio.

In a case where said other herbicidal compound is carfentrazone-ethyl, the mixing ratio of (a) the compound A to (b) carfentrazone-ethyl is usually from 1:100 to 100:1, preferably from 1:10 to 10:1, more preferably from 1:1 to 10:1 by the weight ratio.

In a case where said other herbicidal compound is pyridate, the mixing ratio of (a) the compound A to (b) pyridate is usually from 1:1 to 1:500, preferably from 1:1 to 1:100, more preferably from 1:10 to 1:30 by the weight ratio.

In a case where said other herbicidal compound is sulcotrione, the mixing ratio of (a) the compound A to (b) sulcotrione is usually from 1:100 to 10:1, preferably from 1:10 to 10:1, more preferably from 1:5 to 2:1 by the weight ratio.

In a case where said other herbicidal compound is mesotrione, the mixing ratio of (a) the compound A to (b) mesotrione is usually from 1:1 to 1:100, preferably from 1:1 to 1:50, more preferably from 1:1 to 1:10 by the weight ratio.

In a case where said other herbicidal compound is a sulfonylurea compound, the mixing ratio of (a) the compound A to (b) the sulfonylurea compound is usually from 1:100 to 100:1, preferably from 1:50 to 50:1, more preferably from 1:25 to 20:1 by the weight ratio.

In a case where said other herbicidal compound is a triazolopyrimidinesulfonamide compound, the mixing ratio of (a) the compound A to (b) the triazolopyrimidinesulfonamide compound is usually from 1:100 to 100:1, preferably from 1:50 to 10:1, more preferably from 1:10 to 5:1 by the weight ratio.

In a case where said other herbicidal compound is an imidazolinone compound, the mixing ratio of (a) the compound A to (b) the imidazolinone compound is usually from 1:100 to 100:1, preferably from 1:50 to 10:1, more preferably from 1:10 to 5:1 by the weight ratio.

In a case where said other herbicidal compound is glyphosate or its salt (such as glyphosate-ammonium), the mixing ratio of (a) the compound A to (b) glyphosate or its salt is usually from 1:1 to 1:500, preferably from 1:1 to 1:50, more preferably from 1:1 to 1:40 by the weight ratio.

In a case where said other herbicidal compound is glufosinate or its salt (such as glufosinate-ammonium), the mixing ratio of (a) the compound A to (b) glufosinate or its salt is usually from 1:1 to 1:500, preferably from 1:1 to 1:100, more preferably from 1:1 to 1:40 by the weight ratio.

In a case where said other herbicidal compound is a dinitroaniline compound, the mixing ratio of (a) the compound A to (b) the dinitroaniline compound is usually from 1:1 to 1:1,000, preferably from 1:1 to 1:100, more preferably from 1:1 to 1:50 by the weight ratio.

In a case where said other herbicidal compound is a chloroacetamide compound, the mixing ratio of (a) the compound A to (b) the chloroacetamide compound is usually from 1:1 to 1:1,000, preferably from 1:1 to 1:500, more preferably from 1:1 to 1:300 by the weight ratio.

In a case where said other herbicidal compound is flufenacet, the mixing ratio of (a) the compound A to (b) flufenacet is usually from 1:1 to 1:500, preferably from 1:5 to 1:100, more preferably from 1:15 to 1:45 by the weight ratio.

In a case where said other herbicidal compound is pyroxasulfone, the mixing ratio of (a) the compound A to (b) pyroxasulfone is usually from 1:1 to 1:500, preferably from 1:1 to 1:100, more preferably from 1:1 to 1:50 by the weight ratio.

The dose of the herbicidally active ingredients in the present invention can not generally be defined, as it varies depending upon various conditions such as the types of the compound A and other herbicidal compound, their mixing ratio, the type of the formulation, the weather conditions, and the type and the growth state of the plants to be controlled. However, the compound A is applied in an amount of usually from 0.1 to 10,000 g/ha, preferably from 1 to 2,000 g/ha, more preferably from 1 to 1,000 g/ha, and said other herbicidal compound is applied in an amount of usually from 0.1 to 50,000 g/ha, preferably from 1 to 10,000 g/ha, more preferably from 1.5 to 10,000 g/ha, and the appropriate dose of the compound A and said other herbicidal compound in total is usually from 0.2 to 60,000 g/ha, preferably from 2 to 12,000 g/ha, more preferably from 2.5 to 11,000 g/ha.

Said other herbicidal compound in the present invention is not limited to a specific compound, and its dose is not limited to a specific range, but as one embodiment of the present invention, doses of some compounds are exemplified. However, the dose may vary depending upon various conditions such as the type of the compound, the type of the formulation, the weather conditions, and the type and the growth state of the plants to be controlled in some cases as described above.

In a case where other herbicidal compound is a phenoxy compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is an aromatic carboxylic acid compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is fluoroxypyr, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is a triazine compound, the dose of said other herbicidal compound is usually from 0.1 to 50,000 g/ha, preferably from 10 to 10,000 g/ha. Further, the appropriate dose of the compound A and said other herbicidal compound in total is usually from 0.2 to 60,000 g/ha, preferably from 11 to 12,000 g/ha.

In a case where other herbicidal compound is a urea compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is a hydroxybenzonitrile compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is bentazone or its salt (such as bentazone-sodium), the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is a diphenylether compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is a cyclic imide compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is carfentrazone-ethyl, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is pyridate, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is sulcotrione, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is mesotrione, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is a sulfonylurea compound, the dose of said other herbicidal compound is usually from 0.1 to 10,000 g/ha, preferably from 1 to 500 g/ha. Further, the appropriate dose of the compound A and said other herbicidal compound in total is usually from 0.2 to 20,000 g/ha, preferably from 2 to 2,500 g/ha.

In a case where other herbicidal compound is a triazolopyrimidinesulfonamide compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is an imidazolinone compound, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is glyphosate or its salt (such as glyphosate-ammonium), the dose of said other herbicidal compound is usually from 0.1 to 50,000 g/ha, preferably from 1 to 5,000 g/ha. Further, the appropriate dose of the compound A and said other herbicidal compound in total is usually from 0.2 to 60,000 g/ha, preferably from 2 to 7,000 g/ha.

In a case where other herbicidal compound is glufosinate or its salt (such as glufosinate-ammonium), the dose of said other herbicidal compound is usually from 0.1 to 50,000 g/ha, preferably from 1 to 5,000 g/ha. Further, the appropriate dose of the compound A and said other herbicidal compound in total is usually from 0.2 to 60,000 g/ha, preferably from 2 to 7,000 g/ha.

In a case where other herbicidal compound is a dinitroaniline compound, the dose of said other herbicidal compound is usually from 0.1 to 10,000 g/ha, preferably from 1 to 5,000 g/ha. Further, the appropriate dose of the compound A and said other herbicidal compound in total is usually from 0.2 to 20,000 g/ha, preferably from 2 to 7,000 g/ha.

In a case where other herbicidal compound is a chloroacetamide compound, the dose of said other herbicidal compound is usually from 0.1 to 50,000 g/ha, preferably from 1 to 10,000 g/ha. Further, the appropriate dose of the compound A and said other herbicidal compound in total is usually from 0.2 to 60,000 g/ha, preferably from 2 to 12,000 g/ha.

In a case where other herbicidal compound is flufenacet, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

In a case where other herbicidal compound is pyroxasulfone, the dose of said other herbicidal compound is usually from 0.1 to 10,000 g/ha, preferably from 1 to 2,000 g/ha. Further, the appropriate dose of the compound A and said other herbicidal compound in total is usually from 0.2 to 20,000 g/ha, preferably from 2 to 4,000 g/ha.

With respect to application, application to undesired plants or application to a place where they grow (either before or after emerging of the plants) may optionally be selected. Further, the compound A and other herbicidal compound may separately be formulated so that they are mixed for use at the time of application, or they may be formulated together. As examples of a specific application method, the following may be mentioned.

1. The compound A and other herbicidal compound are formulated together, and the formulation is applied as it is.
2. The compound A and other herbicidal compound are formulated together, the formulation is diluted to a predetermined concentration with e.g. water, and as the case requires, a spreader (such as a surfactant, a vegetable oil or a mineral oil) is added for application.
3. The compound A and other herbicidal compound are separately formulated and applied as they are.
4. The compound A and other herbicidal compound are separately formulated, and they are diluted to a predetermined concentration with e.g. water, and as the case requires, a spreader (such as a surfactant, a vegetable oil or a mineral oil) is added for application.
5. The compound A and other herbicidal compound are separately formulated, and the formulations are mixed when diluted to a predetermined concentration with e.g. water, and as the case requires, a spreader (such as a surfactant, a vegetable oil or a mineral oil) is added for application.

The herbicidal composition of the present invention may be prepared by mixing the compound A and other herbicidal compound, as active ingredients, with various agricultural additives in accordance with conventional formulation methods for agricultural chemicals, and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, the compound A and other herbicidal compound may be mixed together for the formulation, or they may be separately formulated.

The additives to be used for the formulation include, for example, a solid carrier such as diatomaceous earth, slaked lime, calcium carbonate, talc, white carbon, kaoline, bentonite, a mixture of kaolinite and sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone or an alcohol; an anionic surfactant such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound A or other herbicidal compound to such various additives may be from 0.1:99.9 to 95:5, preferably from 0.2:99.8 to 85:15.

The herbicidal composition of the present invention may be mixed with or may be used in combination with other agricultural chemicals, fertilizers or phytotoxicity-reducing agents, whereby synergistic effects or activities may sometimes be obtained. Such other agricultural chemicals include, for example, a fungicide, an antibiotic, a plant hormone and an insecticide.

Now, examples of preferred embodiments of the present invention will be given below, but it should be understood that the present invention is by no means restricted thereto.

(1) A herbicidal composition comprising as active ingredients a herbicidal benzoylpyrazole compound of the formula (I) or its salt wherein Q is —C(O)SR$^3$, and other herbicidal compound.

(2) The herbicidal composition according to the above (1), which comprises as active ingredients the herbicidal benzoylpyrazole compound of the formula (I) or its salt wherein R$^1$ is alkyl or cycloalkyl, R$^2$ is a hydrogen atom or alkyl, R$^3$ is alkyl; cycloalkyl; haloalkyl; alkoxyalkyl; alkenyl; or aralkyl which may be substituted by R$^8$, R$^4$ is alkyl; haloalkyl; alkoxy; halogen; nitro; cyano; alkylthio; alkylsulfinyl; or alkylsulfonyl, R$^5$ is a hydrogen atom; alkyl; halogen; cyano; cyanoalkyl; haloalkyl; alkoxyalkyl; haloalkoxyalkyl; alkoxy; haloalkoxy; alkoxyalkoxy; haloalkoxyalkoxy; alkoxyhaloalkoxy; alkoxyalkoxyalkyl; alkylthio; alkoxyalkylthio; haloalkoxyalkylthio; alkylthioalkylthio; haloalkylthioalkylthio; alkylthioalkoxy; alkylsulfonyl; alkylsulfonylalkyl; alkoxycarbonylalkyl; alkoxycarbonylalkoxy; heterocyclyloxy; heterocyclylalkoxy; heterocyclylalkoxyalkyl; —OC(O)SR$^7$; —OC(O)OR$^7$; —C(O)OR$^7$; —C(O)SR$^7$; or 4,5-dihydroisoxazol-3-yl which may be substituted by R$^9$, R$^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, and other herbicidal compound.

(3) The herbicidal composition according to the above (2), which comprises as active ingredients the herbicidal benzoylpyrazole compound of the formula (I) or its salt wherein $R^1$ is alkyl or cycloalkyl, $R^2$ is a hydrogen atom or alkyl, $R^3$ is alkyl; cycloalkyl; haloalkyl; alkoxyalkyl; or arylalkyl which may be substituted by $R^8$, $R^4$ is alkyl; haloalkyl; alkoxy; halogen; nitro; cyano; alkylthio; alkylsulfinyl; or alkylsulfonyl, $R^5$ is alkyl; haloalkyl; alkoxyalkyl; haloalkoxyalkyl; alkoxy; haloalkoxy; alkoxyalkoxy; haloalkoxyalkoxy; heterocyclyloxy; heterocyclylalkoxy; heterocyclylalkoxyalkyl; —OC(O)SR$^7$; —OC(O)OR$^7$; —C(O)OR$^7$; —C(O)SR$^7$; or 4,5-dihydroisoxazol-3-yl which may be substituted by $R^9$, $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, and other herbicidal compound.

(4) The herbicidal composition according to the above (3), which comprises as active ingredients the herbicidal benzoylpyrazole compound of the formula (I) or its salt wherein $R^1$ is alkyl, $R^2$ is a hydrogen atom, $R^3$ is alkyl, $R^4$ is alkyl, $R^5$ is alkoxy; haloalkoxy; alkoxyalkoxy; —C(O)OR$^7$; or 4,5-dihydroisoxazol-3-yl, and $R^6$ is alkylsulfonyl, and other herbicidal compound.

(5) The herbicidal composition, which comprises as active ingredients the herbicidal benzoylpyrazole compound of the formula (I) or its salt wherein Q is a hydrogen atom, and other herbicidal compound.

(6) The herbicidal composition according to the above (5), which comprises as active ingredients the herbicidal benzoylpyrazole compound of the formula (I) or its salt wherein $R^1$ is alkyl or cycloalkyl, $R^2$ is a hydrogen atom or alkyl, $R^4$ is alkyl; haloalkyl; alkoxy; halogen; nitro; cyano; alkylthio; alkylsulfinyl; or alkylsulfonyl, $R^5$ is haloalkyl; alkoxyalkyl; haloalkoxyalkyl; alkoxy; haloalkoxy; alkoxyalkoxy; haloalkoxyalkoxy; heterocyclyloxy; heterocyclylalkoxy; heterocyclylalkoxyalkyl; —OC(O)SR$^7$; —OC(O)OR$^7$; —C(O)OR$^7$; or —C(O)SR$^7$; $R^6$ is haloalkyl; halogen; nitro; cyano; alkylthio; alkylsulfinyl; or alkylsulfonyl, $R^7$ is alkyl; haloalkyl; alkoxyalkyl; alkenyl; haloalkenyl; alkynyl; or arylalkyl which may be substituted by $R^{10}$, and each of $R^8$, $R^9$ and $R^{10}$ which are independent of one another, is halogen; alkyl; or alkoxy, and other herbicidal compound.

(7) The herbicidal composition according to the above (6), which comprises as active ingredients the herbicidal benzoylpyrazole compound of the formula (I) or its salt wherein $R^1$ is alkyl, $R^2$ is a hydrogen atom, $R^4$ is alkyl, $R^5$ is alkoxyalkyl; alkoxy; haloalkoxy; alkoxyalkoxy; or —C(O)OR$^7$, and $R^6$ is alkylsulfonyl, and other herbicidal compound.

(8) The herbicidal composition, which comprises as active ingredients the compound A and other herbicidal compound which is at least one compound selected from the group consisting of a phenoxy compound, an aromatic carboxylic acid compound, a urea compound, a triazine compound, a uracil compound, an anilide compound, a carbamate compound, a hydroxybenzonitrile compound, a quaternary ammonium salt compound, a diphenylether compound, a cyclic imide compound, a pyridazinone compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, an amide compound, an organic phosphorus compound, a phenyl carbamate compound, a cumylamine compound, a chloroacetamide compound, a thiocarbamate compound, naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, chlorflurenol-methyl, pyridate, bentazone, bentazone-sodium, amicarbazone, methazole, pentanochlor, oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone, amitrole, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachlortole, benzobicyclon, picolinafen, beflubutamid, flamprop-M, flamprop-M-methyl, flamprop-M-isopropyl, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, cinmethylin, asulam, asulam-sodium, dithiopyr, thiazopyr, chlorthal, chlorthal-dimethyl, diphenamid, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium, trichloroacetic acid, MSMA, DSMA, CMA, endothall, endothall-dipotassium, endothall-sodium, endothall-mono (N,N-dimethylalkylammonium), ethofumesate, sodium chlorate, pelargonic acid, fosamine, fosamine-ammonium, pinoxaden, HOK-201, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid and urea sulfate.

(9) The herbicidal composition, which comprises as active ingredients the compound A and other herbicidal compound which is at least one compound selected from the group consisting of (b-1) a compound selectively controlling undesired plants in a corn field, (b-2) a compound selectively controlling undesired plants in a wheat, a barley or a rye field, (b-3) a compound selectively controlling undesired plants in a rice field, and (b-4) a compound nonselectively controlling undesired plants.

(10) The herbicidal composition according to the above (9), wherein said other herbicidal compound is at least one compound selected from the group consisting of a phenoxy compound, an aromatic carboxylic acid compound, a urea compound, a triazine compound, a uracil compound, an anilide compound, a carbamate compound, a hydroxybenzonitrile compound, a quaternary ammonium salt compound, a diphenylether compound, a cyclic imide compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, an organic phosphorus compound, a phenyl carbamate compound, a cumylamine compound, a chloroacetamide compound, a thiocarbamate compound, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, chlorflurenol-methyl, pyridate, bentazone, bentazone-sodium, amicarbazone, pentanochlor, oxadiargyl, oxadiazon, carfentrazone-ethyl, thidiazimin, pentoxazone, pyraflufen-ethyl, butafenacil, saflufenacil, flupoxam, fluazolate, pyraclonil, flufenpyr-ethyl, bencarbazone, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachiortole, benzobicyclon, picolinafen, beflubutamid, flamprop-M, flamprop-M-methyl, flamprop-M-isopropyl, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, cinmethylin, asulam, asulam-sodium, dithiopyr, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium, trichloroacetic acid, CMA, fosamine, fosamine-ammonium, pinoxaden, HOK-201, ammonium sulfamate, borax, chloroacetic acid, sodium chloroacete, methylarsonic acid, dimethylarsinic acid, sodium dimethylarsinate, dinoterb, dinoterb-ammonium, dinoterb-diolamine, dinoterb-acetate, DNOC, flupropanate, flupropanate-sodium, isoxaben, mefluidide, mefluidide-diolamine, pentachlorophenol, sodium pentachlorophenoxide, pentachlorophenol laurate and quinoclamine.

(11) The herbicidal composition according to the above (10), wherein the phenoxy compound is at least one compound selected from the group consisting of 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide and clomeprop; the aromatic carboxylic acid compound is at least one compound selected from the group consisting of 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium and aminopyralid; the urea compound is at least one compound selected from the group consisting of chlorotoluron, diuron, linuron, isoproturon, metobenzuron, tebuthiuron, dimefuron, isouron, karbutilate, methabenzthiazuron, metoxuron, monolinuron and neburon; the triazine compound is at least one compound selected from the group consisting of simazine, atrazine, simetryn, prometryn, dimethametryn, hexazinone, metribuzin, terbuthylazine, cyanazine, ametryn, triaziflam, terbutryn, propazine and prometon; the uracil compound is at least one compound selected from the group consisting of bromacil and bromacyl-lithium; the anilide compound is at least one compound selected from the group consisting of propanil and cypromid; the carbamate compound is swep, the hydroxybenzonitrile compound is at least one compound selected from the group consisting of bromoxynil, bromoxynil-octanoate, bromoxynil-heptanoate, ioxynil, ioxynil-octanoate, ioxynil-potassium and ioxynil-sodium; the quaternary ammonium salt compound is at least one compound selected from the group consisting of paraquat and diquat; the diphenylether compound is at least one compound selected from the group consisting of nitrofen, chlomethoxyfen, bifenox, acifluorfen-sodium, acifluorfen, oxyfluorfen, aclonifen, ethoxyfen-ethyl, fluoroglycofen-ethyl and fluoroglycofen; the cyclic imide compound is at least one compound selected from the group consisting of flumiclorac-pentyl, cinidon-ethyl and fluthiacet-methyl; the pyrazole compound is at least one compound selected from the group consisting of pyrazolynate, pyrazoxyfen, benzofenap, topramezone and pyrasulfotole; the aryloxyphenoxypropionic acid compound is at least one compound selected from the group consisting of diclofop, diclofop-methyl, cyhalofop-butyl, fenoxaprop-ethyl, fenoxaprop-P, fenoxaprop-P-ethyl, metamifop, metamifop-propyl, clodinafop-propargyl and clodinafop; the cyclohexanedione compound is at least one compound selected from the group consisting of tralkoxydim, butroxydim and profoxydim; the sulfonylurea compound is at least one compound selected from the group consisting of sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, halosulfuron-methyl, halosulfuron, thifensulfuron-methyl, thifensulfuron, ethoxysulfuron, iodosulfuron-methyl-sodium, iodosulfuron, sulfosulfuron, triasulfuron, tribenuron-methyl, tribenuron, tritosulfuron, foramsulfuron, mesosulfuron-methyl, mesosulfuron, orthosulfamuron, flucetosulfuron, amidosulfuron and TH-547; the triazolopyrimidinesulfonamide compound is at least one compound selected from the group consisting of flumetsulam, metosulam, florasulam and penoxsulam; the imidazolinone compound is at least one compound selected from the group consisting of imazapyr, imazapyr-isopropylammonium, imazamox, imazamox-ammonium, imazamethabenz, imazamethabenz-methyl and imazapic; the pyrimidinylsalicylic acid compound is at least one compound selected from the group consisting of bispyribac-sodium, pyriminobac-methyl, pyribenzoxim, pyriftalid and pyrimisulfan; the sulfonylaminocarbonitriletriazolinone compound is at least one compound selected from the group consisting of flucarbazone, propoxycarbazone-sodium, propoxycarbazone-sodium and propoxycarbazone; the dinitroaniline compound is at least one compound selected from the group consisting of oryzalin, pendimethalin, ethalfluralin, prodiamine and butralin; the organic phosphorus compound is at least one compound selected from the group consisting of butamifos, anilofos and piperophos; the phenyl carbamate compound is barban; the cumylamine compound is at least one compound selected from the group consisting of daimuron, cumyluron and bromobutide; the chloroacetamide compound is at least one compound selected from the group consisting of alachlor, metazachlor, butachlor, pretilachlor, metolachlor, S-metolachlor, thenylchlor, pethoxamid, acetochlor, propachlor, dimethenamid and dimethenamid-P; and the thiocarbamate compound is at least one compound selected from the group consisting of molinate, dimepiperate, pyributicarb, EPTC, butylate, prosulfocarb, esprocarb, thiobencarb, tri-allate and orbencarb.

(12) The herbicidal composition according to the above (8) or (10), wherein said other herbicidal compound is at least one compound selected from the group consisting of a phenoxy compound, an aromatic carboxylic acid compound, a urea compound, a triazine compound, a hydroxybenzonitrile compound, a diphenylether compound, a cyclic imide compound, a sulfonylurea compound, a dinitroaniline compound, a chloroacetamide compound, fluoroxypyr, pyridate, bentazone, bentazone-sodium, carfentrazone-ethyl, sulcotrione, mesotrione, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium and flufenacet.

(13) The herbicidal composition according to the above (12), wherein the phenoxy compound is at least one compound selected from the group consisting of 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide and clomeprop; the aromatic carboxylic acid compound is at least one compound selected from the group consisting of 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium and aminopyralid; the urea compound is at least one compound selected from the group consisting of chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton and trietazine; the triazine compound is at least one compound selected from the group consisting of simazine, atrazine, atratone, simetryn, prometryn, dimethametryn, hexazinone, metribuzin, terbuthylazine, cyanazine, ametryn, cybutryne, triaziflam, terbutryn, propazine, metamitron and prometon; the hydroxybenzonitrile compound is at least one compound selected from the group consisting of bromoxynil, bromoxynil-octanoate, bromoxynil-heptanoate, ioxynil, ioxynil-octanoate, ioxynil-potassium and ioxynil-sodium; the diphenylether compound is at least one compound selected from the group consisting of nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl and fluoroglycofen; the cyclic imide compound is at least one compound selected from the group consisting of chlorphthalim, flumioxazin, flumiclorac, flumiclorac-pentyl, cinidon-ethyl and fluthiacet-methyl; the sulfonylurea compound is at least one compound selected from the group consisting of chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron and TH-547; the dinitroaniline compound is at least one compound selected from the group consisting of trifluralin, oryzalin, nitralin, pendimethalin, ethalfluralin, benfluralin, prodiamine, butralin and dinitramine; and the chloroacetamide compound is at least one compound selected from the group consisting of alachlor, metazachlor, butachlor, pretilachlor, metolachlor, S-metolachlor, thenylchlor, pethoxamid, acetochlor, propachlor, dimethenamid, dimethenamid-P, propisochlor and dimethachlor.

(14) The herbicidal composition according to the above (13), wherein said other herbicidal compound is at least one compound selected from the group consisting of 2,4-D, 2,4-D-ethyl, dicamba, dicamba-dimethylammonium, clopyralid, clopyralid-olamine, fluoroxypyr, linuron, atrazine, metribuzin, terbuthylazine, terbutryn, bromoxynil, bromoxynil-octanoate, pyridate, bentazone, bentazone-sodium, aclonifen, cinidon-ethyl, carfentrazone-ethyl, sulcotrione, mesotrione, rimsulfuron, nicosulfuron, prosulfuron, halosulfuron-methyl, thifensulfuron-methyl, iodosulfuron, iodosulfuron-methyl-sodium, triasulfuron, foramsulfuron, flumetsulam, metosulam, florasulam, imazamox, imazamox-ammonium, glyphosate, glyphosate-sodium, glyphosate-potassium, glyphosate-ammonium, glyphosate-isopropylammonium, glufosinate, glufosinate-ammonium, alachlor, metolachlor, S-metolachlor, acetochlor, flufenacet, dimethenamid and pyroxasulfone.

(15) The herbicidal composition according to the above (14), wherein said other herbicidal compound is at least one compound selected from the group consisting of 2,4-D-ethyl, dicamba-dimethylammonium, clopyralid-olamine, linuron, atrazine, metribuzin, terbuthylazine, bromoxynil, bromoxynil-octanoate, pyridate, bentazone-sodium, carfentrazone-ethyl, sulcotrione, rimsulfuron, nicosulfuron, prosulfuron, iodosulfuron-methyl-sodium, tritosulfuron, foramsulfuron, glyphosate-ammonium, glufosinate-ammonium, pendimethalin, S-metolachlor, pethoxamid, acetochlor, flufenacet and dimethenamid.

(16) The herbicidal composition, which comprises as active ingredients the compound A and other herbicidal compound which is a compound which inhibits photosynthesis of plants.

(17) The herbicidal composition according to the above (16), wherein said other herbicidal compound is at least one compound selected from the group consisting of a urea compound, a triazine compound, a uracil compound, an anilide compound, a carbamate compound, a hydroxybenzonitrile compound, pyridate, bentazone, bentazone-sodium, amicarbazone, methazole and pentanochlor.

(18) The herbicidal composition according to the above (17), wherein the urea compound is at least one compound selected from the group consisting of chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton and trietazine; the triazine compound is at least one compound selected from the group consisting of simazine, atrazine, atratone, simetryn, prometryn, dimethametryn, hexazinone, metribuzin, terbuthylazine, cyanazine, ametryn, cybutryne, triaziflam, terbutryn, propazine, metamitron and prometon; the uracil compound is at least one compound selected from the group consisting of bromacil, bromacyl-lithium, lenacil and terbacil; the anilide compound is at least one compound selected from the group consisting of propanil and cypromid; the carbamate compound is at least one compound selected from the group consisting of swep, desmedipham and phenmedipham; and the hydroxybenzonitrile compound is at least one compound selected from the group consisting of bromoxynil, bromoxynil-octanoate, bromoxynil-heptanoate, ioxynil, ioxynil-octanoate, ioxynil-potassium and ioxynil-sodium.

(19) The herbicidal composition, which comprises as active ingredients the compound A and other herbicidal compound which is a compound which inhibits amino acid biosynthesis of plants.

(20) The herbicidal composition according to the above (19), wherein said other herbicidal compound is at least one compound selected from the group consisting of a sulfonylurea compound, a triazolopyrimidinesulfonamide compound, an imidazolinone compound, a pyrimidinylsalicylic acid compound, a sulfonylaminocarbonyltriazolinone compound, glyphosate, glyphosate-sodium, glyphosate-potassium, glyphosate-ammonium, glyphosate-diammonium, glyphosate-isopropylammonium, glyphosate-trimesium (sulfosate), glyphosate-sesquisodium, glufosinate, glufosinate-ammonium, bilanafos, bilanafos-sodium and cinmethylin.

(21) The herbicidal composition according to the above (20), wherein the sulfonylurea compound is at least one compound selected from the group consisting of chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, TH-547 and a compound disclosed in claims of WO2005092104; the triazolopyrimidinesulfonamide compound is at least one compound selected from the group consisting of flumetsulam, metosulam, diclosulam, cloransulam-methyl, florasulam and penoxsulam; the imidazolinone compound is at least one compound selected from the group consisting of imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl and imazapic; the pyrimidinylsalicylic acid compound is at least one compound selected from the group consisting of pyrithiobac-sodium, bispyribac-sodium, pyriminobac-methyl, pyribenzoxim, pyriftalid and pyrimisulfan; and the sulfonylaminocarbonyltriazolinone compound is at least one compound selected from the group consisting of flucarbazone, flucarbazone-sodium, propoxycarbazone-sodium and propoxycarbazone.

(22) The herbicidal composition, which comprises as active ingredients the compound A and other herbicidal compound which is a compound which exhibits herbicidal effects by disturbing hormone activities of plants.

(23) The herbicidal composition according to the above (22), wherein said other herbicidal compound is at least one compound selected from the group consisting of a phenoxy compound, an aromatic carboxylic acid compound, naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol and chlorflurenol-methyl.

(24) The herbicidal composition according to the above (23), wherein the phenoxy compound is at least one compound selected from the group consisting of 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide and clomeprop; the aromatic carboxylic acid compound is at least one compound selected from the group consisting of 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium and aminopyralid.

(25) The herbicidal composition, which comprises as active ingredients the compound A and other herbicidal compound which is a compound which exhibits herbicidal effects characterized by bleaching activities by inhibiting chromogenesis of plants such as carotenoids.

(26) The herbicidal composition according to the above (25), wherein said other herbicidal compound is at least one compound selected from the group consisting of a pyridazinone compound, a pyrazole compound, amitrole, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachlortole, benzobicyclon, picolinafen and beflubutamid.

(27) The herbicidal composition according to the above (26), wherein the pyridazinone compound is at least one compound selected from the group consisting of norflurazon, chloridazon and metflurazon; and the pyrazole compound is at least one compound selected from the group consisting of pyrazolynate, pyrazoxyfen, benzofenap, topramezone and pyrasulfotole.

(28) The herbicidal composition, which comprises as active ingredients the compound A and other herbicidal compound which is a compound which exhibits herbicidal effects by inhibiting protein biosynthesis or lipid biosynthesis of plants.

(29) The herbicidal composition according to the above (28), wherein said other herbicidal compound is at least one compound selected from the group consisting of a chloroacetamide compound, a thiocarbamate compound, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium and trichloroacetic acid.

(30) The herbicidal composition according to the above (29), wherein the chloroacetamide compound is at least one compound selected from the group consisting of alachlor, metazachlor, butachlor, pretilachlor, metolachlor, S-metolachlor, thenylchlor, pethoxamid, acetochlor, propachlor, dimethenamid, dimethenamid-P, propisochior and dimethachlor; and the thiocarbamate compound is at least one compound selected from the group consisting of molinate, dimepiperate, pyributicarb, EPTC, butylate, vernolate, pebulate, cycloate, prosulfocarb, esprocarb, thiobencarb, diallate, triallate and orbencarb.

(31) A method for controlling undesired plants, which comprises applying a herbicidally effective amount of the herbicidal composition according to the above (1) to (30) to the undesired plants or to a place where they grow.

(32) A method for controlling undesired plants, which comprises applying a herbicidally effective amount of the compound A and a herbicidally effective amount of other herbicidal compound to the undesired plants or to a place where they grow.

(33) The method according to the above (31) or (32), wherein the undesired plants are controlled in a corn field.

(34) The method according to the above (33), wherein the corn is a genetically-modified one.

(35) The method according to the above (31) or (32), wherein the undesired plants are controlled in a wheat, a barley or a rye field.

(36) The method according to the above (31) or (32), wherein the undesired plants are controlled in a rice field.

(37) The method according to the above (31) or (32), wherein the undesired plants are nonselectively controlled.

Now, Preparation Examples for representative examples of the compound A are described below.

Preparation Example 1

Preparation of 5-(ethylthio)carbonyloxy-1-methylpyrazol-4-yl 3-(methoxycarbonyl)-2-methyl-4-(methylsulfonyl)phenyl ketone (Compound No. 1 as described hereinafter)

5-Hydroxy-1-methylpyrazol-4-yl 3-(methoxycarbonyl)-2-methyl-4-(methylsulfonyl)phenyl ketone (290 mg, 0.82 mmol) was dissolved in dry tetrahydrofuran (15 mL), and triethylamine (166 mg, 1.64 mmol) was added thereto. A solution (4 mL) of 96% S-ethyl chlorothiolformate (107 mg) dissolved in dry tetrahydrofuran was added thereto little by little under cooling with ice water. The reaction mixture was stirred for 90 minutes while the reaction temperature was allowed to warm to room temperature. The reaction solution was poured into ice water, followed by extraction with ethyl acetate. The extract was dried over anhydrous sodium sulfate, and the solvent was distilled off under reduced pressure. The residue was purified by silica gel column chromatography (n-hexane:ethyl acetate=6:4) to obtain the desired product as an amorphous solid (202 mg, 0.46 mmol) (yield: 56%).

Preparation Example 2

Preparation of 1-ethyl-5-(ethylthio)carbonyloxypyrazol-4-yl 3-(methoxycarbonyl)-2-methyl-4-(methylsulfonyl)phenyl ketone (Compound No. 2 as described hereinafter)

5-Hydroxy-1-ethylpyrazol-4-yl 3-(methoxycarbonyl)-2-methyl-4-(methylsulfonyl)phenyl ketone (510 mg, 1.39 mmol) was dissolved in dry tetrahydrofuran (20 mL), and triethylamine (281 mg, 2.78 mmol) was added thereto. A solution (4 mL) of 96% S-ethyl chlorothiolformate (217 mg) dissolved in dry tetrahydrofuran was added thereto little by little under cooling with ice water. The reaction mixture was stirred for 90 minutes while the reaction temperature was allowed to warm to room temperature. The reaction mixture was poured into ice water, followed by extraction with ethyl acetate. The organic layer was dried over anhydrous sodium sulfate, and the solvent was distilled off under reduced pressure. The residue was purified by silica gel column chromatography (n-hexane:ethyl acetate=6:4) to obtain the desired product as an oil (417 mg, 0.92 mmol) (yield: 66%).

Preparation Example 3

Preparation of 5-(ethylthio)carbonyloxy-1-methylpyrazol-4-yl 3-(methoxy)-2-methyl-4-(methylsulfonyl)phenyl ketone (Compound No. 35 as described hereinafter)

(1) To a stirred mixture of 3-methoxy-2-methyl-4-(methylsulfonyl)benzoic acid (340 mg, 1.39 mmol) and 5-hydroxy-1-methylpyrazole hydrochloride (230 mg) in anhydrous methylene chloride (10 mL) were added DCC (dicyclohexylcarbodiimide) (315 mg) and triethylamine (260 mg) at room temperature, followed by stirring for 2 hours. The reaction mixture was subjected to filtration through Celite, the filtrate was concentrated, and the obtained residue was dissolved in 10 mL of anhydrous acetonitrile. Triethylamine (260 mg) and acetone cyanohydrin in a catalytic amount were added thereto, and the reaction solution was stirred overnight at room temperature. 150 mL of ethyl acetate was added to the reaction mixture, and the solution was washed once with a 1N hydrochloric acid aqueous solution and washed once with a saturated brine. The organic layer was dried over anhydrous sodium sulfate, and then the solvent was distilled off under reduced pressure. The obtained residue was purified by silica gel column chromatography (ethyl acetate:methanol=9:1) to obtain 5-hydroxy-1-methylpyrazol-4-yl 3-methoxy-2-methyl-4-(methylsulfonyl)phenyl ketone (115 mg).

$^1$H-NMR (400 MHz CDCl$_3$ δ ppm): 2.31 (s, 3H), 3.20 (s, 3H), 3.66 (s, 3H), 3.92 (s, 3H), 7.1 (br s, 1H), 7.29 (d, 1H, J=7.6 Hz), 7.30 (s, 1H), 7.85 (d, 1H, J=7.6 Hz).

(2) To a solution of 5-hydroxy-1-methylpyrazol-4-yl 3-methoxy-2-methyl-4-(methylsulfonyl)phenyl ketone (100 mg, 0.3 mmol) in dry tetrahydrofuran (5 mL) were added triethylamine (61 mg) and 96% S-ethyl chlorothiolformate (50 mg) at room temperature. After the reaction solution was stirred for 1 hour, 150 mL of ethyl acetate was added. The mixture was washed twice with a saturated brine, the organic layer was dried over anhydrous sodium sulfate, and the solvent was distilled off under reduced pressure. The residue was purified by silica gel column chromatography (n-hexane:ethyl acetate=2:1) to obtain the desired product as an oil.

Preparation Example 4

Preparation of 5-(ethylthio)carbonyloxy-1-methylpyrazol-4-yl 2-methyl-4-(methylsulfonyl)-3-(4,5-dihydroisoxazol-3-yl)phenyl ketone (Compound No. 39 as described hereinafter)

To a solution of 5-hydroxy-1-methylpyrazol-4-yl 3-(4,5-dihydroisoxazol-3-yl)-2-methyl-4-(methylsulfonyl)phenyl ketone (100 mg, $2.75 \times 10^{-4}$ mol) in anhydrous tetrahydrofuran (5 mL) were added triethylamine (55 mg) and 96% S-ethyl chlorothiolformate (45 mg) at room temperature. After the reaction solution was stirred for 1 hour, 150 mL of ethyl acetate was added, and the solution was washed twice with a saturated brine. The organic layer was dried over anhydrous sodium sulfate, and the solvent was distilled off under reduced pressure. The residue was purified by silica gel column chromatography (n-hexane:ethyl acetate=6:4) to obtain the desired product (82 mg) as an oil.

Preparation Example 5

Preparation of 5-(ethylthio)carbonyloxy-1-methylpyrazol-4-yl 3-(difluoromethoxy)-2-methyl-4-(methylsulfonyl)phenyl ketone (Compound No. 38 as described hereinafter)

(1) To a stirred mixture of 3-(difluoromethoxy)-2-methyl-4-(methylsulfonyl)benzoic acid (500 mg, 1.78 mmol) and 5-hydroxy-1-methylpyrazole hydrochloride (288 mg) in anhydrous acetonitrile (10 mL) were added 1-ethyl-3-(3-dimethylaminopropyl)carbodiimide hydrochloride (443 mg), triethylamine (360 mg) and dimethylaminopyridine (217 mg) at room temperature. After being stirred for 12 hours, the reaction mixture was concentrated under reduced pressure, and the residue was dissolved in 100 mL of methylene chloride. This solution was washed with 100 mL of water, and the organic layer was dried over anhydrous sodium sulfate, and the solvent was distilled off under reduced pressure. The residue was dissolved in 10 mL of anhydrous acetonitrile, and triethylamine (260 mg) and acetone cyanohydrin in a catalytic amount were added, followed by stirring overnight at room temperature. 150 mL of methylene chloride was added to the reaction mixture, followed by extraction with a 1N potassium carbonate aqueous solution, and the aqueous layer was acidified by 2N hydrochloric acid. The obtained acidic aqueous solution was extracted twice with methylene chloride (100 mL), the combined organic layer was dried over anhydrous sodium sulfate, and the solvent was distilled off under reduced pressure. The obtained crude product was purified by silica gel column chromatography (ethyl acetate:hexane=1:1 to 9:1) to obtain 5-hydroxy-1-methylpyrazol-4-yl 3-(difluoromethoxy)-2-methyl-4-(methylsulfonyl)phenyl ketone as an oil.

$^1$H-NMR (400 MHz acetone-$d_6$ δ ppm): 2.37 (s, 3H), 3.28 (s, 3H), 3.61 (s, 3H), 6.90 (d, 1H, J=75.2 Hz), 7.27 (s, 1H), 7.59 (d, 1H, J=8.4 Hz), 7.96 (d, 1H, J=8.4 Hz).

(2) To a solution of 5-hydroxy-1-methylpyrazol-4-yl 3-(difluoromethoxy)-2-methyl-4-(methylsulfonyl)phenyl ketone (89 mg) obtained in the above step (1) in dry tetrahydrofuran (5 mL) were added triethylamine (50 mg) and 96% S-ethyl chlorothiolformate (40 mg) at room temperature. After the reaction solution was stirred for 1 hour, 150 mL of ethyl acetate was added. The mixture was washed twice with a saturated brine, the organic layer was dried over anhydrous sodium sulfate, and the solvent was distilled off under reduced pressure. The residue was purified by silica gel column chromatography (n-hexane:ethyl acetate=2:1) to obtain the desired product as an oil.

Preparation Example 6

Preparation of 5-(ethylthio)carbonyloxy-1-methylpyrazol-4-yl 3-(2-methoxyethoxy)-2-methyl-4-(methylsulfonyl)phenyl ketone (Compound No. 55 as described hereinafter)

(1) To a stirred suspension of sodium hydride (60%, 220 mg, 5.32 mmol) in anhydrous N,N-dimethylformamide (10 mL) was added methyl 3-hydroxy-2-methyl-4-(methylsulfonyl) benzoate (1 g, 4.09 mmol) under nitrogen atmosphere at room temperature. After stirring for 30 minutes, 2-bromoethyl methyl ether (1.13 g, 8.18 mmol) and potassium iodide in a catalytic amount were added thereto, and the reaction solution was stirred at 60° C. for 12 hours. 200 mL of ethyl acetate was added to the reaction solution, and the solution was washed twice with a saturate brine. The organic layer was dried over anhydrous sodium sulfate and concentrated under reduced pressure. The residue was purified by silica gel column chromatography (n-hexane:ethyl acetate=1:2) to obtain methyl 3-(2-methoxyethoxy)-2-methyl-4-(methylsulfonyl) benzoate as an oil (680 mg).

$^1$H-NMR 400 MHz (CDCl$_3$ δ ppm): 2.53 (s, 3H), 3.26 (s, 3H), 3.46 (s, 3H), 3.78 (m, 2H), 3.91 (s, 3H), 4.19 (m, 2H), 7.71 (d, 1H, J=8.4 Hz), 7.84 (d, 1H, J=8.4 Hz).

(2) Methyl 3-(2-methoxyethoxy)-2-methyl-4-(methylsulfonyl)benzoate (680 mg, 2.25 mmol) obtained in the above step (1) was dissolved in methanol (10 mL), and an aqueous sodium hydroxide solution (2 mL) at a concentration of 20 wt % was added thereto at room temperature. After stirring for 30 minutes, 100 mL of 1N hydrochloric acid was added to the reaction solution, followed by extraction with ethyl acetate (200 mL). The organic layer was washed twice with a saturated brine and dried over anhydrous sodium sulfate. The solvent was distilled off under reduced pressure to obtain 3-(2-methoxyethoxy)-2-methyl-4-(methylsulfonyl)benzoic acid (570 mg) as a white solid.

$^1$H-NMR 400 MHz (acetone-$d_6$ δ ppm): 2.56 (s, 3H), 3.31 (s, 3H), 3.41 (s, 3H), 3.80 (m, 2H), 4.21 (m, 2H), 7.81 (s, 2H).

(3) To a solution of 3-(2-methoxyethoxy)-2-methyl-4-(methylsulfonyl)benzoic acid (195 mg, 6.76 mmol) in chloroform (15 mL) were added oxalyl chloride (0.5 mL) and DMF in a catalytic amount. The reaction mixture was stirred for 30 minutes at room temperature, and the solvent was distilled off under reduced pressure. The residue was dissolved in anhydrous THF (20 mL), and 5-hydroxy-1-methylpyrazole hydrochloride (136 mg, 1.01 mmol), triethylamine (136 mg) and N,N-dimethylaminopyridine (250 mg) were added, followed by reflux with heating for 1 hour. The reaction mixture was allowed to cool to room temperature, and diluted with ethyl acetate (200 mL). The mixture was washed twice with a saturated brine. The organic layer was dried over anhydrous sodium sulfate, and the solvent was distilled off under reduced pressure. The residue was dissolved in anhydrous acetonitrile (10 mL), and triethylamine (136 mg) and acetone cyanohydrin in a catalytic amount were added. The mixture was stirred for 12 hours at room temperature. The solvent was distilled off under reduced pressure to obtain crude 5-hydroxy-1-methylpyrazol-4-yl 3-(2-methoxyethoxy)-2-methyl-4-(methylsulfonyl)phenyl ketone.

$^1$H-NMR (400 MHz CDCl$_3$ δ ppm): 2.39 (s, 3H), 3.29 (s, 3H), 3.46 (s, 3H), 3.71 (s, 3H), 3.81 (m, 2H), 4.24 (m, 2H), 7.34 (s, 1H), 7.35 (d, 1H, J=7.6 Hz), 7.92 (d, 1H, J=7.6 Hz).

(4) The crude 5-hydroxy-1-methylpyrazol-4-yl 3-(2-methoxyethoxy)-2-methyl-4-(methylsulfonyl)phenyl ketone obtained in the same manner as the above step (3) was dissolved in anhydrous THF (10 mL), and triethylamine (190 mg) and 96% S-ethyl chlorothiolformate (151 mg) were added, followed by stirring for 1 hour at room temperature. Ethyl acetate (200 mL) was added to the reaction mixture, and the mixture was washed twice with a saturated brine. The organic layer was dried over anhydrous sodium sulfate, and the solvent was distilled off under reduced pressure. The residue was purified by silica gel column chromatography (n-hexane:ethyl acetate=1:1) to obtain the desired product (250 mg).

Preparation Example 7

Preparation of 5-(ethylthio)carbonyloxy-1-ethylpyrazol-4-yl 3-(2-methoxyethoxy)-2-methyl-4-(methylsulfonyl)phenyl ketone (Compound No. 16 as described hereinafter)

(1) To a solution of 3-(2-methoxyethoxy)-2-methyl-4-(methylsulfonyl)benzoic acid (200 mg, 6.90×10$^{-4}$ mol) in chloroform (15 mL) were added oxalyl chloride (0.5 mL) and DMF in a catalytic amount. The reaction mixture was stirred at room temperature for 30 minutes, and the solvent was distilled off under reduced pressure. The residue was dissolved in anhydrous THF (20 mL), and 5-hydroxy-1-ethylpyrazole hydrochloride (134 mg, 9.01×10$^{-4}$ mol), triethylamine (139 mg) and N,N-dimethylaminopyridine (170 mg) were added. The mixture was heated at refluxed temperature for 1 hour. The reaction mixture was allowed to cool to room temperature, and then ethyl acetate (200 mL) was added. The mixture was washed twice with a saturated brine, and the organic layer was dried over anhydrous sodium sulfate. The solvent was distilled off under reduced pressure. The residue was dissolved in anhydrous acetonitrile (10 mL), and triethylamine (139 mg) and acetone cyanohydrin in a catalytic amount were added, followed by stirring for 12 hours at room temperature. The solvent was distilled off under reduced pressure to obtain crude 5-hydroxy-1-ethylpyrazol-4-yl 3-(2-methoxyethoxy)-2-methyl-4-(methylsulfonyl)phenyl ketone.

$^1$H-NMR (400 MHz CDCl$_3$ δ ppm): 1.40 (t, 3H, J=7.0 Hz), 2.39 (s, 3H), 3.25 (s, 3H), 3.42 (s, 3H), 3.76 (m, 2H), 4.02 (q, 2H, J=7.0 Hz), 4.20 (m, 2H), 7.28 (s, 1H), 7.31 (d, 1H, J=7.6 Hz), 7.87 (d, 1H, J=7.6 Hz).

(2) The crude 5-hydroxy-1-ethylpyrazol-4-yl 3-(2-methoxyethoxy)-2-methyl-4-(methylsulfonyl)phenyl ketone obtained in the above step (1) was dissolved in anhydrous THF (10 mL), and triethylamine (139 mg) and 96% S-ethyl chlorothiolformate (111 mg) were added, followed by stirring for 1 hour at room temperature. Ethyl acetate (200 mL) was added to the obtained reaction mixture, and the mixture was washed twice with a saturated brine. The organic layer was dried over anhydrous sodium sulfate, and the solvent was distilled off under reduced pressure. The residue was purified by silica gel column chromatography (n-hexane:ethyl acetate=1:1) to obtain the desired product (170 mg).

Preparation Example 8

Preparation of 5-(ethylthio)carbonyloxy-1-methylpyrazol-4-yl 3-(2,2-dimethoxyethoxy)-2-methyl-4-(methylsulfonyl)phenyl ketone (Compound No. 209 as described hereinafter)

(1) 3-Hydroxy-2-methyl-4-(methylsulfonyl)benzoic acid (300 mg, 1.30 mmol) was dissolved in N,N-dimethylformamide (10 mL), and potassium carbonate (360 mg, 2.72 mmol) and bromoacetaldehyde dimethyl acetal (660 mg, 3.90 mmol) were added at room temperature. The reaction mixture was heated at 80° C., followed by stirring for 32 hours. The reaction mixture was allowed to cool to room temperature, and 100 mL of water and a 0.5N sodium hydroxide aqueous solution (10 mL) were added. Then, extraction with ethyl acetate (200 mL) was carried out, and the organic layer was dried over anhydrous sodium sulfate. The solvent was distilled off under reduced pressure to obtain 2,2-dimethoxyethyl 3-(2,2-dimethoxyethoxy)-2-methyl-4-(methylsulfonyl)benzoate as an oil.

$^1$H-NMR 400 MHz (CDCl$_3$ δ ppm): 2.54 (s, 3H), 3.31 (s, 1H), 3.39 (s, 6H), 3.44 (s, 6H), 4.06 (d, 2H, J=5.4 Hz), 4.31 (d, 2H, J=5.4 Hz), 4.73 (t, 1H, J=5.4 Hz), 4.87 (t, 1H, J=5.4 Hz), 7.76 (d, 1H, J=8.4 Hz), 7.82 (d, 1H, J=8.4 Hz).

(2) The 2,2-dimethoxyethyl 3-(2,2-dimethoxyethoxy)-2-methyl-4-(methylsulfonyl)benzoate obtained in the above step (1) was dissolved in methanol (20 mL), and an aqueous sodium hydroxide solution (2 mL) at a concentration of 20 wt % was added thereto at room temperature. After stirring for 30 minutes, 100 mL of 1N hydrochloric acid was added to the reaction solution, followed by extraction with ethyl acetate (200 mL). The organic layer was washed twice with a saturated brine and dried over anhydrous sodium sulfate. The solvent was distilled off under reduced pressure to obtain 3-(2,2-dimethoxyethoxy)-2-methyl-4-(methylsulfonyl)benzoic acid (390 mg) as a white solid.

$^1$H-NMR 400 MHz (acetone-d$_6$ δ ppm): 2.56 (s, 3H), 3.31 (s, 3H), 3.44 (s, 6H), 4.06 (d, 2H, J=5.2 Hz), 4.88 (t, 1H, J=5.2 Hz), 7.82 (br s, 2H).

(3) 3-(2,2-Dimethoxyethoxy)-2-methyl-4-(methylsulfonyl)benzoic acid (390 mg, 1.23 mmol) obtained in the above step (2) was dissolved in chloroform (15 mL), and oxalyl chloride (0.5 mL) and DMF in a catalytic amount were added thereto. The reaction mixture was stirred at room temperature for 30 minutes, and the solvent was distilled off under reduced pressure. The residue was dissolved in anhydrous THF (20 mL), and 5-hydroxy-1-methylpyrazole (132 mg, 1.35 mmol), triethylamine (250 mg) and N,N-dimethylaminopyridine (300 mg) were added, followed by reflux with heating for 1 hour. The reaction mixture was allowed to cool to room temperature, and ethyl acetate (200 mL) was added. The mixture was washed twice with a saturated brine. The organic layer was dried over anhydrous sodium sulfate, and the solvent was distilled off under reduced pressure. The residue was dissolved in anhydrous acetonitrile (10 mL), and triethylamine (250 mg) and acetone cyanohydrin in a catalytic amount were added, followed by stirring for 12 hours at room temperature. The solvent was distilled off under reduced pressure to obtain crude 5-hydroxy-1-methylpyrazol-4-yl 3-(2,2-dimethoxyethoxy)-2-methyl-4-(methylsulfonyl)phenyl ketone.

$^1$H-NMR (400 MHz CDCl$_3$ δ ppm): 2.38 (s, 3H), 3.29 (s, 3H), 3.47 (s, 6H), 3.70 (s, 3H), 4.09 (d, 2H, J=5.2 Hz), 4.1 (br s, 1H), 4.83 (t, 1H, J=5.2 Hz), 7.32 (s, 1H), 7.35 (d, 1H, J=8.4 Hz), 7.91 (d, 1H, J=8.4 Hz).

(4) The crude 5-hydroxy-1-methylpyrazol-4-yl 3-(2,2-dimethoxyethoxy)-2-methyl-4-(methylsulfonyl)phenyl ketone obtained in the above step (3) was dissolved in anhydrous THF (10 mL), and triethylamine (250 mg) and 96% S-ethyl chlorothiolformate (200 mg) were added, followed by stirring for 1 hour at room temperature. Ethyl acetate (200 mL) was added to the obtained reaction mixture, and the mixture was washed twice with a saturated brine. The organic layer was dried over anhydrous sodium sulfate, and the solvent was distilled off under reduced pressure. The residue was purified by silica gel column chromatography (n-hexane:ethyl acetate=1:1) to obtain the desired product (150 mg).

Now, typical examples among the compounds of the above formula (I) wherein Q is —C(O)SR$^3$ are shown in Table 1, and their $^1$H-NMR spectrum data are shown in Table 2. Further, typical examples among the compounds of the above formula (I) wherein Q is a hydrogen atom are shown in Table 3, and their $^1$H-NMR spectrum data are shown in Table 4. These compounds can be prepared in accordance with the above Preparation Examples or the above various processes for production of the compounds of the above formula (I). In Tables 1 to 4, No. represents the Compound No. In Tables 1 and 3, Me represents a methyl group, Et an ethyl group, n-Pr a normal-propyl group, i-Pr an isopropyl group, c-Pr a cyclopropyl group, s-Bu a secondary butyl group, t-Bu a tertiary butyl group, Ph a phenyl group, and Bn a benzyl group, respectively.

TABLE 1

(I-2)

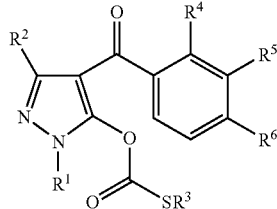

| No. | R$^1$ | R$^2$ | R$^3$ | R$^4$ | R$^5$ | R$^6$ |
|---|---|---|---|---|---|---|
| 1 | Me | H | Et | Me | CO$_2$Me | SO$_2$Me |
| 2 | Et | H | Et | Me | CO$_2$Me | SO$_2$Me |
| 3 | Me | H | Me | Me | CO$_2$Me | SO$_2$Me |
| 4 | Et | H | Me | Me | CO$_2$Me | SO$_2$Me |
| 5 | n-Pr | H | Et | Me | CO$_2$Me | SO$_2$Me |
| 6 | c-Pr | H | Et | Me | CO$_2$Me | SO$_2$Me |
| 7 | n-Pr | H | Me | Me | CO$_2$Me | SO$_2$Me |
| 8 | c-Pr | H | Me | Me | CO$_2$Me | SO$_2$Me |
| 9 | t-Bu | H | Et | Me | CO$_2$Me | SO$_2$Me |
| 10 | t-Bu | H | Me | Me | CO$_2$Me | SO$_2$Me |
| 11 | Me | Me | Et | Me | CO$_2$Me | SO$_2$Me |
| 12 | Et | H | Et | Me | CO$_2$(i-Pr) | SO$_2$Me |
| 13 | Me | H | Et | Me | CO$_2$Et | SO$_2$Me |
| 14 | Et | H | Et | Me | CO$_2$Me | NO$_2$ |
| 15 | Et | H | Et | SO$_2$Me | CO$_2$Me | CF$_3$ |
| 16 | Et | H | Et | Me | OCH$_2$CH$_2$OMe | SO$_2$Me |
| 17 | Et | H | Et | Cl | OCH$_2$CH$_2$OMe | SO$_2$Me |
| 18 | Et | H | Et | Me | CO$_2$Me | CN |
| 19 | Me | H | Et | Me | C(O)SMe | SO$_2$Me |
| 20 | Et | H | Et | Me | C(O)SMe | SO$_2$Me |
| 21 | Me | H | Me | Me | C(O)SEt | SO$_2$Me |
| 22 | Et | H | Me | Me | C(O)SEt | SO$_2$Me |
| 23 | Me | H | Et | Me | 2-(2-Oxolanyl)ethoxy | SO$_2$Me |
| 24 | Me | H | Et | Me | 2-(2-(1,3-Dioxolanyl))ethoxy | SO$_2$Me |
| 25 | Et | H | Et | Me | CH$_2$OMe | SO$_2$Me |
| 26 | Et | H | Et | Me | 2-Oxolanylmethoxymethyl | SO$_2$Me |
| 27 | Me | H | Et | Cl | CO$_2$Me | SO$_2$Me |
| 28 | Et | H | Et | Cl | CO$_2$Me | SO$_2$Et |
| 29 | Me | H | Me | Cl | CO$_2$Me | SO$_2$Me |
| 30 | Et | H | Me | Br | CO$_2$Me | SO$_2$Me |
| 31 | Me | H | Et | Cl | C(O)SMe | SO$_2$Me |
| 32 | Et | H | Et | Cl | C(O)SMe | SO$_2$Me |
| 33 | Me | H | Et | Cl | C(O)SEt | SO$_2$Me |
| 34 | Et | H | Et | Cl | C(O)SEt | SO$_2$Me |
| 35 | Me | H | Et | Me | OMe | SO$_2$Me |
| 36 | Me | H | Et | Me | OEt | SO$_2$Me |
| 37 | Me | H | Et | Me | O(i-Pr) | SO$_2$Me |
| 38 | Me | H | Et | Me | OCHF$_2$ | SO$_2$Me |
| 39 | Me | H | Et | Me | (4,5-Dihydroisoxazol-3-yl) | SO$_2$Me |
| 40 | Me | H | Me | Me | (4,5-Dihydroisoxazol-3-yl) | SO$_2$Me |
| 41 | Me | H | Et | Me | O(n-Pr) | SO$_2$Et |
| 42 | Me | H | Et | Cl | CH$_2$OMe | SO$_2$Me |
| 43 | Me | H | Et | Me | OCO$_2$Me | SO$_2$Me |
| 44 | Et | H | Et | Me | OCO$_2$Me | SO$_2$Me |
| 45 | Me | H | Me | Me | OCO$_2$Me | SO$_2$Me |
| 46 | Et | H | Me | Me | OCO$_2$Me | SO$_2$Me |
| 47 | Me | H | Et | Me | OC(O)SMe | SO$_2$Me |
| 48 | Et | H | Et | Me | OC(O)SMe | SO$_2$Me |
| 49 | Me | H | Me | Me | OC(O)SMe | SO$_2$Me |

TABLE 1-continued (I-2)

| No. | R¹ | R² | R³ | R⁴ | R⁵ | R⁶ |
|---|---|---|---|---|---|---|
| 50 | Et | H | Me | Me | OC(O)SMe | $SO_2Me$ |
| 51 | Me | H | Et | Me | OC(O)SEt | $SO_2Me$ |
| 52 | Et | H | Et | Me | OC(O)SEt | $SO_2Me$ |
| 53 | Me | H | Me | Me | OC(O)SEt | $SO_2Me$ |
| 54 | Et | H | Me | Me | OC(O)SEt | $SO_2Me$ |
| 55 | Me | H | Et | Me | $OCH_2CH_2OMe$ | $SO_2Me$ |
| 56 | Me | H | Me | Me | $OCH_2CH_2OMe$ | $SO_2Et$ |
| 57 | Me | H | Et | Cl | $OCH_2CH_2OMe$ | $SO_2Me$ |
| 58 | Et | H | Et | Me | OEt | $SO_2Me$ |
| 59 | Et | H | Et | Cl | $CO_2Et$ | $SO_2Me$ |
| 60 | Et | H | Et | Cl | $CO_2(n\text{-Pr})$ | $SO_2Me$ |
| 61 | Et | H | Et | Me | $CO_2Et$ | $SO_2Me$ |
| 62 | Et | H | Me | Me | $CO_2Et$ | $SO_2Me$ |
| 63 | Me | H | Et | Me | $CH_2OMe$ | $SO_2Me$ |
| 64 | Me | H | Et | Me | $CH_2CO_2Me$ | $SO_2Me$ |
| 65 | Me | H | Et | Me | $OCH_2CO_2Et$ | $SO_2Me$ |
| 66 | Me | H | Et | Me | O(n-Pr) | $SO_2Me$ |
| 67 | Et | H | Et | Me | O(n-Pr) | $SO_2Me$ |
| 68 | Et | H | Et | $SO_2Me$ | H | $CF_3$ |
| 69 | Me | H | Et | Me | $CH_2OCH_2CF_3$ | $SO_2Me$ |
| 70 | Me | H | Et | Cl | $CH_2OCH_2CF_3$ | $SO_2Me$ |
| 71 | Et | H | Et | Me | Cl | $SO_2Me$ |
| 72 | Me | H | Et | Me | $CH_2SO_2Me$ | $SO_2Me$ |
| 73 | Me | H | Et | Me | $CH_2OEt$ | $SO_2Me$ |
| 74 | Me | H | Me | Cl | $CH_2OMe$ | $SO_2Me$ |
| 75 | Me | H | Et | Me | $CH_2CH_2OMe$ | $SO_2Me$ |
| 76 | Me | H | Et | Me | $CH_2OCH_2CH_2OMe$ | $SO_2Me$ |
| 77 | Me | H | Et | Me | $OCH_2CH_2OEt$ | $SO_2Me$ |
| 78 | Me | H | Et | Me | $OCH_2CH_2Cl$ | $SO_2Me$ |
| 79 | Me | H | Et | Me | $OCH_2CF_3$ | $SO_2Me$ |
| 80 | Me | H | Et | Me | $CH_2OCH_2OMe$ | $SO_2Me$ |
| 81 | Me | H | Et | Me | $OCH_2CH_2SMe$ | $SO_2Me$ |
| 82 | Me | H | Et | Me | CN | $SO_2Me$ |
| 83 | Me | H | Et | Me | $CH_2CN$ | $SO_2Me$ |
| 84 | Me | H | n-Pr | Me | $CO_2Me$ | $SO_2Me$ |
| 85 | Et | H | n-Pr | Me | $CO_2Me$ | $SO_2Me$ |
| 86 | Me | H | i-Pr | Me | $CO_2Me$ | $SO_2Me$ |
| 87 | Et | H | i-Pr | Me | $CO_3Me$ | $SO_2Me$ |
| 88 | Me | H | s-Bu | Me | $CO_2Me$ | $SO_2Me$ |
| 89 | Et | H | s-Bu | Me | $CO_2Me$ | $SO_2Me$ |
| 90 | Me | H | t-Bu | Me | $CO_2Me$ | $SO_2Me$ |
| 91 | Et | H | t-Bu | Me | $CO_2Me$ | $SO_2Me$ |
| 92 | Me | H | Bn | Me | $CO_2Me$ | $SO_2Me$ |
| 93 | Et | H | Bn | Me | $CO_2Me$ | $SO_2Me$ |
| 94 | Me | H | Et | Br | $CO_2Me$ | $SO_2Me$ |
| 95 | Et | H | Et | Cl | $CO_2Me$ | $SO_2Me$ |
| 96 | Me | H | Me | Br | $CO_2Me$ | $SO_2Me$ |
| 97 | Et | H | Me | Cl | $CO_2Me$ | $SO_2Me$ |
| 98 | Me | H | Allyl | Me | $CO_2Me$ | $SO_2Me$ |
| 99 | Et | H | Allyl | Me | $CO_2Me$ | $SO_2Me$ |
| 100 | Me | H | $CH_2CH(CH_3)=CH_2$ | Me | $CO_2Me$ | $SO_2Me$ |
| 101 | Et | H | $CH_2CH(CH_3)=CH_2$ | Me | $CO_2Me$ | $SO_2Me$ |
| 102 | Me | H | Et | Cl | $OCH_2CH_2OCF_3$ | $SO_2Me$ |
| 103 | Et | H | Et | Cl | $OCH_2CH_2OCF_3$ | $SO_2Me$ |
| 104 | Me | H | Et | Me | $OCH_2CH_2OCF_3$ | $SO_2Me$ |
| 105 | Et | H | Et | Me | $OCH_2CH_2OCF_3$ | $SO_2Me$ |
| 106 | Me | H | Et | $CF_3$ | $OCH_2CH_2OCF_3$ | $SO_2Me$ |
| 107 | Et | H | Et | $CF_3$ | $OCH_2CH_2OCF_3$ | $SO_2Me$ |
| 108 | Me | H | Et | Br | $OCH_2CH_2OCF_3$ | $SO_2Me$ |
| 109 | Et | H | Et | Br | $OCH_2CH_2OCF_3$ | $SO_2Me$ |
| 110 | Me | H | Et | $SO_2Me$ | $OCH_2CH_2OCF_3$ | $CF_3$ |
| 111 | Et | H | Et | $SO_2Me$ | $OCH_2CH_2OCF_3$ | $CF_3$ |
| 112 | Me | H | Et | Cl | $OCH_2CH_2OCHClF$ | $SO_2Me$ |
| 113 | Et | H | Et | Cl | $OCH_2CH_2OCHClF$ | $SO_2Me$ |
| 114 | Me | H | Et | Me | $OCH_2CH_2OCHClF$ | $SO_2Me$ |
| 115 | Et | H | Et | Me | $OCH_2CH_2OCHClF$ | $SO_2Me$ |

TABLE 1-continued (I-2)

| No. | R¹ | R² | R³ | R⁴ | R⁵ | R⁶ |
|---|---|---|---|---|---|---|
| 116 | Me | H | Et | CF₃ | OCH₂CH₂OCHClF | SO₂Me |
| 117 | Et | H | Et | CF₃ | OCH₂CH₃OCHClF | SO₂Me |
| 118 | Me | H | Et | Br | OCH₂CH₂OCHClF | SO₂Me |
| 119 | Et | H | Et | Br | OCH₂CH₂OCHClF | SO₂Me |
| 120 | Me | H | Et | SO₂Me | OCH₂CH₂OCHClF | CF₃ |
| 121 | Et | H | Et | SO₂Me | OCH₂CH₂OCHClF | CF₃ |
| 122 | Me | H | Et | Cl | OCH₂CHFOCF₃ | SO₂Me |
| 123 | Et | H | Et | Cl | OCH₂CHFOCF₃ | SO₂Me |
| 124 | Me | H | Et | Me | OCH₂CHFOCF₃ | SO₂Me |
| 125 | Me | H | Et | Cl | OCH₂CHFOMe | SO₂Me |
| 126 | Et | H | Et | Cl | OCH₂CHFOMe | SO₂Me |
| 127 | Me | H | Et | Me | OCH₂CHFOMe | SO₂Me |
| 128 | Et | H | Et | Me | OCH₂CHFOMe | SO₂Me |
| 129 | Me | H | Et | CF₃ | OCH₂CHFOMe | SO₂Me |
| 130 | Et | H | Et | CF₃ | OCH₂CHFOMe | SO₂Me |
| 131 | Me | H | Et | Br | OCH₂CHFOMe | SO₂Me |
| 132 | Et | H | Et | Br | OCH₂CHFOMe | SO₂Me |
| 133 | Me | H | Et | SO₂Me | OCH₂CHFOMe | CF₃ |
| 134 | Et | H | Et | SO₂Me | OCH₂CHFOMe | CF₃ |
| 135 | Me | H | Et | Cl | OCHFCH₂OCF₃ | SO₂Me |
| 136 | Et | H | Et | Cl | OCHFCH₂OCF₃ | SO₂Me |
| 137 | Me | H | Et | Cl | OCH₂CH₂OCF₂Cl | SO₂Me |
| 138 | Et | H | Et | Cl | OCH₂CH₂OCF₂Cl | SO₂Me |
| 139 | Me | H | Et | Me | OCH₂CH₂OCF₂Cl | SO₂Me |
| 140 | Et | H | Et | Me | OCH₂CH₂OCF₂Cl | SO₂Me |
| 141 | Me | H | Et | CF₃ | OCH₂CH₂OCF₂Cl | SO₂Me |
| 142 | Et | H | Et | CF₃ | OCH₂CH₂OCF₂Cl | SO₂Me |
| 143 | Me | H | Et | Br | OCH₂CH₂OCF₂Cl | SO₂Me |
| 144 | Et | H | Et | Br | OCH₂CH₂OCF₂Cl | SO₂Me |
| 145 | Me | H | Et | SO₂Me | OCH₂CH₂OCF₂Cl | CF₃ |
| 146 | Et | H | Et | SO₂Me | OCH₂CH₂OCF₂Cl | CF₃ |
| 147 | Me | H | Et | Cl | SCH₂CH₂OCH₃ | SO₂Me |
| 148 | Et | H | Et | Cl | SCH₂CH₂OCH₃ | SO₂Me |
| 149 | Me | H | Et | Me | SCH₂CH₂OCH₃ | SO₂Me |
| 150 | Et | H | Et | Me | SCH₂CH₂OCH₃ | SO₂Me |
| 151 | Me | H | Et | CF₃ | SCH₂CH₂OCH₃ | SO₂Me |
| 152 | Et | H | Et | CF₃ | SCH₂CH₂OCH₃ | SO₂Me |
| 153 | Me | H | Et | Br | SCH₂CH₂OCH₃ | SO₂Me |
| 154 | Et | H | Et | Br | SCH₂CH₂OCH₃ | SO₂Me |
| 155 | Me | H | Et | SO₂Me | SCH₂CH₂OCH₃ | CF₃ |
| 156 | Et | H | Et | SO₂Me | SCH₂CH₂OCH₃ | CF₃ |
| 157 | Me | H | Et | Cl | SCH₂CH₂OCF₃ | SO₂Me |
| 158 | Et | H | Et | Cl | SCH₂CH₂OCF₃ | SO₂Me |
| 159 | Me | H | Et | Me | SCH₂CH₂OCF₃ | SO₂Me |
| 160 | Et | H | Et | Me | SCH₂CH₂OCF₃ | SO₂Me |
| 161 | Me | H | Et | CF₃ | SCH₂CH₂OCF₃ | SO₂Me |
| 162 | Et | H | Et | CF₃ | SCH₂CH₂OCF₃ | SO₂Me |
| 163 | Me | H | Et | Br | SCH₂CH₂OCF₃ | SO₂Me |
| 164 | Et | H | Et | Br | SCH₂CH₂OCF₃ | SO₂Me |
| 165 | Me | H | Et | SO₂Me | SCH₂CH₂OCF₃ | CF₃ |
| 166 | Et | H | Et | SO₂Me | SCH₂CH₂OCF₃ | CF₃ |
| 167 | Me | H | Et | Cl | SCH₂CH₂SCH₃ | SO₂Me |
| 168 | Et | H | Et | Cl | SCH₂CH₂SCH₃ | SO₂Me |
| 169 | Me | H | Et | Me | SCH₂CH₂SCH₃ | SO₂Me |
| 170 | Et | H | Et | Me | SCH₂CH₂SCH₃ | SO₂Me |
| 171 | Me | H | Et | CF₃ | SCH₂CH₂SCH₃ | SO₂Me |
| 172 | Et | H | Et | CF₃ | SCH₂CH₂SCH₃ | SO₂Me |
| 173 | Me | H | Et | Br | SCH₂CH₂SCH₃ | SO₂Me |
| 174 | Et | H | Et | Br | SCH₂CH₂SCH₃ | SO₂Me |
| 175 | Me | H | Et | SO₂Me | SCH₂CH₂SCH₃ | CF₃ |
| 176 | Et | H | Et | SO₂Me | SCH₂CH₂SCH₃ | CF₃ |
| 177 | Me | H | Et | Cl | SCH₂CH₂SCF₃ | SO₂Me |
| 178 | Et | H | Et | Cl | SCH₂CH₂SCF₃ | SO₂Me |
| 179 | Me | H | Et | Me | SCH₂CH₂SCF₃ | SO₂Me |
| 180 | Et | H | Et | Me | SCH₂CH₂SCF₃ | SO₂Me |
| 181 | Me | H | Et | CF₃ | SCH₂CH₂SCF₃ | SO₂Me |

TABLE 1-continued (I-2)

| No. | R¹ | R² | R³ | R⁴ | R⁵ | R⁶ |
|---|---|---|---|---|---|---|
| 182 | Et | H | Et | $CF_3$ | $SCH_2CH_2SCF_3$ | $SO_2Me$ |
| 183 | Me | H | Et | Br | $SCH_2CH_2SCF_3$ | $SO_2Me$ |
| 184 | Et | H | Et | Br | $SCH_2CH_2SCF_3$ | $SO_2Me$ |
| 185 | Me | H | Et | $SO_2Me$ | $SCH_2CH_2SCF_3$ | $CF_3$ |
| 186 | Et | H | Et | $SO_2Me$ | $SCH_2CH_2SCF_3$ | $CF_3$ |
| 187 | Me | H | Et | Cl | $OCH_2CH(CH_3)OCH_3$ | $SO_2Me$ |
| 188 | Et | H | Et | Cl | $OCH_2CH(CH_3)OCH_3$ | $SO_2Me$ |
| 189 | Me | H | Et | Me | $OCH_2CH(CH_3)OCH_3$ | $SO_2Me$ |
| 190 | Et | H | Et | Me | $OCH_2CH(CH_3)OCH_3$ | $SO_2Me$ |
| 191 | Me | H | Et | $CF_3$ | $OCH_2CH(CH_3)OCH_3$ | $SO_2Me$ |
| 192 | Et | H | Et | $CF_3$ | $OCH_2CH(CH_3)OCH_3$ | $SO_2Me$ |
| 193 | Me | H | Et | Br | $OCH_2CH(CH_3)OCH_3$ | $SO_2Me$ |
| 194 | Et | H | Et | Br | $OCH_2CH(CH_3)OCH_3$ | $SO_2Me$ |
| 195 | Me | H | Et | $SO_2Me$ | $OCH_2CH(CH_3)OCH_3$ | $CF_3$ |
| 196 | Et | H | Et | $SO_2Me$ | $OCH_2CH(CH_3)OCH_3$ | $CF_3$ |
| 197 | Me | H | Et | Cl | $OCH_2CF_2OCH_3$ | $SO_2Me$ |
| 198 | Et | H | Et | Cl | $OCH_2CF_2OCH_3$ | $SO_2Me$ |
| 199 | Me | H | Et | Me | $OCH_2CF_2OCH_3$ | $SO_2Me$ |
| 200 | Et | H | Et | Me | $OCH_2CF_2OCH_3$ | $SO_2Me$ |
| 201 | Me | H | Et | $CF_3$ | $OCH_2CF_2OCH_3$ | $SO_2Me$ |
| 202 | Et | H | Et | $CF_3$ | $OCH_2CF_2OCH_3$ | $SO_2Me$ |
| 203 | Me | H | Et | Br | $OCH_2CF_2OCH_3$ | $SO_2Me$ |
| 204 | Et | H | Et | Br | $OCH_2CF_2OCH_3$ | $SO_2Me$ |
| 205 | Me | H | Et | $SO_2Me$ | $OCH_2CF_2OCH_3$ | $CF_3$ |
| 206 | Et | H | Et | $SO_2Me$ | $OCH_2CF_2OCH_3$ | $CF_3$ |
| 207 | Me | H | i-Pr | Me | $OCH_2CH_2OCH_3$ | $SO_2Me$ |
| 208 | Et | H | i-Pr | Me | $OCH_2CH_2OCH_3$ | $SO_2Me$ |
| 209 | Me | H | Et | Me | $OCH_2CH(OCH_3)_2$ | $SO_2Me$ |
| 210 | Me | H | Et | Me | $CH_2N(Me)CH_2CN$ | $SO_2Me$ |
| 211 | Me | H | Et | Me | (Tetrahydrofuran-2-yl)methoxy | $SO_2Me$ |
| 212 | Me | H | Et | Cl | SMe | $SO_2Me$ |
| 213 | Me | H | Et | Cl | Cl | $SO_2Me$ |
| 214 | Me | H | Et | Cl | OMe | $SO_2Me$ |
| 215 | Me | H | Et | Me | (Tetrahydro-2H-pyran-2-yl)methoxy | $SO_2Me$ |
| 216 | Me | H | Et | Cl | $OCH_2CH_2OMe$ | $SO_2Me$ |
| 217 | Me | H | Et | Me | Tetrahydrofuran-3-yloxy | $SO_2Me$ |
| 218 | Me | H | Et | Me | $OCH_2CH_2OMe$ | $SO_2Me$ |
| 219 | Me | H | n-Pr | Me | $OCH_2CH_2OMe$ | $SO_2Me$ |
| 220 | Et | H | s-Bu | Cl | C(O)OMe | Me |
| 221 | Et | H | Et | Cl | 2-(1,3-Dioxolan-2-yl)ethoxy | $SO_2Me$ |
| 222 | Me | H | Et | Me | Propargyloxy | $SO_2Me$ |
| 223 | Me | H | Et | Me | (Tetrahydrofuran-3-yloxy)methyl | $SO_2Me$ |
| 224 | Me | H | Et | Cl | $SO_2Me$ | $SO_2Me$ |
| 225 | Me | H | Et | Me | $(CH_2)_6Me$ | $SO_2Me$ |
| 226 | Me | H | Et | Me | $CH_2CH_2CH_2OMe$ | $SO_2Me$ |
| 227 | Et | H | Et | Cl | (1,3-Dioxolan-2-yl)methoxy | $SO_2Me$ |
| 228 | Me | H | Et | Me | $CH_2N[C(O)SEt]CH_2CN$ | $SO_2Me$ |
| 229 | Me | H | Et | Me | CH=CHCN | $SO_2Me$ |
| 230 | Me | H | Et | Me | $CH_2CH_2CN$ | $SO_2Me$ |
| 231 | Me | H | Et | Me | $CH_2SCN$ | $SO_2Me$ |
| 232 | Me | H | Et | Me | $CH_2C(S)NH_2$ | $SO_2Me$ |
| 233 | Me | H | Me | Me | $OCH_2CH_2OMe$ | $SO_2Me$ |
| 234 | Et | H | Me | Me | $OCH_2CH_2OMe$ | $SO_2Me$ |
| 235 | Et | H | n-Pr | Me | $OCH_2CH_2OMe$ | $SO_2Me$ |
| 236 | Me | H | Et | Me | $OCH(CH_3)CH_2OMe$ | $SO_2Me$ |
| 237 | Et | H | Et | Me | $OCH_2CH(Et)OMe$ | $SO_2Me$ |
| 238 | Me | H | Et | Me | (1,3-Dioxolan-2-yl)methyl | $SO_2Me$ |
| 239 | Me | H | s-Bu | Me | $OCH_2CH_2OMe$ | $SO_2Me$ |
| 240 | Me | H | Et | Me | $CH_2O$(i-Pr) | $SO_2Me$ |
| 241 | Me | H | t-Bu | Me | $OCH_2CH_2OMe$ | $SO_2Me$ |
| 242 | Me | H | $CH_2CO_2Me$ | Me | $OCH_2CH_2OMe$ | $SO_2Me$ |
| 243 | Et | H | c-Pr | Me | $CO_2Me$ | $SO_2Me$ |
| 244 | Et | H | c-Pr | Me | $CO_2$(i-Pr) | $SO_2Me$ |
| 245 | Et | H | c-Pr | Me | $OCH_2CH_2OMe$ | $SO_2Me$ |
| 246 | Et | H | c-Pr | $SO_2Me$ | $CO_2Me$ | CN |
| 247 | Me | H | c-Pr | Me | C(O)SMe | $SO_2Me$ |

TABLE 1-continued

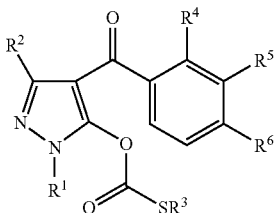

(I-2)

| No. | $R^1$ | $R^2$ | $R^3$ | $R^4$ | $R^5$ | $R^6$ |
|---|---|---|---|---|---|---|
| 248 | Me | H | c-Pr | Me | C(O)SEt | $SO_2Me$ |
| 249 | Me | H | c-Pr | Me | 2-(2-Oxolanyl)ethoxy | $SO_2Me$ |
| 250 | Me | H | c-Pr | Me | 2-(2-(1,3-Dioxolanyl))ethoxy | $SO_2Me$ |
| 251 | Et | H | c-Pr | Me | $CH_2OMe$ | $SO_2Me$ |
| 252 | Et | H | c-Pr | Me | 2-Oxolanylmethoxymethyl | $SO_2Me$ |
| 253 | Me | H | c-Pr | Cl | $CO_2Me$ | $SO_2Me$ |
| 254 | Et | H | c-Pr | Cl | $CO_2Me$ | $SO_2Et$ |
| 255 | Me | H | c-Pr | Cl | C(O)SMe | $SO_2Me$ |
| 256 | Me | H | c-Pr | Cl | C(O)SEt | $SO_2Me$ |
| 257 | Me | H | c-Pr | Me | OMe | $SO_2Me$ |
| 258 | Me | H | c-Pr | Me | OEt | $SO_2Me$ |
| 259 | Me | H | c-Pr | Me | O(i-Pr) | $SO_2Me$ |
| 260 | Me | H | c-Pr | Me | $OCHF_2$ | $SO_2Me$ |
| 261 | Me | H | c-Pr | Me | (4,5-Dihydroisoxazol-3-yl) | $SO_2Me$ |
| 262 | Me | H | c-Pr | Me | O(n-Pr) | $SO_2Et$ |
| 263 | Me | H | c-Pr | Cl | $CH_2OMe$ | $SO_2Me$ |
| 264 | Me | H | c-Pr | Me | $OCO_2Me$ | $SO_2Me$ |
| 265 | Me | H | c-Pr | Me | OC(O)SMe | $SO_2Me$ |
| 266 | Me | H | c-Pr | Me | OC(O)SEt | $SO_2Me$ |
| 267 | Me | H | c-Pr | Me | $OCH_2CH_2OMe$ | $SO_2Me$ |
| 268 | Et | H | c-Pr | Me | OEt | $SO_2Me$ |
| 269 | Et | H | c-Pr | Cl | $CO_2Et$ | $SO_2Me$ |
| 270 | Et | H | c-Pr | Cl | $CO_2(n-Pr)$ | $SO_2Me$ |
| 271 | Et | H | c-Pr | Me | $CO_2Et$ | $SO_2Me$ |
| 272 | Me | H | c-Pr | CN | $CO_2Me$ | $SO_2Me$ |
| 273 | Et | H | c-Pr | CN | $CO_2(i-Pr)$ | $SO_2Me$ |
| 274 | Me | H | c-Pr | Me | $CH_2CO_2Me$ | $SO_2Me$ |
| 275 | Me | H | c-Pr | Me | $OCH_2CO_2Et$ | $SO_2Me$ |
| 276 | Me | H | c-Pr | Me | O(n-Pr) | $SO_2Me$ |
| 277 | Et | H | c-Pr | $SO_2Me$ | H | $CF_3$ |
| 278 | Me | H | c-Pr | Me | $CH_2OCH_2CF_3$ | $SO_2Me$ |
| 279 | Me | H | c-Pr | Cl | $CH_2OCH_2CF_3$ | $SO_2Me$ |
| 280 | Et | H | c-Pr | Me | Cl | $SO_2Me$ |
| 281 | Me | H | c-Pr | Me | $CH_2SO_2Me$ | $SO_2Me$ |
| 282 | Me | H | c-Pr | Me | $CH_2OEt$ | $SO_2Me$ |
| 283 | Me | H | c-Pr | Cl | $CH_2OMe$ | $SO_2Me$ |
| 284 | Me | H | c-Pr | Me | $CH_2CH_2OMe$ | $SO_2Me$ |
| 285 | Me | H | c-Pr | Me | $CH_2OCH_2CH_2OMe$ | $SO_2Me$ |
| 286 | Me | H | c-Pr | Me | $OCH_2CH_2OEt$ | $SO_2Me$ |
| 287 | Me | H | c-Pr | Me | $OCH_2CH_2Cl$ | $SO_2Me$ |
| 288 | Me | H | c-Pr | Me | $OCH_2CF_3$ | $SO_2Me$ |
| 289 | Me | H | c-Pr | Me | $CH_2OCH_2OMe$ | $SO_2Me$ |
| 290 | Me | H | c-Pr | Me | $OCH_2CH_2SMe$ | $SO_2Me$ |
| 291 | Me | H | c-Pr | Me | CN | $SO_2Me$ |
| 292 | Me | H | c-Pr | Me | $CH_2CN$ | $SO_2Me$ |
| 293 | Me | H | c-Pr | Br | $CO_3Me$ | $SO_2Me$ |
| 294 | Et | H | c-Pr | Cl | $CO_2Me$ | $SO_2Me$ |
| 295 | Me | H | c-Pr | Br | $CO_2Et$ | $SO_2Me$ |
| 296 | Me | H | c-Pr | Cl | $OCH_2CH_2OCF_3$ | $SO_2Me$ |
| 297 | Et | H | c-Pr | Cl | $OCH_2CH_2OCF_3$ | $SO_2Me$ |
| 298 | Me | H | c-Pr | Me | $OCH_2CH_2OCF_3$ | $SO_2Me$ |
| 299 | Et | H | c-Pr | Me | $OCH_2CH_2OCF_3$ | $SO_2Me$ |
| 300 | Me | H | c-Pr | $CF_3$ | $OCH_2CH_2OCF_3$ | $SO_2Me$ |
| 301 | Et | H | c-Pr | $CF_3$ | $OCH_2CH_2OCF_3$ | $SO_2Me$ |
| 302 | Me | H | c-Pr | Br | $OCH_2CH_2OCF_3$ | $SO_2Me$ |
| 303 | Et | H | c-Pr | Br | $OCH_2CH_2OCF_3$ | $SO_2Me$ |
| 304 | Me | H | c-Pr | $SO_2Me$ | $OCH_2CH_2OCF_3$ | $CF_3$ |
| 305 | Et | H | c-Pr | $SO_2Me$ | $OCH_2CH_2OCF_3$ | $CF_3$ |
| 306 | Me | H | c-Pr | Cl | $OCH_2CH_2OCHClF$ | $SO_2Me$ |
| 307 | Et | H | c-Pr | Cl | $OCH_2CH_2OCHClF$ | $SO_2Me$ |
| 308 | Me | H | c-Pr | Me | $OCH_2CH_2OCHClF$ | $SO_2Me$ |
| 309 | Et | H | c-Pr | Me | $OCH_2CH_2OCHClF$ | $SO_2Me$ |
| 310 | Me | H | c-Pr | $CF_3$ | $OCH_2CH_2OCHClF$ | $SO_2Me$ |
| 311 | Et | H | c-Pr | $CF_3$ | $OCH_2CH_2OCHClF$ | $SO_2Me$ |
| 312 | Me | H | c-Pr | Br | $OCH_2CH_2OCHClF$ | $SO_2Me$ |
| 313 | Et | H | c-Pr | Br | $OCH_2CH_2OCHClF$ | $SO_2Me$ |

TABLE 1-continued (I-2)

| No. | R¹ | R² | R³ | R⁴ | R⁵ | R⁶ |
|---|---|---|---|---|---|---|
| 314 | Me | H | c-Pr | SO₂Me | OCH₂CH₂OCHClF | CF₃ |
| 315 | Et | H | c-Pr | SO₂Me | OCH₂CH₂OCHClF | CF₃ |
| 316 | Me | H | c-Pr | Cl | OCH₂CHFOCF₃ | SO₂Me |
| 317 | Et | H | c-Pr | Cl | OCH₂CHFOCF₃ | SO₂Me |
| 318 | Me | H | c-Pr | Me | OCH₂CHFOCF₃ | SO₂Me |
| 319 | Me | H | c-Pr | Cl | OCH₂CHFOMe | SO₂Me |
| 320 | Et | H | c-Pr | Cl | OCH₂CHFOMe | SO₂Me |
| 321 | Me | H | c-Pr | Me | OCH₂CHFOMe | SO₂Me |
| 322 | Et | H | c-Pr | Me | OCH₂CHFOMe | SO₂Me |
| 323 | Me | H | c-Pr | CF₃ | OCH₂CHFOMe | SO₂Me |
| 324 | Et | H | c-Pr | CF₃ | OCH₂CHFOMe | SO₂Me |
| 325 | Me | H | c-Pr | Br | OCH₂CHFOMe | SO₂Me |
| 326 | Et | H | c-Pr | Br | OCH₂CHFOMe | SO₂Me |
| 327 | Me | H | c-Pr | SO₂Me | OCH₂CHFOMe | CF₃ |
| 328 | Et | H | c-Pr | SO₂Me | OCH₂CHFOMe | CF₃ |
| 329 | Me | H | c-Pr | Cl | OCHFCH₂OCF₃ | SO₂Me |
| 330 | Et | H | c-Pr | Cl | OCHFCH₂OCF₃ | SO₂Me |
| 331 | Me | H | c-Pr | Cl | OCH₂CH₂OCF₂Cl | SO₂Me |
| 332 | Et | H | c-Pr | Cl | OCH₂CH₃OCF₂Cl | SO₂Me |
| 333 | Me | H | c-Pr | Me | OCH₂CH₂OCF₂Cl | SO₂Me |
| 334 | Me | H | c-Pr | CN | OCH₂CH₂OCF₃ | SO₂Me |
| 335 | Et | H | c-Pr | Me | OCH₂CH₂OCF₂Cl | SO₂Me |
| 336 | Me | H | c-Pr | CF₃ | OCH₂CH₂OCF₂Cl | SO₂Me |
| 337 | Et | H | c-Pr | CF₃ | OCH₂CH₂OCF₂Cl | SO₂Me |
| 338 | Me | H | c-Pr | Br | OCH₂CH₂OCF₂Cl | SO₂Me |
| 339 | Et | H | c-Pr | Br | OCH₂CH₂OCF₂Cl | SO₂Me |
| 340 | Me | H | c-Pr | SO₂Me | OCH₂CH₂OCF₂Cl | CF₃ |
| 341 | Et | H | c-Pr | SO₂Me | OCH₂CH₂OCF₂Cl | CF₃ |
| 342 | Me | H | c-Pr | Cl | SCH₂CH₂OCH₃ | SO₂Me |
| 343 | Et | H | c-Pr | Cl | SCH₂CH₂OCH₃ | SO₂Me |
| 344 | Me | H | c-Pr | Me | SCH₂CH₂OCH₃ | SO₂Me |
| 345 | Et | H | c-Pr | Me | SCH₂CH₂OCH₃ | SO₂Me |
| 346 | Me | H | c-Pr | CF₃ | SCH₂CH₂OCH₃ | SO₂Me |
| 347 | Et | H | c-Pr | CF₃ | SCH₂CH₂OCH₃ | SO₂Me |
| 348 | Me | H | c-Pr | Br | SCH₂CH₂OCH₃ | SO₂Me |
| 349 | Et | H | c-Pr | Br | SCH₂CH₂OCH₃ | SO₂Me |
| 350 | Me | H | c-Pr | SO₂Me | SCH₂CH₂OCH₃ | CF₃ |
| 351 | Et | H | c-Pr | SO₂Me | SCH₂CH₂OCH₃ | CF₃ |
| 352 | Me | H | c-Pr | Cl | SCH₂CH₃OCF₃ | SO₂Me |
| 353 | Et | H | c-Pr | Cl | SCH₂CH₂OCF₃ | SO₂Me |
| 354 | Me | H | c-Pr | Me | SCH₂CH₂OCF₃ | SO₂Me |
| 355 | Et | H | c-Pr | Me | SCH₂CH₂OCF₃ | SO₂Me |
| 356 | Me | H | c-Pr | CF₃ | SCH₂CH₂OCF₃ | SO₂Me |
| 357 | Et | H | c-Pr | CF₃ | SCH₂CH₂OCF₃ | SO₂Me |
| 358 | Me | H | c-Pr | Br | SCH₂CH₂OCF₃ | SO₂Me |
| 359 | Et | H | c-Pr | Br | SCH₂CH₂OCF₃ | SO₂Me |
| 360 | Me | H | c-Pr | SO₂Me | SCH₂CH₂OCF₃ | CF₃ |
| 361 | Et | H | c-Pr | SO₂Me | SCH₂CH₂OCF₃ | CF₃ |
| 362 | Me | H | c-Pr | Cl | SCH₂CH₂SCH₃ | SO₂Me |
| 363 | Et | H | c-Pr | Cl | SCH₂CH₂SCH₃ | SO₂Me |
| 364 | Me | H | c-Pr | Me | SCH₂CH₂SCH₃ | SO₂Me |
| 365 | Et | H | c-Pr | Me | SCH₂CH₂SCH₃ | SO₂Me |
| 366 | Me | H | c-Pr | CF₃ | SCH₂CH₂SCH₃ | SO₂Me |
| 367 | Et | H | c-Pr | CF₃ | SCH₂CH₂SCH₃ | SO₂Me |
| 368 | Me | H | c-Pr | Br | SCH₂CH₂SCH₃ | SO₂Me |
| 369 | Et | H | c-Pr | Br | SCH₂CH₂SCH₃ | SO₂Me |
| 370 | Me | H | c-Pr | SO₂Me | SCH₂CH₂SCH₃ | CF₃ |
| 371 | Et | H | c-Pr | SO₂Me | SCH₂CH₂SCH₃ | CF₃ |
| 372 | Me | H | c-Pr | Cl | SCH₂CH₂SCF₃ | SO₂Me |
| 373 | Et | H | c-Pr | Cl | SCH₂CH₂SCF₃ | SO₂Me |
| 374 | Me | H | c-Pr | Me | SCH₂CH₂SCF₃ | SO₂Me |
| 375 | Et | H | c-Pr | Me | SCH₂CH₂SCF₃ | SO₂Me |
| 376 | Me | H | c-Pr | CF₃ | SCH₂CH₂SCF₃ | SO₂Me |
| 377 | Et | H | c-Pr | CF₃ | SCH₂CH₂SCF₃ | SO₂Me |
| 378 | Me | H | c-Pr | Br | SCH₂CH₂SCF₃ | SO₂Me |
| 379 | Et | H | c-Pr | Br | SCH₂CH₂SCF₃ | SO₂Me |

TABLE 1-continued (I-2)

| No. | R¹ | R² | R³ | R⁴ | R⁵ | R⁶ |
|---|---|---|---|---|---|---|
| 380 | Me | H | c-Pr | SO₂Me | SCH₂CH₂SCF₃ | CF₃ |
| 381 | Et | H | c-Pr | SO₂Me | SCH₂CH₂SCF₃ | CF₃ |
| 382 | Me | H | c-Pr | Cl | OCH₂CH(CH₃)OCH₃ | SO₂Me |
| 383 | Et | H | c-Pr | Cl | OCH₂CH(CH₃)OCH₃ | SO₂Me |
| 384 | Me | H | c-Pr | Me | OCH₂CH(CH₃)OCH₃ | SO₂Me |
| 385 | Et | H | c-Pr | Me | OCH₂CH(CH₃)OCH₃ | SO₂Me |
| 386 | Me | H | c-Pr | CF₃ | OCH₂CH(CH₃)OCH₃ | SO₂Me |
| 387 | Et | H | c-Pr | CF₃ | OCH₂CH(CH₃)OCH₃ | SO₂Me |
| 388 | Me | H | c-Pr | Br | OCH₂CH(CH₃)OCH₃ | SO₂Me |
| 389 | Et | H | c-Pr | Br | OCH₂CH(CH₃)OCH₃ | SO₂Me |
| 390 | Me | H | c-Pr | SO₂Me | OCH₂CH(CH₃)OCH₃ | CF₃ |
| 391 | Et | H | c-Pr | SO₂Me | OCH₂CH(CH₃)OCH₃ | CF₃ |
| 392 | Me | H | c-Pr | Cl | OCH₂CF₂OCH₃ | SO₂Me |
| 393 | Et | H | c-Pr | Cl | OCH₂CF₂OCH₃ | SO₂Me |
| 394 | Me | H | c-Pr | Me | OCH₂CF₂OCH₃ | SO₂Me |
| 395 | Et | H | c-Pr | Me | OCH₂CF₂OCH₃ | SO₂Me |
| 396 | Me | H | c-Pr | CF₃ | OCH₂CF₂OCH₃ | SO₂Me |
| 397 | Et | H | c-Pr | CF₃ | OCH₂CF₂OCH₃ | SO₂Me |
| 398 | Me | H | c-Pr | Br | OCH₂CF₂OCH₃ | SO₂Me |
| 399 | Et | H | c-Pr | Br | OCH₂CF₂OCH₃ | SO₂Me |
| 400 | Me | H | c-Pr | SO₂Me | OCH₂CF₂OCH₃ | CF₃ |
| 401 | Et | H | c-Pr | SO₂Me | OCH₂CF₂OCH₃ | CF₃ |
| 402 | Me | H | c-Pr | Me | OCH₂CH₂OCH₃ | SO₂Me |
| 403 | Et | H | c-Pr | Me | OCH₂CH₂OCH₃ | SO₂Me |
| 404 | Me | H | c-Pr | Me | OCH₂CH(OCH₃)₂ | SO₂Me |
| 405 | Me | H | c-Pr | Me | CH₂N(Me)CH₂CN | SO₂Me |
| 406 | Me | H | c-Pr | Me | (Tetrahydrofuran-2-yl)methoxy | SO₂Me |
| 407 | Me | H | c-Pr | Cl | SMe | SO₂Me |
| 408 | Me | H | c-Pr | Cl | Cl | SO₂Me |
| 409 | Me | H | c-Pr | Cl | OMe | SO₂Me |
| 410 | Me | H | c-Pr | Me | (Tetrahydro-2H-pyran-2-yl)methoxy | SO₂Me |
| 411 | Me | H | c-Pr | Cl | OCH₂CH₃OMe | SO₂Me |
| 412 | Me | H | c-Pr | Me | Tetrahydrofuran-3-yloxy | SO₂Me |
| 413 | Me | H | c-Pr | Me | OCH₂CH₂CH₂OMe | SO₂Me |
| 414 | Me | H | c-Pr | CN | OCH₂CH₂OMe | SO₂Me |
| 415 | Et | H | c-Pr | Cl | 2-(1,3-Dioxolan-2-yl)ethoxy | SO₂Me |
| 416 | Me | H | c-Pr | Me | Propargyloxy | SO₂Me |
| 417 | Me | H | c-Pr | Me | Tetrahydrofuran-3-yloxy)methyl | SO₂Me |
| 418 | Me | H | c-Pr | Cl | SO₂Me | SO₂Me |
| 419 | Me | H | c-Pr | Me | (CH₂)₆Me | SO₂Me |
| 420 | Me | H | c-Pr | Me | CH₂CH₂CH₂OMe | SO₂Me |
| 421 | Et | H | c-Pr | Cl | (1,3-Dioxolan-2-yl)methoxy | SO₂Me |
| 422 | Me | H | c-Pr | Me | CH₂N[C(O)SEt]CH₂CN | SO₂Me |
| 423 | Me | H | c-Pr | Me | CH=CHCN | SO₂Me |
| 424 | Me | H | c-Pr | Me | CH₂CH₂CN | SO₂Me |
| 425 | Me | H | c-Pr | Me | CH₂SCN | SO₂Me |
| 426 | Me | H | c-Pr | Me | CH₂C(S)NH₂ | SO₂Me |
| 427 | Me | H | c-Pr | NO₂ | OCH₂CH₂OMe | SO₂Me |
| 428 | Et | H | c-Pr | NO₂ | OCH₂CH₂OMe | SO₂Me |
| 429 | Me | H | c-Pr | Me | OCH(CH₃)CH₂OMe | SO₂Me |
| 430 | Et | H | c-Pr | Me | OCH₂CH(Et)OMe | SO₂Me |
| 431 | Me | H | c-Pr | Me | (1,3-Dioxolan-2-yl)methyl | SO₂Me |
| 432 | Me | H | c-Pr | Me | CH₂O(i-Pr) | SO₂Me |
| 433 | Et | H | s-Bu | Me | CO₂(i-Pr) | SO₂Me |
| 434 | Me | H | s-Bu | Cl | CO₂Et | SO₂Me |
| 435 | Et | H | s-Bu | Me | CO₂Me | CF₃ |
| 436 | Me | H | s-Bu | Me | OCH₂CH₂OMe | SO₂Me |
| 437 | Et | H | s-Bu | SO₂Me | CO₂Me | CN |
| 438 | Me | H | s-Bu | Me | C(O)SMe | SO₂Me |
| 439 | Me | H | s-Bu | Me | C(O)SEt | SO₂Me |
| 440 | Me | H | s-Bu | Me | 2-(2-Oxolanyl)ethoxy | SO₂Me |
| 441 | Me | H | s-Bu | Me | 2-(2-(1,3-Dioxolanyl)ethoxy | SO₂Me |
| 442 | Et | H | s-Bu | Me | CH₂OMe | SO₂Me |
| 443 | Et | H | s-Bu | Me | 2-Oxolanylmethoxymethyl | SO₂Me |
| 444 | Me | H | s-Bu | Cl | CO₂Me | SO₂Me |
| 445 | Et | H | s-Bu | Cl | CO₂Me | SO₂Et |

TABLE 1-continued (I-2)

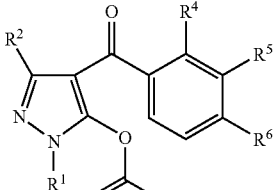

| No. | R¹ | R² | R³ | R⁴ | R⁵ | R⁶ |
|---|---|---|---|---|---|---|
| 446 | Me | H | s-Bu | Cl | C(O)SMe | $SO_2Me$ |
| 447 | Me | H | s-Bu | Cl | C(O)SEt | $SO_2Me$ |
| 448 | Me | H | s-Bu | Me | OMe | $SO_2Me$ |
| 449 | Me | H | s-Bu | Me | OEt | $SO_2Me$ |
| 450 | Me | H | s-Bu | Me | O(i-Pr) | $SO_2Me$ |
| 451 | Me | H | s-Bu | Me | $OCHF_2$ | $SO_2Me$ |
| 452 | Me | H | s-Bu | Me | (4,5-Dihydroisoxazol-3-yl) | $SO_2Me$ |
| 453 | Me | H | s-Bu | Me | O(n-Pr) | $SO_2Et$ |
| 454 | Me | H | s-Bu | Cl | $CH_2OMe$ | $SO_2Me$ |
| 455 | Me | H | s-Bu | Me | $OCO_2Me$ | $SO_2Me$ |
| 456 | Me | H | s-Bu | Me | OC(O)SMe | $SO_2Me$ |
| 457 | Me | H | s-Bu | Me | OC(O)SEt | $SO_2Me$ |
| 458 | Et | H | s-Bu | Me | OEt | $SO_2Me$ |
| 459 | Et | H | s-Bu | Cl | $CO_2Et$ | $SO_2Me$ |
| 460 | Et | H | s-Bu | Cl | $CO_2(n-Pr)$ | $SO_2Me$ |
| 461 | Et | H | s-Bu | Me | $CO_2Et$ | $SO_2Me$ |
| 462 | Me | H | s-Bu | Me | $CH_2CO_2Me$ | $SO_2Me$ |
| 463 | Me | H | s-Bu | Me | $OCH_2CO_2Et$ | $SO_2Me$ |
| 464 | Me | H | s-Bu | Me | O(n-Pr) | $SO_2Me$ |
| 465 | Et | H | s-Bu | $SO_2Me$ | H | $CF_3$ |
| 466 | Me | H | s-Bu | Me | $CH_2OCH_2CF_3$ | $SO_2Me$ |
| 467 | Me | H | s-Bu | Cl | $CH_2OCH_2CF_3$ | $SO_2Me$ |
| 468 | Et | H | s-Bu | Me | Cl | $SO_2Me$ |
| 469 | Me | H | s-Bu | Me | $CH_2SO_2Me$ | $SO_2Me$ |
| 470 | Me | H | s-Bu | Me | $CH_2OEt$ | $SO_2Me$ |
| 471 | Me | H | s-Bu | Cl | $CH_2OMe$ | $SO_2Me$ |
| 472 | Me | H | s-Bu | Me | $CH_2CH_2OMe$ | $SO_2Me$ |
| 473 | Me | H | s-Bu | Me | $CH_2OCH_2CH_2OMe$ | $SO_2Me$ |
| 474 | Me | H | s-Bu | Me | $OCH_2CH_2OEt$ | $SO_2Me$ |
| 475 | Me | H | s-Bu | Me | $OCH_2CH_2Cl$ | $SO_2Me$ |
| 476 | Me | H | s-Bu | Me | $OCH_2CF_3$ | $SO_2Me$ |
| 477 | Me | H | s-Bu | Me | $CH_2OCH_2OMe$ | $SO_2Me$ |
| 478 | Me | H | s-Bu | Me | $OCH_2CH_2SMe$ | $SO_2Me$ |
| 479 | Me | H | s-Bu | Me | CN | $SO_2Me$ |
| 480 | Me | H | s-Bu | Me | $CH_2CN$ | $SO_2Me$ |
| 481 | Me | H | s-Bu | Br | $CO_2Me$ | $SO_2Me$ |
| 482 | Et | H | s-Bu | Cl | $CO_2Me$ | $SO_2Me$ |
| 483 | Me | H | s-Bu | CN | $CO_2Me$ | $SO_2Me$ |
| 484 | Me | H | s-Bu | Cl | $OCH_2CH_2OCF_3$ | $SO_2Me$ |
| 485 | Et | H | s-Bu | Cl | $OCH_2CH_2OCF_3$ | $SO_2Me$ |
| 486 | Me | H | s-Bu | Me | $OCH_2CH_2OCF_3$ | $SO_2Me$ |
| 487 | Et | H | s-Bu | Me | $OCH_2CH_2OCF_3$ | $SO_2Me$ |
| 488 | Me | H | s-Bu | $CF_3$ | $OCH_2CH_2OCF_3$ | $SO_2Me$ |
| 489 | Et | H | s-Bu | $CF_3$ | $OCH_2CH_2OCF_3$ | $SO_2Me$ |
| 490 | Me | H | s-Bu | Br | $OCH_2CH_2OCF_3$ | $SO_2Me$ |
| 491 | Et | H | s-Bu | Br | $OCH_2CH_2OCF_3$ | $SO_2Me$ |
| 492 | Me | H | s-Bu | $SO_2Me$ | $OCH_2CH_2OCF_3$ | $CF_3$ |
| 493 | Et | H | s-Bu | $SO_2Me$ | $OCH_2CH_2OCF_3$ | $CF_3$ |
| 494 | Me | H | s-Bu | Cl | $OCH_2CH_2OCHClF$ | $SO_2Me$ |
| 495 | Et | H | s-Bu | Cl | $OCH_2CH_2OCHClF$ | $SO_2Me$ |
| 496 | Me | H | s-Bu | Me | $OCH_2CH_2OCHClF$ | $SO_2Me$ |
| 497 | Et | H | s-Bu | Me | $OCH_2CH_2OCHClF$ | $SO_2Me$ |
| 498 | Me | H | s-Bu | $CF_3$ | $OCH_2CH_2OCHClF$ | $SO_2Me$ |
| 499 | Et | H | s-Bu | $CF_3$ | $OCH_2CH_2OCHClF$ | $SO_2Me$ |
| 500 | Me | H | s-Bu | Br | $OCH_2CH_2OCHClF$ | $SO_2Me$ |
| 501 | Et | H | s-Bu | Br | $OCH_2CH_2OCHClF$ | $SO_2Me$ |
| 502 | Me | H | s-Bu | $SO_2Me$ | $OCH_2CH_2OCHClF$ | $CF_3$ |
| 503 | Et | H | s-Bu | $SO_2Me$ | $OCH_2CH_2OCHClF$ | $CF_3$ |
| 504 | Me | H | s-Bu | Cl | $OCH_2CHFOCF_3$ | $SO_2Me$ |
| 505 | Et | H | s-Bu | Cl | $OCH_2CHFOCF_3$ | $SO_2Me$ |
| 506 | Me | H | s-Bu | Me | $OCH_2CHFOCF_3$ | $SO_2Me$ |
| 507 | Me | H | s-Bu | Cl | $OCH_2CHFOMe$ | $SO_2Me$ |
| 508 | Et | H | s-Bu | Cl | $OCH_2CHFOMe$ | $SO_2Me$ |
| 509 | Me | H | s-Bu | Me | $OCH_2CHFOMe$ | $SO_2Me$ |
| 510 | Et | H | s-Bu | Me | $OCH_2CHFOMe$ | $SO_2Me$ |
| 511 | Me | H | s-Bu | $CF_3$ | $OCH_2CHFOMe$ | $SO_2Me$ |

TABLE 1-continued (I-2)

| No. | R¹ | R² | R³ | R⁴ | R⁵ | R⁶ |
|---|---|---|---|---|---|---|
| 512 | Et | H | s-Bu | CF₃ | OCH₂CHFOMe | SO₂Me |
| 513 | Me | H | s-Bu | Br | OCH₂CHFOMe | SO₂Me |
| 514 | Et | H | s-Bu | Br | OCH₂CHFOMe | SO₂Me |
| 515 | Me | H | s-Bu | SO₂Me | OCH₂CHFOMe | CF₃ |
| 516 | Et | H | s-Bu | SO₂Me | OCH₂CHFOMe | CF₃ |
| 517 | Me | H | s-Bu | Cl | OCHFCH₂OCF₃ | SO₂Me |
| 518 | Et | H | s-Bu | Cl | OCHFCH₂OCF₃ | SO₂Me |
| 519 | Me | H | s-Bu | Cl | OCH₂CH₂OCF₂Cl | SO₂Me |
| 520 | Et | H | s-Bu | Cl | OCH₂CH₂OCF₂Cl | SO₂Me |
| 521 | Me | H | s-Bu | Me | OCH₂CH₂OCF₂Cl | SO₂Me |
| 522 | Et | H | s-Bu | Me | OCH₂CH₂OCF₂Cl | SO₂Me |
| 523 | Me | H | s-Bu | CF₃ | OCH₂CH₂OCF₂Cl | SO₂Me |
| 524 | Et | H | s-Bu | CF₃ | OCH₂CH₂OCF₂Cl | SO₂Me |
| 525 | Me | H | s-Bu | Br | OCH₂CH₂OCF₂Cl | SO₂Me |
| 526 | Et | H | s-Bu | Br | OCH₂CH₂OCF₂Cl | SO₂Me |
| 527 | Me | H | s-Bu | SO₂Me | OCH₂CH₂OCF₂Cl | CF₃ |
| 528 | Et | H | s-Bu | SO₂Me | OCH₂CH₃OCF₂Cl | CF₃ |
| 529 | Me | H | s-Bu | Cl | SCH₂CH₂OCH₃ | SO₂Me |
| 530 | Et | H | s-Bu | Cl | SCH₂CH₂OCH₃ | SO₂Me |
| 531 | Me | H | s-Bu | Me | SCH₂CH₂OCH₃ | SO₂Me |
| 532 | Et | H | s-Bu | Me | SCH₂CH₃OCH₃ | SO₂Me |
| 533 | Me | H | s-Bu | CF₃ | SCH₂CH₂OCH₃ | SO₂Me |
| 534 | Et | H | s-Bu | CF₃ | SCH₂CH₃OCH₃ | SO₂Me |
| 535 | Me | H | s-Bu | Br | SCH₂CH₃OCH₃ | SO₂Me |
| 536 | Et | H | s-Bu | Br | SCH₂CH₂OCH₃ | SO₂Me |
| 537 | Me | H | s-Bu | SO₂Me | SCH₂CH₂OCH₃ | CF₃ |
| 538 | Et | H | s-Bu | SO₂Me | SCH₂CH₂OCH₃ | CF₃ |
| 539 | Me | H | s-Bu | Cl | SCH₂CH₂OCF₃ | SO₂Me |
| 540 | Et | H | s-Bu | Cl | SCH₂CH₂OCF₃ | SO₂Me |
| 541 | Me | H | s-Bu | Me | SCH₂CH₂OCF₃ | SO₂Me |
| 542 | Et | H | s-Bu | Me | SCH₂CH₂OCF₃ | SO₂Me |
| 543 | Me | H | s-Bu | CF₃ | SCH₂CH₂OCF₃ | SO₂Me |
| 544 | Et | H | s-Bu | CF₃ | SCH₂CH₂OCF₃ | SO₂Me |
| 545 | Me | H | s-Bu | Br | SCH₂CH₂OCF₃ | SO₂Me |
| 546 | Et | H | s-Bu | Br | SCH₂CH₂OCF₃ | SO₂Me |
| 547 | Me | H | s-Bu | SO₂Me | SCH₂CH₂OCF₃ | CF₃ |
| 548 | Et | H | s-Bu | SO₂Me | SCH₂CH₂OCF₃ | CF₃ |
| 549 | Me | H | s-Bu | Cl | SCH₂CH₂SCH₃ | SO₂Me |
| 550 | Et | H | s-Bu | Cl | SCH₂CH₂SCH₃ | SO₂Me |
| 551 | Me | H | s-Bu | Me | SCH₂CH₂SCH₃ | SO₂Me |
| 552 | Et | H | s-Bu | Me | SCH₂CH₂SCH₃ | SO₂Me |
| 553 | Me | H | s-Bu | CF₃ | SCH₂CH₂SCH₃ | SO₂Me |
| 554 | Et | H | s-Bu | CF₃ | SCH₂CH₂SCH₃ | SO₂Me |
| 555 | Me | H | s-Bu | Br | SCH₂CH₂SCH₃ | SO₂Me |
| 556 | Et | H | s-Bu | Br | SCH₂CH₂SCH₃ | SO₂Me |
| 557 | Me | H | s-Bu | SO₂Me | SCH₂CH₂SCH₃ | CF₃ |
| 558 | Et | H | s-Bu | SO₂Me | SCH₂CH₂SCH₃ | CF₃ |
| 559 | Me | H | s-Bu | Cl | SCH₂CH₂SCF₃ | SO₂Me |
| 560 | Et | H | s-Bu | Cl | SCH₂CH₂SCF₃ | SO₂Me |
| 561 | Me | H | s-Bu | Me | SCH₂CH₂SCF₃ | SO₂Me |
| 562 | Et | H | s-Bu | Me | SCH₂CH₂SCF₃ | SO₂Me |
| 563 | Me | H | s-Bu | CF₃ | SCH₂CH₂SCF₃ | SO₂Me |
| 564 | Et | H | s-Bu | CF₃ | SCH₂CH₂SCF₃ | SO₂Me |
| 565 | Me | H | s-Bu | Br | SCH₂CH₂SCF₃ | SO₂Me |
| 566 | Et | H | s-Bu | Br | SCH₂CH₂SCF₃ | SO₂Me |
| 567 | Me | H | s-Bu | SO₂Me | SCH₂CH₂SCF₃ | CF₃ |
| 568 | Et | H | s-Bu | SO₂Me | SCH₂CH₂SCF₃ | CF₃ |
| 569 | Me | H | s-Bu | Cl | OCH₂CH(CH₃)OCH₃ | SO₂Me |
| 570 | Et | H | s-Bu | Cl | OCH₂CH(CH₃)OCH₃ | SO₂Me |
| 571 | Me | H | s-Bu | Me | OCH₂CH(CH₃)OCH₃ | SO₂Me |
| 572 | Et | H | s-Bu | Me | OCH₂CH(CH₃)OCH₃ | SO₂Me |
| 573 | Me | H | s-Bu | CF₃ | OCH₂CH(CH₃) OCH₃ | SO₂Me |
| 574 | Et | H | s-Bu | CF₃ | OCH₂CH(CH₃) OCH₃ | SO₂Me |
| 575 | Me | H | s-Bu | Br | OCH₂CH(CH₃)OCH₃ | SO₂Me |
| 576 | Et | H | s-Bu | Br | OCH₂CH(CH₃)OCH₃ | SO₂Me |
| 577 | Me | H | s-Bu | SO₂Me | OCH₂CH(CH₃)OCH₃ | CF₃ |

TABLE 1-continued (I-2)

| No. | R¹ | R² | R³ | R⁴ | R⁵ | R⁶ |
|---|---|---|---|---|---|---|
| 578 | Et | H | s-Bu | SO₂Me | OCH₂CH(CH₃)OCH₃ | CF₃ |
| 579 | Me | H | s-Bu | Cl | OCH₂CF₂OCH₃ | SO₂Me |
| 580 | Et | H | s-Bu | Cl | OCH₂CF₂OCH₃ | SO₂Me |
| 581 | Me | H | s-Bu | Me | OCH₂CF₂OCH₃ | SO₂Me |
| 582 | Et | H | s-Bu | Me | OCH₂CF₂OCH₃ | SO₂Me |
| 583 | Me | H | s-Bu | CF₃ | OCH₂CF₂OCH₃ | SO₂Me |
| 584 | Et | H | s-Bu | CF₃ | OCH₂CF₂OCH₃ | SO₂Me |
| 585 | Me | H | s-Bu | Br | OCH₂CF₂OCH₃ | SO₂Me |
| 586 | Et | H | s-Bu | Br | OCH₂CF₂OCH₃ | SO₂Me |
| 587 | Me | H | s-Bu | SO₂Me | OCH₂CF₂OCH₃ | CF₃ |
| 588 | Et | H | s-Bu | SO₂Me | OCH₂CF₂OCH₃ | CF₃ |
| 589 | Me | H | s-Bu | Me | OCH₂CH₂OCH₃ | SO₂Me |
| 590 | Et | H | s-Bu | Me | OCH₂CH₂OCH₃ | SO₂Me |
| 591 | Me | H | s-Bu | Me | OCH₂CH(OCH₃)₂ | SO₂Me |
| 592 | Me | H | s-Bu | Me | CH₂N(Me)CH₂CN | SO₂Me |
| 593 | Me | H | s-Bu | Me | (Tetrahydrofuran-2-yl)methoxy | SO₂Me |
| 594 | Me | H | s-Bu | Cl | SMe | SO₂Me |
| 595 | Me | H | s-Bu | Cl | Cl | SO₂Me |
| 596 | Me | H | s-Bu | Cl | OMe | SO₂Me |
| 597 | Me | H | s-Bu | Me | (Tetrahydro-2H-pyran-2-yl)methoxy | SO₂Me |
| 598 | Me | H | s-Bu | Cl | OCH₂CH₂OMe | SO₂Me |
| 599 | Me | H | s-Bu | Me | Tetrahydrofuran-3-yloxy | SO₂Me |
| 600 | Me | H | s-Bu | Me | OCH₂CH₂CH₂OMe | SO₂Me |
| 601 | Me | H | s-Bu | Me | OCH₂CH₂OMe | SO₂Me |
| 602 | Me | H | s-Bu | OCHF₂ | OCH₂CH₂OMe | SO₂Me |
| 603 | Et | H | s-Bu | Cl | 2-(1,3-Dioxolan-2-yl)ethoxy | SO₂Me |
| 604 | Me | H | s-Bu | Me | Propargyloxy | SO₂Me |
| 605 | Me | H | s-Bu | Me | (Tetrahydrofuran-3-yloxy)methyl | SO₂Me |
| 606 | Me | H | s-Bu | Cl | SO₂Me | SO₂Me |
| 607 | Me | H | s-Bu | Me | (CH₂)₆Me | SO₂Me |
| 608 | Me | H | s-Bu | Me | CH₂CH₂CH₂OMe | SO₂Me |
| 609 | Et | H | s-Bu | Cl | (1,3-Dioxolan-2-yl)methoxy | SO₂Me |
| 610 | Me | H | s-Bu | Me | CH₂N[C(O)SEt]CH₂CN | SO₂Me |
| 611 | Me | H | s-Bu | Me | CH=CHCN | SO₂Me |
| 612 | Me | H | s-Bu | Me | CH₂CH₂CN | SO₂Me |
| 613 | Me | H | s-Bu | Me | CH₂SCN | SO₂Me |
| 614 | Me | H | s-Bu | Me | CH₂C(S)NH₂ | SO₂Me |
| 615 | Me | H | s-Bu | Me | OCH₂CH₂OMe | SO₂Me |
| 616 | Et | H | s-Bu | Me | OCH₂CH₂OMe | SO₂Me |
| 617 | Me | H | s-Bu | Me | OCH(CH₃)CH₂OMe | SO₂Me |
| 618 | Et | H | s-Bu | Me | OCH₂CH(Et)OMe | SO₂Me |
| 619 | Me | H | s-Bu | Me | (1,3-Dioxolan-2-yl)methyl | SO₂Me |
| 620 | Me | H | s-Bu | Me | CH₂O(i-Pr) | SO₂Me |
| 621 | Me | H | s-Bu | OCHF₂ | CH₂OMe | SO₂Me |
| 622 | Me | H | s-Bu | CHF₂ | CH₂OMe | SO₂Me |
| 623 | Et | H | t-Bu | Me | CO₂(i-Pr) | SO₂Me |
| 624 | Me | H | t-Bu | Cl | CO₂Et | SO₂Me |
| 625 | Et | H | t-Bu | Me | CO₂Me | CF₃ |
| 626 | Et | H | t-Bu | Me | OCH₂CH₂OMe | SO₂Me |
| 627 | Et | H | t-Bu | SO₂Me | CO₂Me | CN |
| 628 | Me | H | t-Bu | Me | C(O)SMe | SO₂Me |
| 629 | Me | H | t-Bu | Me | C(O)SEt | SO₂Me |
| 630 | Me | H | t-Bu | Me | 2-(2-Oxolanyl)ethoxy | SO₂Me |
| 631 | Me | H | t-Bu | Me | 2-(2-(1,3-Dioxolanyl))ethoxy | SO₂Me |
| 632 | Et | H | t-Bu | Me | CH₂OMe | SO₂Me |
| 633 | Et | H | t-Bu | Me | 2-Oxolanylmethoxymethyl | SO₂Me |
| 634 | Me | H | t-Bu | Cl | CO₂Me | SO₂Me |
| 635 | Et | H | t-Bu | Cl | CO₂Me | SO₂Et |
| 636 | Me | H | t-Bu | Cl | C(O)SMe | SO₂Me |
| 637 | Me | H | t-Bu | Cl | C(O)SEt | SO₂Me |
| 638 | Me | H | t-Bu | Me | OMe | SO₂Me |
| 639 | Me | H | t-Bu | Me | OEt | SO₂Me |
| 640 | Me | H | t-Bu | Me | O(i-Pr) | SO₂Me |
| 641 | Me | H | t-Bu | Me | OCHF₂ | SO₂Me |
| 642 | Me | H | t-Bu | Me | (4,5-Dihydroisoxazol-3-yl) | SO₂Me |
| 643 | Me | H | t-Bu | Me | O(n-Pr) | SO₂Et |

TABLE 1-continued (I-2)

| No. | R¹ | R² | R³ | R⁴ | R⁵ | R⁶ |
|---|---|---|---|---|---|---|
| 644 | Me | H | t-Bu | Cl | CH$_2$OMe | SO$_2$Me |
| 645 | Me | H | t-Bu | Me | OCO$_2$Me | SO$_2$Me |
| 646 | Me | H | t-Bu | Me | OC(O)SMe | SO$_2$Me |
| 647 | Me | H | t-Bu | Me | OC(O)SEt | SO$_2$Me |
| 648 | Me | H | t-Bu | Me | OCH$_2$CH$_2$OMe | SO$_2$Me |
| 649 | Et | H | t-Bu | Me | OEt | SO$_2$Me |
| 650 | Et | H | t-Bu | Cl | CO$_2$Et | SO$_2$Me |
| 651 | Et | H | t-Bu | Cl | CO$_2$(n-Pr) | SO$_2$Me |
| 652 | Et | H | t-Bu | Me | CO$_2$Et | SO$_2$Me |
| 653 | Me | H | t-Bu | Me | CH$_2$CO$_2$Me | SO$_2$Me |
| 654 | Me | H | t-Bu | Me | OCH$_2$CO$_2$Et | SO$_2$Me |
| 655 | Me | H | t-Bu | Me | O(n-Pr) | SO$_2$Me |
| 656 | Et | H | t-Bu | SO$_2$Me | H | CF$_3$ |
| 657 | Me | H | t-Bu | Me | CH$_2$OCH$_2$CF$_3$ | SO$_2$Me |
| 658 | Me | H | t-Bu | Cl | CH$_2$OCH$_2$CF$_3$ | SO$_2$Me |
| 659 | Et | H | t-Bu | Me | Cl | SO$_2$Me |
| 660 | Me | H | t-Bu | Me | CH$_2$SO$_2$Me | SO$_2$Me |
| 661 | Me | H | t-Bu | Me | CH$_2$OEt | SO$_2$Me |
| 662 | Me | H | t-Bu | Cl | CH$_2$OMe | SO$_2$Me |
| 663 | Me | H | t-Bu | Me | CH$_2$CH$_2$OMe | SO$_2$Me |
| 664 | Me | H | t-Bu | Me | CH$_2$OCH$_2$CH$_2$OMe | SO$_2$Me |
| 665 | Me | H | t-Bu | Me | OCH$_2$CH$_2$OEt | SO$_2$Me |
| 666 | Me | H | t-Bu | Me | OCH$_2$CH$_2$Cl | SO$_2$Me |
| 667 | Me | H | t-Bu | Me | OCH$_2$CF$_3$ | SO$_2$Me |
| 668 | Me | H | t-Bu | Me | CH$_2$OCH$_2$OMe | SO$_2$Me |
| 669 | Me | H | t-Bu | Me | OCH$_2$CH$_2$SMe | SO$_2$Me |
| 670 | Me | H | t-Bu | Me | CN | SO$_2$Me |
| 671 | Me | H | t-Bu | Me | CH$_2$CN | SO$_2$Me |
| 672 | Me | H | t-Bu | Br | CO$_2$Me | SO$_2$Me |
| 673 | Et | H | t-Bu | Cl | CO$_2$Me | SO$_2$Me |
| 674 | Me | H | t-Bu | Br | CO$_2$Me | SO$_2$Me |
| 675 | Me | H | t-Bu | Cl | OCH$_2$CH$_2$OCF$_3$ | SO$_2$Me |
| 676 | Et | H | t-Bu | Cl | OCH$_2$CH$_2$OCF$_3$ | SO$_2$Me |
| 677 | Me | H | t-Bu | Me | OCH$_2$CH$_2$OCF$_3$ | SO$_2$Me |
| 678 | Et | H | t-Bu | Me | OCH$_2$CH$_2$OCF$_3$ | SO$_2$Me |
| 679 | Me | H | t-Bu | CF$_3$ | OCH$_2$CH$_2$OCF$_3$ | SO$_2$Me |
| 680 | Et | H | t-Bu | CF$_3$ | OCH$_2$CH$_2$OCF$_3$ | SO$_2$Me |
| 681 | Me | H | t-Bu | Br | OCH$_2$CH$_2$OCF$_3$ | SO$_2$Me |
| 682 | Et | H | t-Bu | Br | OCH$_2$CH$_2$OCF$_3$ | SO$_2$Me |
| 683 | Me | H | t-Bu | SO$_2$Me | OCH$_2$CH$_2$OCF$_3$ | CF$_3$ |
| 684 | Et | H | t-Bu | SO$_2$Me | OCH$_2$CH$_2$OCF$_3$ | CF$_3$ |
| 685 | Me | H | t-Bu | Cl | OCH$_2$CH$_2$OCHClF | SO$_2$Me |
| 686 | Et | H | t-Bu | Cl | OCH$_2$CH$_2$OCHClF | SO$_2$Me |
| 687 | Me | H | t-Bu | Me | OCH$_2$CH$_2$OCHClF | SO$_2$Me |
| 688 | Et | H | t-Bu | Me | OCH$_2$CH$_2$OCHClF | SO$_2$Me |
| 689 | Me | H | t-Bu | CF$_3$ | OCH$_2$CH$_2$OCHClF | SO$_2$Me |
| 690 | Et | H | t-Bu | CF$_3$ | OCH$_2$CH$_2$OCHClF | SO$_2$Me |
| 691 | Me | H | t-Bu | Br | OCH$_2$CH$_2$OCHClF | SO$_2$Me |
| 692 | Et | H | t-Bu | Br | OCH$_2$CH$_2$OCHClF | SO$_2$Me |
| 693 | Me | H | t-Bu | SO$_2$Me | OCH$_2$CH$_2$OCHClF | CF$_3$ |
| 694 | Et | H | t-Bu | SO$_2$Me | OCH$_2$CH$_2$OCHClF | CF$_3$ |
| 695 | Me | H | t-Bu | Cl | OCH$_2$CHFOCF$_3$ | SO$_2$Me |
| 696 | Et | H | t-Bu | Cl | OCH$_2$CHFOCF$_3$ | SO$_2$Me |
| 697 | Me | H | t-Bu | Me | OCH$_2$CHFOCF$_3$ | SO$_2$Me |
| 698 | Me | H | t-Bu | Cl | OCH$_2$CHFOMe | SO$_2$Me |
| 699 | Et | H | t-Bu | Cl | OCH$_2$CHFOMe | SO$_2$Me |
| 700 | Me | H | t-Bu | Me | OCH$_2$CHFOMe | SO$_2$Me |
| 701 | Et | H | t-Bu | Me | OCH$_2$CHFOMe | SO$_2$Me |
| 702 | Me | H | t-Bu | CF$_3$ | OCH$_2$CHFOMe | SO$_2$Me |
| 703 | Et | H | t-Bu | CF$_3$ | OCH$_2$CHFOMe | SO$_2$Me |
| 704 | Me | H | t-Bu | Br | OCH$_2$CHFOMe | SO$_2$Me |
| 705 | Et | H | t-Bu | Br | OCH$_2$CHFOMe | SO$_2$Me |
| 706 | Me | H | t-Bu | SO$_2$Me | OCH$_2$CHFOMe | CF$_3$ |
| 707 | Et | H | t-Bu | SO$_2$Me | OCH$_2$CHFOMe | CF$_3$ |
| 708 | Me | H | t-Bu | Cl | OCHFCH$_2$OCF$_3$ | SO$_2$Me |
| 709 | Et | H | t-Bu | Cl | OCHFCH$_2$OCF$_3$ | SO$_2$Me |

TABLE 1-continued (I-2)

| No. | R¹ | R² | R³ | R⁴ | R⁵ | R⁶ |
|---|---|---|---|---|---|---|
| 710 | Me | H | t-Bu | Cl | OCH$_2$CH$_2$OCF$_2$Cl | SO$_2$Me |
| 711 | Et | H | t-Bu | Cl | OCH$_2$CH$_2$OCF$_2$Cl | SO$_2$Me |
| 712 | Me | H | t-Bu | Me | OCH$_2$CH$_2$OCF$_2$Cl | SO$_2$Me |
| 713 | Et | H | t-Bu | Me | OCH$_2$CH$_2$OCF$_2$Cl | SO$_2$Me |
| 714 | Me | H | t-Bu | CF$_3$ | OCH$_2$CH$_2$OCF$_2$Cl | SO$_2$Me |
| 715 | Et | H | t-Bu | CF$_3$ | OCH$_2$CH$_2$OCF$_2$Cl | SO$_2$Me |
| 716 | Me | H | t-Bu | Br | OCH$_2$CH$_2$OCF$_2$Cl | SO$_2$Me |
| 717 | Et | H | t-Bu | Br | OCH$_2$CH$_2$OCF$_2$Cl | SO$_2$Me |
| 718 | Me | H | t-Bu | SO$_2$Me | OCH$_2$CH$_2$OCF$_2$Cl | CF$_3$ |
| 719 | Et | H | t-Bu | SO$_2$Me | OCH$_2$CH$_2$OCF$_2$Cl | CF$_3$ |
| 720 | Me | H | t-Bu | Cl | SCH$_2$CH$_2$OCH$_3$ | SO$_2$Me |
| 721 | Et | H | t-Bu | Cl | SCH$_2$CH$_2$OCH$_3$ | SO$_2$Me |
| 722 | Me | H | t-Bu | Me | SCH$_2$CH$_2$OCH$_3$ | SO$_2$Me |
| 723 | Et | H | t-Bu | Me | SCH$_2$CH$_2$OCH$_3$ | SO$_2$Me |
| 724 | Me | H | t-Bu | CF$_3$ | SCH$_2$CH$_2$OCH$_3$ | SO$_2$Me |
| 725 | Et | H | t-Bu | CF$_3$ | SCH$_2$CH$_2$OCH$_3$ | SO$_2$Me |
| 726 | Me | H | t-Bu | Br | SCH$_2$CH$_2$OCH$_3$ | SO$_2$Me |
| 727 | Et | H | t-Bu | Br | SCH$_2$CH$_2$OCH$_3$ | SO$_2$Me |
| 728 | Me | H | t-Bu | SO$_2$Me | SCH$_2$CH$_2$OCH$_3$ | CF$_3$ |
| 729 | Et | H | t-Bu | SO$_2$Me | SCH$_2$CH$_2$OCH$_3$ | CF$_3$ |
| 730 | Me | H | t-Bu | Cl | SCH$_2$CH$_3$OCF$_3$ | SO$_2$Me |
| 731 | Et | H | t-Bu | Cl | SCH$_2$CH$_2$OCF$_3$ | SO$_2$Me |
| 732 | Me | H | t-Bu | Me | SCH$_2$CH$_2$OCF$_3$ | SO$_2$Me |
| 733 | Et | H | t-Bu | Me | SCH$_2$CH$_2$OCF$_3$ | SO$_2$Me |
| 734 | Me | H | t-Bu | CF$_3$ | SCH$_2$CH$_2$OCF$_3$ | SO$_2$Me |
| 735 | Et | H | t-Bu | CF$_3$ | SCH$_2$CH$_2$OCF$_3$ | SO$_2$Me |
| 736 | Me | H | t-Bu | Br | SCH$_2$CH$_2$OCF$_3$ | SO$_2$Me |
| 737 | Et | H | t-Bu | Br | SCH$_2$CH$_2$OCF$_3$ | SO$_2$Me |
| 738 | Me | H | t-Bu | SO$_2$Me | SCH$_2$CH$_2$OCF$_3$ | CF$_3$ |
| 739 | Et | H | t-Bu | SO$_2$Me | SCH$_2$CH$_2$OCF$_3$ | CF$_3$ |
| 740 | Me | H | t-Bu | Cl | SCH$_2$CH$_2$SCH$_3$ | SO$_2$Me |
| 741 | Et | H | t-Bu | Cl | SCH$_2$CH$_2$SCH$_3$ | SO$_2$Me |
| 742 | Me | H | t-Bu | Me | SCH$_2$CH$_2$SCH$_3$ | SO$_2$Me |
| 743 | Et | H | t-Bu | Me | SCH$_2$CH$_2$SCH$_3$ | SO$_2$Me |
| 744 | Me | H | t-Bu | CF$_3$ | SCH$_2$CH$_2$SCH$_3$ | SO$_2$Me |
| 745 | Et | H | t-Bu | CF$_3$ | SCH$_2$CH$_2$SCH$_3$ | SO$_2$Me |
| 746 | Me | H | t-Bu | Br | SCH$_2$CH$_2$SCH$_3$ | SO$_2$Me |
| 747 | Et | H | t-Bu | Br | SCH$_2$CH$_2$SCH$_3$ | SO$_2$Me |
| 748 | Me | H | t-Bu | SO$_2$Me | SCH$_2$CH$_2$SCH$_3$ | CF$_3$ |
| 749 | Et | H | t-Bu | SO$_2$Me | SCH$_2$CH$_2$SCH$_3$ | CF$_3$ |
| 750 | Me | H | t-Bu | Cl | SCH$_2$CH$_2$SCF$_3$ | SO$_2$Me |
| 751 | Et | H | t-Bu | Cl | SCH$_2$CH$_2$SCF$_3$ | SO$_2$Me |
| 752 | Me | H | t-Bu | Me | SCH$_2$CH$_2$SCF$_3$ | SO$_2$Me |
| 753 | Et | H | t-Bu | Me | SCH$_2$CH$_2$SCF$_3$ | SO$_2$Me |
| 754 | Me | H | t-Bu | CF$_3$ | SCH$_2$CH$_2$SCF$_3$ | SO$_2$Me |
| 755 | Et | H | t-Bu | CF$_3$ | SCH$_2$CH$_2$SCF$_3$ | SO$_2$Me |
| 756 | Me | H | t-Bu | Br | SCH$_2$CH$_2$SCF$_3$ | SO$_2$Me |
| 757 | Et | H | t-Bu | Br | SCH$_2$CH$_2$SCF$_3$ | SO$_2$Me |
| 758 | Me | H | t-Bu | SO$_2$Me | SCH$_2$CH$_2$SCF$_3$ | CF$_3$ |
| 759 | Et | H | t-Bu | SO$_2$Me | SCH$_2$CH$_2$SCF$_3$ | CF$_3$ |
| 760 | Me | H | t-Bu | Cl | OCH$_2$CH(CH$_3$)OCH$_3$ | SO$_2$Me |
| 761 | Et | H | t-Bu | Cl | OCH$_2$CH(CH$_3$)OCH$_3$ | SO$_2$Me |
| 762 | Me | H | t-Bu | Me | OCH$_2$CH(CH$_3$)OCH$_3$ | SO$_2$Me |
| 763 | Et | H | t-Bu | Me | OCH$_2$CH(CH$_3$)OCH$_3$ | SO$_2$Me |
| 764 | Me | H | t-Bu | CF$_3$ | OCH$_2$CH(CH$_3$)OCH$_3$ | SO$_2$Me |
| 765 | Et | H | t-Bu | CF$_3$ | OCH$_2$CH(CH$_3$)OCH$_3$ | SO$_2$Me |
| 766 | Me | H | t-Bu | Br | OCH$_2$CH(CH$_3$)OCH$_3$ | SO$_2$Me |
| 767 | Et | H | t-Bu | Br | OCH$_2$CH(CH$_3$)OCH$_3$ | SO$_2$Me |
| 768 | Me | H | t-Bu | SO$_2$Me | OCH$_2$CH (CH$_3$)OCH$_3$ | CF$_3$ |
| 769 | Et | H | t-Bu | SO$_2$Me | OCH$_2$CH (CH$_3$)OCH$_3$ | CF$_3$ |
| 770 | Me | H | t-Bu | Cl | OCH$_2$CF$_2$OCH$_3$ | SO$_2$Me |
| 771 | Et | H | t-Bu | Cl | OCH$_2$CF$_2$OCH$_3$ | SO$_2$Me |
| 772 | Me | H | t-Bu | Me | OCH$_2$CF$_2$OCH$_3$ | SO$_2$Me |
| 773 | Et | H | t-Bu | Me | OCH$_2$CF$_2$OCH$_3$ | SO$_2$Me |
| 774 | Me | H | tDu | CF$_3$ | OCH$_2$CF$_2$OCH$_3$ | SO$_2$Me |
| 775 | Et | H | t-Bu | CF$_3$ | OCH$_2$CF$_2$OCH$_3$ | SO$_2$Me |

TABLE 1-continued (I-2)

$$\text{Structure with } R^1, R^2, R^3, R^4, R^5, R^6 \text{ substituents on pyrazole-benzoyl scaffold with OC(O)SR}^3 \text{ group}$$

| No. | R¹ | R² | R³ | R⁴ | R⁵ | R⁶ |
|---|---|---|---|---|---|---|
| 776 | Me | H | t-Bu | Br | OCH₂CF₂OCH₃ | SO₂Me |
| 777 | Et | H | t-Bu | Br | OCH₂CF₂OCH₃ | SO₂Me |
| 778 | Me | H | t-Bu | SO₂Me | OCH₂CF₂OCH₃ | CF₃ |
| 779 | Et | H | t-Bu | SO₂Me | OCH₂CF₂OCH₃ | CF₃ |
| 780 | Et | H | t-Bu | CN | OCH₂CF₂OCH₃ | SO₂Me |
| 781 | Et | H | t-Bu | Me | OCH₂CH₂OCH₃ | SO₂Me |
| 782 | Me | H | t-Bu | Me | OCH₂CH(OCH₃)₂ | SO₂Me |
| 783 | Me | H | t-Bu | Me | CH₂N(Me)CH₂CN | SO₂Me |
| 784 | Me | H | t-Bu | Me | (Tetrahydrofuran-2-yl)methoxy | SO₂Me |
| 785 | Me | H | t-Bu | Cl | SMe | SO₂Me |
| 786 | Me | H | t-Bu | Cl | Cl | SO₂Me |
| 787 | Me | H | t-Bu | Cl | OMe | SO₂Me |
| 788 | Me | H | t-Bu | Me | (Tetrahydro-2H-pyran-2-yl)methoxy | SO₂Me |
| 789 | Me | H | t-Bu | Cl | OCH₂CH₂OMe | SO₂Me |
| 790 | Me | H | t-Bu | Me | Tetrahydrofuran-3-yloxy | SO₂Me |
| 791 | Me | H | t-Bu | Me | OCH₂CH₂CH₂OMe | SO₂Me |
| 792 | Me | H | t-Bu | Me | OCH₂CH₂OMe | SO₂Me |
| 793 | Et | H | t-Bu | Cl | (1,3-Dioxolan-2-yl)ethoxy | SO₂Me |
| 794 | Me | H | t-Bu | Me | Propargyloxy | SO₂Me |
| 795 | Me | H | t-Bu | Me | (Tetrahydrofuran-3-yloxy)methyl | SO₂Me |
| 796 | Me | H | t-Bu | Cl | SO₂Me | SO₂Me |
| 797 | Me | H | t-Bu | Me | (CH₂)₆Me | SO₂Me |
| 798 | Me | H | t-Bu | Me | CH₂CH₂CH₂OMe | SO₂Me |
| 799 | Et | H | t-Bu | Cl | (1,3-Dioxolan-2-yl)methoxy | SO₂Me |
| 800 | Me | H | t-Bu | Me | CH₂N[C(O)SEt]CH₂CN | SO₂Me |
| 801 | Me | H | t-Bu | Me | CH=CHCN | SO₂Me |
| 802 | Me | H | t-Bu | Me | CH₂CH₂CN | SO₂Me |
| 803 | Me | H | t-Bu | Me | CH₂SCN | SO₂Me |
| 804 | Me | H | t-Bu | Me | CH₂C(S)NH₂ | SO₂Me |
| 805 | Me | H | t-Bu | Me | OCH₂CH₂OMe | SO₂Me |
| 806 | Et | H | t-Bu | Me | OCH₂CH₂OMe | SO₂Me |
| 807 | Me | H | t-Bu | Me | OCH(CH₃)CH₂OMe | SO₂Me |
| 808 | Et | H | t-Bu | Me | OCH₂CH(Et)OMe | SO₂Me |
| 809 | Me | H | t-Bu | Me | (1,3-Dioxolan-2-yl)methyl | SO₂Me |
| 810 | Me | H | t-Bu | Me | CH₂O(i-Pr) | SO₂Me |
| 811 | Me | Me | t-Bu | Me | CO₂Me | SO₂Me |
| 812 | Et | Me | t-Bu | Me | CO₂Me | SO₂Me |
| 813 | Et | Me | t-Bu | Me | CO₂(i-Pr) | SO₂Me |
| 814 | Me | Me | t-Bu | Cl | CO₂Et | SO₂Me |
| 815 | Et | Me | t-Bu | Me | CO₂Me | CF₃ |
| 816 | Et | Me | t-Bu | Me | OCH₂CH₂OMe | SO₂Me |
| 817 | Et | Me | t-Bu | SO₂Me | CO₂Me | CN |
| 818 | Me | Me | t-Bu | Me | C(O)SMe | SO₂Me |
| 819 | Me | Me | t-Bu | Me | C(O)SEt | SO₂Me |
| 820 | Me | Me | t-Bu | Me | 2-(2-Oxolanyl)ethoxy | SO₂Me |
| 821 | Me | Me | t-Bu | Me | 2-(2-(1,3-Dioxolanyl))ethoxy | SO₂Me |
| 822 | Et | Me | t-Bu | Me | CH₂OMe | SO₂Me |
| 823 | Et | Me | t-Bu | Me | 2-Oxolanylmethoxymethyl | SO₂Me |
| 824 | Me | Me | t-Bu | Cl | CO₂Me | SO₂Me |
| 825 | Et | Me | t-Bu | Cl | CO₂Me | SO₂Et |
| 826 | Me | Me | t-Bu | Cl | C(O)SMe | SO₂Me |
| 827 | Me | Me | t-Bu | Cl | C(O)SEt | SO₂Me |
| 828 | Me | Me | t-Bu | Me | OMe | SO₂Me |
| 829 | Me | Me | t-Bu | Me | OEt | SO₂Me |
| 830 | Me | Me | t-Bu | Me | O(i-Pr) | SO₂Me |
| 831 | Me | Me | t-Bu | Me | OCHF₂ | SO₂Me |
| 832 | Me | Me | t-Bu | Me | (4,5-Dihydroisoxazol-3-yl) | SO₂Me |
| 833 | Me | Me | t-Bu | Me | O(n-Pr) | SO₂Et |
| 834 | Me | Me | t-Bu | Cl | CH₂OMe | SO₂Me |
| 835 | Me | Me | t-Bu | Me | OCO₂Me | SO₂Me |
| 836 | Me | Me | t-Bu | Me | OC(O)SMe | SO₂Me |
| 837 | Me | Me | t-Bu | Me | OC(O)SEt | SO₂Me |
| 838 | Me | Me | t-Bu | Me | OCH₂CH₂OMe | SO₂Me |
| 839 | Et | Me | t-Bu | Me | OEt | SO₂Me |
| 840 | Et | Me | t-Bu | Cl | CO₂Et | SO₂Me |
| 841 | Et | Me | t-Bu | Cl | CO₂(n-Pr) | SO₂Me |

TABLE 1-continued (I-2)

|No.|R¹|R²|R³|R⁴|R⁵|R⁶|
|---|---|---|---|---|---|---|
|842|Et|Me|t-Bu|Me|CO₂Et|SO₂Me|
|843|Me|Me|t-Bu|Me|CH₂CO₂Me|SO₂Me|
|844|Me|Me|t-Bu|Me|OCH₂CO₂Et|SO₂Me|
|845|Me|Me|t-Bu|Me|O(n-Pr)|SO₂Me|
|846|Et|Me|t-Bu|SO₂Me|H|CF₃|
|847|Me|Me|t-Bu|Me|CH₂OCH₂CF₃|SO₂Me|
|848|Me|Me|t-Bu|Cl|CH₂OCH₂CF₃|SO₂Me|
|849|Et|Me|t-Bu|Me|Cl|SO₂Me|
|850|Me|Me|t-Bu|Me|CH₂SO₂Me|SO₂Me|
|851|Me|Me|t-Bu|Me|CH₂OEt|SO₂Me|
|852|Me|Me|t-Bu|Cl|CH₂OMe|SO₂Me|
|853|Me|Me|t-Bu|Me|CH₂CH₂OMe|SO₂Me|
|854|Me|Me|t-Bu|Me|CH₂OCH₂CH₂OMe|SO₂Me|
|855|Me|Me|t-Bu|Me|OCH₂CH₂OEt|SO₂Me|
|856|Me|Me|t-Bu|Me|OCH₂CH₂Cl|SO₂Me|
|857|Me|Me|t-Bu|Me|OCH₂CF₃|SO₂Me|
|858|Me|Me|t-Bu|Me|CH₂OCH₂OMe|SO₂Me|
|859|Me|Me|t-Bu|Me|OCH₂CH₂SMe|SO₂Me|
|860|Me|Me|t-Bu|Me|CN|SO₂Me|
|861|Me|Me|t-Bu|Me|CH₂CN|SO₂Me|
|862|Me|Me|t-Bu|Br|CO₂Me|SO₂Me|
|863|Et|Me|t-Bu|Cl|CO₂Me|SO₂Me|
|864|Me|Me|t-Bu|Br|CO₂Me|SO₂Me|
|865|Me|Me|t-Bu|Cl|OCH₂CH₂OCF₃|SO₂Me|
|866|Et|Me|t-Bu|Cl|OCH₂CH₂OCF₃|SO₂Me|
|867|Me|Me|t-Bu|Me|OCH₂CH₂OCF₃|SO₂Me|
|868|Et|Me|t-Bu|Me|OCH₂CH₂OCF₃|SO₂Me|
|869|Me|Me|t-Bu|CF₃|OCH₂CH₂OCF₃|SO₂Me|
|870|Et|Me|t-Bu|CF₃|OCH₂CH₂OCF₃|SO₂Me|
|871|Me|Me|t-Bu|Br|OCH₂CH₂OCF₃|SO₂Me|
|872|Et|Me|t-Bu|Br|OCH₂CH₂OCF₃|SO₂Me|
|873|Me|Me|t-Bu|SO₂Me|OCH₂CH₂OCF₃|CF₃|
|874|Et|Me|t-Bu|SO₂Me|OCH₂CH₂OCF₃|CF₃|
|875|Me|Me|t-Bu|Cl|OCH₂CH₂OCHClF|SO₂Me|
|876|Et|Me|t-Bu|Cl|OCH₂CH₂OCHClF|SO₂Me|
|877|Me|Me|t-Bu|Me|OCH₂CH₂OCHClF|SO₂Me|
|878|Et|Me|t-Bu|Me|OCH₂CH₂OCHClF|SO₂Me|
|879|Me|Me|t-Bu|CF₃|OCH₂CH₂OCHClF|SO₂Me|
|880|Et|Me|t-Bu|CF₃|OCH₂CH₂OCHClF|SO₂Me|
|881|Me|Me|t-Bu|Br|OCH₂CH₂OCHClF|SO₂Me|
|882|Et|Me|t-Bu|Br|OCH₂CH₂OCHClF|SO₂Me|
|883|Me|Me|t-Bu|SO₂Me|OCH₂CH₂OCHClF|CF₃|
|884|Et|Me|t-Bu|SO₂Me|OCH₂CH₂OCHClF|CF₃|
|885|Me|Me|t-Bu|Cl|OCH₂CHFOCF₃|SO₂Me|
|886|Et|Me|t-Bu|Cl|OCH₂CHFOCF₃|SO₂Me|
|887|Me|Me|t-Bu|Me|OCH₂CHFOCF₃|SO₂Me|
|888|Me|Me|t-Bu|Cl|OCH₂CHFOMe|SO₂Me|
|889|Et|Me|t-Bu|Cl|OCH₂CHFOMe|SO₂Me|
|890|Me|Me|t-Bu|Me|OCH₂CHFOMe|SO₂Me|
|891|Et|Me|t-Bu|Me|OCH₂CHFOMe|SO₂Me|
|892|Me|Me|t-Bu|CF₃|OCH₂CHFOMe|SO₂Me|
|893|Et|Me|t-Bu|CF₃|OCH₂CHFOMe|SO₂Me|
|894|Me|Me|t-Bu|Br|OCH₂CHFOMe|SO₂Me|
|895|Et|Me|t-Bu|Br|OCH₂CHFOMe|SO₂Me|
|896|Me|Me|t-Bu|SO₂Me|OCH₂CHFOMe|CF₃|
|897|Et|Me|t-Bu|SO₂Me|OCH₂CHFOMe|CF₃|
|898|Me|Me|t-Bu|Cl|OCHFCH₂OCF₃|SO₂Me|
|899|Et|Me|t-Bu|Cl|OCHFCH₂OCF₃|SO₂Me|
|900|Me|Me|t-Bu|Cl|OCH₂CH₂OCF₂Cl|SO₂Me|
|901|Et|Me|t-Bu|Cl|OCH₂CH₂OCF₂Cl|SO₂Me|
|902|Me|Me|t-Bu|Me|OCH₂CH₂OCF₂Cl|SO₂Me|
|903|Et|Me|t-Bu|Me|OCH₂CH₂OCF₂Cl|SO₂Me|
|904|Me|Me|t-Bu|CF₃|OCH₂CH₂OCF₂Cl|SO₂Me|
|905|Et|Me|t-Bu|CF₃|OCH₂CH₂OCF₂Cl|SO₂Me|
|906|Me|Me|t-Bu|Br|OCH₂CH₂OCF₂Cl|SO₂Me|
|907|Et|Me|t-Bu|Br|OCH₂CH₂OCF₂Cl|SO₂Me|

TABLE 1-continued (I-2)

| No. | R¹ | R² | R³ | R⁴ | R⁵ | R⁶ |
|---|---|---|---|---|---|---|
| 908 | Me | Me | t-Bu | SO$_2$Me | OCH$_2$CH$_2$OCF$_2$Cl | CF$_3$ |
| 909 | Et | Me | t-Bu | SO$_2$Me | OCH$_2$CH$_2$OCF$_2$Cl | CF$_3$ |
| 910 | Me | Me | t-Bu | Cl | SCH$_2$CH$_2$OCH$_3$ | SO$_2$Me |
| 911 | Et | Me | t-Bu | Cl | SCH$_2$CH$_2$OCH$_3$ | SO$_2$Me |
| 912 | Me | Me | t-Bu | Me | SCH$_2$CH$_2$OCH$_3$ | SO$_2$Me |
| 913 | Et | Me | t-Bu | Me | SCH$_2$CH$_2$OCH$_3$ | SO$_2$Me |
| 914 | Me | Me | t-Bu | CF$_3$ | SCH$_2$CH$_2$OCH$_3$ | SO$_2$Me |
| 915 | Et | Me | t-Bu | CF$_3$ | SCH$_2$CH$_2$OCH$_3$ | SO$_2$Me |
| 916 | Me | Me | t-Bu | Br | SCH$_2$CH$_2$OCH$_3$ | SO$_2$Me |
| 917 | Et | Me | t-Bu | Br | SCH$_2$CH$_2$OCH$_3$ | SO$_2$Me |
| 918 | Me | Me | t-Bu | SO$_2$Me | SCH$_2$CH$_2$OCH$_3$ | CF$_3$ |
| 919 | Et | Me | t-Bu | SO$_2$Me | SCH$_2$CH$_2$OCH$_3$ | CF$_3$ |
| 920 | Me | Me | t-Bu | Cl | SCH$_2$CH$_2$OCF$_3$ | SO$_2$Me |
| 921 | Et | Me | t-Bu | Cl | SCH$_2$CH$_2$OCF$_3$ | SO$_2$Me |
| 922 | Me | Me | t-Bu | Me | SCH$_2$CH$_2$OCF$_3$ | SO$_2$Me |
| 923 | Et | Me | t-Bu | Me | SCH$_2$CH$_2$OCF$_3$ | SO$_2$Me |
| 924 | Me | Me | t-Bu | CF$_3$ | SCH$_2$CH$_2$OCF$_3$ | SO$_2$Me |
| 925 | Et | Me | t-Bu | CF$_3$ | SCH$_2$CH$_2$OCF$_3$ | SO$_2$Me |
| 926 | Me | Me | t-Bu | Br | SCH$_2$CH$_2$OCF$_3$ | SO$_2$Me |
| 927 | Et | Me | t-Bu | Br | SCH$_2$CH$_2$OCF$_3$ | SO$_2$Me |
| 928 | Me | Me | t-Bu | SO$_2$Me | SCH$_2$CH$_2$OCF$_3$ | CF$_3$ |
| 929 | Et | Me | t-Bu | SO$_2$Me | SCH$_2$CH$_2$OCF$_3$ | CF$_3$ |
| 930 | Me | Me | t-Bu | Cl | SCH$_2$CH$_2$SCH$_3$ | SO$_2$Me |
| 931 | Et | Me | t-Bu | Cl | SCH$_2$CH$_2$SCH$_3$ | SO$_2$Me |
| 932 | Me | Me | t-Bu | Me | SCH$_2$CH$_2$SCH$_3$ | SO$_2$Me |
| 933 | Et | Me | t-Bu | Me | SCH$_2$CH$_2$SCH$_3$ | SO$_2$Me |
| 934 | Me | Me | t-Bu | CF$_3$ | SCH$_2$CH$_2$SCH$_3$ | SO$_2$Me |
| 935 | Et | Me | t-Bu | CF$_3$ | SCH$_2$CH$_2$SCH$_3$ | SO$_2$Me |
| 936 | Me | Me | t-Bu | Br | SCH$_2$CH$_2$SCH$_3$ | SO$_2$Me |
| 937 | Et | Me | t-Bu | Br | SCH$_2$CH$_2$SCH$_3$ | SO$_2$Me |
| 938 | Me | Me | t-Bu | SO$_2$Me | SCH$_2$CH$_2$SCH$_3$ | CF$_3$ |
| 939 | Et | Me | t-Bu | SO$_2$Me | SCH$_2$CH$_2$SCH$_3$ | CF$_3$ |
| 940 | Me | Me | t-Bu | Cl | SCH$_2$CH$_2$SCF$_3$ | SO$_2$Me |
| 941 | Et | Me | t-Bu | Cl | SCH$_2$CH$_2$SCF$_3$ | SO$_2$Me |
| 942 | Me | Me | t-Bu | Me | SCH$_2$CH$_2$SCF$_3$ | SO$_2$Me |
| 943 | Et | Me | t-Bu | Me | SCH$_2$CH$_2$SCF$_3$ | SO$_2$Me |
| 944 | Me | Me | t-Bu | CF$_3$ | SCH$_2$CH$_2$SCF$_3$ | SO$_2$Me |
| 945 | Et | Me | t-Bu | CF$_3$ | SCH$_2$CH$_2$SCF$_3$ | SO$_2$Me |
| 946 | Me | Me | t-Bu | Br | SCH$_2$CH$_2$SCF$_3$ | SO$_2$Me |
| 947 | Et | Me | t-Bu | Br | SCH$_2$CH$_2$SCF$_3$ | SO$_2$Me |
| 948 | Me | Me | t-Bu | SO$_2$Me | SCH$_2$CH$_2$SCF$_3$ | CF$_3$ |
| 949 | Et | Me | t-Bu | SO$_2$Me | SCH$_2$CH$_2$SCF$_3$ | CF$_3$ |
| 950 | Me | Me | t-Bu | Cl | OCH$_2$CH(CH$_3$)OCH$_3$ | SO$_2$Me |
| 951 | Et | Me | t-Bu | Cl | OCH$_2$CH(CH$_3$)OCH$_3$ | SO$_2$Me |
| 952 | Me | Me | t-Bu | Me | OCH$_2$CH(CH$_3$)OCH$_3$ | SO$_2$Me |
| 953 | Et | Me | t-Bu | Me | OCH$_2$CH(CH$_3$)OCH$_3$ | SO$_2$Me |
| 954 | Me | Me | t-Bu | CF$_3$ | OCH$_2$CH(CH$_3$)OCH$_3$ | SO$_2$Me |
| 955 | Et | Me | t-Bu | CF$_3$ | OCH$_2$CH(CH$_3$)OCH$_3$ | SO$_2$Me |
| 956 | Me | Me | t-Bu | Br | OCH$_2$CH(CH$_3$)OCH$_3$ | SO$_2$Me |
| 957 | Et | Me | t-Bu | Br | OCH$_2$CH(CH$_3$)OCH$_3$ | SO$_2$Me |
| 958 | Me | Me | t-Bu | SO$_2$Me | OCH$_2$CH(CH$_3$)OCH$_3$ | CF$_3$ |
| 959 | Et | Me | t-Bu | SO$_2$Me | OCH$_2$CH(CH$_3$)OCH$_3$ | CF$_3$ |
| 960 | Me | Me | t-Bu | Cl | OCH$_2$CF$_2$OCH$_3$ | SO$_2$Me |
| 961 | Et | Me | t-Bu | Cl | OCH$_2$CF$_2$OCH$_3$ | SO$_2$Me |
| 962 | Me | Me | t-Bu | Me | OCH$_2$CF$_2$OCH$_3$ | SO$_2$Me |
| 963 | Et | Me | t-Bu | Me | OCH$_2$CF$_2$OCH$_3$ | SO$_2$Me |
| 964 | Me | Me | t-Bu | CF$_3$ | OCH$_2$CF$_2$OCH$_3$ | SO$_2$Me |
| 965 | Et | Me | t-Bu | CF$_3$ | OCH$_2$CF$_2$OCH$_3$ | SO$_2$Me |
| 966 | Me | Me | t-Bu | Br | OCH$_2$CF$_2$OCH$_3$ | SO$_2$Me |
| 967 | Et | Me | t-Bu | Br | OCH$_2$CF$_2$OCH$_3$ | SO$_2$Me |
| 968 | Me | Me | t-Bu | SO$_2$Me | OCH$_2$CF$_2$OCH$_3$ | CF$_3$ |
| 969 | Et | Me | t-Bu | SO$_2$Me | OCH$_2$CF$_2$OCH$_3$ | CF$_3$ |
| 970 | Me | Me | t-Bu | Me | OCH$_2$CH$_3$OCH$_3$ | SO$_2$Me |
| 971 | Et | Me | t-Bu | Me | OCH$_2$CH$_3$OCH$_3$ | SO$_2$Me |
| 972 | Me | Me | t-Bu | Me | OCH$_2$CH(OCH$_3$)$_2$ | SO$_2$Me |
| 973 | Me | Me | t-Bu | Me | CH$_2$N(Me)CH$_3$CN | SO$_2$Me |

TABLE 1-continued (I-2)

| No. | R¹ | R² | R³ | R⁴ | R⁵ | R⁶ |
|---|---|---|---|---|---|---|
| 974 | Me | Me | t-Bu | Me | (Tetrahydrofuran-2-yl)methoxy | $SO_2Me$ |
| 975 | Me | Me | t-Bu | Cl | SMe | $SO_2Me$ |
| 976 | Me | Me | t-Bu | Cl | Cl | $SO_2Me$ |
| 977 | Me | Me | t-Bu | Cl | OMe | $SO_2Me$ |
| 978 | Me | Me | t-Bu | Me | (Tetrahydro-2H-pyran-2-yl)methoxy | $SO_2Me$ |
| 979 | Me | Me | t-Bu | Cl | $OCH_2CH_2OMe$ | $SO_2Me$ |
| 980 | Me | Me | t-Bu | Me | Tetrahydrofuran-3-yloxy | $SO_2Me$ |
| 981 | Me | Me | t-Bu | Me | $OCH_2CH_2CH_2OMe$ | $SO_2Me$ |
| 982 | Me | Me | t-Bu | Me | $OCH_2CH_2OMe$ | $SO_2Me$ |
| 983 | Et | Me | t-Bu | Cl | (1,3-Dioxolan-2-yl)ethoxy | $SO_2Me$ |
| 984 | Me | Me | t-Bu | Me | Propargyloxy | $SO_2Me$ |
| 985 | Me | Me | t-Bu | Me | (Tetrahydrofuran-3-yloxy)methyl | $SO_2Me$ |
| 986 | Me | Me | t-Bu | Cl | $SO_2Me$ | $SO_2Me$ |
| 987 | Me | Me | t-Bu | Me | $(CH_2)_6Me$ | $SO_2Me$ |
| 988 | Me | Me | t-Bu | Me | $CH_2CH_2CH_2OMe$ | $SO_2Me$ |
| 989 | Et | Me | t-Bu | Cl | (1,3-Dioxolan-2-yl)methoxy | $SO_2Me$ |
| 990 | Me | Me | t-Bu | Me | $CH_2N[C(O)SEt]CH_2CN$ | $SO_2Me$ |
| 991 | Me | Me | t-Bu | Me | CH=CHCN | $SO_2Me$ |
| 992 | Me | Me | t-Bu | Me | $CH_2CH_2CN$ | $SO_2Me$ |
| 993 | Me | Me | t-Bu | Me | $CH_2SCN$ | $SO_2Me$ |
| 994 | Me | Me | t-Bu | Me | $CH_2C(S)NH_2$ | $SO_2Me$ |
| 995 | Me | Me | t-Bu | Me | $OCH_2CH_2OMe$ | $SO_2Me$ |
| 996 | Et | Me | t-Bu | Me | $OCH_2CH_2OMe$ | $SO_2Me$ |
| 997 | Me | Me | t-Bu | Me | $OCH(CH_3)CH_2OMe$ | $SO_2Me$ |
| 998 | Et | Me | t-Bu | Me | $OCH_2CH(Et)OMe$ | $SO_2Me$ |
| 999 | Me | Me | t-Bu | Me | (1,3-Dioxolan-2-yl)methyl | $SO_2Me$ |
| 1000 | Me | Me | t-Bu | Me | $CH_2O$(i-Pr) | $SO_2Me$ |
| 1001 | Me | H | $CH(Et)_2$ | Me | $CO_2Me$ | $SO_2Me$ |
| 1002 | Et | H | $CH(Et)_2$ | Me | $CO_2Me$ | $SO_2Me$ |
| 1003 | Et | H | $CH(Et)_2$ | Me | $CO_2$(i-Pr) | $SO_2Me$ |
| 1004 | Me | H | $CH(Et)_2$ | Cl | $CO_2Et$ | $SO_2Me$ |
| 1005 | Et | H | $CH(Et)_2$ | Me | $CO_2Me$ | $CF_3$ |
| 1006 | Et | H | $CH(Et)_2$ | Me | $OCH_2CH_2OMe$ | $SO_2Me$ |
| 1007 | Et | H | $CH(Et)_2$ | $SO_2Me$ | $CO_2Me$ | CN |
| 1008 | Me | H | $CH(Et)_2$ | Me | C(O)SMe | $SO_2Me$ |
| 1009 | Me | H | $CH(Et)_2$ | Me | C(O)SEt | $SO_2Me$ |
| 1010 | Me | H | $CH(Et)_2$ | Me | 2-(2-Oxolanyl)ethoxy | $SO_2Me$ |
| 1011 | Me | H | $CH(Et)_2$ | Me | 2-(2-(1,3-Dioxolanyl))ethoxy | $SO_2Me$ |
| 1012 | Et | H | $CH(Et)_2$ | Me | $CH_2OMe$ | $SO_2Me$ |
| 1013 | Et | H | $CH(Et)_2$ | Me | 2-Oxolanylmethoxymethyl | $SO_2Me$ |
| 1014 | Me | H | $CH(Et)_2$ | Cl | $CO_2Me$ | $SO_2Me$ |
| 1015 | Et | H | $CH(Et)_2$ | Cl | $CO_2Me$ | $SO_2Et$ |
| 1016 | Me | H | $CH(Et)_2$ | Cl | C(O)SMe | $SO_2Me$ |
| 1017 | Me | H | $CH(Et)_2$ | Cl | C(O)SEt | $SO_2Me$ |
| 1018 | Me | H | $CH(Et)_2$ | Me | OMe | $SO_2Me$ |
| 1019 | Me | H | $CH(Et)_2$ | Me | OEt | $SO_2Me$ |
| 1020 | Me | H | $CH(Et)_2$ | Me | O(i-Pr) | $SO_2Me$ |
| 1021 | Me | H | $CH(Et)_2$ | Me | $OCHF_2$ | $SO_2Me$ |
| 1022 | Me | H | $CH(Et)_2$ | Me | (4,5-Dihydroisoxazol-3-yl) | $SO_2Me$ |
| 1023 | Me | H | $CH(Et)_2$ | Me | O(n-Pr) | $SO_2Et$ |
| 1024 | Me | H | $CH(Et)_2$ | Cl | $CH_2OMe$ | $SO_2Me$ |
| 1025 | Me | H | $CH(Et)_2$ | Me | $OCO_2Me$ | $SO_2Me$ |
| 1026 | Me | H | $CH(Et)_2$ | Me | OC(O)SMe | $SO_2Me$ |
| 1027 | Me | H | $CH(Et)_2$ | Me | OC(O)SEt | $SO_2Me$ |
| 1028 | Me | H | $CH(Et)_2$ | Me | $OCH_2CH_2OMe$ | $SO_2Me$ |
| 1029 | Et | H | $CH(Et)_2$ | Me | OEt | $SO_2Me$ |
| 1030 | Et | H | $CH(Et)_2$ | Cl | $CO_2Et$ | $SO_2Me$ |
| 1031 | Et | H | $CH(Et)_2$ | Cl | $CO_2$(n-Pr) | $SO_2Me$ |
| 1032 | Et | H | $CH(Et)_2$ | Me | $CO_2Et$ | $SO_2Me$ |
| 1033 | Me | H | $CH(Et)_2$ | Me | $CH_2CO_2Me$ | $SO_2Me$ |
| 1034 | Me | H | $CH(Et)_2$ | Me | $OCH_2CO_2Et$ | $SO_2Me$ |
| 1035 | Me | H | $CH(Et)_2$ | Me | O(n-Pr) | $SO_2Me$ |
| 1036 | Et | H | $CH(Et)_2$ | $SO_2Me$ | H | $CF_3$ |
| 1037 | Me | H | $CH(Et)_2$ | Me | $CH_2OCH_2CF_3$ | $SO_2Me$ |
| 1038 | Me | H | $CH(Et)_2$ | Cl | $CH_2OCH_2CF_3$ | $SO_2Me$ |
| 1039 | Et | H | $CH(Et)_2$ | Me | Cl | $SO_2Me$ |

TABLE 1-continued

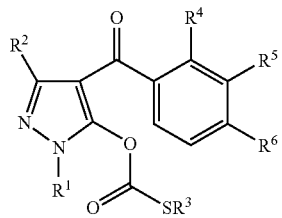

(I-2)

| No. | R¹ | R² | R³ | R⁴ | R⁵ | R⁶ |
|---|---|---|---|---|---|---|
| 1040 | Me | H | CH(Et)$_2$ | Me | CH$_2$SO$_2$Me | SO$_2$Me |
| 1041 | Me | H | CH(Et)$_2$ | Me | CH$_2$OEt | SO$_2$Me |
| 1042 | Me | H | CH(Et)$_2$ | Cl | CH$_2$OMe | SO$_2$Me |
| 1043 | Me | H | CH(Et)$_2$ | Me | CH$_2$CH$_2$OMe | SO$_2$Me |
| 1044 | Me | H | CH(Et)$_2$ | Me | CH$_2$OCH$_2$CH$_2$OMe | SO$_2$Me |
| 1045 | Me | H | CH(Et)$_2$ | Me | OCH$_2$CH$_2$OEt | SO$_2$Me |
| 1046 | Me | H | CH(Et)$_2$ | Me | OCH$_2$CH$_2$Cl | SO$_2$Me |
| 1047 | Me | H | CH(Et)$_2$ | Me | OCH$_2$CF$_3$ | SO$_2$Me |
| 1048 | Me | H | CH(Et)$_2$ | Me | CH$_2$OCH$_2$OMe | SO$_2$Me |
| 1049 | Me | H | CH(Et)$_2$ | Me | OCH$_2$CH$_2$SMe | SO$_2$Me |
| 1050 | Me | H | CH(Et)$_2$ | Me | CN | SO$_2$Me |
| 1051 | Me | H | CH(Et)$_2$ | Me | CH$_2$CN | SO$_2$Me |
| 1052 | Me | H | CH(Et)$_2$ | Br | CO$_2$Me | SO$_2$Me |
| 1053 | Et | H | CH(Et)$_2$ | Cl | CO$_2$Me | SO$_2$Me |
| 1054 | Me | H | CH(Et)$_2$ | Br | CO$_2$Me | SO$_2$Me |
| 1055 | Me | H | CH(Et)$_2$ | Cl | OCH$_2$CH$_2$OCF$_3$ | SO$_2$Me |
| 1056 | Et | H | CH(Et)$_2$ | Cl | OCH$_2$CH$_2$OCF$_3$ | SO$_2$Me |
| 1057 | Me | H | CH(Et)$_2$ | Me | OCH$_2$CH$_2$OCF$_3$ | SO$_2$Me |
| 1058 | Et | H | CH(Et)$_2$ | Me | OCH$_2$CH$_2$OCF$_3$ | SO$_2$Me |
| 1059 | Me | H | CH(Et)$_2$ | CF$_3$ | OCH$_2$CH$_2$OCF$_3$ | SO$_2$Me |
| 1060 | Et | H | CH(Et)$_2$ | CF$_3$ | OCH$_2$CH$_2$OCF$_3$ | SO$_2$Me |
| 1061 | Me | H | CH(Et)$_2$ | Br | OCH$_2$CH$_2$OCF$_3$ | SO$_2$Me |
| 1062 | Et | H | CH(Et)$_2$ | Br | OCH$_2$CH$_2$OCF$_3$ | SO$_2$Me |
| 1063 | Me | H | CH(Et)$_2$ | SO$_2$Me | OCH$_2$CH$_2$OCF$_3$ | CF$_3$ |
| 1064 | Et | H | CH(Et)$_2$ | SO$_2$Me | OCH$_2$CH$_2$OCF$_3$ | CF$_3$ |
| 1065 | Me | H | CH(Et)$_2$ | Cl | OCH$_2$CH$_2$OCHClF | SO$_2$Me |
| 1066 | Et | B | CH(Et)$_2$ | Cl | OCH$_2$CH$_2$OCHClF | SO$_2$Me |
| 1067 | Me | H | CH(Et)$_2$ | Me | OCH$_2$CH$_2$OCHClF | SO$_2$Me |
| 1068 | Et | H | CH(Et)$_2$ | Me | OCH$_2$CH$_2$OCHClF | SO$_2$Me |
| 1069 | Me | H | CH(Et)$_2$ | CF$_3$ | OCH$_2$CH$_2$OCHClF | SO$_2$Me |
| 1070 | Et | H | CH(Et)$_2$ | CF$_3$ | OCH$_2$CH$_2$OCHClF | SO$_2$Me |
| 1071 | Me | H | CH(Et)$_2$ | Br | OCH$_2$CH$_2$OCHClF | SO$_2$Me |
| 1072 | Et | H | CH(Et)$_2$ | Br | OCH$_2$CH$_3$OCHClF | SO$_2$Me |
| 1073 | Me | H | CH(Et)$_2$ | SO$_2$Me | OCH$_2$CH$_2$OCHClF | CF$_3$ |
| 1074 | Et | H | CH(Et)$_2$ | SO$_2$Me | OCH$_2$CH$_2$OCHClF | CF$_3$ |
| 1075 | Me | H | CH(Et)$_2$ | Cl | OCH$_2$CHFOCF$_3$ | SO$_2$Me |
| 1076 | Et | H | CH(Et)$_2$ | Cl | OCH$_2$CHFOCF$_3$ | SO$_2$Me |
| 1077 | Me | H | CH(Et)$_2$ | Me | OCH$_2$CHFOCF$_3$ | SO$_2$Me |
| 1078 | Me | H | CH(Et)$_2$ | Cl | OCH$_2$CHFOMe | SO$_2$Me |
| 1079 | Et | H | CH(Et)$_2$ | Cl | OCH$_2$CHFOMe | SO$_2$Me |
| 1080 | Me | H | CH(Et)$_2$ | Me | OCH$_2$CHFOMe | SO$_2$Me |
| 1081 | Et | H | CH(Et)$_2$ | Me | OCH$_2$CHFOMe | SO$_2$Me |
| 1082 | Me | H | CH(Et)$_2$ | CF$_3$ | OCH$_2$CHFOMe | SO$_2$Me |
| 1083 | Et | H | CH(Et)$_2$ | CF$_3$ | OCH$_2$CHFOMe | SO$_2$Me |
| 1084 | Me | H | CH(Et)$_2$ | Br | OCH$_2$CHFOMe | SO$_2$Me |
| 1085 | Et | H | CH(Et)$_2$ | Br | OCH$_2$CHFOMe | SO$_2$Me |
| 1086 | Me | H | CH(Et)$_2$ | SO$_2$Me | OCH$_2$CHFOMe | CF$_3$ |
| 1087 | Et | H | CH(Et)$_2$ | SO$_2$Me | OCH$_2$CHFOMe | CF$_3$ |
| 1088 | Me | H | CH(Et)$_2$ | Cl | OCHFCH$_3$OCF$_3$ | SO$_2$Me |
| 1089 | Et | H | CH(Et)$_2$ | Cl | OCHFCH$_3$OCF$_3$ | SO$_2$Me |
| 1090 | Me | H | CH(Et)$_2$ | Cl | OCH$_2$CH$_2$OCF$_2$Cl | SO$_2$Me |
| 1091 | Et | H | CH(Et)$_2$ | Cl | OCH$_2$CH$_2$OCF$_2$Cl | SO$_2$Me |
| 1092 | Me | H | CH(Et)$_2$ | Me | OCH$_2$CH$_2$OCF$_2$Cl | SO$_2$Me |
| 1093 | Et | H | CH(Et)$_2$ | Me | OCH$_2$CH$_2$OCF$_2$Cl | SO$_2$Me |
| 1094 | Me | H | CH(Et)$_2$ | CF$_3$ | OCH$_2$CH$_2$OCF$_2$Cl | SO$_2$Me |
| 1095 | Et | H | CH(Et)$_2$ | CF$_3$ | OCH$_2$CH$_2$OCF$_2$Cl | SO$_2$Me |
| 1096 | Me | H | CH(Et)$_2$ | Br | OCH$_2$CH$_2$OCF$_2$Cl | SO$_2$Me |
| 1097 | Et | H | CH(Et)$_2$ | Br | OCH$_2$CH$_2$OCF$_2$Cl | SO$_2$Me |
| 1098 | Me | H | CH(Et)$_2$ | SO$_2$Me | OCH$_2$CH$_2$OCF$_2$Cl | CF$_3$ |
| 1099 | Et | H | CH(Et)$_2$ | SO$_2$Me | OCH$_2$CH$_2$OCF$_2$Cl | CF$_3$ |
| 1100 | Me | H | CH(Et)$_2$ | Cl | SCH$_2$CH$_2$OCH$_3$ | SO$_2$Me |
| 1101 | Et | H | CH(Et)$_2$ | Cl | SCH$_2$CH$_2$OCH$_3$ | SO$_2$Me |
| 1102 | Me | H | CH(Et)$_2$ | Me | SCH$_2$CH$_2$OCH$_3$ | SO$_2$Me |
| 1103 | Et | H | CH(Et)$_2$ | Me | SCH$_2$CH$_2$OCH$_3$ | SO$_2$Me |
| 1104 | Me | H | CH(Et)$_2$ | CF$_3$ | SCH$_2$CH$_2$OCH$_3$ | SO$_2$Me |
| 1105 | Et | H | CH(Et)$_2$ | CF$_3$ | SCH$_2$CH$_2$OCH$_3$ | SO$_2$Me |

TABLE 1-continued

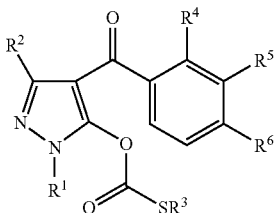

(I-2)

| No. | R$^1$ | R$^2$ | R$^3$ | R$^4$ | R$^5$ | R$^6$ |
|---|---|---|---|---|---|---|
| 1106 | Me | H | CH(Et)$_2$ | Br | SCH$_2$CH$_2$OCH$_3$ | SO$_2$Me |
| 1107 | Et | H | CH(Et)$_2$ | Br | SCH$_2$CH$_2$OCH$_3$ | SO$_2$Me |
| 1108 | Me | H | CH(Et)$_2$ | SO$_2$Me | SCH$_2$CH$_2$OCH$_3$ | CF$_3$ |
| 1109 | Et | H | CH(Et)$_2$ | SO$_2$Me | SCH$_2$CH$_2$OCH$_3$ | CF$_3$ |
| 1110 | Me | H | CH(Et)$_2$ | Cl | SCH$_2$CH$_2$OCF$_3$ | SO$_2$Me |
| 1111 | Et | H | CH(Et)$_2$ | Cl | SCH$_2$CH$_2$OCF$_3$ | SO$_2$Me |
| 1112 | Me | H | CH(Et)$_2$ | Me | SCH$_2$CH$_2$OCF$_3$ | SO$_2$Me |
| 1113 | Et | H | CH(Et)$_2$ | Me | SCH$_2$CH$_2$OCF$_3$ | SO$_2$Me |
| 1114 | Me | H | CH(Et)$_2$ | CF$_3$ | SCH$_2$CH$_2$OCF$_3$ | SO$_2$Me |
| 1115 | Et | H | CH(Et)$_2$ | CF$_3$ | SCH$_2$CH$_2$OCF$_3$ | SO$_2$Me |
| 1116 | Me | H | CH(Et)$_2$ | Br | SCH$_2$CH$_2$OCF$_3$ | SO$_2$Me |
| 1117 | Et | H | CH(Et)$_2$ | Br | SCH$_2$CH$_2$OCF$_3$ | SO$_2$Me |
| 1118 | Me | H | CH(Et)$_2$ | SO$_2$Me | SCH$_2$CH$_2$OCF$_3$ | CF$_3$ |
| 1119 | Et | H | CH(Et)$_2$ | SO$_2$Me | SCH$_2$CH$_2$OCF$_3$ | CF$_3$ |
| 1120 | Me | H | CH(Et)$_2$ | Cl | SCH$_2$CH$_2$SCH$_3$ | SO$_2$Me |
| 1121 | Et | H | CH(Et)$_2$ | Cl | SCH$_2$CH$_2$SCH$_3$ | SO$_2$Me |
| 1122 | Me | H | CH(Et)$_2$ | Me | SCH$_2$CH$_2$SCH$_3$ | SO$_2$Me |
| 1123 | Et | H | CH(Et)$_2$ | Me | SCH$_2$CH$_2$SCH$_3$ | SO$_2$Me |
| 1124 | Me | H | CH(Et)$_2$ | CF$_3$ | SCH$_2$CH$_2$SCH$_3$ | SO$_2$Me |
| 1125 | Et | H | CH(Et)$_2$ | CF$_3$ | SCH$_2$CH$_2$SCH$_3$ | SO$_2$Me |
| 1126 | Me | H | CH(Et)$_2$ | Br | SCH$_2$CH$_2$SCH$_3$ | SO$_2$Me |
| 1127 | Et | H | CH(Et)$_2$ | Br | SCH$_2$CH$_2$SCH$_3$ | SO$_2$Me |
| 1128 | Me | H | CH(Et)$_2$ | SO$_2$Me | SCH$_2$CH$_2$SCH$_3$ | CF$_3$ |
| 1129 | Et | H | CH(Et)$_2$ | SO$_2$Me | SCH$_2$CH$_2$SCH$_3$ | CF$_3$ |
| 1130 | Me | H | CH(Et)$_2$ | Cl | SCH$_2$CH$_2$SCF$_3$ | SO$_2$Me |
| 1131 | Et | H | CH(Et)$_2$ | Cl | SCH$_2$CH$_2$SCF$_3$ | SO$_2$Me |
| 1132 | Me | H | CH(Et)$_2$ | Me | SCH$_2$CH$_2$SCF$_3$ | SO$_2$Me |
| 1133 | Et | H | CH(Et)$_2$ | Me | SCH$_2$CH$_2$SCF$_3$ | SO$_2$Me |
| 1134 | Me | H | CH(Et)$_2$ | CF$_3$ | SCH$_2$CH$_2$SCF$_3$ | SO$_2$Me |
| 1135 | Et | H | CH(Et)$_2$ | CF$_3$ | SCH$_2$CH$_2$SCF$_3$ | SO$_2$Me |
| 1136 | Me | H | CH(Et)$_2$ | Br | SCH$_2$CH$_2$SCF$_3$ | SO$_2$Me |
| 1137 | Et | H | CH(Et)$_2$ | Br | SCH$_2$CH$_2$SCF$_3$ | SO$_2$Me |
| 1138 | Me | H | CH(Et)$_2$ | SO$_2$Me | SCH$_2$CH$_2$SCF$_3$ | CF$_3$ |
| 1139 | Et | H | CH(Et)$_2$ | SO$_2$Me | SCH$_2$CH$_2$SCF$_3$ | CF$_3$ |
| 1140 | Me | H | CH(Et)$_2$ | Cl | OCH$_2$CH(CH$_3$)OCH$_3$ | SO$_2$Me |
| 1141 | Et | H | CH(Et)$_2$ | Cl | OCH$_2$CH(CH$_3$)OCH$_3$ | SO$_2$Me |
| 1142 | Me | H | CH(Et)$_2$ | Me | OCH$_2$CH(CH$_3$)OCH$_3$ | SO$_2$Me |
| 1143 | Et | H | CH(Et)$_2$ | Me | OCH$_2$CH(CH$_3$)OCH$_3$ | SO$_2$Me |
| 1144 | Me | H | CH(Et)$_2$ | CF$_3$ | OCH$_2$CH(CH$_3$)OCH$_2$ | SO$_2$Me |
| 1145 | Et | H | CH(Et)$_2$ | CF$_3$ | OCH$_2$CH(CH$_3$)OCH$_3$ | SO$_2$Me |
| 1146 | Me | H | CH(Et)$_2$ | Br | OCH$_2$CH(CH$_3$)OCH$_3$ | SO$_2$Me |
| 1147 | Et | H | CH(Et)$_2$ | Br | OCH$_2$CH(CH$_3$)OCH$_3$ | SO$_2$Me |
| 1148 | Me | H | CH(Et)$_2$ | SO$_2$Me | OCH$_2$CH(CH$_3$)OCH$_3$ | CF$_3$ |
| 1149 | Et | H | CH(Et)$_2$ | SO$_2$Me | OCH$_2$CH(CH$_3$)OCH$_3$ | CF$_3$ |
| 1150 | Me | H | CH(Et)$_2$ | Cl | OCH$_2$CF$_2$OCH$_3$ | SO$_2$Me |
| 1151 | Et | H | CH(Et)$_2$ | Cl | OCH$_2$CF$_2$OCH$_3$ | SO$_2$Me |
| 1152 | Me | H | CH(Et)$_2$ | Me | OCH$_2$CF$_2$OCH$_3$ | SO$_2$Me |
| 1153 | Et | H | CH(Et)$_2$ | Me | OCH$_2$CF$_2$OCH$_3$ | SO$_2$Me |
| 1154 | Me | H | CH(Et)$_2$ | CF$_3$ | OCH$_2$CF$_2$OCH$_3$ | SO$_2$Me |
| 1155 | Et | H | CH(Et)$_2$ | CF$_3$ | OCH$_2$CF$_2$OCH$_3$ | SO$_2$Me |
| 1156 | Me | H | CH(Et)$_2$ | Br | OCH$_2$CF$_2$OCH$_3$ | SO$_2$Me |
| 1157 | Et | H | CH(Et)$_2$ | Br | OCH$_2$CF$_2$OCH$_3$ | SO$_2$Me |
| 1158 | Me | H | CH(Et)$_2$ | SO$_2$Me | OCH$_2$CF$_2$OCH$_3$ | CF$_3$ |
| 1159 | Et | H | CH(Et)$_2$ | SO$_2$Me | OCH$_2$CF$_2$OCH$_3$ | CF$_3$ |
| 1160 | Me | H | CH(Et)$_2$ | CN | OCH$_2$CH$_2$OCH$_3$ | SO$_2$Me |
| 1161 | Et | H | CH(Et)$_2$ | Me | OCH$_2$CH$_2$OCH$_3$ | SO$_2$Me |
| 1162 | Me | H | CH(Et)$_2$ | Me | OCH$_2$CH(OCH$_3$)$_2$ | SO$_2$Me |
| 1163 | Me | H | CH(Et)$_2$ | Me | CH$_2$N(Me)CH$_2$CN | SO$_2$Me |
| 1164 | Me | H | CH(Et)$_2$ | Me | (Tetrahydrofuran-2-yl)methoxy | SO$_2$Me |
| 1165 | Me | H | CH(Et)$_2$ | Cl | SMe | SO$_2$Me |
| 1166 | Me | H | CH(Et)$_2$ | Cl | Cl | SO$_2$Me |
| 1167 | Me | H | CH(Et)$_2$ | Cl | OMe | SO$_2$Me |
| 1168 | Me | H | CH(Et)$_2$ | Me | (Tetrahydro-2H-pyran-2-yl)methoxy | SO$_2$Me |
| 1169 | Me | H | CH(Et)$_2$ | Cl | OCH$_2$CH$_2$OMe | SO$_2$Me |
| 1170 | Me | H | CH(Et)$_2$ | Me | Tetrahydrofuran-3-yloxy | SO$_2$Me |
| 1171 | Me | H | CH(Et)$_2$ | Me | OCH$_2$CH$_2$CH$_2$OMe | SO$_2$Me |

TABLE 1-continued (I-2)

| No. | R¹ | R² | R³ | R⁴ | R⁵ | R⁶ |
|---|---|---|---|---|---|---|
| 1172 | Me | H | CH(Et)$_2$ | NO$_2$ | OCH$_2$CH$_2$OMe | SO$_2$Me |
| 1173 | Et | H | CH(Et)$_2$ | Cl | (1,3-Dioxolan-2-yl)ethoxy | SO$_2$Me |
| 1174 | Me | H | CH(Et)$_2$ | Me | Propargyloxy | SO$_2$Me |
| 1175 | Me | H | CH(Et)$_2$ | Me | (Tetrahydrofuran-3-yloxy)methyl | SO$_2$Me |
| 1176 | Me | H | CH(Et)$_2$ | Cl | SO$_2$Me | SO$_2$Me |
| 1177 | Me | H | CH(Et)$_2$ | Me | (CH$_2$)$_6$Me | SO$_2$Me |
| 1178 | Me | H | CH(Et)$_2$ | Me | CH$_2$CH$_2$CH$_2$OMe | SO$_2$Me |
| 1179 | Et | H | CH(Et)$_2$ | Cl | (1,3-Dioxolan-2-yl)methoxy | SO$_2$Me |
| 1180 | Me | H | CH(Et)$_2$ | Me | CH$_2$N[C(O)SEt]CH$_2$CN | SO$_2$Me |
| 1181 | Me | H | CH(Et)$_2$ | Me | CH=CHCN | SO$_2$Me |
| 1182 | Me | H | CH(Et)$_2$ | Me | CH$_2$CH$_2$CN | SO$_2$Me |
| 1183 | Me | H | CH(Et)$_2$ | Me | CH$_2$SCN | SO$_2$Me |
| 1184 | Me | H | CH(Et)$_2$ | Me | CH$_2$C(S)NH$_2$ | SO$_2$Me |
| 1185 | Me | H | CH(Et)$_2$ | Me | OCH$_2$CH$_2$OMe | SO$_2$Me |
| 1186 | Et | H | CH(Et)$_2$ | Me | OCH$_2$CH$_2$OMe | SO$_2$Me |
| 1187 | Me | H | CH(Et)$_2$ | Me | OCH(CH$_3$)CH$_2$OMe | SO$_2$Me |
| 1188 | Et | H | CH(Et)$_2$ | Me | OCH$_2$CH(Et)OMe | SO$_2$Me |
| 1189 | Me | H | CH(Et)$_2$ | Me | (1,3-Dioxolan-2-yl)methyl | SO$_2$Me |
| 1190 | Me | H | CH(Et)$_2$ | Me | CH$_2$O(i-Pr) | SO$_2$Me |
| 1191 | i-Pr | H | Et | Me | CO$_2$Me | SO$_2$Me |
| 1192 | t-Bu | H | Et | Me | CO$_2$Me | SO$_2$Me |
| 1193 | t-Bu | H | Me | Me | CO$_2$(i-Pr) | SO$_2$Me |
| 1194 | i-Pr | H | Me | Cl | CO$_2$Et | SO$_2$Me |
| 1195 | t-Bu | H | Et | Me | CO$_2$Me | CF$_3$ |
| 1196 | t-Bu | H | Et | Me | OCH$_2$CH$_2$OMe | SO$_2$Me |
| 1197 | t-Bu | H | Me | SO$_2$Me | CO$_2$Me | CN |
| 1198 | i-Pr | H | Me | Me | C(O)SMe | SO$_2$Me |
| 1199 | i-Pr | H | Et | Me | C(O)SEt | SO$_2$Me |
| 1200 | i-Pr | H | Me | Me | 2-(2-Oxolanyl)ethoxy | SO$_2$Me |
| 1201 | i-Pr | H | Et | Me | 2-(2-(1,3-Dioxolanyl))ethoxy | SO$_2$Me |
| 1202 | t-Bu | H | Et | Me | CH$_2$OMe | SO$_2$Me |
| 1203 | t-Bu | H | Et | Me | 2-Oxolanylmethoxymethyl | SO$_2$Me |
| 1204 | i-Pr | H | Et | Cl | CO$_2$Me | SO$_2$Me |
| 1205 | t-Bu | H | Et | Cl | CO$_2$Me | SO$_2$Et |
| 1206 | i-Pr | H | Et | Cl | C(O)SMe | SO$_2$Me |
| 1207 | i-Pr | H | Et | Cl | C(O)SEt | SO$_2$Me |
| 1208 | i-Pr | H | Et | Me | OMe | SO$_2$Me |
| 1209 | i-Pr | H | Et | Me | OEt | SO$_2$Me |
| 1210 | i-Pr | H | Et | Me | O(i-Pr) | SO$_2$Me |
| 1211 | i-Pr | H | Me | Me | OCHF$_2$ | SO$_2$Me |
| 1212 | i-Pr | H | Me | Me | (4,5-Dihydroisoxazol-3-yl) | SO$_2$Me |
| 1213 | i-Pr | H | Et | Me | O(n-Pr) | SO$_2$Et |
| 1214 | i-Pr | H | Et | Cl | CH$_2$OMe | SO$_2$Me |
| 1215 | i-Pr | H | Et | Me | OCO$_2$Me | SO$_2$Me |
| 1216 | i-Pr | H | Et | Me | OC(O)SMe | SO$_2$Me |
| 1217 | i-Pr | H | Et | Me | OC(O)SEt | SO$_2$Me |
| 1218 | i-Pr | H | Et | Me | OCH$_2$CH$_2$OMe | SO$_2$Me |
| 1219 | t-Bu | H | Et | Me | OEt | SO$_2$Me |
| 1220 | t-Bu | H | Me | Cl | CO$_2$Et | SO$_2$Me |
| 1221 | t-Bu | H | Me | Cl | CO$_2$(n-Pr) | SO$_2$Me |
| 1222 | t-Bu | H | Et | Me | CO$_2$Et | SO$_2$Me |
| 1223 | i-Pr | H | Et | Me | CH$_2$CO$_2$Me | SO$_2$Me |
| 1224 | i-Pr | H | Me | Me | OCH$_2$CO$_2$Et | SO$_2$Me |
| 1225 | i-Pr | H | Me | Me | O(n-Pr) | SO$_2$Me |
| 1226 | t-Bu | H | Et | SO$_2$Me | H | CF$_3$ |
| 1227 | i-Pr | H | Me | Me | CH$_2$OCH$_2$CF$_3$ | SO$_2$Me |
| 1228 | i-Pr | H | Et | Cl | CH$_2$OCH$_2$CF$_3$ | SO$_2$Me |
| 1229 | t-Bu | H | Et | Me | Cl | SO$_2$Me |
| 1230 | i-Pr | H | Et | Me | CH$_2$SO$_2$Me | SO$_2$Me |
| 1231 | i-Pr | H | Et | Me | CH$_2$OEt | SO$_2$Me |
| 1232 | i-Pr | H | Et | CN | CH$_2$OMe | SO$_2$Me |
| 1233 | i-Pr | H | Et | Me | CH$_2$CH$_2$OMe | SO$_2$Me |
| 1234 | i-Pr | H | Et | Me | CH$_2$OCH$_2$CH$_2$OMe | SO$_2$Me |
| 1235 | i-Pr | H | Et | Me | OCH$_2$CH$_2$OEt | SO$_2$Me |
| 1236 | i-Pr | H | Et | Me | OCH$_2$CH$_2$Cl | SO$_2$Me |
| 1237 | i-Pr | H | Et | Me | OCH$_2$CF$_3$ | SO$_2$Me |

TABLE 1-continued

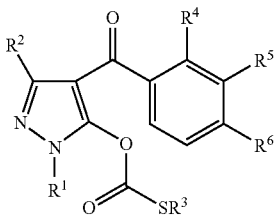

(I-2)

| No. | R¹ | R² | R³ | R⁴ | R⁵ | R⁶ |
|---|---|---|---|---|---|---|
| 1238 | i-Pr | H | Me | Me | CH$_2$OCH$_2$OMe | SO$_2$Me |
| 1239 | i-Pr | H | Me | Me | OCH$_2$CH$_2$SMe | SO$_2$Me |
| 1240 | i-Pr | H | Et | Me | CN | SO$_2$Me |
| 1241 | i-Pr | H | Et | Me | CH$_2$CN | SO$_2$Me |
| 1242 | i-Pr | H | Et | Br | CO$_2$Me | SO$_2$Me |
| 1243 | t-Bu | H | Et | Cl | CO$_2$Me | SO$_2$Me |
| 1244 | i-Pr | H | Et | Br | CO$_2$Me | SO$_2$Me |
| 1245 | i-Pr | H | Et | Cl | OCH$_2$CH$_2$OCF$_3$ | SO$_2$Me |
| 1246 | t-Bu | H | Et | Cl | OCH$_2$CH$_2$OCF$_3$ | SO$_2$Me |
| 1247 | i-Pr | H | Me | Me | OCH$_2$CH$_2$OCF$_3$ | SO$_2$Me |
| 1248 | t-Bu | H | Me | Me | OCH$_2$CH$_2$OCF$_3$ | SO$_2$Me |
| 1249 | i-Pr | H | Et | CF$_3$ | OCH$_2$CH$_2$OCF$_3$ | SO$_2$Me |
| 1250 | t-Bu | H | Et | CF$_3$ | OCH$_2$CH$_2$OCF$_3$ | SO$_2$Me |
| 1251 | i-Pr | H | Me | Br | OCH$_2$CH$_2$OCF$_3$ | SO$_2$Me |
| 1252 | t-Bu | H | Me | Br | OCH$_2$CH$_2$OCF$_3$ | SO$_2$Me |
| 1253 | i-Pr | H | Et | SO$_2$Me | OCH$_2$CH$_2$OCF$_3$ | CF$_3$ |
| 1254 | t-Bu | H | Me | SO$_2$Me | OCH$_2$CH$_2$OCF$_3$ | CF$_3$ |
| 1255 | i-Pr | H | Et | Cl | OCH$_2$CH$_2$OCHClF | SO$_2$Me |
| 1256 | t-Bu | H | Et | Cl | OCH$_2$CH$_2$OCHClF | SO$_2$Me |
| 1257 | i-Pr | H | Et | Me | OCH$_2$CH$_2$OCHClF | SO$_2$Me |
| 1258 | t-Bu | H | Et | Me | OCH$_2$CH$_2$OCHClF | SO$_2$Me |
| 1259 | i-Pr | H | Et | CF$_3$ | OCH$_2$CH$_2$OCHClF | SO$_2$Me |
| 1260 | t-Bu | H | Et | CF$_3$ | OCH$_2$CH$_2$OCHClF | SO$_2$Me |
| 1261 | i-Pr | H | Et | Br | OCH$_2$CH$_2$OCHClF | SO$_2$Me |
| 1262 | t-Bu | H | Et | Br | OCH$_2$CH$_2$OCHClF | SO$_2$Me |
| 1263 | i-Pr | H | Et | SO$_2$Me | OCH$_2$CH$_2$OCHClF | CF$_3$ |
| 1264 | t-Bu | H | Et | SO$_2$Me | OCH$_2$CH$_2$OCHClF | CF$_3$ |
| 1265 | i-Pr | H | Me | Cl | OCH$_2$CHFOCF$_3$ | SO$_2$Me |
| 1266 | t-Bu | H | Me | Cl | OCH$_2$CHFOCF$_3$ | SO$_2$Me |
| 1267 | i-Pr | H | Et | Me | OCH$_2$CHFOCF$_3$ | SO$_2$Me |
| 1268 | i-Pr | H | Et | Cl | OCH$_2$CHFOMe | SO$_2$Me |
| 1269 | t-Bu | H | Et | Cl | OCH$_2$CHFOMe | SO$_2$Me |
| 1270 | i-Pr | H | Et | Me | OCH$_2$CHFOMe | SO$_2$Me |
| 1271 | t-Bu | H | Et | Me | OCH$_2$CHFOMe | SO$_2$Me |
| 1272 | i-Pr | H | Et | CF$_3$ | OCH$_2$CHFOMe | SO$_2$Me |
| 1273 | t-Bu | H | Et | CF$_3$ | OCH$_2$CHFOMe | SO$_2$Me |
| 1274 | i-Pr | H | Me | Br | OCH$_2$CHFOMe | SO$_2$Me |
| 1275 | t-Bu | H | Me | Br | OCH$_2$CHFOMe | SO$_2$Me |
| 1276 | i-Pr | H | Et | SO$_2$Me | OCH$_2$CHFOMe | CF$_3$ |
| 1277 | t-Bu | H | Et | SO$_2$Me | OCH$_2$CHFOMe | CF$_3$ |
| 1278 | i-Pr | H | Me | Cl | OCHFCH$_2$OCF$_3$ | SO$_2$Me |
| 1279 | t-Bu | H | Me | Cl | OCHFCH$_2$OCF$_3$ | SO$_2$Me |
| 1280 | i-Pr | H | Et | Cl | OCH$_2$CH$_2$OCF$_2$Cl | SO$_2$Me |
| 1281 | t-Bu | H | Me | Cl | OCH$_2$CH$_2$OCF$_2$Cl | SO$_2$Me |
| 1282 | i-Pr | H | Et | Me | OCH$_2$CH$_2$OCF$_2$Cl | SQ2Me |
| 1283 | t-Bu | H | Et | Me | OCH$_2$CH$_2$OCF$_2$Cl | SO$_2$Me |
| 1284 | i-Pr | H | Et | CF$_3$ | OCH$_2$CH$_2$OCF$_2$Cl | SO$_2$Me |
| 1285 | t-Bu | H | Et | CF$_3$ | OCH$_2$CH$_2$OCF$_2$Cl | SO$_2$Me |
| 1286 | i-Pr | H | Et | Br | OCH$_2$CH$_2$OCF$_2$Cl | SO$_2$Me |
| 1287 | t-Bu | H | Et | Br | OCH$_2$CH$_2$OCF$_2$Cl | SO$_2$Me |
| 1288 | i-Pr | H | Et | SO$_2$Me | OCH$_2$CH$_2$OCF$_2$Cl | CF$_3$ |
| 1289 | t-Bu | H | Et | SO$_2$Me | OCH$_2$CH$_2$OCF$_2$Cl | CF$_3$ |
| 1290 | i-Pr | H | Et | Cl | SCH$_2$CH$_2$OCH$_3$ | SO$_2$Me |
| 1291 | t-Bu | H | Et | Cl | SCH$_2$CH$_3$OCH$_3$ | SO$_2$Me |
| 1292 | i-Pr | H | Me | Me | SCH$_2$CH$_3$OCH$_3$ | SO$_2$Me |
| 1293 | t-Bu | H | Me | Me | SCH$_2$CH$_3$OCH$_3$ | SO$_2$Me |
| 1294 | i-Pr | H | Et | CF$_3$ | SCH$_2$CH$_2$OCH$_3$ | SO$_2$Me |
| 1295 | t-Bu | H | Et | CF$_3$ | SCH$_2$CH$_2$OCH$_3$ | SO$_2$Me |
| 1296 | i-Pr | H | Et | Br | SCH$_2$CH$_2$OCH$_3$ | SO$_2$Me |
| 1297 | t-Bu | H | Et | Br | SCH$_2$CH$_2$OCH$_3$ | SO$_2$Me |
| 1298 | i-Pr | H | Et | SO$_2$Me | SCH$_2$CH$_2$OCH$_3$ | CF$_3$ |
| 1299 | t-Bu | H | Et | SO$_2$Me | SCH$_2$CH$_2$OCH$_3$ | CF$_3$ |
| 1300 | i-Pr | H | Et | Cl | SCH$_2$CH$_2$OCF$_3$ | SO$_2$Me |
| 1301 | t-Bu | H | Me | Cl | SCH$_2$CH$_2$OCF$_3$ | SO$_2$Me |
| 1302 | i-Pr | H | Me | Me | SCH$_2$CH$_2$OCF$_3$ | SO$_2$Me |
| 1303 | t-Bu | H | Et | Me | SCH$_2$CH$_2$OCF$_3$ | SO$_2$Me |

TABLE 1-continued (I-2)

| No. | R¹ | R² | R³ | R⁴ | R⁵ | R⁶ |
|---|---|---|---|---|---|---|
| 1304 | i-Pr | H | Et | $CF_3$ | $SCH_2CH_2OCF_3$ | $SO_2Me$ |
| 1305 | t-Bu | H | Me | $CF_3$ | $SCH_2CH_2OCF_3$ | $SO_2Me$ |
| 1306 | i-Pr | H | Me | Br | $SCH_2CH_2OCF_3$ | $SO_2Me$ |
| 1307 | t-Bu | H | Et | Br | $SCH_2CH_2OCF_3$ | $SO_2Me$ |
| 1308 | i-Pr | H | Me | $SO_2Me$ | $SCH_2CH_2OCF_3$ | $CF_3$ |
| 1309 | t-Bu | H | Et | $SO_2Me$ | $SCH_2CH_2OCF_3$ | $CF_3$ |
| 1310 | i-Pr | H | Et | Cl | $SCH_2CH_2SCH_3$ | $SO_2Me$ |
| 1311 | t-Bu | H | Et | Cl | $SCH_2CH_2SCH_3$ | $SO_2Me$ |
| 1312 | i-Pr | H | Et | Me | $SCH_2CH_2SCH_3$ | $SO_2Me$ |
| 1313 | t-Bu | H | Et | Me | $SCH_2CH_2SCH_3$ | $SO_2Me$ |
| 1314 | i-Pr | H | Et | $CF_3$ | $SCH_2CH_2SCH_3$ | $SO_2Me$ |
| 1315 | t-Bu | H | Et | $CF_3$ | $SCH_2CH_2SCH_3$ | $SO_2Me$ |
| 1316 | i-Pr | H | Et | Br | $SCH_2CH_2SCH_3$ | $SO_2Me$ |
| 1317 | t-Bu | H | Et | Br | $SCH_2CH_2SCH_3$ | $SO_2Me$ |
| 1318 | i-Pr | H | Et | $SO_2Me$ | $SCH_2CH_2SCH_3$ | $CF_3$ |
| 1319 | t-Bu | H | Me | $SO_2Me$ | $SCH_2CH_2SCH_3$ | $CF_3$ |
| 1320 | i-Pr | H | Me | Cl | $SCH_2CH_2SCF_3$ | $SO_2Me$ |
| 1321 | t-Bu | H | Et | Cl | $SCH_2CH_2SCF_3$ | $SO_2Me$ |
| 1322 | i-Pr | H | Et | Me | $SCH_2CH_2SCF_3$ | $SO_2Me$ |
| 1323 | t-Bu | H | Et | Me | $SCH_2CH_2SCF_3$ | $SO_2Me$ |
| 1324 | i-Pr | H | Et | $CF_3$ | $SCH_2CH_2SCF_3$ | $SO_2Me$ |
| 1325 | t-Bu | H | Et | $CF_3$ | $SCH_2CH_2SCF_3$ | $SO_2Me$ |
| 1326 | i-Pr | H | Et | Br | $SCH_2CH_2SCF_3$ | $SO_2Me$ |
| 1327 | t-Bu | H | Et | Br | $SCH_2CH_2SCF_3$ | $SO_2Me$ |
| 1328 | i-Pr | H | Me | $SO_2Me$ | $SCH_2CH_2SCF_3$ | $CF_3$ |
| 1329 | t-Bu | H | Me | $SO_2Me$ | $SCH_2CH_2SCF_3$ | $CF_3$ |
| 1330 | i-Pr | H | Et | Cl | $OCH_2CH(CH_3)OCH_3$ | $SO_2Me$ |
| 1331 | t-Bu | H | Et | Cl | $OCH_2CH(CH_3)OCH_3$ | $SO_2Me$ |
| 1332 | i-Pr | H | Me | Me | $OCH_2CH(CH_3)OCH_3$ | $SO_2Me$ |
| 1333 | t-Bu | H | Me | Me | $OCH_2CH(CH_3)OCH_3$ | $SO_2Me$ |
| 1334 | i-Pr | H | Et | $CF_3$ | $OCH_2CH(CH_3)OCH_3$ | $SO_2Me$ |
| 1335 | t-Bu | H | Me | $CF_3$ | $OCH_2CH(CH_3)OCH_3$ | $SO_2Me$ |
| 1336 | i-Pr | H | Et | Br | $OCH_2CH(CH_3)OCH_3$ | $SO_2Me$ |
| 1337 | t-Bu | H | Et | Br | $OCH_2CH(CH_3)OCH_3$ | $SO_2Me$ |
| 1338 | i-Pr | H | Et | $SO_2Me$ | $OCH_2CH(CH_3)OCH_3$ | $CF_3$ |
| 1339 | t-Bu | H | Et | $SO_2Me$ | $OCH_2CH(CH_3)OCH_3$ | $CF_3$ |
| 1340 | i-Pr | H | Et | Cl | $OCH_2CF_2OCH_3$ | $SO_2Me$ |
| 1341 | t-Bu | H | Et | Cl | $OCH_2CF_2OCH_3$ | $SO_2Me$ |
| 1342 | i-Pr | H | Et | Me | $OCH_2CF_2OCH_3$ | $SO_2Me$ |
| 1343 | t-Bu | H | Et | Me | $OCH_2CF_2OCH_3$ | $SO_2Me$ |
| 1344 | i-Pr | H | Et | $CF_3$ | $OCH_2CF_2OCH_3$ | $SO_2Me$ |
| 1345 | t-Bu | H | Et | $CF_3$ | $OCH_2CF_2OCH_3$ | $SO_2Me$ |
| 1346 | i-Pr | H | Me | Br | $OCH_2CF_2OCH_3$ | $SO_2Me$ |
| 1347 | t-Bu | H | Me | Br | $OCH_2CF_2OCH_3$ | $SO_2Me$ |
| 1348 | i-Pr | H | Et | $SO_2Me$ | $OCH_2CF_2OCH_3$ | $CF_3$ |
| 1349 | t-Bu | H | Et | $SO_2Me$ | $OCH_2CF_2OCH_3$ | $CF_3$ |
| 1350 | i-Pr | H | Et | Me | $OCH_2CH_2OCH_3$ | $SO_2Me$ |
| 1351 | t-Bu | H | Et | Me | $OCH_2CH_2OCH_3$ | $SO_2Me$ |
| 1352 | i-Pr | H | Et | Me | $OCH_2CH(OCH_3)_2$ | $SO_2Me$ |
| 1353 | i-Pr | H | Et | Me | $CH_2NMeCH_2CN$ | $SO_2Me$ |
| 1354 | i-Pr | H | Et | Me | (Tetrahydrofuran-2-yl)methoxy | $SO_2Me$ |
| 1355 | i-Pr | H | Me | Cl | SMe | $SO_2Me$ |
| 1356 | i-Pr | H | Me | Cl | Cl | $SO_2Me$ |
| 1357 | i-Pr | H | Et | Cl | OMe | $SO_2Me$ |
| 1358 | i-Pr | H | Et | Me | (Tetrahydro-2H-pyran-2-yl)methoxy | $SO_2Me$ |
| 1359 | i-Pr | H | Me | Cl | $OCH_2CH_2OMe$ | $SO_2Me$ |
| 1360 | i-Pr | H | Me | Me | Tetrahydrofuran-3-yloxy | $SO_2Me$ |
| 1361 | i-Pr | H | Et | Me | $OCH_2CH_2CH_2OMe$ | $SO_2Me$ |
| 1362 | i-Pr | H | Me | Me | $OCH_2CH_2OMe$ | $SO_2Me$ |
| 1363 | t-Bu | H | Et | Cl | (1,3-Dioxolan-2-yl)ethoxy | $SO_2Me$ |
| 1364 | i-Pr | H | Et | Me | Propargyloxy | $SO_2Me$ |
| 1365 | i-Pr | H | Et | Me | (Tetrahydrofuran-3-yloxy)methyl | $SO_2Me$ |
| 1366 | i-Pr | H | Et | Cl | $SO_2Me$ | $SO_2Me$ |
| 1367 | i-Pr | H | Et | Me | $(CH_2)_6Me$ | $SO_2Me$ |
| 1368 | i-Pr | H | Et | Me | $CH_2CH_2CH_2OMe$ | $SO_2Me$ |
| 1369 | t-Bu | H | Et | Cl | (1,3-Dioxolan-2-yl)methoxy | $SO_2Me$ |

TABLE 1-continued (I-2)

| No. | R¹ | R² | R³ | R⁴ | R⁵ | R⁶ |
|---|---|---|---|---|---|---|
| 1370 | i-Pr | H | Et | Me | CH₂N[C(O)SEt]CH₂CN | SO₂Me |
| 1371 | i-Pr | H | Et | Me | CH=CHCN | SO₂Me |
| 1372 | i-Pr | H | Et | Me | CH₂CH₂CN | SO₂Me |
| 1373 | i-Pr | H | Me | Me | CH₂SCN | SO₂Me |
| 1374 | i-Pr | H | Me | Me | CH₂C(S)NH₂ | SO₂Me |
| 1375 | i-Pr | H | Et | Me | OCH₂CH₂OMe | SO₂Me |
| 1376 | t-Bu | H | Et | Me | OCH₂CH₂OMe | SO₂Me |
| 1377 | i-Pr | H | Et | Me | OCH(CH₃)CH₂OMe | SO₂Me |
| 1378 | t-Bu | H | Et | Me | OCH₂CH(Et)OMe | SO₂Me |
| 1379 | i-Pr | H | Et | Me | (1,3-Dioxolan-2-yl)methyl | SO₂Me |
| 1380 | i-Pr | H | Et | Me | CH₂O(i-Pr) | SO₂Me |
| 1381 | Et | H | i-Pr | Me | CO₂(i-Pr) | SO₂Me |
| 1382 | Me | H | i-Pr | Cl | CO₂Et | SO₂Me |
| 1383 | Et | H | i-Pr | Me | CO₂Me | CF₃ |
| 1384 | Et | H | i-Pr | SO₂Me | CO₂Me | CN |
| 1385 | i-Pr | H | i-Pr | Me | C(O)SMe | SO₂Me |
| 1386 | Me | H | i-Pr | Me | C(O)SEt | SO₂Me |
| 1387 | Me | H | i-Pr | Me | 2-(2-Oxolanyl)ethoxy | SO₂Me |
| 1388 | Me | H | i-Pr | Me | 2-(2-(1,3-Dioxolanyl))ethoxy | SO₂Me |
| 1389 | Et | H | i-Pr | Me | CH₂OMe | SO₂Me |
| 1390 | Et | H | i-Pr | Me | 2-Oxolanylmethoxymethyl | SO₂Me |
| 1391 | Me | H | i-Pr | Cl | CO₂Me | SO₂Me |
| 1392 | Et | H | i-Pr | Cl | CO₂Me | SO₂Et |
| 1393 | Me | H | i-Pr | Cl | C(O)SMe | SO₂Me |
| 1394 | Me | H | i-Pr | Cl | C(O)SEt | SO₂Me |
| 1395 | Me | H | i-Pr | Me | OMe | SO₂Me |
| 1396 | Me | H | i-Pr | Me | OEt | SO₂Me |
| 1397 | Me | H | i-Pr | Me | O(i-Pr) | SO₂Me |
| 1398 | Me | H | i-Pr | Me | OCHF₂ | SO₂Me |
| 1399 | Me | H | i-Pr | Me | (4,5-Dihydrosioxazol-3-yl) | SO₂Me |
| 1400 | Me | H | i-Pr | Me | O(n-Pr) | SO₂Et |
| 1401 | Me | H | i-Pr | Cl | CH₂OMe | SO₂Me |
| 1402 | Me | H | i-Pr | Me | OCO₂Me | SO₂Me |
| 1403 | Me | H | i-Pr | Me | OC(O)SMe | SO₂Me |
| 1404 | Me | H | i-Pr | Me | OC(O)SEt | SO₂Me |
| 1405 | Et | H | i-Pr | Me | OEt | SO₂Me |
| 1406 | Et | H | i-Pr | Cl | CO₂Et | SO₂Me |
| 1407 | Et | H | i-Pr | Cl | CO₂(n-Pr) | SO₂Me |
| 1408 | Et | H | i-Pr | Me | CO₂Et | SO₂Me |
| 1409 | Me | H | i-Pr | Me | CH₂CO₂Me | SO₂Me |
| 1410 | Me | H | i-Pr | Me | OCH₂CO₂Et | SO₂Me |
| 1411 | Me | H | i-Pr | Me | O(n-Pr) | SO₂Me |
| 1412 | Et | H | i-Pr | SO₂Me | H | CF₃ |
| 1413 | Me | H | i-Pr | Me | CH₂OCH₂CF₃ | SO₂Me |
| 1414 | Me | H | i-Pr | Cl | CH₂OCH₂CF₃ | SO₂Me |
| 1415 | Et | H | i-Pr | Me | Cl | SO₂Me |
| 1416 | Me | H | i-Pr | Me | CH₂SO₂Me | SO₂Me |
| 1417 | Me | H | i-Pr | Me | CH₂OEt | SO₂Me |
| 1418 | Me | H | i-Pr | Cl | CH₂OMe | SO₂Me |
| 1419 | Me | H | i-Pr | Me | CH₂CH₂OMe | SO₂Me |
| 1420 | Me | H | i-Pr | Me | CH₂OCH₂CH₂OMe | SO₂Me |
| 1421 | Me | H | i-Pr | Me | OCH₂CH₂OEt | SO₂Me |
| 1422 | Me | H | i-Pr | Me | OCH₂CH₂Cl | SO₂Me |
| 1423 | Me | H | i-Pr | Me | OCH₂CF₃ | SO₂Me |
| 1424 | Me | H | i-Pr | Me | CH₂OCH₂OMe | SO₂Me |
| 1425 | Me | H | i-Pr | Me | OCH₂CH₂SMe | SO₂Me |
| 1426 | Me | H | i-Pr | Me | CN | SO₂Me |
| 1427 | Me | H | i-Pr | Me | CH₂CN | SO₂Me |
| 1428 | Me | H | i-Pr | Br | CO₂Me | SO₂Me |
| 1429 | Et | H | i-Pr | Cl | CO₂Me | SO₂Me |
| 1430 | Me | H | i-Pr | Br | CO₂Me | SO₂Me |
| 1431 | Me | H | i-Pr | Cl | OCH₂CH₂OCF₃ | SO₂Me |
| 1432 | Et | H | i-Pr | Cl | OCH₂CH₂OCF₃ | SO₂Me |
| 1433 | Me | H | i-Pr | Me | OCH₂CH₂OCF₃ | SO₂Me |
| 1434 | Et | H | i-Pr | Me | OCH₂CH₂OCF₃ | SO₂Me |
| 1435 | Me | H | i-Pr | CF₃ | OCH₂CH₂OCF₃ | SO₂Me |

TABLE 1-continued (I-2)

| No. | R¹ | R² | R³ | R⁴ | R⁵ | R⁶ |
|---|---|---|---|---|---|---|
| 1436 | Et | H | i-Pr | CF$_3$ | OCH$_2$CH$_2$OCF$_3$ | SO$_2$Me |
| 1437 | Me | H | i-Pr | Br | OCH$_2$CH$_2$OCF$_3$ | SO$_2$Me |
| 1438 | Et | H | i-Pr | Br | OCH$_2$CH$_2$OCF$_3$ | SO$_2$Me |
| 1439 | Me | H | i-Pr | SO$_2$Me | OCH$_2$CH$_2$OCF$_3$ | CF$_3$ |
| 1440 | Et | H | i-Pr | SO$_2$Me | OCH$_2$CH$_2$OCF$_3$ | CF$_3$ |
| 1441 | Me | H | i-Pr | Cl | OCH$_2$CH$_3$OCHClF | SO$_2$Me |
| 1442 | Et | H | i-Pr | Cl | OCH$_2$CH$_3$OCHClF | SO$_2$Me |
| 1443 | Me | H | i-Pr | Me | OCH$_2$CH$_2$OCHClF | SO$_2$Me |
| 1444 | Et | H | i-Pr | Me | OCH$_2$CH$_2$OCHClF | SO$_2$Me |
| 1445 | Me | H | i-Pr | CF$_3$ | OCH$_2$CH$_2$OCHClF | SO$_2$Me |
| 1446 | Et | H | i-Pr | CF$_3$ | OCH$_2$CH$_2$OCHClF | SO$_2$Me |
| 1447 | Me | H | i-Pr | Br | OCH$_2$CH$_2$OCHClF | SO$_2$Me |
| 1448 | Et | H | i-Pr | Br | OCH$_2$CH$_2$OCHClF | SO$_2$Me |
| 1449 | Me | H | i-Pr | SO$_2$Me | OCH$_2$CH$_2$OCHClF | CF$_3$ |
| 1450 | Et | H | i-Pr | SO$_2$Me | OCH$_2$CH$_2$OCHClF | CF$_3$ |
| 1451 | Me | H | i-Pr | Cl | OCH$_2$CHFOCF$_3$ | SO$_2$Me |
| 1452 | Et | H | i-Pr | Cl | OCH$_2$CHFOCF$_3$ | SO$_2$Me |
| 1453 | Me | H | i-Pr | Me | OCH$_2$CHFOCF$_3$ | SO$_2$Me |
| 1454 | Me | H | i-Pr | Cl | OCH$_2$CHFOMe | SO$_2$Me |
| 1455 | Et | H | i-Pr | Cl | OCH$_2$CHFOMe | SO$_2$Me |
| 1456 | Me | H | i-Pr | Me | OCH$_2$CHFOMe | SO$_2$Me |
| 1457 | Et | H | i-Pr | Me | OCH$_2$CHFOMe | SO$_2$Me |
| 1458 | Me | H | i-Pr | CF$_3$ | OCH$_2$CHFOMe | SO$_2$Me |
| 1459 | Et | H | i-Pr | CF$_3$ | OCH$_2$CHFOMe | SO$_2$Me |
| 1460 | Me | H | i-Pr | Br | OCH$_2$CHFOMe | SO$_2$Me |
| 1461 | Et | H | i-Pr | Br | OCH$_2$CHFOMe | SO$_2$Me |
| 1462 | Me | H | i-Pr | SO$_2$Me | OCH$_2$CHFOMe | CF$_3$ |
| 1463 | Et | H | i-Pr | SO$_2$Me | OCH$_2$CHFOMe | CF$_3$ |
| 1464 | Me | H | i-Pr | Cl | OCHFCH$_2$OCF$_3$ | SO$_2$Me |
| 1465 | Et | H | i-Pr | Cl | OCHFCH$_2$OCF$_3$ | SO$_2$Me |
| 1466 | Me | H | i-Pr | Cl | OCH$_2$CH$_2$OCF$_2$Cl | SO$_2$Me |
| 1467 | Et | H | i-Pr | Cl | OCH$_2$CH$_2$OCF$_2$Cl | SO$_2$Me |
| 1468 | Me | H | i-Pr | Me | OCH$_2$CH$_2$OCF$_2$Cl | SO$_2$Me |
| 1469 | Et | H | i-Pr | Me | OCH$_2$CH$_2$OCF$_2$Cl | SO$_2$Me |
| 1470 | Me | H | i-Pr | CF$_3$ | OCH$_2$CH$_2$OCF$_2$Cl | SO$_2$Me |
| 1471 | Et | H | i-Pr | CF$_3$ | OCH$_2$CH$_2$OCF$_2$Cl | SO$_2$Me |
| 1472 | Me | H | i-Pr | Br | OCH$_2$CH$_2$OCF$_2$Cl | SO$_2$Me |
| 1473 | Et | H | i-Pr | Br | OCH$_2$CH$_2$OCF$_2$Cl | SO$_2$Me |
| 1474 | Me | H | i-Pr | SO$_2$Me | OCH$_2$CH$_2$OCF$_2$Cl | CF$_3$ |
| 1475 | Et | H | i-Pr | SO$_2$Me | OCH$_2$CH$_3$OCF$_2$Cl | CF$_3$ |
| 1476 | Me | H | i-Pr | Cl | SCH$_2$CH$_2$OCH$_3$ | SO$_2$Me |
| 1477 | Et | H | i-Pr | Cl | SCH$_2$CH$_2$OCH$_3$ | SO$_2$Me |
| 1478 | Me | H | i-Pr | Me | SCH$_2$CH$_2$OCH$_3$ | SO$_2$Me |
| 1479 | Et | H | i-Pr | Me | SCH$_2$CH$_2$OCH$_3$ | SO$_2$Me |
| 1480 | Me | H | i-Pr | CF$_3$ | SCH$_2$CH$_2$OCH$_3$ | SO$_2$Me |
| 1481 | Et | H | i-Pr | CF$_3$ | SCH$_2$CH$_2$OCH$_3$ | SO$_2$Me |
| 1482 | Me | H | i-Pr | Br | SCH$_2$CH$_2$OCH$_3$ | SO$_2$Me |
| 1483 | Et | H | i-Pr | Br | SCH$_2$CH$_2$OCH$_3$ | SO$_2$Me |
| 1484 | Me | H | i-Pr | SO$_2$Me | SCH$_2$CH$_2$OCH$_3$ | CF$_3$ |
| 1485 | Et | H | i-Pr | SO$_2$Me | SCH$_2$CH$_2$OCH$_3$ | CF$_3$ |
| 1486 | Me | H | i-Pr | Cl | SCH$_2$CH$_2$OCF$_3$ | SO$_2$Me |
| 1487 | Et | H | i-Pr | Cl | SCH$_2$CH$_2$OCF$_3$ | SO$_2$Me |
| 1488 | Me | H | i-Pr | Me | SCH$_2$CH$_2$OCF$_3$ | SO$_2$Me |
| 1489 | Et | H | i-Pr | Me | SCH$_2$CH$_2$OCF$_3$ | SO$_2$Me |
| 1490 | Me | H | i-Pr | CF$_3$ | SCH$_2$CH$_2$OCF$_3$ | SO$_2$Me |
| 1491 | Et | H | i-Pr | CF$_3$ | SCH$_2$CH$_2$OCF$_3$ | SO$_2$Me |
| 1492 | Me | H | i-Pr | Br | SCH$_2$CH$_2$OCF$_3$ | SO$_2$Me |
| 1493 | Et | H | i-Pr | Br | SCH$_2$CH$_2$OCF$_3$ | SO$_2$Me |
| 1494 | Me | H | i-Pr | SO$_2$Me | SCH$_2$CH$_3$OCF$_3$ | CF$_3$ |
| 1495 | Et | H | i-Pr | SO$_2$Me | SCH$_2$CH$_2$OCF$_3$ | CF$_3$ |
| 1496 | Me | H | i-Pr | Cl | SCH$_2$CH$_2$SCH$_3$ | SO$_2$Me |
| 1497 | Et | H | i-Pr | Cl | SCH$_2$CH$_2$SCH$_3$ | SO$_2$Me |
| 1498 | Me | H | i-Pr | Me | SCH$_2$CH$_2$SCH$_3$ | SO$_2$Me |
| 1499 | Et | H | i-Pr | Me | SCH$_2$CH$_2$SCH$_3$ | SO$_2$Me |
| 1500 | Me | H | i-Pr | CF$_3$ | SCH$_2$CH$_2$SCH$_3$ | SO$_2$Me |
| 1501 | Et | H | i-Pr | CF$_3$ | SCH$_2$CH$_2$SCH$_3$ | SO$_2$Me |

TABLE 1-continued

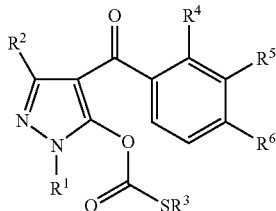

(I-2)

| No. | $R^1$ | $R^2$ | $R^3$ | $R^4$ | $R^5$ | $R^6$ |
|---|---|---|---|---|---|---|
| 1502 | Me | H | i-Pr | Br | $SCH_2CH_2SCH_3$ | $SO_2Me$ |
| 1503 | Et | H | i-Pr | Br | $SCH_2CH_2SCH_3$ | $SO_2Me$ |
| 1504 | Me | H | i-Pr | $SO_2Me$ | $SCH_2CH_2SCH_3$ | $CF_3$ |
| 1505 | Et | H | i-Pr | $SO_2Me$ | $SCH_2CH_2SCH_3$ | $CF_3$ |
| 1506 | Me | H | i-Pr | Cl | $SCH_2CH_2SCF_3$ | $SO_2Me$ |
| 1507 | Et | H | i-Pr | Cl | $SCH_2CH_2SCF_3$ | $SO_2Me$ |
| 1508 | Me | H | i-Pr | Me | $SCH_2CH_2SCF_3$ | $SO_2Me$ |
| 1509 | Et | H | i-Pr | Me | $SCH_2CH_2SCF_3$ | $SO_2Me$ |
| 1510 | Me | H | i-Pr | $CF_3$ | $SCH_2CH_2SCF_3$ | $SO_2Me$ |
| 1511 | Et | H | i-Pr | $CF_3$ | $SCH_2CH_2SCF_3$ | $SO_2Me$ |
| 1512 | Me | H | i-Pr | Br | $SCH_2CH_2SCF_3$ | $SO_2Me$ |
| 1513 | Et | H | i-Pr | Br | $SCH_2CH_2SCF_3$ | $SO_2Me$ |
| 1514 | Me | H | i-Pr | $SO_2Me$ | $SCH_2CH_2SCF_3$ | $CF_3$ |
| 1515 | Et | H | i-Pr | $SO_2Me$ | $SCH_2CH_2SCF_3$ | $CF_3$ |
| 1516 | Me | H | i-Pr | Cl | $OCH_2CH(CH_3)OCH_3$ | $SO_2Me$ |
| 1517 | Et | H | i-Pr | Cl | $OCH_2CH(CH_3)OCH_3$ | $SO_2Me$ |
| 1518 | Me | H | i-Pr | Me | $OCH_2CH(CH_3)OCH_3$ | $SO_2Me$ |
| 1519 | Et | H | i-Pr | Me | $OCH_2CH(CH_3)OCH_3$ | $SO_2Me$ |
| 1520 | Me | H | i-Pr | $CF_3$ | $OCH_2CH(CH_3)OCH_3$ | $SO_2Me$ |
| 1521 | Et | H | i-Pr | $CF_3$ | $OCH_2CH(CH_3)OCH_3$ | $SO_2Me$ |
| 1522 | Me | H | i-Pr | Br | $OCH_2CH(CH_3)OCH_3$ | $SO_2Me$ |
| 1523 | Et | H | i-Pr | Br | $OCH_2CH(CH_3)OCH_3$ | $SO_2Me$ |
| 1524 | Me | H | i-Pr | $SO_2Me$ | $OCH_2CH(CH_3)OCH_3$ | $CF_3$ |
| 1525 | Et | H | i-Pr | $SO_2Me$ | $OCH_2CH(CH_3)OCH_3$ | $CF_3$ |
| 1526 | Me | H | i-Pr | Cl | $OCH_2CF_2OCH_3$ | $SO_2Me$ |
| 1527 | Et | H | i-Pr | Cl | $OCH_2CF_2OCH_3$ | $SO_2Me$ |
| 1528 | Me | H | i-Pr | Me | $OCH_2CF_2OCH_3$ | $SO_2Me$ |
| 1529 | Et | H | i-Pr | Me | $OCH_2CF_2OCH_3$ | $SO_2Me$ |
| 1530 | Me | H | i-Pr | $CF_3$ | $OCH_2CF_2OCH_3$ | $SO_2Me$ |
| 1531 | Et | H | i-Pr | $CF_3$ | $OCH_2CF_2OCH_3$ | $SO_2Me$ |
| 1532 | Me | H | i-Pr | Br | $OCH_2CF_2OCH_3$ | $SO_2Me$ |
| 1533 | Et | H | i-Pr | Br | $OCH_2CF_2OCH_3$ | $SO_2Me$ |
| 1534 | Me | H | i-Pr | $SO_2Me$ | $OCH_2CF_2OCH_3$ | $CF_3$ |
| 1535 | Et | H | i-Pr | $SO_2Me$ | $OCH_2CF_2OCH_3$ | $CF_3$ |
| 1536 | Me | H | i-Pr | Me | $OCH_2CH_2OCH_3$ | $SO_2Me$ |
| 1537 | Et | H | i-Pr | Me | $OCH_2CH_2OCH_3$ | $SO_2Me$ |
| 1538 | Me | H | i-Pr | Me | $OCH_2CH(OCH_3)_2$ | $SO_2Me$ |
| 1539 | Me | H | i-Pr | Me | $CH_2N(Me)CH_2CN$ | $SO_2Me$ |
| 1540 | Me | H | i-Pr | Me | (Tetrahydrofuran-2-yl)methoxy | $SO_2Me$ |
| 1541 | Me | H | i-Pr | Cl | SMe | $SO_2Me$ |
| 1542 | Me | H | i-Pr | Cl | Cl | $SO_2Me$ |
| 1543 | Me | H | i-Pr | Cl | OMe | $SO_2Me$ |
| 1544 | Me | H | i-Pr | Me | (Tetrahydro-2H-pyran-2-yl)methoxy | $SO_2Me$ |
| 1545 | Me | H | i-Pr | Cl | $OCH_2CH_2OMe$ | $SO_2Me$ |
| 1546 | Me | H | i-Pr | Me | Tetrahydrofuran-3-yloxy | $SO_2Me$ |
| 1547 | Me | H | i-Pr | Me | $OCH_2CH_2CH_2OMe$ | $SO_2Me$ |
| 1548 | Me | H | i-Pr | Me | $OCH_2CH_2OMe$ | $SO_2Me$ |
| 1549 | Et | H | i-Pr | Cl | (1,3-Dioxolan-2-yl)ethoxy | $SO_2Me$ |
| 1550 | Me | H | i-Pr | Me | Propargyloxy | $SO_2Me$ |
| 1551 | Me | H | i-Pr | Me | (Tetrahydrofuran-3-yloxy)methyl | $SO_2Me$ |
| 1552 | Me | H | i-Pr | Cl | $SO_2Me$ | $SO_2Me$ |
| 1553 | Me | H | i-Pr | Me | $(CH_2)_6Me$ | $SO_2Me$ |
| 1554 | Me | H | i-Pr | Me | $CH_2CH_2OMe$ | $SO_2Me$ |
| 1555 | Et | H | i-Pr | Cl | (1,3-Dioxolan-2-yl)methoxy | $SO_2Me$ |
| 1556 | Me | H | i-Pr | Me | $CH_2N[C(O)SEt]CH_2CN$ | $SO_2Me$ |
| 1557 | Me | H | i-Pr | Me | CHCHCN | $SO_2Me$ |
| 1558 | Me | H | i-Pr | Me | $CH_2CH_2CN$ | $SO_2Me$ |
| 1559 | Me | H | i-Pr | Me | $CH_2SCN$ | $SO_2Me$ |
| 1560 | Me | H | i-Pr | Me | $CH_2C(S)NH_2$ | $SO_2Me$ |
| 1561 | Me | H | i-Pr | Me | $OCH_2CH_2OMe$ | $SO_2Me$ |
| 1562 | Et | H | i-Pr | Me | $OCH_2CH_2OMe$ | $SO_2Me$ |
| 1563 | Me | H | i-Pr | Me | $OCH(CH_3)CH_2OMe$ | $SO_2Me$ |
| 1564 | Et | H | i-Pr | Me | $OCH_2CH(Et)OMe$ | $SO_2Me$ |
| 1565 | Me | H | i-Pr | Me | (1,3-Dioxolan-2-yl)methyl | $SO_2Me$ |
| 1566 | Me | H | i-Pr | Me | $CH_2O(i-Pr)$ | $SO_2Me$ |
| 1567 | Me | Me | Et | Me | $CO_2Me$ | $SO_2Me$ |

TABLE 1-continued

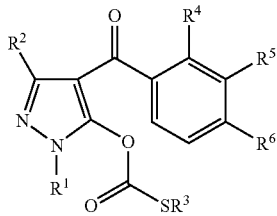

(I-2)

| No. | R$^1$ | R$^2$ | R$^3$ | R$^4$ | R$^5$ | R$^6$ |
|---|---|---|---|---|---|---|
| 1568 | Et | Me | Et | Me | CO$_2$Me | SO$_2$Me |
| 1569 | Me | Me | Me | Me | CO$_2$Me | SO$_2$Me |
| 1570 | Et | Me | Me | Me | CO$_2$Me | SO$_2$Me |
| 1571 | n-Pr | Me | Et | Me | CO$_2$Me | SO$_2$Me |
| 1572 | c-Pr | Me | Et | Me | CO$_2$Me | SO$_2$Me |
| 1573 | n-Pr | Me | Me | Me | CO$_2$Me | SO$_2$Me |
| 1574 | c-Pr | Me | Me | Me | CO$_2$Me | SO$_2$Me |
| 1575 | t-Bu | Me | Et | Me | CO$_2$Me | SO$_2$Me |
| 1576 | t-Bu | Me | Me | Me | CO$_2$Me | SO$_2$Me |
| 1577 | Et | Me | Et | Me | CO$_2$(i-Pr) | SO$_2$Me |
| 1578 | Me | Me | Et | Me | CO$_2$Et | SO$_2$Me |
| 1579 | Et | Me | Et | Me | CO$_2$Me | NO$_2$ |
| 1580 | Et | Me | Et | SO$_2$Me | CO$_2$Me | CF$_3$ |
| 1581 | Et | Me | Et | Me | OCH$_2$CH$_2$OMe | SO$_2$Me |
| 1582 | Et | Me | Et | Cl | OCH$_2$CH$_2$OMe | SO$_2$Me |
| 1583 | Et | Me | Et | Me | CO$_2$Me | CN |
| 1584 | Me | Me | Et | Me | C(O)SMe | SO$_2$Me |
| 1585 | Et | Me | Et | Me | C(O)SMe | SO$_2$Me |
| 1586 | Me | Me | Me | Me | C(O)SEt | SO$_2$Me |
| 1587 | Et | Me | Me | Me | C(O)SEt | SO$_2$Me |
| 1588 | Me | Me | Et | Me | 2-(2-Oxolanyl)ethoxy | SO$_2$Me |
| 1589 | Me | Me | Et | Me | 2-(2-(1,3-Dioxolanyl))ethoxy | SO$_2$Me |
| 1590 | Et | Me | Et | Me | CH$_2$OMe | SO$_2$Me |
| 1591 | Et | Me | Et | Me | 2-Oxolanylmethoxymethyl | SO$_2$Me |
| 1592 | Me | Me | Et | Cl | CO$_2$Me | SO$_2$Me |
| 1593 | Et | Me | Et | Cl | CO$_2$Me | SO$_2$Et |
| 1594 | Me | Me | Me | Cl | CO$_2$Me | SO$_2$Me |
| 1595 | Et | Me | Me | Br | CO$_2$Me | SO$_2$Me |
| 1596 | Me | Me | Et | Cl | C(O)SMe | SO$_2$Me |
| 1597 | Et | Me | Et | Cl | C(O)SMe | SO$_2$Me |
| 1598 | Me | Me | Et | Cl | C(O)SEt | SO$_2$Me |
| 1599 | Et | Me | Et | Cl | C(O)SEt | SO$_2$Me |
| 1600 | Me | Me | Et | Me | OMe | SO$_2$Me |
| 1601 | Me | Me | Et | Me | OEt | SO$_2$Me |
| 1602 | Me | Me | Et | Me | O(i-Pr) | SO$_2$Me |
| 1603 | Me | Me | Et | Me | OCHF$_2$ | SO$_2$Me |
| 1604 | Me | Me | Et | Me | (4,5-Dihydroisoxazol-3-yl) | SO$_2$Me |
| 1605 | Me | Me | Me | Me | (4,5-Dihydroisoxazol-3-yl) | SO$_2$Me |
| 1606 | Me | Me | Et | Me | O(n-Pr) | SO$_2$Et |
| 1607 | Me | Me | Et | Cl | CH$_2$OMe | SO$_2$Me |
| 1608 | Me | Me | Et | Me | OCO$_2$Me | SO$_2$Me |
| 1609 | Et | Me | Et | Me | OCO$_2$Me | SO$_2$Me |
| 1610 | Me | Me | Me | Me | OCO$_2$Me | SO$_2$Me |
| 1611 | Et | Me | Me | Me | OCO$_2$Me | SO$_2$Me |
| 1612 | Me | Me | Et | Me | OC(O)SMe | SO$_2$Me |
| 1613 | Et | Me | Et | Me | OC(O)SMe | SO$_2$Me |
| 1614 | Me | Me | Me | Me | OC(O)SMe | SO$_2$Me |
| 1615 | Et | Me | Me | Me | OC(O)SMe | SO$_2$Me |
| 1616 | Me | Me | Et | Me | OC(O)SEt | SO$_2$Me |
| 1617 | Et | Me | Et | Me | OC(O)SEt | SO$_2$Me |
| 1618 | Me | Me | Me | Me | OC(O)SEt | SO$_2$Me |
| 1619 | Et | Me | Me | Me | OC(O)SEt | SO$_2$Me |
| 1620 | Me | Me | Et | Me | OCH$_2$CH$_2$OMe | SO$_2$Me |
| 1621 | Me | Me | Me | Me | OCH$_2$CH$_2$OMe | SO$_2$Et |
| 1622 | Me | Me | Et | Cl | OCH$_2$CH$_2$OMe | SO$_2$Me |
| 1623 | Et | Me | Et | Me | OEt | SO$_2$Me |
| 1624 | Et | Me | Et | Cl | CO$_2$Et | SO$_2$Me |
| 1625 | Et | Me | Et | Cl | CO$_2$(n-Pr) | SO$_2$Me |
| 1626 | Et | Me | Et | Me | CO$_2$Et | SO$_2$Me |
| 1627 | Et | Me | Me | Me | CO$_2$Et | SO$_2$Me |
| 1628 | Me | Me | Et | Me | CH$_2$OMe | SO$_2$Me |
| 1629 | Me | Me | Et | Me | CH$_2$CO$_2$Me | SO$_2$Me |
| 1630 | Me | Me | Et | Me | OCH$_2$CO$_2$Et | SO$_2$Me |
| 1631 | Me | Me | Et | Me | O(n-Pr) | SO$_2$Me |
| 1632 | Et | Me | Et | Me | O(n-Pr) | SO$_2$Me |
| 1633 | Et | Me | Et | SO$_2$Me | H | CF$_3$ |

TABLE 1-continued (I-2)

| No. | R¹ | R² | R³ | R⁴ | R⁵ | R⁶ |
|---|---|---|---|---|---|---|
| 1634 | Me | Me | Et | Me | $CH_2OCH_2CF_3$ | $SO_2Me$ |
| 1635 | Me | Me | Et | Cl | $CH_2OCH_2CF_3$ | $SO_2Me$ |
| 1636 | Et | Me | Et | Me | Cl | $SO_2Me$ |
| 1637 | Me | Me | Et | Me | $CH_2SO_2Me$ | $SO_2Me$ |
| 1638 | Me | Me | Et | Me | $CH_2OEt$ | $SO_2Me$ |
| 1639 | Me | Me | Me | Cl | $CH_2OMe$ | $SO_2Me$ |
| 1640 | Me | Me | Et | Me | $CH_2CH_2OMe$ | $SO_2Me$ |
| 1641 | Me | Me | Et | Me | $CH_2OCH_2CH_2OMe$ | $SO_2Me$ |
| 1642 | Me | Me | Et | Me | $OCH_2CH_2OEt$ | $SO_2Me$ |
| 1643 | Me | Me | Et | Me | $OCH_2CH_2Cl$ | $SO_2Me$ |
| 1644 | Me | Me | Et | Me | $OCH_2CF_3$ | $SO_2Me$ |
| 1645 | Me | Me | Et | Me | $CH_2OCH_2OMe$ | $SO_2Me$ |
| 1646 | Me | Me | Et | Me | $OCH_2CH_2SMe$ | $SO_2Me$ |
| 1647 | Me | Me | Et | Me | CN | $SO_2Me$ |
| 1648 | Me | Me | Et | Me | $CH_2CN$ | $SO_2Me$ |
| 1649 | Me | Me | n-Pr | Me | $CO_2Me$ | $SO_2Me$ |
| 1650 | Et | Me | n-Pr | Me | $CO_2Me$ | $SO_2Me$ |
| 1651 | Me | Me | i-Pr | Me | $CO_2Me$ | $SO_2Me$ |
| 1652 | Et | Me | i-Pr | Me | $CO_2Me$ | $SO_2Me$ |
| 1653 | Me | Me | s-Bu | Me | $CO_2Me$ | $SO_2Me$ |
| 1654 | Et | Me | s-Bu | Me | $CO_2Me$ | $SO_2Me$ |
| 1655 | Me | Me | Bn | Me | $CO_2Me$ | $SO_2Me$ |
| 1656 | Et | Me | Bn | Me | $CO_2Me$ | $SO_2Me$ |
| 1657 | Me | Me | Et | Br | $CO_2Me$ | $SO_2Me$ |
| 1658 | Et | Me | Et | Cl | $CO_2Me$ | $SO_2Me$ |
| 1659 | Me | Me | Me | Br | $CO_2Me$ | $SO_2Me$ |
| 1660 | Et | Me | Me | Cl | $CO_2Me$ | $SO_2Me$ |
| 1661 | Me | Me | Allyl | Me | $CO_2Me$ | $SO_2Me$ |
| 1662 | Et | Me | Allyl | Me | $CO_2Me$ | $SO_2Me$ |
| 1663 | Me | Me | $CH_2CH(CH_3)=CH_2$ | Me | $CO_2Me$ | $SO_2Me$ |
| 1664 | Et | Me | $CH_2CH(CH_3)=CH_2$ | Me | $CO_2Me$ | $SO_2Me$ |
| 1665 | Me | Me | Et | Cl | $OCH_2CH_2OCF_3$ | $SO_2Me$ |
| 1666 | Et | Me | Et | Cl | $OCH_2CH_2OCF_3$ | $SO_2Me$ |
| 1667 | Me | Me | Et | Me | $OCH_2CH_2OCF_3$ | $SO_2Me$ |
| 1668 | Et | Me | Et | Me | $OCH_2CH_2OCF_3$ | $SO_2Me$ |
| 1669 | Me | Me | Et | $CF_3$ | $OCH_2CH_2OCF_3$ | $SO_2Me$ |
| 1670 | Et | Me | Et | $CF_3$ | $OCH_2CH_2OCF_3$ | $SO_2Me$ |
| 1671 | Me | Me | Et | Br | $OCH_2CH_2OCF_3$ | $SO_2Me$ |
| 1672 | Et | Me | Et | Br | $OCH_2CH_2OCF_3$ | $SO_2Me$ |
| 1673 | Me | Me | Et | $SO_2Me$ | $OCH_2CH_2OCF_3$ | $CF_3$ |
| 1674 | Et | Me | Et | $SO_2Me$ | $OCH_2CH_2OCF_3$ | $CF_3$ |
| 1675 | Me | Me | Et | Cl | $OCH_2CH_2OCHClF$ | $SO_2Me$ |
| 1676 | Et | Me | Et | Cl | $OCH_2CH_2OCHClF$ | $SO_2Me$ |
| 1677 | Me | Me | Et | Me | $OCH_2CH_2OCHClF$ | $SO_2Me$ |
| 1678 | Et | Me | Et | Me | $OCH_2CH_2OCHClF$ | $SO_2Me$ |
| 1679 | Me | Me | Et | $CF_3$ | $OCH_2CH_2OCHClF$ | $SO_2Me$ |
| 1680 | Et | Me | Et | $CF_3$ | $OCH_2CH_2OCHClF$ | $SO_2Me$ |
| 1681 | Me | Me | Et | Br | $OCH_2CH_2OCHClF$ | $SO_2Me$ |
| 1682 | Et | Me | Et | Br | $OCH_2CH_2OCHClF$ | $SO_2Me$ |
| 1683 | Me | Me | Et | $SO_2Me$ | $OCH_2CH_2OCHClF$ | $CF_3$ |
| 1684 | Et | Me | Et | $SO_2Me$ | $OCH_2CH_2OCHClF$ | $CF_3$ |
| 1685 | Me | Me | Et | Cl | $OCH_2CHFOCF_3$ | $SO_2Me$ |
| 1686 | Et | Me | Et | Cl | $OCH_2CHFOCF_3$ | $SO_2Me$ |
| 1687 | Me | Me | Et | Me | $OCH_2CHFOCF_3$ | $SO_2Me$ |
| 1688 | Me | Me | Et | Cl | $OCH_2CHFOMe$ | $SO_2Me$ |
| 1689 | Et | Me | Et | Cl | $OCH_2CHFOMe$ | $SO_2Me$ |
| 1690 | Me | Me | Et | Me | $OCH_2CHFOMe$ | $SO_2Me$ |
| 1691 | Et | Me | Et | Me | $OCH_2CHFOMe$ | $SO_2Me$ |
| 1692 | Me | Me | Et | $CF_3$ | $OCH_2CHFOMe$ | $SO_2Me$ |
| 1693 | Et | Me | Et | $CF_3$ | $OCH_2CHFOMe$ | $SO_2Me$ |
| 1694 | Me | Me | Et | Br | $OCH_2CHFOMe$ | $SO_2Me$ |
| 1695 | Et | Me | Et | Br | $OCH_2CHFOMe$ | $SO_2Me$ |
| 1696 | Me | Me | Et | $SO_2Me$ | $OCH_2CHFOMe$ | $CF_3$ |
| 1697 | Et | Me | Et | $SO_2Me$ | $OCH_2CHFOMe$ | $CF_3$ |
| 1698 | Me | Me | Et | Cl | $OCHFCH_2OCF_3$ | $SO_2Me$ |
| 1699 | Et | Me | Et | Cl | $OCHFCH_2OCF_3$ | $SO_2Me$ |

TABLE 1-continued (I-2)

| No. | R¹ | R² | R³ | R⁴ | R⁵ | R⁶ |
|---|---|---|---|---|---|---|
| 1700 | Me | Me | Et | Cl | OCH$_2$CH$_2$OCF$_2$Cl | SO$_2$Me |
| 1701 | Et | Me | Et | Cl | OCH$_2$CH$_2$OCF$_2$Cl | SO$_2$Me |
| 1702 | Me | Me | Et | Me | OCH$_2$CH$_2$OCF$_2$Cl | SO$_2$Me |
| 1703 | Et | Me | Et | Me | OCH$_2$CH$_2$OCF$_2$Cl | SO$_2$Me |
| 1704 | Me | Me | Et | CF$_3$ | OCH$_2$CH$_2$OCF$_2$Cl | SO$_2$Me |
| 1705 | Et | Me | Et | CF$_3$ | OCH$_2$CH$_2$OCF$_2$Cl | SO$_2$Me |
| 1706 | Me | Me | Et | Br | OCH$_2$CH$_2$OCF$_2$Cl | SO$_2$Me |
| 1707 | Et | Me | Et | Br | OCH$_2$CH$_2$OCF$_2$Cl | SO$_2$Me |
| 1708 | Me | Me | Et | SO$_2$Me | OCH$_2$CH$_2$OCF$_2$Cl | CF$_3$ |
| 1709 | Et | Me | Et | SO$_2$Me | OCH$_2$CH$_2$OCF$_2$Cl | CF$_3$ |
| 1710 | Me | Me | Et | Cl | SCH$_2$CH$_2$OCH$_3$ | SO$_2$Me |
| 1711 | Et | Me | Et | Cl | SCH$_2$CH$_2$OCH$_3$ | SO$_2$Me |
| 1712 | Me | Me | Et | Me | SCH$_2$CH$_2$OCH$_3$ | SO$_2$Me |
| 1713 | Et | Me | Et | Me | SCH$_2$CH$_2$OCH$_3$ | SO$_2$Me |
| 1714 | Me | Me | Et | CF$_3$ | SCH$_2$CH$_2$OCH$_3$ | SO$_2$Me |
| 1715 | Et | Me | Et | CF$_3$ | SCH$_2$CH$_2$OCH$_3$ | SO$_2$Me |
| 1716 | Me | Me | Et | Br | SCH$_2$CH$_2$OCH$_3$ | SO$_2$Me |
| 1717 | Et | Me | Et | Br | SCH$_2$CH$_2$OCH$_3$ | SO$_2$Me |
| 1718 | Me | Me | Et | SO$_2$Me | SCH$_2$CH$_2$OCH$_3$ | CF$_3$ |
| 1719 | Et | Me | Et | SO$_2$Me | SCH$_2$CH$_2$OCH$_3$ | CF$_3$ |
| 1720 | Me | Me | Et | Cl | SCH$_2$CH$_2$OCF$_3$ | SO$_2$Me |
| 1721 | Et | Me | Et | Cl | SCH$_2$CH$_2$OCF$_3$ | SO$_2$Me |
| 1722 | Me | Me | Et | Me | SCH$_2$CH$_2$OCF$_3$ | SO$_2$Me |
| 1723 | Et | Me | Et | Me | SCH$_2$CH$_2$OCF$_3$ | SO$_2$Me |
| 1724 | Me | Me | Et | CF$_3$ | SCH$_2$CH$_2$OCF$_3$ | SO$_2$Me |
| 1725 | Et | Me | Et | CF$_3$ | SCH$_2$CH$_2$OCF$_3$ | SO$_2$Me |
| 1726 | Me | Me | Et | Br | SCH$_2$CH$_2$OCF$_3$ | SO$_2$Me |
| 1727 | Et | Me | Et | Br | SCH$_2$CH$_2$OCF$_3$ | SO$_2$Me |
| 1728 | Me | Me | Et | SO$_2$Me | SCH$_2$CH$_2$OCF$_3$ | CF$_3$ |
| 1729 | Et | Me | Et | SO$_2$Me | SCH$_2$CH$_2$OCF$_3$ | CF$_3$ |
| 1730 | Me | Me | Et | Cl | SCH$_2$CH$_2$SCH$_3$ | SO$_2$Me |
| 1731 | Et | Me | Et | Cl | SCH$_2$CH$_2$SCH$_3$ | SO$_2$Me |
| 1732 | Me | Me | Et | Me | SCH$_2$CH$_2$SCH$_3$ | SO$_2$Me |
| 1733 | Et | Me | Et | Me | SCH$_2$CH$_2$SCH$_3$ | SO$_2$Me |
| 1734 | Me | Me | Et | CF$_3$ | SCH$_2$CH$_2$SCH$_3$ | SO$_2$Me |
| 1735 | Et | Me | Et | CF$_3$ | SCH$_2$CH$_2$SCH$_3$ | SO$_2$Me |
| 1736 | Me | Me | Et | Br | SCH$_2$CH$_2$SCH$_3$ | SO$_2$Me |
| 1737 | Et | Me | Et | Br | SCH$_2$CH$_2$SCH$_3$ | SO$_2$Me |
| 1738 | Me | Me | Et | SO$_2$Me | SCH$_2$CH$_2$SCH$_3$ | CF$_3$ |
| 1739 | Et | Me | Et | SO$_2$Me | SCH$_2$CH$_2$SCH$_3$ | CF$_3$ |
| 1740 | Me | Me | Et | Cl | SCH$_2$CH$_2$SCF$_3$ | SO$_2$Me |
| 1741 | Et | Me | Et | Cl | SCH$_2$CH$_2$SCF$_3$ | SO$_2$Me |
| 1742 | Me | Me | Et | Me | SCH$_2$CH$_2$SCF$_3$ | SO$_2$Me |
| 1743 | Et | Me | Et | Me | SCH$_2$CH$_2$SCF$_3$ | SO$_2$Me |
| 1744 | Me | Me | Et | CF$_3$ | SCH$_2$CH$_2$SCF$_3$ | SO$_2$Me |
| 1745 | Et | Me | Et | CF$_3$ | SCH$_2$CH$_2$SCF$_3$ | SO$_2$Me |
| 1746 | Me | Me | Et | Br | SCH$_2$CH$_2$SCF$_3$ | SO$_2$Me |
| 1747 | Et | Me | Et | Br | SCH$_2$CH$_2$SCF$_3$ | SO$_2$Me |
| 1748 | Me | Me | Et | SO$_2$Me | SCH$_2$CH$_2$SCF$_3$ | CF$_3$ |
| 1749 | Et | Me | Et | SO$_2$Me | SCH$_2$CH$_2$SCF$_3$ | CF$_3$ |
| 1750 | Me | Me | Et | Cl | OCH$_2$CH(CH$_3$)OCH$_3$ | SO$_2$Me |
| 1751 | Et | Me | Et | Cl | OCH$_2$CH(CH$_3$)OCH$_3$ | SO$_2$Me |
| 1752 | Me | Me | Et | Me | OCH$_2$CH(CH$_3$)OCH$_3$ | SO$_2$Me |
| 1753 | Et | Me | Et | Me | OCH$_2$CH(CH$_3$)OCH$_3$ | SO$_2$Me |
| 1754 | Me | Me | Et | CF$_3$ | OCH$_2$CH(CH$_3$)OCH$_3$ | SO$_2$Me |
| 1755 | Et | Me | Et | CF$_3$ | OCH$_2$CH(CH$_3$)OCH$_3$ | SO$_2$Me |
| 1756 | Me | Me | Et | Br | OCH$_2$CH(CH$_3$)OCH$_3$ | SO$_2$Me |
| 1757 | Et | Me | Et | Br | OCH$_2$CH(CH$_3$)OCH$_3$ | SO$_2$Me |
| 1758 | Me | Me | Et | SO$_2$Me | OCH$_2$CH(CH$_3$)OCH$_3$ | CF$_3$ |
| 1759 | Et | Me | Et | SO$_2$Me | OCH$_2$CH(CH$_3$)OCH$_3$ | CF$_3$ |
| 1760 | Me | Me | Et | Cl | OCH$_2$CF$_2$OCH$_3$ | SO$_2$Me |
| 1761 | Et | Me | Et | Cl | OCH$_2$CF$_2$OCH$_3$ | SO$_2$Me |
| 1762 | Me | Me | Et | Me | OCH$_2$CF$_2$OCH$_3$ | SO$_2$Me |
| 1763 | Et | Me | Et | Me | OCH$_2$CF$_2$OCH$_3$ | SO$_2$Me |
| 1764 | Me | Me | Et | CF$_3$ | OCH$_2$CF$_2$OCH$_3$ | SO$_2$Me |
| 1765 | Et | Me | Et | CF$_3$ | OCH$_2$CF$_2$OCH$_3$ | SO$_2$Me |

TABLE 1-continued

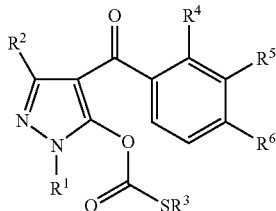

(I-2)

| No. | R¹ | R² | R³ | R⁴ | R⁵ | R⁶ |
|---|---|---|---|---|---|---|
| 1766 | Me | Me | Et | Br | OCH$_2$CF$_2$OCH$_3$ | SO$_2$Me |
| 1767 | Et | Me | Et | Br | OCH$_2$CF$_2$OCH$_3$ | SO$_2$Me |
| 1768 | Me | Me | Et | SO$_2$Me | OCH$_2$CF$_2$OCH$_3$ | CF$_3$ |
| 1769 | Et | Me | Et | SO$_2$Me | OCH$_2$CF$_2$OCH$_3$ | CF$_3$ |
| 1770 | Me | Me | i-Pr | Me | OCH$_2$CH$_2$OCH$_3$ | SO$_2$Me |
| 1771 | Et | Me | i-Pr | Me | OCH$_2$CH$_2$OCH$_3$ | SO$_2$Me |
| 1772 | Me | Me | Et | Me | OCH$_2$CH(OCH$_3$)$_2$ | SO$_2$Me |
| 1773 | Me | Me | Et | Me | CH$_2$N(Me)CH$_2$CN | SO$_2$Me |
| 1774 | Me | Me | Et | Me | (Tetrahydrofuran-2-yl)methoxy | SO$_2$Me |
| 1775 | Me | Me | Et | Cl | SMe | SO$_2$Me |
| 1776 | Me | Me | Et | Cl | Cl | SO$_2$Me |
| 1777 | Me | Me | Et | Cl | OMe | SO$_2$Me |
| 1778 | Me | Me | Et | Me | (Tetrahydro-2H-pyran-2-yl)methoxy | SO$_2$Me |
| 1779 | Me | Me | Et | CN | OCH$_2$CH$_2$OMe | SO$_2$Me |
| 1780 | Me | Me | Et | Me | Tetrahydrofuran-3-yloxy | SO$_2$Me |
| 1781 | Me | Me | Et | Me | OCH$_2$CH$_2$OMe | SO$_2$Me |
| 1782 | Me | Me | n-Pr | Me | OCH$_2$CH$_2$OMe | SO$_2$Me |
| 1783 | Et | Me | s-Bu | Cl | C(O)OMe | SO$_2$Me |
| 1784 | Et | Me | Et | Cl | 2-(1,3-Dioxolan-2-yl)ethoxy | SO$_2$Me |
| 1785 | Me | Me | Et | Me | Propargyloxy | SO$_2$Me |
| 1786 | Me | Me | Et | Me | (Tetrahydrofuran-3-yloxy)methyl | SO$_2$Me |
| 1787 | Me | Me | Et | Cl | SO$_2$Me | SO$_2$Me |
| 1788 | Me | Me | Et | Me | (CH$_2$)$_6$Me | SO$_2$Me |
| 1789 | Me | Me | Et | Me | CH$_2$CH$_2$CH$_2$OMe | SO$_2$Me |
| 1790 | Et | Me | Et | Cl | (1,3-Dioxolan-2-yl)methoxy | SO$_2$Me |
| 1791 | Me | Me | Et | Me | CH$_2$N[C(O)SEt]CH$_2$CN | SO$_2$Me |
| 1792 | Me | Me | Et | Me | CH=CHCN | SO$_2$Me |
| 1793 | Me | Me | Et | Me | CH$_2$CH$_2$CN | SO$_2$Me |
| 1794 | Me | Me | Et | Me | CH$_2$SCN | SO$_2$Me |
| 1795 | Me | Me | Et | Me | CH$_2$C(S)NH$_2$ | SO$_2$Me |
| 1796 | Me | Me | Me | Me | OCH$_2$CH$_2$OMe | SO$_2$Me |
| 1797 | Et | Me | Me | Me | OCH$_2$CH$_2$OMe | SO$_2$Me |
| 1798 | Et | Me | n-Pr | Me | OCH$_2$CH$_2$OMe | SO$_2$Me |
| 1799 | Me | Me | Et | Me | OCH(CH$_3$)CH$_2$OMe | SO$_2$Me |
| 1800 | Et | Me | Et | Me | OCH$_2$CH(Et)OMe | SO$_2$Me |
| 1801 | Me | Me | Et | Me | (1,3-Dioxolan-2-yl)methyl | SO$_2$Me |
| 1802 | Me | Me | s-Bu | Me | OCH$_2$CH$_2$OMe | SO$_2$Me |
| 1803 | Me | Me | Et | Me | CH$_2$O(i-Pr) | SO$_2$Me |
| 1804 | Me | H | CH$_2$CF$_3$ | Cl | CO$_2$Et | SO$_2$Me |
| 1805 | Et | H | CH$_2$CF$_3$ | Me | CO$_2$Me | CF$_3$ |
| 1806 | Et | H | CH$_2$CF$_3$ | SO$_2$Me | CO$_2$Me | CN |
| 1807 | Me | H | CH$_2$CF$_3$ | Me | C(O)SMe | SO$_2$Me |
| 1808 | Me | H | CH$_2$CF$_3$ | Me | C(O)SEt | SO$_2$Me |
| 1809 | Me | H | CH$_2$CF$_3$ | Me | 2-(2-Oxolanyl)ethoxy | SO$_2$Me |
| 1810 | Me | H | CH$_2$CF$_3$ | Me | 2-(2-(1,3-Dioxolanyl))ethoxy | SO$_2$Me |
| 1811 | Et | H | CH$_2$CF$_3$ | Me | CH$_2$OMe | SO$_2$Me |
| 1812 | Et | H | CH$_2$CF$_3$ | Me | 2-Oxolanylmethoxymethyl | SO$_2$Me |
| 1813 | Me | H | CH$_2$CF$_3$ | Cl | CO$_2$Me | SO$_2$Me |
| 1814 | Et | H | CH$_2$CF$_3$ | Cl | CO$_2$Me | SO$_2$Et |
| 1815 | Me | H | CH$_2$CF$_3$ | Cl | C(O)SMe | SO$_2$Me |
| 1816 | Me | H | CH$_2$CF$_3$ | Cl | C(O)SEt | SO$_2$Me |
| 1817 | Me | H | CH$_2$CF$_3$ | Me | OMe | SO$_2$Me |
| 1818 | Me | H | CH$_2$CF$_3$ | Me | OEt | SO$_2$Me |
| 1819 | Me | H | CH$_2$CF$_3$ | Me | O(i-Pr) | SO$_2$Me |
| 1820 | Me | H | CH$_2$CF$_3$ | Me | OCHF$_2$ | SO$_2$Me |
| 1821 | Me | H | CH$_2$CF$_3$ | Me | (4,5-Dihydroisoxazol-3-yl) | SO$_2$Me |
| 1822 | Me | H | CH$_2$CF$_3$ | Me | O(n-Pr) | SO$_2$Et |
| 1823 | Me | H | CH$_2$CF$_3$ | Cl | CH$_2$OMe | SO$_2$Me |
| 1824 | Me | H | CH$_2$CF$_3$ | Me | OCO$_2$Me | SO$_2$Me |
| 1825 | Me | H | CH$_2$CF$_3$ | Me | OC(O)SMe | SO$_2$Me |
| 1826 | Me | H | CH$_2$CF$_3$ | Me | OC(O)SEt | SO$_2$Me |
| 1827 | Et | H | CH$_2$CF$_3$ | Me | OEt | SO$_2$Me |
| 1828 | Et | H | CH$_2$CF$_3$ | Cl | CO$_2$Et | SO$_2$Me |
| 1829 | Et | H | CH$_2$CF$_3$ | Cl | CO$_2$(n-Pr) | SO$_2$Me |
| 1830 | Et | H | CH$_2$CF$_3$ | Me | CO$_2$Et | SO$_2$Me |
| 1831 | Me | H | CH$_2$CF$_3$ | Me | CH$_2$CO$_2$Me | SO$_2$Me |

TABLE 1-continued (I-2)

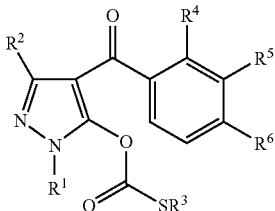

| No. | R¹ | R² | R³ | R⁴ | R⁵ | R⁶ |
|---|---|---|---|---|---|---|
| 1832 | Me | H | CH₂CF₃ | Me | OCH₂CO₂Et | SO₂Me |
| 1833 | Me | H | CH₂CF₃ | Me | O(n-Pr) | SO₂Me |
| 1834 | Et | H | CH₂CF₃ | SO₂Me | H | CF₃ |
| 1835 | Me | H | CH₂CF₃ | Me | CH₂OCH₂CF₃ | SO₂Me |
| 1836 | Me | H | CH₂CF₃ | Cl | CH₂OCH₂CF₃ | SO₂Me |
| 1837 | Et | H | CH₂CF₃ | Me | Cl | SO₂Me |
| 1838 | Me | H | CH₂CF₃ | Me | CH₂SO₂Me | SO₂Me |
| 1839 | Me | H | CH₂CF₃ | Me | CH₂OEt | SO₂Me |
| 1840 | Me | H | CH₂CF₃ | Cl | CH₂OMe | SO₂Me |
| 1841 | Me | H | CH₂CF₃ | Me | CH₂CH₂OMe | SO₂Me |
| 1842 | Me | H | CH₂CF₃ | Me | CH₂OCH₂CH₂OMe | SO₂Me |
| 1843 | Me | H | CH₂CF₃ | Me | OCH₂CH₂OEt | SO₂Me |
| 1844 | Me | H | CH₂CF₃ | Me | OCH₂CH₂Cl | SO₂Me |
| 1845 | Me | H | CH₂CF₃ | Me | OCH₂CF₃ | SO₂Me |
| 1846 | Me | H | CH₂CF₃ | Me | CH₂OCH₂OMe | SO₂Me |
| 1847 | Me | H | CH₂CF₃ | Me | OCH₂CH₂SMe | SO₂Me |
| 1848 | Me | H | CH₂CF₃ | Me | CN | SO₂Me |
| 1849 | Me | H | CH₂CF₃ | Me | CH₂CN | SO₂Me |
| 1850 | Me | H | CH₂CF₃ | Br | CO₂Me | SO₂Me |
| 1851 | Et | H | CH₂CF₃ | Cl | CO₂Me | SO₂Me |
| 1852 | Me | H | CH₂CF₃ | CN | CO₂Me | SO₂Me |
| 1853 | Me | H | CH₂CF₃ | Cl | OCH₂CH₂OCF₃ | SO₂Me |
| 1854 | Et | H | CH₂CF₃ | Cl | OCH₂CH₂OCF₃ | SO₂Me |
| 1855 | Me | H | CH₂CF₃ | Me | OCH₂CH₂OCF₃ | SO₂Me |
| 1856 | Et | H | CH₂CF₃ | Me | OCH₂CH₂OCF₃ | SO₂Me |
| 1857 | Me | H | CH₂CF₃ | CF₃ | OCH₂CH₂OCF₃ | SO₂Me |
| 1858 | Et | H | CH₂CF₃ | CF₃ | OCH₂CH₂OCF₃ | SO₂Me |
| 1859 | Me | H | CH₂CF₃ | Br | OCH₂CH₂OCF₃ | SO₂Me |
| 1860 | Et | H | CH₂CF₃ | Br | OCH₂CH₂OCF₃ | SO₂Me |
| 1861 | Me | H | CH₂CF₃ | SO₂Me | OCH₂CH₂OCF₃ | CF₃ |
| 1862 | Et | H | CH₂CF₃ | SO₂Me | OCH₂CH₂OCF₃ | CF₃ |
| 1863 | Me | H | CH₂CF₃ | Cl | OCH₂CH₂OCHClF | SO₂Me |
| 1864 | Et | H | CH₂CF₃ | Cl | OCH₂CH₂OCHClF | SO₂Me |
| 1865 | Me | H | CH₂CF₃ | Me | OCH₂CH₂OCHClF | SO₂Me |
| 1866 | Et | H | CH₂CF₃ | Me | OCH₂CH₂OCHClF | SO₂Me |
| 1867 | Me | H | CH₂CF₃ | CF₃ | OCH₂CH₂OCHClF | SO₂Me |
| 1868 | Et | H | CH₂CF₃ | CF₃ | OCH₂CH₂OCHClF | SO₂Me |
| 1869 | Me | H | CH₂CF₃ | Br | OCH₂CH₂OCHClF | SO₂Me |
| 1870 | Et | H | CH₂CF₃ | Br | OCH₂CH₂OCHClF | SO₂Me |
| 1871 | Me | H | CH₂CF₃ | SO₂Me | OCH₂CH₂OCHClF | CF₃ |
| 1872 | Et | H | CH₂CF₃ | SO₂Me | OCH₂CH₂OCHClF | CF₃ |
| 1873 | Me | H | CH₂CF₃ | Cl | OCH₂CHFOCF₃ | SO₂Me |
| 1874 | Et | H | CH₂CF₃ | Cl | OCH₂CHFOCF₃ | SO₂Me |
| 1875 | Me | H | CH₂CF₃ | Me | OCH₂CHFOCF₃ | SO₂Me |
| 1876 | Me | H | CH₂CF₃ | Cl | OCH₂CHFOMe | SO₂Me |
| 1877 | Et | H | CH₂CF₃ | Cl | OCH₂CHFOMe | SO₂Me |
| 1878 | Me | H | CH₂CF₃ | Me | OCH₂CHFOMe | SO₂Me |
| 1879 | Et | H | CH₂CF₃ | Me | OCH₂CHFOMe | SO₂Me |
| 1880 | Me | H | CH₂CF₃ | CF₃ | OCH₂CHFOMe | SO₂Me |
| 1881 | Et | H | CH₂CF₃ | CF₃ | OCH₂CHFOMe | SO₂Me |
| 1882 | Me | H | CH₂CF₃ | Br | OCH₂CHFOMe | SO₂Me |
| 1883 | Et | H | CH₂CF₃ | Br | OCH₂CHFOMe | SO₂Me |
| 1884 | Me | H | CH₂CF₃ | SO₂Me | OCH₂CHFOMe | CF₃ |
| 1885 | Et | H | CH₂CF₃ | SO₂Me | OCH₂CHFOMe | CF₃ |
| 1886 | Me | H | CH₂CF₃ | Cl | OCHFCH₂OCF₃ | SO₂Me |
| 1887 | Et | H | CH₂CF₃ | Cl | OCHFCH₂OCF₃ | SO₂Me |
| 1888 | Me | H | CH₂CF₃ | Cl | OCH₂CH₂OCF₂Cl | SO₂Me |
| 1889 | Et | H | CH₂CF₃ | Cl | OCH₂CH₂OCF₂Cl | SO₂Me |
| 1890 | Me | H | CH₂CF₃ | Me | OCH₂CH₂OCF₂Cl | SO₂Me |
| 1891 | Et | H | CH₂CF₃ | Me | OCH₂CH₂OCF₂Cl | SO₂Me |
| 1892 | Me | H | CH₂CF₃ | CF₃ | OCH₂CH₂OCF₂Cl | SO₂Me |
| 1893 | Et | H | CH₂CF₃ | CF₃ | OCH₂CH₂OCF₂Cl | SO₂Me |
| 1894 | Me | H | CH₂CF₃ | Br | OCH₂CH₂OCF₂Cl | SO₂Me |
| 1895 | Et | H | CH₂CF₃ | Br | OCH₂CH₂OCF₂Cl | SO₂Me |
| 1896 | Me | H | CH₂CF₃ | SO₂Me | OCH₂CH₂OCF₂Cl | CF₃ |
| 1897 | Et | H | CH₂CF₃ | SO₂Me | OCH₂CH₂OCF₂Cl | CF₃ |

TABLE 1-continued

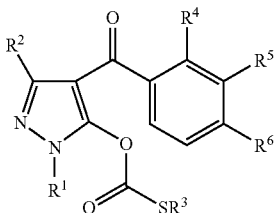

(I-2)

| No. | R¹ | R² | R³ | R⁴ | R⁵ | R⁶ |
|---|---|---|---|---|---|---|
| 1898 | Me | H | $CH_2CF_3$ | Cl | $SCH_2CH_2OCH_3$ | $SO_2Me$ |
| 1899 | Et | H | $CH_2CF_3$ | Cl | $SCH_2CH_2OCH_3$ | $SO_2Me$ |
| 1900 | Me | H | $CH_2CF_3$ | Me | $SCH_2CH_2OCH_3$ | $SO_2Me$ |
| 1901 | Et | H | $CH_2CF_3$ | Me | $SCH_2CH_2OCH_3$ | $SO_2Me$ |
| 1902 | Me | H | $CH_2CF_3$ | $CF_3$ | $SCH_2CH_2OCH_3$ | $SO_2Me$ |
| 1903 | Et | H | $CH_2CF_3$ | $CF_3$ | $SCH_2CH_2OCH_3$ | $SO_2Me$ |
| 1904 | Me | H | $CH_2CF_3$ | Br | $SCH_2CH_2OCH_3$ | $SO_2Me$ |
| 1905 | Et | H | $CH_2CF_3$ | Br | $SCH_2CH_2OCH_3$ | $SO_2Me$ |
| 1906 | Me | H | $CH_2CF_3$ | $SO_2Me$ | $SCH_2CH_2OCH_3$ | $CF_3$ |
| 1907 | Et | H | $CH_2CF_3$ | $SO_2Me$ | $SCH_2CH_2OCH_3$ | $CF_3$ |
| 1908 | Me | H | $CH_2CF_3$ | Cl | $SCH_2CH_2OCF_3$ | $SO_2Me$ |
| 1909 | Et | H | $CH_2CF_3$ | Cl | $SCH_2CH_2OCF_3$ | $SO_2Me$ |
| 1910 | Me | H | $CH_2CF_3$ | Me | $SCH_2CH_2OCF_3$ | $SO_2Me$ |
| 1911 | Et | H | $CH_2CF_3$ | Me | $SCH_2CH_2OCF_3$ | $SO_2Me$ |
| 1912 | Me | H | $CH_2CF_3$ | $CF_3$ | $SCH_2CH_2OCF_3$ | $SO_2Me$ |
| 1913 | Et | H | $CH_2CF_3$ | $CF_3$ | $SCH_2CH_2OCF_3$ | $SO_2Me$ |
| 1914 | Me | H | $CH_2CF_3$ | Br | $SCH_2CH_2OCF_3$ | $SO_2Me$ |
| 1915 | Et | H | $CH_2CF_3$ | Br | $SCH_2CH_2OCF_3$ | $SO_2Me$ |
| 1916 | Me | H | $CH_2CF_3$ | $SO_2Me$ | $SCH_2CH_2OCF_3$ | $CF_3$ |
| 1917 | Et | H | $CH_2CF_3$ | $SO_2Me$ | $SCH_2CH_2OCF_3$ | $CF_3$ |
| 1918 | Me | H | $CH_2CF_3$ | Cl | $SCH_2CH_2SCH_3$ | $SO_2Me$ |
| 1919 | Et | H | $CH_2CF_3$ | Cl | $SCH_2CH_2SCH_3$ | $SO_2Me$ |
| 1920 | Me | H | $CH_2CF_3$ | Me | $SCH_2CH_2SCH_3$ | $SO_2Me$ |
| 1921 | Et | H | $CH_2CF_3$ | Me | $SCH_2CH_2SCH_3$ | $SO_2Me$ |
| 1922 | Me | H | $CH_2CF_3$ | $CF_3$ | $SCH_2CH_2SCH_3$ | $SO_2Me$ |
| 1923 | Et | H | $CH_2CF_3$ | $CF_3$ | $SCH_2CH_2SCH_3$ | $SO_2Me$ |
| 1924 | Me | H | $CH_2CF_3$ | Br | $SCH_2CH_2SCH_3$ | $SO_2Me$ |
| 1925 | Et | H | $CH_2CF_3$ | Br | $SCH_2CH_2SCH_3$ | $SO_2Me$ |
| 1926 | Me | H | $CH_2CF_3$ | $SO_2Me$ | $SCH_2CH_2SCH_3$ | $CF_3$ |
| 1927 | Et | H | $CH_2CF_3$ | $SO_2Me$ | $SCH_2CH_2SCH_3$ | $CF_3$ |
| 1928 | Me | H | $CH_2CF_3$ | Cl | $SCH_2CH_2SCF_3$ | $SO_2Me$ |
| 1929 | Et | H | $CH_2CF_3$ | Cl | $SCH_2CH_2SCF_3$ | $SO_2Me$ |
| 1930 | Me | H | $CH_2CF_3$ | Me | $SCH_2CH_2SCF_3$ | $SO_2Me$ |
| 1931 | Et | H | $CH_2CF_3$ | Me | $SCH_2CH_2SCF_3$ | $SO_2Me$ |
| 1932 | Me | H | $CH_2CF_3$ | $CF_3$ | $SCH_2CH_2SCF_3$ | $SO_2Me$ |
| 1933 | Et | H | $CH_2CF_3$ | $CF_3$ | $SCH_2CH_2SCF_3$ | $SO_2Me$ |
| 1934 | Me | H | $CH_2CF_3$ | Br | $SCH_2CH_2SCF_3$ | $SO_2Me$ |
| 1935 | Et | H | $CH_2CF_3$ | Br | $SCH_2CH_2SCF_3$ | $SO_2Me$ |
| 1936 | Me | H | $CH_2CF_3$ | $SO_2Me$ | $SCH_2CH_2SCF_3$ | $CF_3$ |
| 1937 | Et | H | $CH_2CF_3$ | $SO_2Me$ | $SCH_2CH_2SCF_3$ | $CF_3$ |
| 1938 | Me | H | $CH_2CF_3$ | Cl | $OCH_2CH(CH_3)OCH_3$ | $SO_2Me$ |
| 1939 | Et | H | $CH_2CF_3$ | Cl | $OCH_2CH(CH_3)OCH_3$ | $SO_2Me$ |
| 1940 | Me | H | $CH_2CF_3$ | Me | $OCH_2CH(CH_3)OCH_3$ | $SO_2Me$ |
| 1941 | Et | H | $CH_2CF_3$ | Me | $OCH_2CH(CH_3)OCH_3$ | $SO_2Me$ |
| 1942 | Me | H | $CH_2CF_3$ | $CF_3$ | $OCH_2CH(CH_3)OCH_3$ | $SO_2Me$ |
| 1943 | Et | H | $CH_2CF_3$ | $CF_3$ | $OCH_2CH(CH_3)OCH_3$ | $SO_2Me$ |
| 1944 | Me | H | $CH_2CF_3$ | Br | $OCH_2CH(CH_3)OCH_3$ | $SO_2Me$ |
| 1945 | Et | H | $CH_2CF_3$ | Br | $OCH_2CH(CH_3)OCH_3$ | $SO_2Me$ |
| 1946 | Me | H | $CH_2CF_3$ | $SO_2Me$ | $OCH_2CH(CH_3)OCH_3$ | $CF_3$ |
| 1947 | Et | H | $CH_2CF_3$ | $SO_2Me$ | $OCH_2CH(CH_3) OCH_3$ | $CF_3$ |
| 1948 | Me | H | $CH_2CF_3$ | Cl | $OCH_2CF_2OCH_3$ | $SO_2Me$ |
| 1949 | Et | H | $CH_2CF_3$ | Cl | $OCH_2CF_2OCH_3$ | $SO_2Me$ |
| 1950 | Me | H | $CH_2CF_3$ | Me | $OCH_2CF_2OCH_3$ | Me |
| 1951 | Et | H | $CH_2CF_3$ | Me | $OCH_2CF_2OCH_3$ | $SO_2Me$ |
| 1952 | Me | H | $CH_2CF_3$ | $CF_3$ | $OCH_2CF_2OCH_3$ | $SO_2Me$ |
| 1953 | Et | H | $CH_2CF_3$ | $CF_3$ | $OCH_2CF_2OCH_3$ | $SO_2Me$ |
| 1954 | Me | H | $CH_2CF_3$ | Br | $OCH_2CF_2OCH_3$ | $SO_2Me$ |
| 1955 | Et | H | $CH_2CF_3$ | Br | $OCH_2CF_2OCH_3$ | $SO_2Me$ |
| 1956 | Me | H | $CH_2CF_3$ | $SO_2Me$ | $OCH_2CF_2OCH_3$ | $CF_3$ |
| 1957 | Et | H | $CH_2CF_3$ | $SO_2Me$ | $OCH_2CF_2OCH_3$ | $CF_3$ |
| 1958 | Me | H | $CH_2CF_3$ | Me | $OCH_2CH_2OCH_3$ | $SO_2Me$ |
| 1959 | Et | H | $CH_2CF_3$ | Me | $OCH_2CH_2OCH_3$ | $SO_2Me$ |
| 1960 | Me | H | $CH_2CF_3$ | Me | $OCH_2CH(OCH_3)_2$ | $SO_2Me$ |
| 1961 | Me | H | $CH_2CF_3$ | Me | $CH_2N(Me)CH_2CN$ | $SO_2Me$ |
| 1962 | Me | H | $CH_2CF_3$ | Me | (Tetrahydrofuran-2-yl)methoxy | $SO_2Me$ |
| 1963 | Me | H | $CH_2CF_3$ | Cl | SMe | $SO_2Me$ |

TABLE 1-continued

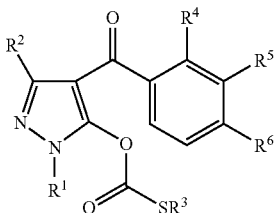

(I-2)

| No. | R¹ | R² | R³ | R⁴ | R⁵ | R⁶ |
|---|---|---|---|---|---|---|
| 1964 | Me | H | $CH_2CF_3$ | Cl | Cl | $SO_2Me$ |
| 1965 | Me | H | $CH_2CF_3$ | Cl | OMe | $SO_2Me$ |
| 1966 | Me | H | $CH_2CF_3$ | Me | (Tetrahydro-2H-pyran-2-yl)methoxy | $SO_2Me$ |
| 1967 | Me | H | $CH_2CF_3$ | Cl | $OCH_2CH_2OMe$ | $SO_2Me$ |
| 1968 | Me | H | $CH_2CF_3$ | Me | Tetrahydrofuran-3-yloxy | $SO_2Me$ |
| 1969 | Me | H | $CH_2CF_3$ | Me | $OCH_2CH_2CH_2OMe$ | $SO_2Me$ |
| 1970 | Me | H | $CH_2CF_3$ | Me | $OCH_2CH_2OMe$ | $SO_2Me$ |
| 1971 | Et | H | $CH_2CF_3$ | Cl | 2-(1,3-Dioxolan-2-yl)ethoxy | $SO_2Me$ |
| 1972 | Me | H | $CH_2CF_3$ | Me | Propargyloxy | $SO_2Me$ |
| 1973 | Me | H | $CH_2CF_3$ | Me | (Tetrahydrofuran-3-yloxy)methyl | $SO_2Me$ |
| 1974 | Me | H | $CH_2CF_3$ | Cl | $SO_2Me$ | $SO_2Me$ |
| 1975 | Me | H | $CH_2CF_3$ | Me | $(CH_2)_6Me$ | $SO_2Me$ |
| 1976 | Me | H | $CH_2CF_3$ | Me | $CH_2CH_2CH_2OMe$ | $SO_2Me$ |
| 1977 | Et | H | $CH_2CF_3$ | Cl | (1,3-Dioxolan-2-yl)methoxy | $SO_2Me$ |
| 1978 | Me | H | $CH_2CF_3$ | Me | $CH_2N[C(O)SEt]CH_2CN$ | $SO_2Me$ |
| 1979 | Me | H | $CH_2CF_3$ | Me | CH=CHCN | $SO_2Me$ |
| 1980 | Me | H | $CH_2CF_3$ | Me | $CH_2CH_2CN$ | $SO_2Me$ |
| 1981 | Me | H | $CH_2CF_3$ | Me | $CH_2SCN$ | $SO_2Me$ |
| 1982 | Me | H | $CH_2CF_3$ | Me | $CH_2C(S)NH_2$ | $SO_2Me$ |
| 1983 | Me | H | $CH_2CF_3$ | CN | $OCH_2CH_2OMe$ | $SO_2Me$ |
| 1984 | Et | H | $CH_2CF_3$ | Me | $OCH_2CH_2OMe$ | $SO_2Me$ |
| 1985 | Me | H | $CH_2CF_3$ | Me | $OCH(CH_3)CH_2OMe$ | $SO_2Me$ |
| 1986 | Et | H | $CH_2CF_3$ | Me | $OCH_2CH(Et)OMe$ | $SO_2Me$ |
| 1987 | Me | H | $CH_2CF_3$ | Me | (1,3-Dioxolan-2-yl)methyl | $SO_2Me$ |
| 1988 | Me | H | $CH_2CF_3$ | Me | $CH_2O(i-Pr)$ | $SO_2Me$ |
| 1989 | Me | H | $CH_2CHF_2$ | Cl | $CO_2Et$ | $SO_2Me$ |
| 1990 | Et | H | $CH_2CHF_2$ | Me | $CO_2Me$ | $CF_3$ |
| 1991 | Et | H | $CH_2CHF_2$ | $SO_2Me$ | $CO_2Me$ | CN |
| 1992 | Me | H | $CH_2CHF_2$ | Me | C(O)SMe | $SO_2Me$ |
| 1993 | Me | H | $CH_2CHF_2$ | Me | C(O)SEt | $SO_2Me$ |
| 1994 | Me | H | $CH_2CHF_2$ | Me | 2-(2-Oxolanyl)ethoxy | $SO_2Me$ |
| 1995 | Me | H | $CH_2CHF_2$ | Me | 2-(2-(1,3-Dioxolanyl))ethoxy | $SO_2Me$ |
| 1996 | Et | H | $CH_2CHF_2$ | Me | $CH_2OMe$ | $SO_2Me$ |
| 1997 | Et | H | $CH_2CHF_2$ | Me | 2-Oxolanylmethoxymethyl | $SO_2Me$ |
| 1998 | Me | H | $CH_2CHF_2$ | Cl | $CO_2Me$ | $SO_2Me$ |
| 1999 | Et | H | $CH_2CHF_2$ | Cl | $CO_2Me$ | $SO_2Et$ |
| 2000 | Me | H | $CH_2CHF_2$ | Cl | C(O)SMe | $SO_2Me$ |
| 2001 | Me | H | $CH_2CHF_2$ | Cl | C(O)SEt | $SO_2Me$ |
| 2002 | Me | H | $CH_2CHF_2$ | Me | OMe | $SO_2Me$ |
| 2003 | Me | H | $CH_2CHF_2$ | Me | OEt | $SO_2Me$ |
| 2004 | Me | H | $CH_2CHF_2$ | Me | O(i-Pr) | $SO_2Me$ |
| 2005 | Me | H | $CH_2CHF_2$ | Me | $OCHF_2$ | $SO_2Me$ |
| 2006 | Me | H | $CH_2CHF_2$ | Me | (4,5-Dihydroisoxazol-3-yl) | $SO_2Me$ |
| 2007 | Me | H | $CH_2CHF_2$ | Me | O(n-Pr) | $SO_2Et$ |
| 2008 | Me | H | $CH_2CHF_2$ | Cl | $CH_2OMe$ | $SO_2Me$ |
| 2009 | Me | H | $CH_2CHF_2$ | Me | $OCO_2Me$ | $SO_2Me$ |
| 2010 | Me | H | $CH_2CHF_2$ | Me | OC(O)SMe | $SO_2Me$ |
| 2011 | Me | H | $CH_2CHF_2$ | Me | OC(O)SEt | $SO_2Me$ |
| 2012 | Et | H | $CH_2CHF_2$ | Me | OEt | $SO_2Me$ |
| 2013 | Et | H | $CH_2CHF_2$ | Cl | $CO_2Et$ | $SO_2Me$ |
| 2014 | Et | H | $CH_2CHF_2$ | Cl | $CO_2(n-Pr)$ | $SO_2Me$ |
| 2015 | Et | H | $CH_2CHF_2$ | Me | $CO_2Et$ | $SO_2Me$ |
| 2016 | Me | H | $CH_2CHF_2$ | Me | $CH_2CO_2Me$ | $SO_2Me$ |
| 2017 | Me | H | $CH_2CHF_2$ | Me | $OCH_2CO_2Et$ | $SO_2Me$ |
| 2018 | Me | H | $CH_2CHF_2$ | Me | O(n-Pr) | $SO_2Me$ |
| 2019 | Et | H | $CH_2CHF_2$ | $SO_2Me$ | H | $CF_3$ |
| 2020 | Me | H | $CH_2CHF_2$ | Me | $CH_2OCH_2CF_3$ | $SO_2Me$ |
| 2021 | Me | H | $CH_2CHF_2$ | Cl | $CH_2OCH_2CF_3$ | $SO_2Me$ |
| 2022 | Et | H | $CH_2CHF_2$ | Me | Cl | $SO_2Me$ |
| 2023 | Me | H | $CH_2CHF_2$ | Me | $CH_2SO_2Me$ | $SO_2Me$ |
| 2024 | Me | H | $CH_2CHF_2$ | Me | $CH_2OEt$ | $SO_2Me$ |
| 2025 | Me | H | $CH_2CHF_2$ | Cl | $CH_2OMe$ | $SO_2Me$ |
| 2026 | Me | H | $CH_2CHF_2$ | Me | $CH_2CH_2OMe$ | $SO_2Me$ |
| 2027 | Me | H | $CH_2CHF_2$ | Me | $CH_2OCH_2CH_2OMe$ | $SO_2Me$ |
| 2028 | Me | H | $CH_2CHF_2$ | Me | $OCH_2CH_2OEt$ | $SO_2Me$ |
| 2029 | Me | H | $CH_2CHF_2$ | Me | $OCH_2CH_2Cl$ | $SO_2Me$ |

TABLE 1-continued

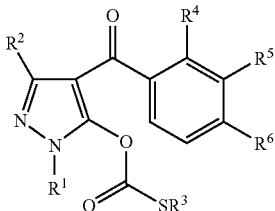

(I-2)

| No. | $R^1$ | $R^2$ | $R^3$ | $R^4$ | $R^5$ | $R^6$ |
|---|---|---|---|---|---|---|
| 2030 | Me | H | $CH_2CHF_2$ | Me | $OCH_2CF_3$ | $SO_2Me$ |
| 2031 | Me | H | $CH_2CHF_2$ | Me | $CH_2OCH_2OMe$ | $SO_2Me$ |
| 2032 | Me | H | $CH_2CHF_2$ | Me | $OCH_2CH_2SMe$ | $SO_2Me$ |
| 2033 | Me | H | $CH_2CHF_2$ | Me | CN | $SO_2Me$ |
| 2034 | Me | H | $CH_2CHF_2$ | Me | $CH_2CN$ | $SO_2Me$ |
| 2035 | Me | H | $CH_2CHF_2$ | Br | $CO_2Me$ | $SO_2Me$ |
| 2036 | Et | H | $CH_2CHF_2$ | Cl | $CO_2Me$ | $SO_2Me$ |
| 2037 | Me | H | $CH_2CHF_2$ | CN | $CO_2Me$ | $SO_2Me$ |
| 2038 | Me | H | $CH_2CHF_2$ | Cl | $OCH_2CH_2OCF_3$ | $SO_2Me$ |
| 2039 | Et | H | $CH_2CHF_2$ | Cl | $OCH_2CH_2OCF_3$ | $SO_2Me$ |
| 2040 | Me | H | $CH_2CHF_2$ | Me | $OCH_2CH_2OCF_3$ | $SO_2Me$ |
| 2041 | Et | H | $CH_2CHF_2$ | Me | $OCH_2CH_2OCF_3$ | $SO_2Me$ |
| 2042 | Me | H | $CH_2CHF_2$ | $CF_3$ | $OCH_2CH_2OCF_3$ | $SO_2Me$ |
| 2043 | Et | H | $CH_2CHF_2$ | $CF_3$ | $OCH_2CH_2OCF_3$ | $SO_2Me$ |
| 2044 | Me | H | $CH_2CHF_2$ | Br | $OCH_2CH_2OCF_3$ | $SO_2Me$ |
| 2045 | Et | H | $CH_2CHF_2$ | Br | $OCH_2CH_2OCF_3$ | $SO_2Me$ |
| 2046 | Me | H | $CH_2CHF_2$ | $SO_2Me$ | $OCH_2CH_2OCF_3$ | $CF_3$ |
| 2047 | Et | H | $CH_2CHF_2$ | $SO_2Me$ | $OCH_2CH_2OCF_3$ | $CF_3$ |
| 2048 | Me | H | $CH_2CHF_2$ | Cl | $OCH_2CH_2OCHClF$ | $SO_2Me$ |
| 2049 | Et | H | $CH_2CHF_2$ | Cl | $OCH_2CH_2OCHClF$ | $SO_2Me$ |
| 2050 | Me | H | $CH_2CHF_2$ | Me | $OCH_2CH_2OCHClF$ | $SO_2Me$ |
| 2051 | Et | H | $CH_2CHF_2$ | Me | $OCH_2CH_2OCHClF$ | $SO_2Me$ |
| 2052 | Me | H | $CH_2CHF_2$ | $CF_3$ | $OCH_2CH_2OCHClF$ | $SO_2Me$ |
| 2053 | Et | H | $CH_2CHF_2$ | $CF_3$ | $OCH_2CH_2OCHClF$ | $SO_2Me$ |
| 2054 | Me | H | $CH_2CHF_2$ | Br | $OCH_2CH_2OCHClF$ | $SO_2Me$ |
| 2055 | Et | H | $CH_2CHF_2$ | Br | $OCH_2CH_2OCHClF$ | $SO_2Me$ |
| 2056 | Me | H | $CH_2CHF_2$ | $SO_2Me$ | $OCH_2CH_2OCHClF$ | $CF_3$ |
| 2057 | Et | H | $CH_2CHF_2$ | $SO_2Me$ | $OCH_2CH_2OCHClF$ | $CF_3$ |
| 2058 | Me | H | $CH_2CHF_2$ | Cl | $OCH_2CHFOCF_3$ | $SO_2Me$ |
| 2059 | Et | H | $CH_2CHF_2$ | Cl | $OCH_2CHFOCF_3$ | $SO_2Me$ |
| 2060 | Me | H | $CH_2CHF_2$ | Me | $OCH_2CHFOCF_3$ | $SO_2Me$ |
| 2061 | Me | H | $CH_2CHF_2$ | Cl | $OCH_2CHFOMe$ | $SO_2Me$ |
| 2062 | Et | H | $CH_2CHF_2$ | Cl | $OCH_2CHFOMe$ | $SO_2Me$ |
| 2063 | Me | H | $CH_2CHF_2$ | Me | $OCH_2CHFOMe$ | $SO_2Me$ |
| 2064 | Et | H | $CH_2CHF_2$ | Me | $OCH_2CHFOMe$ | $SO_2Me$ |
| 2065 | Me | H | $CH_2CHF_2$ | $CF_3$ | $OCH_2CHFOMe$ | $SO_2Me$ |
| 2066 | Et | H | $CH_2CHF_2$ | $CF_3$ | $OCH_2CHFOMe$ | $SO_2Me$ |
| 2067 | Me | H | $CH_2CHF_2$ | Br | $OCH_2CHFOMe$ | $SO_2Me$ |
| 2068 | Et | H | $CH_2CHF_2$ | Br | $OCH_2CHFOMe$ | $SO_2Me$ |
| 2069 | Me | H | $CH_2CHF_2$ | $SO_2Me$ | $OCH_2CHFOMe$ | $CF_3$ |
| 2070 | Et | H | $CH_2CHF_2$ | $SO_2Me$ | $OCH_2CHFOMe$ | $CF_3$ |
| 2071 | Me | H | $CH_2CHF_2$ | Cl | $OCHFCH_2OCF_3$ | $SO_2Me$ |
| 2072 | Et | H | $CH_2CHF_2$ | Cl | $OCHFCH_2OCF_3$ | $SO_2Me$ |
| 2073 | Me | H | $CH_2CHF_2$ | Cl | $OCH_2CH_2OCF_2Cl$ | $SO_2Me$ |
| 2074 | Et | H | $CH_2CHF_2$ | Cl | $OCH_2CH_2OCF_2Cl$ | $SO_2Me$ |
| 2075 | Me | H | $CH_2CHF_2$ | Me | $OCH_2CH_2OCF_2Cl$ | $SO_2Me$ |
| 2076 | Et | H | $CH_2CHF_2$ | Me | $OCH_2CH_2OCF_2Cl$ | $SO_2Me$ |
| 2077 | Me | H | $CH_2CHF_2$ | $CF_3$ | $OCH_2CH_2OCF_2Cl$ | $SO_2Me$ |
| 2078 | Et | H | $CH_2CHF_2$ | $CF_3$ | $OCH_2CH_2OCF_2Cl$ | SO Me |
| 2079 | Me | H | $CH_2CHF_2$ | Br | $OCH_2CH_2OCF_2Cl$ | $SO_2Me$ |
| 2080 | Et | H | $CH_2CHF_2$ | Br | $OCH_2CH_2OCF_2Cl$ | $SO_2Me$ |
| 2081 | Me | H | $CH_2CHF_2$ | $SO_2Me$ | $OCH_2CH_2OCF_2Cl$ | $CF_3$ |
| 2082 | Et | H | $CH_2CHF_2$ | $SO_2Me$ | $OCH_2CH_2OCF_2Cl$ | $CF_3$ |
| 2083 | Me | H | $CH_2CHF_2$ | Cl | $SCH_2CH_2OCH_3$ | $SO_2Me$ |
| 2084 | Et | H | $CH_2CHF_2$ | Cl | $SCH_2CH_2OCH_3$ | $SO_2Me$ |
| 2085 | Me | H | $CH_2CHF_2$ | Me | $SCH_2CH_2OCH_3$ | $SO_2Me$ |
| 2086 | Et | H | $CH_2CHF_2$ | Me | $SCH_2CH_2OCH_3$ | $SO_2Me$ |
| 2087 | Me | H | $CH_2CHF_2$ | $CF_3$ | $SCH_2CH_2OCH_3$ | $SO_2Me$ |
| 2088 | Et | H | $CH_2CHF_2$ | $CF_3$ | $SCH_2CH_2OCH_3$ | $SO_2Me$ |
| 2089 | Me | H | $CH_2CHF_2$ | Br | $SCH_2CH_2OCH_3$ | $SO_2Me$ |
| 2090 | Et | H | $CH_2CHF_2$ | Br | $SCH_2CH_2OCH_3$ | $SO_2Me$ |
| 2091 | Me | H | $CH_2CHF_2$ | $SO_2Me$ | $SCH_2CH_2OCH_3$ | $CF_3$ |
| 2092 | Et | H | $CH_2CHF_2$ | $SO_2Me$ | $SCH_2CH_2OCH_3$ | $CF_3$ |
| 2093 | Me | H | $CH_2CHF_2$ | Cl | $SCH_2CH_2OCF_3$ | $SO_2Me$ |
| 2094 | Et | H | $CH_2CHF_2$ | Cl | $SCH_2CH_2OCF_3$ | $SO_2Me$ |
| 2095 | Me | H | $CH_2CHF_2$ | Me | $SCH_2CH_2OCF_3$ | $SO_2Me$ |

TABLE 1-continued (I-2)

| No. | R¹ | R² | R³ | R⁴ | R⁵ | R⁶ |
|---|---|---|---|---|---|---|
| 2096 | Et | H | CH₂CHF₂ | Me | SCH₂CH₂OCF₃ | SO₂Me |
| 2097 | Me | H | CH₂CHF₂ | CF₃ | SCH₂CH₂OCF₃ | SO₂Me |
| 2098 | Et | H | CH₂CHF₂ | CF₃ | SCH₂CH₂OCF₃ | SO₂Me |
| 2099 | Me | H | CH₂CHF₂ | Br | SCH₂CH₂OCF₃ | SO₂Me |
| 2100 | Et | H | CH₂CHF₂ | Br | SCH₂CH₂OCF₃ | SO₂Me |
| 2101 | Me | H | CH₂CHF₂ | SO₂Me | SCH₂CH₂OCF₃ | CF₃ |
| 2102 | Et | H | CH₂CHF₂ | SO₂Me | SCH₂CH₂OCF₃ | CF₃ |
| 2103 | Me | H | CH₂CHF₂ | Cl | SCH₂CH₂SCH₃ | SO₂Me |
| 2104 | Et | H | CH₂CHF₂ | Cl | SCH₂CH₂SCH₃ | SO₂Me |
| 2105 | Me | H | CH₂CHF₂ | Me | SCH₂CH₂SCH₃ | SO₂Me |
| 2106 | Et | H | CH₂CHF₂ | Me | SCH₂CH₂SCH₃ | SO₂Me |
| 2107 | Me | H | CH₂CHF₂ | CF₃ | SCH₂CH₂SCH₃ | SO₂Me |
| 2108 | Et | H | CH₂CHF₂ | CF₃ | SCH₂CH₂SCH₃ | SO₂Me |
| 2109 | Me | H | CH₂CHF₂ | Br | SCH₂CH₂SCH₃ | SO₂Me |
| 2110 | Et | H | CH₂CHF₂ | Br | SCH₂CH₂SCH₃ | SO₂Me |
| 2111 | Me | H | CH₂CHF₂ | SO₂Me | SCH₂CH₂SCH₃ | CF₃ |
| 2112 | Et | H | CH₂CHF₂ | SO₂Me | SCH₂CH₂SCH₃ | CF₃ |
| 2113 | Me | H | CH₂CHF₂ | Cl | SCH₂CH₂SCF₃ | SO₂Me |
| 2114 | Et | H | CH₂CHF₂ | Cl | SCH₂CH₂SCF₃ | SO₂Me |
| 2115 | Me | H | CH₂CHF₂ | Me | SCH₂CH₂SCF₃ | SO₂Me |
| 2116 | Et | H | CH₂CHF₂ | Me | SCH₂CH₂SCF₃ | SO₂Me |
| 2117 | Me | H | CH₂CHF₂ | CF₃ | SCH₂CH₂SCF₃ | SO₂Me |
| 2118 | Et | H | CH₂CHF₂ | CF₃ | SCH₂CH₂SCF₃ | SO₂Me |
| 2119 | Me | H | CH₂CHF₂ | Br | SCH₂CH₂SCF₃ | SO₂Me |
| 2120 | Et | H | CH₂CHF₂ | Br | SCH₂CH₂SCF₃ | SO₂Me |
| 2121 | Me | H | CH₂CHF₂ | SO₂Me | SCH₂CH₂SCF₃ | CF₃ |
| 2122 | Et | H | CH₂CHF₂ | SO₂Me | SCH₂CH₂SCF₃ | CF₃ |
| 2123 | Me | H | CH₂CHF₂ | Cl | OCH₂CH(CH₃)OCH₃ | SO₂Me |
| 2124 | Et | H | CH₂CHF₂ | Cl | OCH₂CH(CH₃)OCH₃ | SO₂Me |
| 2125 | Me | H | CH₂CHF₂ | Me | OCH₂CH(CH₃)OCH₃ | SO₂Me |
| 2126 | Et | H | CH₂CHF₂ | Me | OCH₂CH(CH₃)OCH₃ | SO₂Me |
| 2127 | Me | H | CH₂CHF₂ | CF₃ | OCH₂CH(CH₃)OCH₃ | SO₂Me |
| 2128 | Et | H | CH₂CHF₂ | CF₃ | OCH₂CH(CH₃)OCH₃ | SO₂Me |
| 2129 | Me | H | CH₂CHF₂ | Br | OCH₂CH(CH₃)OCH₃ | SO₂Me |
| 2130 | Et | H | CH₂CHF₂ | Br | OCH₂CH(CH₃)OCH₃ | SO₂Me |
| 2131 | Me | H | CH₂CHF₂ | SO₂Me | OCH₂CH(CH₃)OCH₃ | CF₃ |
| 2132 | Et | H | CH₂CHF₂ | SO₂Me | OCH₂CH(CH₃)OCH₃ | CF₃ |
| 2133 | Me | H | CH₂CHF₂ | Cl | OCH₂CF₂OCH₃ | SO₂Me |
| 2134 | Et | H | CH₂CHF₂ | Cl | OCH₂CF₂OCH₃ | SO₂Me |
| 2135 | Me | H | CH₂CHF₂ | Me | OCH₂CF₂OCH₃ | SO₂Me |
| 2136 | Et | H | CH₂CHF₂ | Me | OCH₂CF₂OCH₃ | SO₂Me |
| 2137 | Me | H | CH₂CHF₂ | CF₃ | OCH₂CF₂OCH₃ | SO₂Me |
| 2138 | Et | H | CH₂CHF₂ | CF₃ | OCH₂CF₂OCH₃ | SO₂Me |
| 2139 | Me | H | CH₂CHF₂ | Br | OCH₂CF₂OCH₃ | SO₂Me |
| 2140 | Et | H | CH₂CHF₂ | Br | OCH₂CF₂OCH₃ | SO₂Me |
| 2141 | Me | H | CH₂CHF₂ | SO₂Me | OCH₂CF₂OCH₃ | CF₃ |
| 2142 | Et | H | CH₂CHF₂ | SO₂Me | OCH₂CF₂OCH₃ | CF₃ |
| 2143 | Me | H | CH₂CHF₂ | Me | OCH₂CH₂OCH₃ | SO₂Me |
| 2144 | Et | H | CH₂CHF₂ | Me | OCH₂CH₂OCH₃ | SO₂Me |
| 2145 | Me | H | CH₂CHF₂ | Me | OCH₂CH(OCH₃)₂ | SO₂Me |
| 2146 | Me | H | CH₂CHF₂ | Me | CH₂N(Me)CH₂CN | SO₂Me |
| 2147 | Me | H | CH₂CHF₂ | Me | (Tetrahydrofuran-2-yl)methoxy | SO₂Me |
| 2148 | Me | H | CH₂CHF₂ | Cl | SMe | SO₂Me |
| 2149 | Me | H | CH₂CHF₂ | Cl | Cl | SO₂Me |
| 2150 | Me | H | CH₂CHF₂ | Cl | OMe | SO₂Me |
| 2151 | Me | H | CH₂CHF₂ | Me | (Tetrahydro-2H-pyran-2-yl)methoxy | SO₂Me |
| 2152 | Me | H | CH₂CHF₂ | Cl | OCH₂CH₂OMe | SO₂Me |
| 2153 | Me | H | CH₂CHF₂ | Me | Tetrahydrofuran-3-yloxy | SO₂Me |
| 2154 | Me | H | CH₂CHF₂ | Me | OCH₂CH₂CH₂OMe | SO₂Me |
| 2155 | Me | H | CH₂CHF₂ | CN | OCH₂CH₂OMe | SO₂Me |
| 2156 | Et | H | CH₂CHF₂ | Cl | 2-(1,3-Dioxolan-2-yl)ethoxy | SO₂Me |
| 2157 | Me | H | CH₂CHF₂ | Me | Propargyloxy | SO₂Me |
| 2158 | Me | H | CH₂CHF₂ | Me | (Tetrahydrofuran-3-yloxy)methyl | SO₂Me |
| 2159 | Me | H | CH₂CHF₂ | Cl | SO₂Me | SO₂Me |
| 2160 | Me | H | CH₂CHF₂ | Me | (CH₂)₆Me | SO₂Me |
| 2161 | Me | H | CH₂CHF₂ | Me | CH₂CH₂CH₂OMe | SO₂Me |

TABLE 1-continued

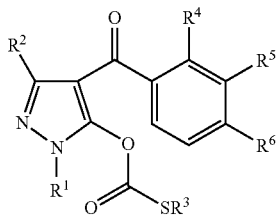

(I-2)

| No. | R¹ | R² | R³ | R⁴ | R⁵ | R⁶ |
|---|---|---|---|---|---|---|
| 2162 | Et | H | $CH_2CHF_2$ | Cl | (1,3-Dioxolan-2-yl)methoxy | $SO_2Me$ |
| 2163 | Me | H | $CH_2CHF_2$ | Me | $CH_2N[C(O)SEt]CH_2CN$ | $SO_2Me$ |
| 2164 | Me | H | $CH_2CHF_2$ | Me | CH=CHCN | $SO_2Me$ |
| 2165 | Me | H | $CH_2CHF_2$ | Me | $CH_2CH_2CN$ | $SO_2Me$ |
| 2166 | Me | H | $CH_2CHF_2$ | Me | $CH_2SCN$ | $SO_2Me$ |
| 2167 | Me | H | $CH_2CHF_2$ | Me | $CH_2C(S)NH_2$ | $SO_2Me$ |
| 2168 | Me | H | $CH_2CHF_2$ | $NO_2$ | $OCH_2CH_2OMe$ | $SO_2Me$ |
| 2169 | Et | H | $CH_2CHF_2$ | Me | $OCH_2CH_2OMe$ | $SO_2Me$ |
| 2170 | Me | H | $CH_2CHF_2$ | Me | $OCH(CH_3)CH_2OMe$ | $SO_2Me$ |
| 2171 | Et | H | $CH_2CHF_2$ | Me | $OCH_2CH(Et)OMe$ | $SO_2Me$ |
| 2172 | Me | H | $CH_2CHF_2$ | Me | (1,3-Dioxolan-2-yl)methyl | $SO_2Me$ |
| 2173 | Me | H | $CH_2CHF_2$ | Me | $CH_2O(i-Pr)$ | $SO_2Me$ |

TABLE 2

| No. | ¹H-NMR δ ppm (solvent: $CDCl_3$, measuring instrument: JEOL-GSX (400 MHz) or VARIAN MERCURY plus(300 MHz)/the same applies hereinafter) |
|---|---|
| 1 | 1.29 (t, 3H), 2.24 (s, 3H), 2.85 (q, 2H), 3.13 (s, 3H), 3.68 (s, 3H), 3.93 (s, 3H), 7.45 (d, 1H), 7.68 (s, 1H), 7.91 (d, 1H). |
| 2 | 1.31 (t, 3H), 1.41 (t, 3H), 2.27 (s, 3H), 2.88 (q, 2H), 3.21 (s, 3H), 3.96 (s, 3H), 4.03 (q, 2H), 7.48 (d, 1H), 7.70 (s, 1H), 7.93 (d, 1H). |
| 3 | 2.26 (s, 3H), 2.36 (s, 3H), 3.16 (s, 3H), 3.70 (s, 3H), 3.97 (s, 3H), 7.46 (d, 1H, J = 8.4 Hz), 7.73 (s, 1H), 7.94 (d, 1H, J = 8.4 Hz). |
| 4 | 1.42 (t, 3H, J = 7.3 Hz), 2.27 (s, 3H), 2.37 (s, 3H), 3.17 (s, 3H), 3.97 (s, 3H), 4.01 (q, 2H, J = 7.3 Hz), 7.47 (d, 1H, J = 7.8 Hz), 7.74 (s, 1H), 7.94 (d, 1H, J = 7.8 Hz). |
| 16 | 1.33 (t, 3H, J = 7.3 Hz), 1.42 (t, 3H, J = 7.3 Hz), 2.30 (s, 3H), 2.89 (q, 2H, J = 7.3 Hz), 3.27 (s, 3H), 3.45 (s, 3H), 3.79 (m, 2H), 4.01 (q, 2H, J = 7.3 Hz), 7.21 (d, 1H, J = 7.8 Hz), 7.65 (s, 1H), 7.86 (d, 1H, J = 7.8 Hz). |
| 27 | 1.32 (t, 3H, J = 7.4 Hz), 2.89 (q, 2H, J = 7.4 Hz), 3.18 (s, 3H), 3.71 (s, 3H), 3.99 (s, 3H), 7.52 (d, 1H, J = 8.2 Hz), 7.75 (s, 1H), 8.01 (d, 1H, J = 8.4 Hz). |
| 29 | 2.38 (s, 3H), 3.18 (s, 3H), 3.71 (s, 3H), 3.99 (s, 3H), 7.52 (d, 1H, J = 8.4 Hz), 7.76 (s, 1H), 8.02 (d, 1H, J = 8.0 Hz). |
| 31 | 1.32 (t, 3H, J = 7.4 Hz), 2.59 (s, 3H), 2.89 (q, 2H, J = 7.4 Hz), 3.16 (s, 3H), 3.71 (s, 3H), 7.52 (d, 1H, J = 7.8 Hz), 7.78 (s, 1H), 8.04 (d, 1H, J = 7.8 Hz). |
| 35 | 1.32 (t, 3H, J = 7.3 Hz), 2.27 (s, 3H), 2.89 (q, 2H, J = 7.3 Hz), 3.23 (s, 3H), 3.72 (s, 3H), 3.95 (s, 3H), 7.19 (d, 1H, J = 7.6 Hz), 7.67 (s, 1H), 7.85 (d, 1H, J = 7.6 Hz) |
| 36 | 1.33 (t, 3H, J = 7.2 Hz), 1.47 (t, 3H, J = 7.2 Hz), 2.26 (s, 3H), 2.88 (q, 2H, J = 7.2 Hz), 3.25 (s, 3H), 3.72 (s, 3H), 4.12 (q, 2H, J = 7.2 Hz), 7.18 (d, 1H, J = 7.9 Hz), 7.69 (s, 1H), 7.85 (d, 1H, J = 7.9 Hz). |
| 37 | 1.33 (m, 9H), 2.24 (s, 3H), 2.91 (q, 2H, J = 7.5 Hz), 3.21 (s, 3H), 3.72 (s, 3H), 4.82 (qq, 1H, J = 6.0, 6.0 Hz), 7.15 (d, 1H, J = 8.0 Hz), 7.63 (s, 1H), 7.90 (d, 1H, J = 8.0 Hz). |
| 38 | 1.33 (t, 3H, J = 7.4 Hz), 2.33 (s, 3H), 2.89 (q, 2H, J = 7.4 Hz), 3.21 (s, 3H), 3.72 (s, 3H), 6.75 (t, 1H, J = 75.2 Hz), 7.35 (d, 1H, J = 8.4 Hz), 7.67 (s, 1H), 7.96 (d, 1H, J = 8.4 Hz). |
| 39 | 1.32 (t, 3H, J = 7.5 Hz), 2.25 (s, 3H), 2.89 (q, 2H, J = 7.5 Hz), 3.18 (s, 3H), 3.3 (br s, 2H), 3.72 (s, 3H), 4.57 (t, 2H, J = 10 Hz), 7.50 (d, 1H, J = 8.4 Hz), 7.70 (s, 1H), 8.04 (d, 1H, J = 8.4 Hz). |
| 40 | 2.15 (s, 3H), 2.37 (s, 3H), 3.18 (s, 3H), 3.3 (br s, 2H), 3.72 (s, 3H), 4.57 (t, 2H, J = 10.2 Hz), 7.49 (d, 1H, J = 8.0 Hz), 7.73 (s, 1H), 8.04 (d, 1H, J = 8.0 Hz). |
| 42 | 1.31 (t, 3H, J = 7.4 Hz), 2.87 (q, 2H, J = 7.4 Hz), 3.25 (s, 3H), 3.49 (s, 3H), 3.70 (s, 3H), 5.09 (s, 2H), 7.42 (d, 1H, J = 8.0 Hz), 7.70 (s, 1H), 8.11 (d, 1H, J = 8.0 Hz). |
| 55 | 1.33 (t, 3H, J = 7.4 Hz), 2.29 (s, 3H), 2.89 (q, 2H, J = 7.4 Hz), 3.28 (s, 3H), 3.45 (s, 3H), 3.72 (s, 3H), 3.79 (m, 2H), 4.23 (m, 2H), 7.20 (d, 1H, J = 8.0 Hz), 7.66 (s, 1H), 7.86 (d, 1H, J = 8.0 Hz). |

TABLE 2-continued

| No. | $^1$H-NMR δ ppm (solvent: CDCl$_3$, measuring instrument: JEOL-GSX (400 MHz) or VARIAN MERCURY plus(300 MHz)/the same applies hereinafter) |
|---|---|
| 58 | 1.33 (t, 3H, J = 7.4 Hz), 1.42 (t, 3H, J = 7.4 Hz), 1.47 (t, 3H, J = 6.8 Hz), 2.26 (s, 3H), 2.89 (q, 2H, J = 7.4 Hz), 3.25 (s, 3H), 4.02 (q, 2H, J = 7.4 Hz), 4.12 (q, 2H, J = 6.8 Hz), 7.19 (d, 1H, J = 8.0 Hz), 7.66 (s, 1H), 7.85 (d, 1H, J = 8.0 Hz). |
| 59 | 1.32 (t, 3H, J = 7.6 Hz), 1.40 (t, 3H, J = 7.2 Hz), 1.43 (t, 3H, J = 7.2 Hz), 2.90 (q, 2H, J = 7.6 Hz), 4.01 (q, 2H, J = 7.3 Hz), 4.47 (q, 2H, J = 7.2 Hz), 7.52 (d, 1H, J = 8.4 Hz), 7.74 (s, 1H), 8.01 (d, 1H, J = 8.4 Hz). |
| 60 | 1.00 (t, 3H, J = 7.6 Hz), 1.33 (t, 3H, J = 7.4 Hz), 1.43 (t, 3H, J = 7.2 Hz), 1.80 (qt, 2H, J = 6.9, 6.9 Hz), 2.90 (q, 2H, J = 7.3 Hz), 3.19 (s, 3H), 4.01 (q, 2H, J = 7.3 Hz), 4.37 (t, 2H, J = 6.8 Hz), 7.52 (d, 1H, J = 8.4 Hz), 7.74 (s, 1H), 8.01 (d, 1H, J = 8.4 Hz). |
| 61 | 1.31 (t, 3H, J = 7.2 Hz), 1.39 (t, 3H, J = 7.2 Hz), 1.42 (t, 3H, J = 7.4 Hz), 2.29 (s, 3H), 2.89 (d, 2H, J = 7.4 Hz), 3.17 (s, 3H), 4.01 (q, 2H, J = 7.2 Hz), 4.44 (d, 2H, J = 7.2 Hz), 7.47 (d, 1H, J = 7.6 Hz), 7.71 (s, 1H), 7.93 (d, 7.6 Hz). |
| 62 | 1.39 (t, 3H, J = 7.4 Hz), 1.42 (t, 3H, J = 7.4 Hz), 2.28 (s, 3H), 2.37 (s, 3H), 3.17 (s, 3H), 4.01 (q, 2H, J = 7.4 Hz), 4.44 (q, 2H, J = 7.1 Hz), 7.47 (d, 1H, J = 8.4 Hz), 7.74 (s, 1H), 7.94 (d, 1H, 8.4 Hz). |
| 63 | 1.31 (t, 3H, J = 7.4 Hz), 2.37 (s, 3H), 2.87 (q, 2H, J = 7.4 Hz), 3.19 (s, 3H), 3.48 (s, 3H), 3.71 (s, 3H), 4.93 (s, 2H), 7.37 (d, 1H, J = 8.2 Hz), 7.64 (s, 1H), 8.03 (d, 1H, J = 8.2 Hz) |
| 64 | 1.35 (t, 3H, J = 7.5 Hz), 2.24 (s, 3H), 2.91 (q, 2H, J = 7.5 Hz), 3.15 (s, 3H), 3.734 (s, 3H), 3.736 (s, 3H), 4.40 (s, 2H), 7.39 (d, 1H, J = 8.1 Hz), 7.65 (s, 1H), 8.05 (d, 1H, J = 8.1 Hz). |
| 65 | 1.31 (t, 3H, J = 7.2 Hz), 1.34 (t, 3H, J = 7.4 Hz), 2.27 (s, 3H), 2.89 (q, 2H, J = 7.3 Hz), 3.35 (s, 3H), 3.19 (s, 3H), 4.29 (q, 2H, J = 7.2 Hz), 4.65 (s, 2H), 7.26 (d, 1H, J = 8.0 Hz), 7.67 (s, 1H), 7.87 (d, 1H, J = 8.0 Hz) |
| 66 | 1.06 (t, 3H, J = 7.6 Hz), 1.32 (t, 3H, J = 7.6 Hz), 1.89 (qt, 2H, J = 6.9, 7.1 Hz), 2.25 (s, 3H), 2.32 (q, 2H, J = 7.3 Hz), 3.33 (s, 3H), 3.71 (s, 3H), 4.03 (t, 2H, J = 6.7 Hz), 7.17 (d, 1H, J = 8.0 Hz), 7.66 (s, 1H), 7.85 (d, 1H, J = 8.0 Hz). |
| 67 | 1.06 (t, 3H, J = 7.2 Hz), 1.34 (t, 3H, J = 7.2 Hz), 1.42 (t, 3H, J = 7.0 Hz), 1.89 (qt, 2H, J = 6.9, 6.9 Hz), 2.26 (s, 3H), 2.89 (q, 2H, J = 7.2 Hz), 3.24 (s, 3H), 3.9-4.0 (m, 4H), 7.19 (d, 1H, J = 8.0 Hz), 7.66 (s, 1H), 7.86 (d, 1H, J = 8.0 Hz). |
| 68 | 1.31 (t, 3H, J = 7.2 Hz), 1.43 (t, 3H, J = 7.4 Hz), 2.87 (q, 2H, J = 7.4 Hz), 3.28 (s, 3H), 3.99 (q, 2H, J = 7.2 Hz), 7.58 (d, 1H, J = 7.6 Hz), 7.69 (s, 1H), 7.93 (d, 1H, J = 7.6 Hz), 8.37 (br s, 1H). |
| 69 | 1.30 (t, 3H, J = 7.2 Hz), 2.38 (s, 3H), 2.86 (q, 2H, J = 7.2 Hz), 3.16 (s, 3H), 3.72 (s, 3H), 4.00 (q, 2H, J = 8.8 Hz), 5.21 (s, 1H), 7.42 (d, 1H, J = 8.2 Hz), 7.67 (s, 1H), 8.05 (d, 1H, J = 8.2 Hz). |
| 70 | 1.32 (t, 3H, J = 7.6 Hz), 2.87 (q, 2H, J = 7.6 Hz), 3.22 (s, 3H), 3.71 (s, 3H), 4.02 (q, 2H, J = 8.8 Hz), 5.35 (s, 2H), 7.48 (d, 1H, J = 8.4 Hz), 7.72 (s, 1H), 8.14 (d, 1H, J = 8.4 Hz). |
| 71 | 1.27 (t, 3H, J = 7.2 Hz), 1.37 (t, 3H, J = 7.2 Hz), 2.33 (s, 3H), 2.83 (q, 2H, J = 7.2 Hz), 3.25 (s, 3H), 3.96 (q, 2H, J = 7.2 Hz), 7.30 (d, 1H, J = 7.8 Hz), 7.65 (s, 1H), 8.03 (d, 1H, J = 7.8 Hz). |
| 72 | 1.33 (t, 3H, J = 7.2 Hz), 2.49 (s, 3H), 2.90 (q, 2H, J = 7.2 Hz), 3.01 (s, 3H), 3.29 (s, 3H), 3.71 (s, 3H), 7.44 (d, 1H, J = 8.0 Hz), 7.63 (s, 1H), 8.02 (d, 1H, J = 8.0 Hz). |
| 73 | 1.24 (t, 3H, J = 6.8 Hz), 1.31 (t, 3H, J = 7.2 Hz), 2.37 (s, 3H), 2.86 (q, 2H, J = 7.2 Hz), 3.29 (s, 3H), 3.67 (q, 2H, J = 6.8 Hz), 3.71 (s, 3H), 4.97 (s, 2H), 7.37 (d, 1H, J = 8.0 Hz), 7.65 (s, 1H), 8.03 (d, 1H, J = 8.0 Hz). |
| 74 | 2.36 (s, 3H), 3.26 (s, 3H), 3.49 (s, 3H), 3.71 (s, 3H), 5.09 (s, 2H), 7.42 (d, 1H, J = 8.0 Hz), 7.71 (s, 1H), 8.12 (d, 1H, J = 8.0 Hz). |
| 75 | 1.33 (t, 3H, J = 7.2 Hz), 2.33 (s, 3H), 2.88 (q, 2H, J = 7.2 Hz), 3.15 (s, 3H), 3.33 (s, 1H), 3.41 (t, 2H, J = 7.4 Hz), 3.63 (t, 2H, J = 7.4 Hz), 3.71 (s, 3H), 7.27 (d, 1H, J = 8.4 Hz), 7.64 (s, 1H), 8.00 (d, 1H, J = 8.4 Hz). |
| 76 | 1.32 (t, 3H, J = 7.2 Hz), 2.38 (s, 3H), 2.88 (q, 2H, J = 7.2 Hz), 3.24 (s, 3H), 3.33 (s, 3H), 3.56 (m, 2H), 3.71 (s, 3H), 3.76 (m, 2H), 5.04 (s, 2H), 7.37 (d, 1H, J = 7.6 Hz), 7.64 (s, 1H), 8.03 (d, 1H, J = 7.6 Hz). |
| 77 | 1.23 (t, 3H, J = 6.8 Hz), 1.33 (t, 3H, J = 7.2 Hz), 2.30 (s, 3H), 2.88 (q, 2H, J = 7.2 Hz), 3.28 (s, 3H), 3.60 (q, 2H, J = 6.8 Hz), 3.71 (s, 3H), 3.82 (m, 2H), 4.24 (m, 2H), 7.18 (d, 1H, J = 7.8 Hz), 7.66 (s, 1H), 7.85 (d, 1H, J = 7.8 Hz). |
| 78 | 1.34 (t, 3H, J = 7.2 Hz), 2.31 (s, 3H), 2.89 (q, 2H, J = 7.2 Hz), 3.26 (s, 3H), 3.72 (s, 3H), 3.91 (t, 2H, J = 5.2 Hz), 4.33 (t, 2H, J = 5.2 Hz), 7.23 (d, 1H, J = 8.0 Hz), 7.67 (s, 1H), 7.87 (d, 1H, J = 8.0 Hz). |
| 79 | 1.35 (t, 3H, J = 7.2 Hz), 2.30 (s, 3H), 2.89 (q, 2H, J = 7.2 Hz), 3.26 (s, 3H), 3.72 (s, 3H), 4.49 (q, 2H, J = 8.4 Hz), 7.30 (d, 1H, J = 8.0 Hz), 7.67 (s, 1H), 7.90 (d, 1H, J = 8.0 Hz). |
| 81 | 1.34 (t, 3H, J = 7.2 Hz), 2.19 (s, 3H), 2.29 (s, 3H), 2.89 (q, 2H, J = 7.2 Hz), 2.96 (t, 2H, J = 6.6 Hz), 3.27 (s, 3H), 3.72 (s, 3H), 4.23 (t, |

TABLE 2-continued

| | $^1$H-NMR δ ppm (solvent: CDCl$_3$, measuring instrument: JEOL-GSX |
|---|---|
| No. | (400 MHz) or VARIAN MERCURY plus(300 MHz)/the same applies hereinafter) |

| No. | |
|---|---|
| | 2H, J = 6.6 Hz), 7.20 (d, 1H, J = 8.4 Hz), 7.67 (s, 1H), 7.87 (d, 1H, J = 8.4 Hz). |
| 82 | 1.34 (t, 3H, J = 7.4 Hz), 2.61 (s, 3H), 2.90 (q, 2H, J = 7.5 Hz), 3.32 (s, 3H), 3.74 (s, 3H), 7.67 (d, 1H, J = 8.1 Hz), 7.72 (s, 1H), 8.12 (d, 1H, J = 8.1 Hz). |
| 83 | 1.34 (t, 3H, J = 7.4 Hz), 2.44 (s, 3H), 2.91 (q, 2H, J = 7.3 Hz), 3.22 (s, 3H), 3.74 (s, 3H), 4.44 (s, 2H), 7.48 (d, 1H, J = 8.1 Hz), 7.69 (s, 1H), 8.10 (d, 1H, J = 8.1 Hz). |
| 84 | 0.99 (t, 3H, J = 7.4 Hz), 1.65 (qt, 2H, J = 7.4, 7.4 Hz), 2.27 (s, 3H), 2.85 (t, 2H, J = 7.2 Hz), 3.16 (s, 3H), 3.71 (s, 3H), 3.97 (s, 3H), 7.47 (d, 1H, J = 8.0 Hz), 7.69 (s, 1H), 7.94 (d, 1H, J = 8.0 Hz) |
| 85 | 0.99 (t, 3H, J = 7.4 Hz), 1.42 (t, 3H, J = 7.2 Hz), 1.67 (qt, 2H, J = 7.4, 7.4 Hz), 2.28 (s, 3H), 2.86 (t, 2H, J = 7.4 Hz), 3.16 (s, 3H), 3.96 (s, 3H), 4.02 (quartet, 2H, J = 7.3 Hz), 7.44 (d, 1H, J = 8.0 Hz), 7.69 (s, 1H), 7.94 (d, 1H, J = 8.0 Hz) |
| 86 | 1.34 (d, 6H, J = 4.8 Hz), 2.28 (s, 3H), 3.16 (s, 3H), 3.50 (quintet, 1H, J = 6.8 Hz), 3.71 (s, 3H), 3.97 (s, 3H), 7.48 (d, 1H, J = 8.0 Hz), 7.69 (s, 1H), 7.94 (d, 1H, J = 8.0 Hz) |
| 87 | 1.34 (d, 6H, J = 4.8 Hz), 1.42 (t, 3H, J = 7.4 Hz), 2.28 (s, 3H), 3.16 (s, 3H), 3.51 (quintet, 1H, J = 6.9 Hz), 3.97 (s, 3H), 4.02 (quartet, 2H, J = 7.3 Hz), 7.48 (d, 1H, J = 8.0 Hz), 7.69 (s, 1H), 7.94 (d, 1H, J = 8.0 Hz) |
| 88 | 0.98 (t, 3H, J = 7.4 Hz), 1.36 (d, 6H, J = 6.8 Hz), 1.61-1.70 (m, 2H), 2.73 (s, 3H), 3.16 (s, 3H), 3.36 (qt, 1H, J = 6.8, 6.8 Hz), 3.71 (s, 3H), 3.96 (s, 3H), 7.48 (d, 1H, J = 7.6 Hz), 7.65 (s, 1H), 7.94 (d, 1H, J = 7.6 Hz) |
| 89 | 0.98 (t, 3H), 1.33 (d, 3H), 1.42 (t, 3H), 1.61-1.69 (m, 2H), 2.28 (s, 3H), 3.16 (s, 3H), 3.35 (m, 1H), 3.96 (s, 3H), 4.04 (q, 2H), 7.49 (d, 1H), 7.64 (s, 1H), 7.93 (d, 1H). |
| 90 | 1.47 (s, 9H), 2.29 (s, 3H), 3.17 (s, 3H), 3.71 (s, 3H), 3.96 (s, 3H), 7.48 (d, 1H, J = 8.0 Hz), 7.67 (s, 1H), 7.94 (d, 1H, J = 8.0 Hz) |
| 91 | 1.42 (t, 3H, J = 7.2 Hz), 1.47 (s, 9H), 2.29 (s, 3H), 3.17 (s, 3H), 3.96 (s, 3H), 4.02 (quartet, 2H, J = 7.3 Hz), 7.49 (d, 1H, J = 8.0 Hz), 7.67 (s, 1H), 7.94 (d, 1H, J = 8.0 Hz) |
| 92 | 2.29 (s, 3H), 3.14 (s, 3H), 3.68 (s, 3H), 3.98 (s, 3H), 4.130 (s, 2H), 7.26-7.33 (m, 5H), 7.47 (d, 1H, J = 8.0 Hz), 7.71 (s, 1H), 7.93 (d, 1H, J = 8.0 Hz) |
| 93 | 1.38 (t, 3H, J = 7.2 Hz), 2.29 (s, 3H), 3.15 (s, 3H), 3.95-4.00 (m, 5H), 4.10 (s, 2H), 7.25-7.34 (m, 5H), 7.43 (d, 1H, J = 8.0 Hz), 7.71 (s, 1H), 7.93 (d, 1H, J = 8.0 Hz) |
| 95 | 1.31 (t, 3H, J = 7.4 Hz), 1.40 (t, 3H, J = 7.4 Hz), 2.88 (q, 2H, J = 7.4 Hz), 3.17 (s, 3H), 3.97 (s, 3H), 3.98 (q, 2H, J = 7.4 Hz), 7.52 (d, 1H, J = 8.0 Hz), 7.73 (s, 1H), 7.97 (d, 1H, J = 8.0 Hz). |
| 97 | 1.42 (t, 3H, J = 7.4 Hz), 2.38 (s, 3H), 3.18 (s, 3H), 4.00 (s, 3H), 4.03 (q, 2H, J = 7.4 Hz), 7.52 (d, 1H, J = 8.0 Hz), 7.75 (s, 1H), 8.00 (d, 1H, J = 8.0 Hz). |
| 99 | 1.41 (t, 3H, J = 7.4 Hz), 2.27 (s, 3H), 3.16 (s, 3H), 3.53 (d, 2H, J = 7.6 Hz), 3.98 (s, 3H), 4.02 (q, 2H, J = 7.4 Hz), 5.19 (d, 1H, 10.9 Hz), 5.30 (d, 1H, J = 18.5 Hz), 5.8-5.9 (m, 1H), 7.48 (d, 1H, J = 8.0 Hz), 7.71 (s, 1H), 7.94 (d, 1H, J = 8.0 Hz). |
| 101 | 1.37 (t, 3H, J = 7.4 Hz), 1.75 (s, 3H), 2.23 (s, 3H), 3.11 (s, 3H), 3.50 (s, 2H), 3.74 (s, 3H), 3.93 (q, 2H, J = 7.4 Hz), 4.86 (s, 1H), 4.96 (s, 1H), 7.44 (d, 1H, J = 8.0 Hz), 7.63 (s, 1H), 7.89 (d, 1H, J = 8.0 Hz). |
| 189 | 1.27 (d, 3H, J = 6.4 Hz), 1.33 (t, 3H, J = 7.8 Hz), 2.29 (s, 3H), 2.89 (q, 2H, J = 7.8 Hz), 3.27 (s, 3H), 3.45 (s, 3H), 3.71 (s, 3H), 3.80 (m, 1H), 4.07 (m, 2H), 7.19 (d, 1H, J = 8.0 Hz), 7.65 (s, 1H), 7.86 (d, 1H, J = 8.0 Hz). |
| 207 | 1.37 (d, 6H, J = 7.0 Hz), 2.29 (s, 3H), 3.27 (s, 3H), 3.45 (s, 3H), 3.50 (tt, 1H, J = 7.0, 7.0 Hz), 3.71 (s, 3H), 3.79 (m, 2H), 4.24 (m, 2H), 7.20 (d, 1H, J = 7.6 Hz), 7.66 (s, 1H), 7.86 (d, 1H, J = 7.6 Hz). |
| 208 | 1.36 (d, 6H, J = 6.8 Hz), 1.42 (t, 3H, J = 7.2 Hz), 2.29 (s, 3H), 3.27 (s, 3H), 3.44 (s, 3H), 3.51 (tt, 1H, J = 6.8, 6.8 Hz), 3.79 (m, 2H), 4.00 (q, 2H, J = 7.2 Hz), 4.23 (m, 2H), 7.20 (d, 1H, J = 8.2 Hz), 7.64 (s, 1H), 7.85 (d, 1H, J = 8.2 Hz). |
| 209 | 1.33 (t, 3H, J = 7.4 Hz), 2.28 (s, 3H), 2.88 (q, 2H, J = 7.4 Hz), 3.27 (s, 3H), 3.47 (s, 6H), 3.71 (s, 3H), 4.09 (d, 2H, J = 5.4 Hz), 4.83 (t, 1H, J = 5.4 Hz), 7.20 (d, 1H, J = 8.2 Hz), 7.66 (s, 1H), 7.86 (d, 1H, J = 8.2 Hz). |
| 210 | 1.34 (t, 3H, J = 7.5 Hz), 2.39 (s, 6H), 2.89 (q, 2H, J = 7.5 Hz), 3.26 (s, 3H), 3.63 (s, 2H), 3.73 (s, 3H), 4.21 (s, 2H), 7.38 (d, 1H, J = 8.1 Hz), 7.67 (s, 1H), 8.08 (d, 1H, J = 8.1 Hz). |
| 211 | 1.33 (t, 3H, J = 7.6 Hz), 1.69 (m, 2H), 1.93 (m, 2H), 2.30 (s, 3H), 2.89 (q, 2H, J = 7.6 Hz), 3.28 (s, 3H), 3.17 (s, 3H), 3.85 (dt, 1H, J = 8.4, 6.8 Hz), 3.94 (dt, 1H, J = 8.4, 6.8 Hz), 4.07 (m, 2H), 4.37 (m, 1H), 7.20 (d, 1H, J = 7.6 Hz), 7.66 (s, 1H), 7.86 (d, 1H, J = 7.6 Hz). |

TABLE 2-continued

| | $^1$H-NMR δ ppm (solvent: CDCl$_3$, measuring instrument: JEOL-GSX |
|No.| (400 MHz) or VARIAN MERCURY plus(300 MHz)/the same applies hereinafter) |

212  1.32 (t, 3H, J = 7.4 Hz), 2.32 (s, 3H), 2.48 (s, 3H), 2.88 (q, 2H,
     J = 7.2 Hz), 3.70 (s, 3H), 7.11 (d, 1H, J = 8.4 Hz), 7.16 (d, 1H, J = 8.4 Hz),
     7.67 (s, 1H).
213  1.33 (t, 3H, J = 7.6 Hz), 2.50 (s, 3H), 2.90 (q, 2H, J = 7.6 Hz),
     3.71 (s, 3H), 7.06 (d, 1H, J = 8.4 Hz), 7.24 (d, 1H, J = 8.4 Hz),
     7.68 (s, 1H)
214  1.32 (t, 3H, J = 7.4 Hz), 2.88 (q, 2H, J = 7.4 Hz), 3.26 (s, 3H),
     3.71 (s, 3H), 4.10 (s, 3H), 7.21 (d, 1H, J = 8.0 Hz), 7.73 (s, 1H),
     7.92 (d, 1H, J = 8.0 Hz).
215  1.33 (t, 3H, J = 7.4 Hz), 1.5-1.9 (m, 6H), 2.29 (s, 3H), 2.89 (q,
     2H, J = 7.4 Hz), 3.27 (s, 3H), 3.52 (m, 1H), 3.71 (s, 3H), 3.81 (m,
     1H), 3.9-4.1 (m, 3H), 7.18 (d, 1H, J = 8.4 Hz), 7.65 (s, 1H),
     7.85 (d, 1H, J = 8.4 Hz).
216  1.33 (t, 3H, J = 7.2 Hz), 2.87 (q, 2H, J = 7.2 Hz), 3.31 (s, 3H),
     3.46 (s, 3H), 3.70 (s, 3H), 3.83 (m, 2H), 4.44 (m, 2H), 7.22 (d, 1H,
     J = 8.0 Hz), 7.72 (s, 1H), 7.94 (d, 1H, J = 8.0 Hz).
217  1.34 (t, 3H, J = 7.2 Hz), 2.12 (m, 1H), 2.40 (m, 1H), 2.90 (q, 2H,
     J = 7.2 Hz), 3.21 (s, 3H), 3.72 (s, 3H), 3.8-3.9 (m, 2H),
     4.1-4.2 (m, 2H), 5.16 (m, 1H), 7.19 (d, 1H, J = 8.4 Hz), 7.67 (s, 1H),
     7.93 (d, 1H, J = 8.4 Hz).
218  1.33 (t, 3H, J = 7.4 Hz), 2.13 (tt, 2H, J = 6.4, 6.4 Hz), 2.26 (s, 3H),
     2.88 (q, 2H, J = 7.4 Hz), 3.23 (s, 3H), 3.35 (s, 3H), 3.59 (t, 2H,
     J = 6.4 Hz), 3.71 (s, 3H), 4.16 (t, 2H, J = 6.4 Hz), 7.18 (d, 1H, J = 8.0 Hz),
     7.67 (s, 1H), 7.85 (d, 1H, J = 8.0 Hz).
219  0.99 (t, 3H, J = 7.4 Hz), 1.68 (qt, 2H, J = 7.4, 7.4 Hz), 2.30 (s, 3H),
     2.86 (t, 2H, J = 7.4 Hz), 3.27 (s, 3H), 3.45 (s, 3H), 3.71 (s, 3H),
     3.79 (m, 2H), 4.23 (m, 2H), 7.19 (d, 1H, J = 8.0 Hz), 7.64 (s, 1H),
     7.86 (d, 1H, J = 8.0 Hz).
220  0.98 (t, 3H, J = 7.4 Hz), 1.36 (d, 3H, J = 7.4 Hz), 1.43 (t, 3H, J = 7.4 Hz),
     1.6-1.7 (m, 2H), 3.15 (s, 3H), 3.3-3.4 (m, 1H), 4.00 (s, 3H),
     4.0-4.1 (m, 2H), 7.54 (d, 1H, J = 8.2 Hz), 7.72 (s, 1H), 8.01 (d,
     1H, J = 8.2 Hz).
221  1.33 (t, 3H, J = 7.4 Hz), 1.42 (t, 3H, J = 7.4 Hz), 2.3-2.3 (m, 2H),
     2.88 (q, 2H, J = 7.4 Hz), 3.28 (s, 3H), 3.8-3.9 (m, 2H), 3.9-4.1 (m,
     4H), 4.43 (t, 2H, J = 5.4 Hz), 5.14 (t, 1H, J = 5.4 Hz), 7.22 (d, 1H,
     J = 8.2 Hz), 7.72 (s, 1H), 7.92 (d, 1H, J = 8.2 Hz).
222  1.33 (t, 3H, J = 7.4 Hz), 2.33 (s, 3H), 2.62 (t, 1H, J = 2.4 Hz),
     3.28 (s, 3H), 3.72 (s, 3H), 4.76 (d, 2H, J = 2.4 Hz), 7.23 (d, 1H, J = 7.2 Hz),
     7.66 (s, 1H), 7.86 (d, 1H, J = 7.2 Hz).
223  1.32 (t, 3H, J = 7.2 Hz), 2.07 (m, 2H), 2.37 (s, 3H), 2.87 (q, 2H, J = 7.2 Hz),
     3.19 (s, 3H), 3.71 (s, 3H), 3.75-3.95 (m, 4H), 4.31 (m,
     1H), 4.97 (d, 2H, J = 10.4 Hz), 5.02 (d, 2H, J = 10.4 Hz), 7.38 (d, 1H,
     J = 8.0 Hz), 7.65 (s, 1H), 8.03 (d, 1H, J = 8.0 Hz).
224  1.28 (t, 3H, J = 7.6 Hz), 2.48 (3H, s), 2.81 (q, 2H, J = 7.6 Hz),
     3.41 (s, 3H), 3.65 (s, 3H), 7.38 (d, 1H, J = 8.4 Hz), 7.70 (s, 1H),
     8.12 (d, 2H, J = 8.4 Hz)
225  0.87 (t, 3H, J = 6.9 Hz), 1.25-1.57 (m, 10H), 1.32 (t, 3H, J = 7.6 Hz),
     2.29 (s, 3H), 2.87 (q, 2H, J = 7.6 Hz), 3.01 (m, 1H), 3.09 (s, 3H),
     3.71 (s, 3H), 7.23 (d, 1H, J = 7.6 Hz), 7.66 (s, 1H), 7.97 (d, 1H,
     J = 7.6 Hz).
226  1.32 (t, 3H, J = 7.6 Hz), 1.97 (m, 2H), 2.31 (s, 3H), 2.86 (q, 2H, J = 7.6 Hz),
     3.11 (s, 3H), 3.12 (m, 2H), 3.36 (s, 3H), 3.50 (t, 2H, J = 6.2 Hz),
     3.70 (s, 3H), 7.24 (d, 1H, J = 8.4 Hz), 7.67 (s, 1H),
     7.97 (d, 1H, J = 8.4 Hz).
227  1.32 (t, 3H, J = 7.4 Hz), 1.42 (t, 3H, J = 7.4 Hz), 2.88 (q, 2H, J = 7.4 Hz),
     3.31 (s, 3H), 3.9-4.1 (m, 6H), 4.29 (d, 2H, J = 5.4 Hz),
     5.47 (t, 1H, J = 5.4 Hz), 7.25 (d, 1H, J = 8.2 Hz), 7.74 (s, 1H), 7.94 (d,
     1H, J = 8.2 Hz).
228  1.31-1.44 (m, 6H), 2.33 (s, 3H), 2.96-3.05 (m, 4H), 3.14 (s, 3H),
     3.74 (s, 3H), 4.37 (s, 2H), 5.21 (s, 2H), 7.50 (d, 1H, J = 8.1 Hz),
     7.62 (s, 1H), 8.10 (d, 1H, J = 8.1 Hz).
229  1.34 (t, 3H, J = 7.5 Hz), 2.30 (s, 3H), 2.89 (q, 2H, J = 7.5 Hz),
     3.06 (s, 3H), 3.74 (s, 3H), 5.68 (d, 1H, J = 17.1 Hz), 7.47 (d, 1H, J = 8.1 Hz),
     7.70 (s, 1H), 8.00 (d, 1H, J = 17.1 Hz), 8.05 (d, 1H, J = 8.1 Hz).
230  1.36 (t, 3H, J = 7.5 Hz), 2.38 (s, 3H), 2.76 (t, 2H, J = 7.8 Hz),
     2.92 (q, 2H, J = 7.5 Hz), 3.14 (s, 3H), 3.43 (q, 2H, J = 7.8 Hz), 3.74 (s,
     3H), 7.37 (d, 1H, J = 8.1 Hz), 7.66 (s, 1H), 8.01 (d, 1H, J = 8.1 Hz).
231  1.36 (t, 3H, J = 7.5 Hz), 2.49 (s, 3H), 2.92 (q, 2H, J = 7.5 Hz),
     3.22 (s, 3H), 3.74 (s, 3H), 4.86 (s, 2H), 7.46 (d, 1H, J = 8.1 Hz),
     7.66 (s, 1H), 8.03 (d, 1H, J = 8.1 Hz).
232  1.37 (t, 3H, J = 7.5 Hz), 2.40 (s, 3H), 2.96 (q, 2H, J = 7.5 Hz),
     3.19 (s, 3H), 3.74 (s, 3H), 4.63 (s, 2H), 7.34 (br, 1H), 7.40 (d, 1H,
     J = 8.1 Hz), 7.49 (br, 1H), 7.62 (s, 1H), 8.06 (d, 1H, J = 8.1 Hz).
233  2.29 (s, 3H), 2.38 (s, 3H), 3.28 (s, 3H), 3.45 (s, 3H), 3.71 (s, 3H),
     3.79 (m, 2H), 4.23 (m, 2H), 7.19 (d, 1H, J = 7.6 Hz), 7.66 (s,
     1H), 7.86 (d, 1H, 7.6 Hz).

TABLE 2-continued $^1$H-NMR δ ppm (solvent: CDCl$_3$, measuring instrument: JEOL-GSX
No. (400 MHz) or VARIAN MERCURY plus(300 MHz)/the same applies hereinafter)

234  1.42 (t, 3H, J = 7.4 Hz), 2.30 (s, 3H), 2.38 (s, 3H), 3.28 (s, 3H), 3.45 (s, 3H), 3.79 (m, 2H), 4.01 (q, 2H, J = 7.6 Hz), 4.23 (m, 2H), 7.22 (d, 1H, J = 8.4 Hz), 7.65 (s, 1H), 7.86 (d, 1H, J = 8.4 Hz).

235  0.99 (t, 3H, J = 7.4 Hz), 1.42 (t, 3H, J = 7.4 Hz), 1.68 (qt, 2H, J = 7.4, 7.4 Hz), 2.29 (s, 3H), 2.86 (t, 2H, J = 7.4 Hz), 3.27 (s, 3H), 3.45 (s, 3H), 3.79 (m, 2H), 4.01 (q, 2H, J = 7.4 Hz), 4.23 (m, 2H), 7.20 (d, 1H, J = 8.4 Hz), 7.63 (s, 1H), 7.85 (d, 1H, J = 8.4 Hz).

236  1.23 (d, 3H, J = 7.4 Hz), 1.37 (t, 3H, J = 7.4 Hz), 2.29 (s, 3H), 2.90-2.96 (m, 2H), 3.23 (s, 3H), 3.35 (s, 3H), 3.51-3.53 (m, 1H), 3.70-3.75 (m, 1H), 3.73 (s, 3H), 4.85-4.90 (m, 1H), 7.18 (d, 1H, J = 8.2 Hz), 7.60 (s, 1H), 7.89 (d, 1H, J = 8.2 Hz).

238  1.33 (t, 3H, J = 7.1 Hz), 2.37 (s, 3H), 2.90 (q, 2H, J = 7.1 Hz), 3.19 (s, 3H), 3.66 (d, 2H, J = 6.0 Hz), 3.71 (s, 3H), 3.78-3.86 (m, 2H), 3.95-4.00 (m, 2H), 5.17 (t, 1H, J = 6.0 Hz), 7.31 (d, 1H, J = 9.4 Hz), 7.66 (s, 1H), 8.01 (d, 1H, J = 9.4 Hz).

239  1.01 (t, 3H, J = 6.8 Hz), 1.39 (d, 3H, J = 7.4 Hz), 1.61-1.75 (m, 2H), 2.32 (s, 3H), 3.30 (s, 3H), 3.39 (m, 1H), 3.48 (s, 3H), 3.74 (s, 3H), 3.77-3.83 (m, 2H), 4.25-4.27 (m, 2H), 7.23 (d, 1H, J = 8.2 Hz), 7.66 (s, 1H), 7.89 (d, 1H, J = 8.2 Hz).

240  1.24 (d, 6H, J = 6.4 Hz), 1.31 (t, 3H, J = 7.2 Hz), 1.42 (t, 3H, J = 7.2 Hz), 2.37 (s, 3H), 2.88 (q, 2H, J = 7.2 Hz), 3.23 (s, 3H), 3.80 (m, 1H), 4.01 (q, 2H, J = 7.2 Hz), 4.97 (s, 2H), 7.38 (d, 1H, J = 8.0 Hz), 7.64 (s, 1H), 8.02 (d, 1H, J = 8.0 Hz).

241  1.47 (s, 9H), 2.29 (s, 3H), 3.23 (s, 3H), 3.45 (s, 3H), 3.67 (s, 3H), 3.79 (m, 2H), 4.24 (m, 2H), 7.18 (d, 1H, J = 8.0 Hz), 7.68 (s, 1H), 7.85 (d, 1H, J = 8.0 Hz).

242  2.29 (s, 3H), 3.27 (s, 3H), 3.44 (s, 3H), 3.72 (s, 2H), 3.73 (s, 3H), 3.78 (s, 3H), 3.79 (m, 2H), 4.23 (m, 2H), 7.20 (d, 1H, J = 8.4 Hz), 7.61 (s, 1H), 7.87 (d, 1H, J = 8.4 Hz).

TABLE 3

(I-1)

| No. | R$^1$ | R$^2$ | R$^4$ | R$^5$ | R$^6$ |
|---|---|---|---|---|---|
| 2-1 | Me | H | Me | CO$_2$Me | SO$_2$Me |
| 2-2 | Et | H | Me | CO$_2$Me | SO$_2$Me |
| 2-3 | Et | H | Me | CO$_2$(i-Pr) | SO$_2$Me |
| 2-4 | Me | H | Cl | CO$_2$Et | SO$_2$Me |
| 2-5 | Et | H | Me | CO$_2$Me | CF$_3$ |
| 2-6 | Et | H | Me | OCH$_2$CH$_2$OMe | SO$_2$Me |
| 2-7 | Et | H | SO$_2$Me | CO$_2$Me | CN |
| 2-8 | Me | H | Me | C(O)SMe | SO$_2$Me |
| 2-9 | Me | H | Me | C(O)SEt | SO$_2$Me |
| 2-10 | Me | H | Me | 2-(2-Oxolanyl)ethoxy | SO$_2$Me |
| 2-11 | Me | H | Me | 2-(2-(1,3-Dioxolanyl)ethoxy | SO$_2$Me |
| 2-12 | Et | H | Me | CH$_2$OMe | SO$_2$Me |
| 2-13 | Et | H | Me | 2-Oxolanylmethoxymethyl | SO$_2$Me |
| 2-14 | Me | H | Cl | CO$_2$Me | SO$_2$Me |
| 2-15 | Et | H | Cl | CO$_2$Me | SO$_2$Et |
| 2-16 | Me | H | Cl | C(O)SMe | SO$_2$Me |
| 2-17 | Me | H | Cl | C(O)SEt | SO$_2$Me |
| 2-18 | Me | H | Me | OMe | SO$_2$Me |
| 2-19 | Me | H | Me | OEt | SO$_2$Me |
| 2-20 | Me | H | Me | O(i-Pr) | SO$_2$Me |
| 2-21 | Me | H | Me | OCHF$_2$ | SO$_2$Me |
| 2-22 | Me | H | Me | (4,5-Dihydroisoxazol-3-yl) | SO$_2$Me |
| 2-23 | Me | H | Me | O(n-Pr) | SO$_2$Et |
| 2-24 | Me | H | Cl | CH$_2$OMe | SO$_2$Me |
| 2-25 | Me | H | Me | OCO$_2$Me | SO$_2$Me |
| 2-26 | Me | H | Me | OC(O)SMe | SO$_2$Me |
| 2-27 | Me | H | Me | OC(O)SEt | SO$_2$Me |
| 2-28 | Me | H | Me | OCH$_2$CH$_2$OMe | SO$_2$Me |
| 2-29 | Et | H | Me | OEt | SO$_2$Me |
| 2-30 | Et | H | Cl | CO$_2$Et | SO$_2$Me |
| 2-31 | Et | H | Cl | CO$_2$(n-Pr) | SO$_2$Me |
| 2-32 | Et | H | Me | CO$_2$Et | SO$_2$Me |
| 2-33 | Me | H | Me | CH$_2$CO$_2$Me | SO$_2$Me |
| 2-34 | Me | H | Me | OCH$_2$CO$_2$Et | SO$_2$Me |
| 2-35 | Me | H | Me | O(n-Pr) | SO$_2$Me |
| 2-36 | Et | H | SO$_2$Me | H | CF$_3$ |
| 2-37 | Me | H | Me | CH$_2$OCH$_2$CF$_3$ | SO$_2$Me |
| 2-38 | Me | H | Cl | CH$_2$OCH$_2$CF$_3$ | SO$_2$Me |
| 2-39 | Et | H | Me | Cl | SO$_2$Me |
| 2-40 | Me | H | Me | CH$_2$SO$_2$Me | SO$_2$Me |
| 2-41 | Me | H | Me | CH$_2$OEt | SO$_2$Me |
| 2-42 | Me | H | Cl | CH$_2$OMe | SO$_2$Me |
| 2-43 | Me | H | Me | CH$_2$OMe | SO$_2$Me |
| 2-44 | Me | H | Me | CH$_2$OCH$_2$CH$_2$OMe | SO$_2$Me |
| 2-45 | Me | H | Me | OCH$_2$CH$_2$OEt | SO$_2$Me |
| 2-46 | Me | H | Me | OCH$_2$CH$_2$Cl | SO$_2$Me |
| 2-47 | Me | H | Me | OCH$_2$CF$_3$ | SO$_2$Me |
| 2-48 | Me | H | Me | CH$_2$OCH$_2$OMe | SO$_2$Me |
| 2-49 | Me | H | Me | OCH$_2$CH$_2$SMe | SO$_2$Me |
| 2-50 | Me | H | Me | CN | SO$_2$Me |
| 2-51 | Me | H | Me | CH$_2$CN | SO$_2$Me |
| 2-52 | Me | H | Br | CO$_2$Me | SO$_2$Me |
| 2-53 | Et | H | Cl | CO$_2$Me | SO$_2$Me |
| 2-54 | Me | H | Br | CO$_2$Me | SO$_2$Me |
| 2-55 | Me | H | Cl | OCH$_2$CH$_2$OCF$_3$ | SO$_2$Me |
| 2-56 | Et | H | Cl | OCH$_2$CH$_2$OCF$_3$ | SO$_2$Me |
| 2-57 | Me | H | Me | OCH$_2$CH$_2$OCF$_3$ | SO$_2$Me |
| 2-58 | Et | H | Me | OCH$_2$CH$_2$OCF$_3$ | SO$_2$Me |

TABLE 3-continued

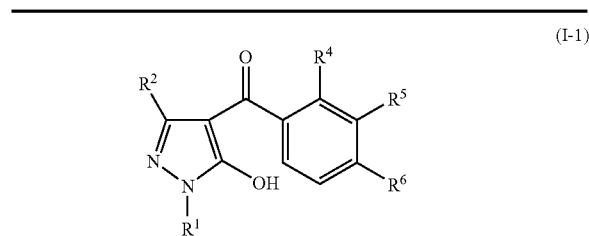

(I-1)

| No. | R¹ | R² | R⁴ | R⁵ | R⁶ |
|---|---|---|---|---|---|
| 2-59 | Me | H | CF₃ | OCH₂CH₂OCF₃ | SO₂Me |
| 2-60 | Et | H | CF₃ | OCH₂CH₂OCF₃ | SO₂Me |
| 2-61 | Me | H | Br | OCH₂CH₂OCF₃ | SO₂Me |
| 2-62 | Et | H | Br | OCH₂CH₂OCF₃ | SO₂Me |
| 2-63 | Me | H | SO₂Me | OCH₂CH₂OCF₃ | CF₃ |
| 2-64 | Et | H | SO₂Me | OCH₂CH₂OCF₃ | CF₃ |
| 2-65 | Me | H | Cl | OCH₂CH₂OCHClF | SO₂Me |
| 2-66 | Et | H | Cl | OCH₂CH₂OCHClF | SO₂Me |
| 2-67 | Me | H | Me | OCH₂CH₂OCHClF | SO₂Me |
| 2-68 | Et | H | Me | OCH₂CH₂OCHClF | SO₂Me |
| 2-69 | Me | H | CF₃ | OCH₂CH₂OCHClF | SO₂Me |
| 2-70 | Et | H | CF₃ | OCH₂CH₂OCHClF | SO₂Me |
| 2-71 | Me | H | Br | OCH₂CH₂OCHClF | SO₂Me |
| 2-72 | Et | H | Br | OCH₂CH₂OCHClF | SO₂Me |
| 2-73 | Me | H | SO₂Me | OCH₂CH₂OCHClF | CF₃ |
| 2-74 | Et | H | SO₂Me | OCH₂CH₂OCHClF | CF₃ |
| 2-75 | Me | H | Cl | OCH₂CHFOCF₃ | SO₂Me |
| 2-76 | Et | H | Cl | OCH₂CHFOCF₃ | SO₂Me |
| 2-77 | Me | H | Me | OCH₂CHFOCF₃ | SO₂Me |
| 2-78 | Me | H | Cl | OCH₂CHFOMe | SO₂Me |
| 2-79 | Et | H | Cl | OCH₂CHFOMe | SO₂Me |
| 2-80 | Me | H | Me | OCH₂CHFOMe | SO₂Me |
| 2-81 | Et | H | Me | OCH₂CHFOMe | SO₂Me |
| 2-82 | Me | H | CF₃ | OCH₂CHFOMe | SO₂Me |
| 2-83 | Et | H | CF₃ | OCH₂CHFOMe | SO₂Me |
| 2-84 | Me | H | Br | OCH₂CHFOMe | SO₂Me |
| 2-85 | Et | H | Br | OCH₂CHFOMe | SO₂Me |
| 2-86 | Me | H | SO₂Me | OCH₂CHFOMe | CF₃ |
| 2-87 | Et | H | SO₂Me | OCH₂CHFOMe | CF₃ |
| 2-88 | Me | H | Cl | OCHFCH₂OCF₃ | SO₂Me |
| 2-89 | Et | H | Cl | OCHFCH₂OCF₃ | SO₂Me |
| 2-90 | Me | H | Cl | OCH₂CH₂OCF₂Cl | SO₂Me |
| 2-91 | Et | H | Cl | OCH₂CH₂OCF₂Cl | SO₂Me |
| 2-92 | Me | H | Me | OCH₂CH₂OCF₂Cl | SO₂Me |
| 2-93 | Et | H | Me | OCH₂CH₂OCF₂Cl | SO₂Me |
| 2-94 | Me | H | CF₃ | OCH₂CH₂OCF₂Cl | SO₂Me |
| 2-95 | Et | H | CF₃ | OCH₂CH₂OCF₂Cl | SO₂Me |
| 2-96 | Me | H | Br | OCH₂CH₂OCF₂Cl | SO₂Me |
| 2-97 | Et | H | Br | OCH₂CH₂OCF₂Cl | SO₂Me |
| 2-98 | Me | H | SO₂Me | OCH₂CH₂OCF₂Cl | CF₃ |
| 2-99 | Et | H | SO₂Me | OCH₂CH₂OCF₂Cl | CF₃ |
| 2-100 | Me | H | Cl | SCH₂CH₂OCH₃ | SO₂Me |
| 2-101 | Et | H | Cl | SCH₂CH₂OCH₃ | SO₂Me |
| 2-102 | Me | H | Me | SCH₂CH₂OCH₃ | SO₂Me |
| 2-103 | Et | H | Me | SCH₂CH₂OCH₃ | SO₂Me |
| 2-104 | Me | H | CF₃ | SCH₂CH₂OCH₃ | SO₂Me |
| 2-105 | Et | H | CF₃ | SCH₂CH₂OCH₃ | SO₂Me |
| 2-106 | Me | H | Br | SCH₂CH₂OCH₃ | SO₂Me |
| 2-107 | Et | H | Br | SCH₂CH₂OCH₃ | SO₂Me |
| 2-108 | Me | H | SO₂Me | SCH₂CH₂OCH₃ | CF₃ |
| 2-109 | Et | H | SO₂Me | SCH₂CH₂OCH₃ | CF₃ |
| 2-110 | Me | H | Cl | SCH₂CH₂OCF₃ | SO₂Me |
| 2-111 | Et | H | Cl | SCH₂CH₂OCF₃ | SO₂Me |
| 2-112 | Me | H | Me | SCH₂CH₂OCF₃ | SO₂Me |
| 2-113 | Et | H | Me | SCH₂CH₂OCF₃ | SO₂Me |
| 2-114 | Me | H | CF₃ | SCH₂CH₂OCF₃ | SO₂Me |
| 2-115 | Et | H | CF₃ | SCH₂CH₂OCF₃ | SO₂Me |
| 2-116 | Me | H | Br | SCH₂CH₂OCF₃ | SO₂Me |
| 2-117 | Et | H | Br | SCH₂CH₂OCF₃ | SO₂Me |
| 2-118 | Me | H | SO₂Me | SCH₂CH₂OCF₃ | CF₃ |
| 2-119 | Et | H | SO₂Me | SCH₂CH₂OCF₃ | CF₃ |
| 2-120 | Me | H | Cl | SCH₂CH₂SCH₃ | SO₂Me |
| 2-121 | Et | H | Cl | SCH₂CH₂SCH₃ | SO₂Me |
| 2-122 | Me | H | Me | SCH₂CH₂SCH₃ | SO₂Me |
| 2-123 | Et | H | Me | SCH₂CH₂SCH₃ | SO₂Me |
| 2-124 | Me | H | CF₃ | SCH₂CH₂SCH₃ | SO₂Me |
| 2-125 | Et | H | CF₃ | SCH₂CH₂SCH₃ | SO₂Me |
| 2-126 | Me | H | Br | SCH₂CH₂SCH₃ | SO₂Me |
| 2-127 | Et | H | Br | SCH₂CH₂SCH₃ | SO₂Me |
| 2-128 | Me | H | SO₂Me | SCH₂CH₂SCH₃ | CF₃ |
| 2-129 | Et | H | SO₂Me | SCH₂CH₂SCH₃ | CF₃ |
| 2-130 | Me | H | Cl | SCH₂CH₂SCF₃ | SO₂Me |
| 2-131 | Et | H | Cl | SCH₂CH₂SCF₃ | SO₂Me |
| 2-132 | Me | H | Me | SCH₂CH₂SCF₃ | SO₂Me |
| 2-133 | Et | H | Me | SCH₂CH₂SCF₃ | SO₂Me |
| 2-134 | Me | H | CF₃ | SCH₂CH₂SCF₃ | SO₂Me |
| 2-135 | Et | H | CF₃ | SCH₂CH₂SCF₃ | SO₂Me |
| 2-136 | Me | H | Br | SCH₂CH₂SCF₃ | SO₂Me |
| 2-137 | Et | H | Br | SCH₂CH₂SCF₃ | SO₂Me |
| 2-138 | Me | H | SO₂Me | SCH₂CH₂SCF₃ | CF₃ |
| 2-139 | Et | H | SO₂Me | SCH₂CH₂SCF₃ | CF₃ |
| 2-140 | Me | H | Cl | OCH₂CH(CH₃)OCH₃ | SO₂Me |
| 2-141 | Et | H | Cl | OCH₂CH(CH₃)OCH₃ | SO₂Me |
| 2-142 | Me | H | Me | OCH₂CH(CH₃)OCH₃ | SO₂Me |
| 2-143 | Et | H | Me | OCH₂CH(CH₃)OCH₃ | SO₂Me |
| 2-144 | Me | H | CF₃ | OCH₂CH(CH₃)OCH₃ | SO₂Me |
| 2-145 | Et | H | CF₃ | OCH₂CH(CH₃)OCH₃ | SO₂Me |
| 2-146 | Me | H | Br | OCH₂CH(CH₃)OCH₃ | SO₂Me |
| 2-147 | Et | H | Br | OCH₂CH(CH₃)OCH₃ | SO₂Me |
| 2-148 | Me | H | SO₂Me | OCH₂CH(CH₃)OCH₃ | CF₃ |
| 2-149 | Et | H | SO₂Me | OCH₂CH(CH₃)OCH₃ | CF₃ |
| 2-150 | Me | H | Cl | OCH₂CF₂OCH₃ | SO₂Me |
| 2-151 | Et | H | Cl | OCH₂CF₂OCH₃ | SO₂Me |
| 2-152 | Me | H | Me | OCH₂CF₂OCH₃ | SO₂Me |
| 2-153 | Et | H | Me | OCH₂CF₂OCH₃ | SO₂Me |
| 2-154 | Me | H | CF₃ | OCH₂CF₂OCH₃ | SO₂Me |
| 2-155 | Et | H | CF₃ | OCH₂CF₂OCH₃ | SO₂Me |
| 2-156 | Me | H | Br | OCH₂CF₂OCH₃ | SO₂Me |
| 2-157 | Et | H | Br | OCH₂CF₂OCH₃ | SO₂Me |
| 2-158 | Me | H | SO₂Me | OCH₂CF₂OCH₃ | CF₃ |
| 2-159 | Et | H | SO₂Me | OCH₂CF₂OCH₃ | CF₃ |
| 2-160 | Me | H | Me | OCH₂CH₂OCH₃ | SO₂Me |
| 2-161 | Et | H | Me | OCH₂CH₂OCH₃ | SO₂Me |
| 2-162 | Me | H | Me | OCH₂CH(OCH₃)₂ | SO₂Me |
| 2-163 | Me | H | Me | CH₂N(Me)CH₂CN | SO₂Me |
| 2-164 | Me | H | Me | (Tetrahydrofuran-2-yl)methoxy | SO₂Me |
| 2-165 | Me | H | Cl | SMe | SO₂Me |
| 2-166 | Me | H | Cl | Cl | SO₂Me |
| 2-167 | Me | H | Cl | OMe | SO₂Me |
| 2-168 | Me | H | Me | (Tetrahydro-2H-pyran-2-yl)methoxy | SO₂Me |
| 2-169 | Me | H | Cl | OCH₂CH₂OMe | SO₂Me |
| 2-170 | Me | H | Me | Tetrahydrofuran-3-yloxy | SO₂Me |
| 2-171 | Me | H | Me | OCH₂CH₂CH₂OMe | SO₂Me |
| 2-172 | Me | H | Me | OCH₂CH₂OMe | SO₂Me |
| 2-173 | Et | H | Cl | (1,3-Dioxolan-2-yl)ethoxy | SO₂Me |
| 2-174 | Me | H | Me | Propargyloxy | SO₂Me |
| 2-175 | Me | H | Me | (Tetrahydrofuran-3-yloxy)methyl | SO₂Me |
| 2-176 | Me | H | Cl | SO₂Me | SO₂Me |
| 2-177 | Me | H | Me | (CH₂)₆Me | SO₂Me |
| 2-178 | Me | H | Me | CH₂CH₂CH₂OMe | SO₂Me |
| 2-179 | Et | H | Cl | (1,3-Dioxolan-2-yl)methoxy | SO₂Me |
| 2-180 | Me | H | Me | CH₂N[C(O)SEt]CH₂CN | SO₂Me |
| 2-181 | Me | H | Me | CHCHCN | SO₂Me |
| 2-182 | Me | H | Me | CH₂CH₂CN | SO₂Me |
| 2-183 | Me | H | Me | CH₂SCN | SO₂Me |
| 2-184 | Me | H | Me | CH₂C(S)NH₂ | SO₂Me |
| 2-185 | Me | H | Me | OCH₂CH₂OMe | SO₂Me |
| 2-186 | Et | H | Me | OCH₂CH₂OMe | SO₂Me |
| 2-187 | Me | H | Me | OCH(CH₃)CH₂OMe | SO₂Me |

TABLE 3-continued

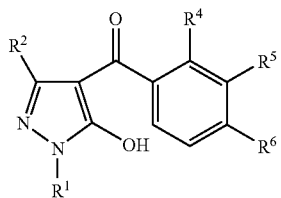
(I-1)

| No. | R¹ | R² | R⁴ | R⁵ | R⁶ |
|---|---|---|---|---|---|
| 2-188 | Me | H | Me | OCH₂CH(Et)OMe | SO₂Me |
| 2-189 | Me | H | Me | (1,3-Dioxolan-2-yl)methyl | SO₂Me |
| 2-190 | Me | H | Me | CH₂O(i-Pr) | SO₂Me |
| 2-191 | Me | H | Me | CH₂OMe | SO₂Me |
| 2-192 | i-Pr | H | Me | OCH₂CH₂OMe | SO₂Me |
| 2-193 | Me | Me | Me | OCH₂CH₂OMe | SO₂Me |
| 2-194 | i-Pr | Me | Me | OCH₂CH₂OMe | SO₂Me |
| 2-195 | Me | Et | Me | OCH₂CH₂OMe | SO₂Me |

TABLE 4

¹H-NMR δ ppm (solvent: CDCl₃ unless otherwise specified, measuring instrument: JEOL-GSX (400 MHz) or VARIAN MERCURY plus (300 MHz)/the same applies hereinafter)

| No. | |
|---|---|
| 2-1 | 2.32 (s, 3H), 3.13 (s, 3H), 3.61 (s, 3H), 3.93 (s, 3H), 7.28 (s, 1H), 7.56 (d, 1H, J = 7.8 Hz), 7.93 (d, 1H, J = 7.8 Hz), 8.44 (br. s, 1H). |
| 2-2 | 1.46 (t, 3H), 2.38 (s, 3H), 3.18 (s, 3H), 3.98 (s, 3H), 4.07 (q, 2H), 7.32 (d, 1H, J = 7.8 Hz), 7.61 (s, 1H), 7.98 (d, 1H, J = 7.8 Hz). |
| 2-19 | 1.48 (t, 3H, J = 7.2 Hz), 2.36 (s, 3H), 3.34 (s, 3H), 3.71 (s, 3H), 4.10 (q, 2H, J = 7.2 Hz), 6.98 (br s, 1H), 7.37 (m, 2H), 7.90 (d, 1H, J = 7.2 Hz). |
| 2-20 | 1.34 (d, 6H, J = 6.4 Hz), 2.33 (s, 3H), 3.22 (s, 3H), 3.70 (s, 3H), 4.82 (qq, 1H, J = 6.4, 6.4 Hz), 6.90 (br s. 1H), 7.29 (d, 1H, J = 7.6 Hz), 7.33 (s, 1H), 7.94 (d, 1H, J = 7.6 Hz). |
| 2-21 | 2.43 (s, 3H), 2.23 (s, 3H), 3.71 (s, 3H), 5.30 (br s, 1H), 6.75 (t, 1H, J = 74.8 Hz), 7.33 (s, 1H), 7.50 (d, 1H, J = 8.0 Hz), 8.00 (d, 1H, J = 8.0 Hz). |
| 2-29 | 1.44 (t, 3H, J = 7.2 Hz), 1.48 (t, 3H, J = 7.2 Hz), 2.36 (s, 3H), 3.27 (s, 3H), 4.06 (q, 2H, J = 7.2 Hz), 4.13 (q, 2H, J = 7.2 Hz), 5.2 (br s, 1H), 7.33 (d, 1H, J = 8.0 Hz), 7.34 (s, 1H), 7.90 (d, 1H, J = 8.0 Hz) |
| 2-30 | (Acetone-d₆) 1.30 (br s, 3H), 1.37 (t, 3H, J = 7.0 Hz), 3.25 (s, 3H), 3.95 (br s, 2H), 4.43 (q, 2H, J = 7.0 Hz), 7.27 (br s, 1H), 7.75 (br s, 1H), 8.07 (br s, 1H). |
| 2-31 | (Acetone-d₆) 1.18 (t, 3H, J = 7.4 Hz), 1.34 (br s, 3H), 1.80 (m, 2H), 3.25 (s, 3H), 3.98 (br s, 2H), 4.33 (t, 2H, J = 5.6 Hz), 7.32 (br s, 1H), 7.81 (br s, 1H), 8.08 (br s, 1H). |
| 2-33 | 2.33 (s, 3H), 3.16 (s, 3H), 3.73 (s, 2H), 3.76 (s, 3H), 4.42 (s, 2H), 7.20-7.60 (br s, 1H), 7.34 (s, 1H), 7.52 (d, 1H, J = 8.1 Hz), 8.10 (d, 1H, J = 8.1 Hz). |
| 2-34 | 1.27 (t, 3H, J = 7.6 Hz), 2.32 (s, 3H), 3.32 (s, 3H), 3.66 (s, 3H), 4.25 (q, 2H, J = 7.6 Hz), 4.61 (s, 2H), 7.30 (s, 1H), 7.35 (d, 1H, J = 8.0 Hz), 7.88 (d, 1H, J = 8.0 Hz). |
| 2-40 | (Acetone-d₆) 2.51 (s, 3H), 3.12 (s, 3H), 3.23 (s, 3H), 3.29 (s, 3H), 5.4 (br s, 2H), 6.8 (br s, 1H), 7.42 (d, 1H, J = 8.0 Hz), 8.00 (d, 1H, J = 8.0 Hz). |
| 2-50 | 2.72 (s, 3H), 3.34 (s, 3H), 3.74 (s, 3H), 5.10-5.60 (br s, 1H), 7.32 (s, 1H), 7.81 (d, 1H, J = 8.1 Hz), 8.16 (d, 1H, J = 8.1 Hz). |
| 2-51 | 2.53 (s, 3H), 3.24 (s, 3H), 3.74 (s, 3H), 4.47 (s, 2H), 6.70-7.20 (br s, 1H), 7.33 (s, 1H), 7.60 (d, 1H, J = 8.1 Hz), 8.14 (d, 1H, J = 8.1 Hz). |
| 2-53 | 1.42 (t, 3H, J = 7.3 Hz), 3.20 (s, 3H), 4.04 (s, 3H), 4.09 (q, 2H, J = 7.3 Hz), 7.34 (s, 1H), 7.64 (d, 1H, J = 7.8 Hz), 8.07 (d, 1H, J = 7.8 Hz). |
| 2-142 | 1.23 (d, 3H, J = 6.4 Hz), 2.34 (s, 3H), 3.24 (s, 3H), 3.41 (s, 3H), 3.65 (s, 3H), 3.77 (m, 2H), 3.99 (dd, 1H, J = 9.2, 4.0 Hz), 4.05 (dd, 1H, J = 9.2, 6.4 Hz), 7.28 (s, 1H), 7.29 (d, 1H, J = 8.4 Hz), 7.86 (d, 1H, J = 8.4 Hz). |
| 2-161 | 1.40 (t, 3H, J = 7.0 Hz), 2.39 (s, 3H), 3.23 (s, 3H), 3.43 (s, 3H), 3.76 (m, 2H), 4.21 (q, 1H, J = 7.0 Hz), 4.19 (m, 2H), 7.29 (s, 1H), 7.31 (d, 1H, J = 8.0 Hz), 7.83 (d, 1H, J = 8.0 Hz). |
| 2-163 | 2.41 (s, 3H), 2.48 (s, 3H), 3.27 (s, 3H), 3.63 (s, 2H), 3.72 (s, 3H), 4.23 (s, 2H), 7.29 (s, 1H), 7.51 (d, 1H, J = 8.1 Hz), 8.12 (d, 1H, J = 8.1 Hz). |
| 2-166 | 2.55 (s, 3H), 3.45 (s, 3H), 7.29-7.33 (m, 2H), 7.35 (d, 1H, J = 8.4 Hz). |
| 2-173 | 1.43 (t, 3H, J = 7.3 Hz), 2.28 (m, 2H), 3.29 (s, 3H), 3.86 (m, 2H), 3.96 (m, 2H), 4.08 (m, 2H), 4.39 (m, 2H), 5.13 (t, 1H, J = 5.5 Hz), 7.32 (s, 1H), 7.33 (d, 1H, J = 7.8 Hz), 7.96 (d, 1H, J = 7.8 Hz). |
| 2-176 | 2.49 (s, 3H), 3.54 (s, 3H), 3.57 (s, 3H), 7.40 (s, 1H), 7.63 (d, 1H, J = 7.6 Hz), 8.06 (d, 1H, J = 7.6 Hz). |
| 2-179 | 1.42 (t, 3H, J = 7.3 Hz), 3.35 (s, 3H), 3.95 (m, 2H), 4.04-4.12 (m, 4H), 4.29 (m, 2H), 5.46 (t, 1H, J = 5.5 Hz), 7.32 (s, 1H), 7.36 (d, 1H, J = 7.8 Hz), 7.98 (d, 1H, J = 7.8 Hz). |
| 2-183 | 2.58 (s, 3H), 2.80-3.20 (br s, 1H), 3.25 (s, 3H), 3.73 (s, 3H), 4.89 (s, 2H), 7.33 (s, 1H), 7.58 (d, 1H, J = 8.1 Hz), 8.07 (d, 1H, J = 8.1 Hz). |
| 2-184 | 2.50 (s, 3H), 3.20 (s, 3H), 3.72 (s, 3H), 4.66 (s, 2H), 7.32 (s, 1H), 7.40-7.50 (br s, 1H), 7.52 (d, 1H, J = 8.1 Hz), 8.11 (d, 1H, J = 8.1 Hz). |
| 2-187 | 1.25 (t, 3H, J = 7.3 Hz), 2.35 (s, 3H), 3.25 (s, 3H), 3.34 (s, 3H), 3.53 (m, 1H), 3.70 (s, 3H), 3.74 (m, 1H), 4.88 (m, 1H), 7.24 (s, 1H), 7.31 (d, 1H, J = 7.8 Hz), 7.85 (d, 1H, J = 7.8 Hz). |
| 2-189 | 2.41 (s, 3H), 3.14 (s, 3H), 3.61 (d, 2H, J = 5.2 Hz), 3.65 (s, 3H), 3.77-3.82 (m, 2H), 3.88-3.96 (m, 2H), 5.12 (t, 1H, J = 4.8 Hz), 5.45 (br s, 1H), 7.24 (s, 1H), 7.37 (d, 1H, J = 8.0 Hz), 8.01 (d, 1H, J = 8.0 Hz). |
| 2-190 | 1.25 (d, 6H, J = 6.4 Hz), 1.44 (t, 3H, J = 7.4 Hz), 2.47 (s, 3H), 3.25 (s, 3H), 3.83 (m, 3H), 4.06 (q, 2H, J = 7.4 Hz), 4.7 (br s, 1H), 5.00 (s, 2H), 7.31 (s, 1H), 7.50 (d, 1H, J = 8.4 Hz), 8.07 (d, 1H, J = 8.4 Hz). |
| 2-192 | 1.48 (d, 6H, J = 6.8 Hz), 2.40 (s, 3H), 3.30 (s, 3H), 3.46 (s, 3H), 3.80 (t, 2H, J = 8.4 Hz), 4.24 (t, 2H, J = 8.4 Hz) 5.89 (m, 1H) 7.35 (d, 1H, J = 8.0 Hz) 7.37 (s, 1H) 7.91 (d, 1H, J = 8.0 Hz). |
| 2-193 | 1.62 (s, 3H), 2.26 (s, 3H), 3.25 (s, 3H), 3.42 (s, 3H), 3.58 (s, 3H), 3.76 (t, 2H, J = 4.4 Hz), 4.19 (t, 2H, J = 4.4 Hz), 7.11 (d, 1H, J = 8.0 Hz), 7.87 (d, 1H, J = 8.0 Hz). |
| 2-194 | 1.46 (d, 6H, J = 6.8 Hz), 1.67 (s, 3H), 2.32 (s, 3H), 3.27 (s, 3H), 3.56 (s, 3H), 3.80 (t, 2H, J = 8.4 Hz) 4.23 (t, 2H, J = 8.4 Hz) 4.55 (m, 1H) 7.15 (d, 1H, J = 8.0 Hz) 7.91 (d, 1H, J = 8.0 Hz). |
| 2-195 | 0.85 (t, 3H, J = 7.2 Hz), 2.00 (q, 2H, J = 7.2 Hz), 2.30 (s, 3H), 3.28 (s, 3H), 3.45 (s, 3H), 3.62 (s, 3H), 3.79 (t, 2H, J = 4.4 Hz), 4.22 (t, 2H, J = 4.4 Hz), 7.16 (d, 1H, J = 8.0 Hz), 7.89 (d, 1H, J = 8.0 Hz). |

EXAMPLES

Example 1

Upland field soil was put into a 1/1,000,000 hectare pot, and seeds of various plants were sown. When the respective plants reached predetermined leaf stage, herbicidal compositions in predetermined amounts were diluted with water in an amount corresponding to 300 L/ha and applied for foliar treatment by a small sprayer.

On the 14th to 28th day after application, the state of growth of the respective plants was visually observed to determine the growth inhibition rate (measured value) in accordance with the following evaluation standard. Further, in accordance with the above Colby's formula, the growth inhibition rate (calculated value) was calculated. The results are shown in Tables 5-1 to 5-137. In Tables, with respect to the compound A, Compound Nos. in Table 1 or 3 are described, and with respect to other herbicidal compounds, common names are described.

Growth inhibition rate (%)=0: equivalent to the non-treated area to 100: complete kill

TABLE 5-1

| Compound | Active ingredient amount (g/ha) | Growth inhibition rate (%) of crabgrass (3.2 to 4.3 leaf stage) (on the 22nd day after application) Measured value | Calculated value |
|---|---|---|---|
| No. 1 | 15 | 65 | — |
|  | 7.5 | 45 | — |
| Atrazine | 250 | 0 | — |
|  | 125 | 0 | — |
| No. 1 + atrazine | 15 + 250 | 70 | 65 |
|  | 7.5 + 125 | 55 | 45 |

TABLE 5-2

| Compound | Active ingredient amount (g/ha) | Growth inhibition rate (%) of velvetleaf (2.4 to 3.2 leaf stage) (on the 22nd day after application) Measured value | Calculated value |
|---|---|---|---|
| No. 1 | 7.5 | 85 | — |
| Atrazine | 125 | 10 | — |
| No. 1 + atrazine | 7.5 + 125 | 100 | 86.5 |

TABLE 5-3

| Compound | Active ingredient amount (g/ha) | Growth inhibition rate (%) of crabgrass (3.2 to 4.3 leaf stage) (on the 22nd day after application) Measured value | Calculated value |
|---|---|---|---|
| No. 1 | 15 | 65 | — |
| Terbuthylazine | 250 | 20 | — |
| No. 1 + terbuthylazine | 15 + 250 | 73 | 72 |

TABLE 5-4

| Compound | Active ingredient amount (g/ha) | Growth inhibition rate (%) of velvetleaf (2.4 to 3.2 leaf stage) (on the 22nd day after application) Measured value | Calculated value |
|---|---|---|---|
| No. 1 | 7.5 | 85 | — |
| Terbuthylazine | 125 | 5 | — |
| No. 1 + terbuthylazine | 7.5 + 125 | 100 | 85.8 |

TABLE 5-5

| Compound | Active ingredient amount (g/ha) | Growth inhibition rate (%) of velvetleaf (2.4 to 3.2 leaf stage) (on the 22nd day after application) Measured value | Calculated value |
|---|---|---|---|
| No. 1 | 7.5 | 85 | — |
| S-Metolachlor | 150 | 0 | — |
| No. 1 + S-metolachlor | 7.5 + 150 | 93 | 85 |

TABLE 5-6

| Compound | Active ingredient amount (g/ha) | Growth inhibition rate (%) of velvetleaf (2.4 to 3.2 leaf stage) (on the 22nd day after application) Measured value | Calculated value |
|---|---|---|---|
| No. 1 | 7.5 | 85 | — |
| Bromoxynil | 62.5 | 35 | — |
| No. 1 + bromoxynil | 7.5 + 62.5 | 100 | 90.3 |

TABLE 5-7

| Compound | Active ingredient amount (g/ha) | Growth inhibition rate (%) of velvetleaf (2.4 to 3.2 leaf stage) (on the 22nd day after application) Measured value | Calculated value |
|---|---|---|---|
| No. 1 | 7.5 | 85 | — |
| 2,4-D-ethyl | 63 | 30 | — |
| No. 1 + 2,4-D-ethyl | 7.5 + 63 | 93 | 89.5 |

TABLE 5-8

| Compound | Active ingredient amount (g/ha) | Growth inhibition rate (%) of velvetleaf (3.0 to 3.5 leaf stage) (on the 21st day after application) Measured value | Calculated value |
|---|---|---|---|
| No. 55 | 15 | 75 | — |
| Nicosulfuron | 15 | 45 | — |
| No. 55 + nicosulfuron | 15 + 15 | 93 | 86.3 |

TABLE 5-9

| Compound | Active ingredient amount (g/ha) | Growth inhibition rate (%) of crabgrass (4.0 to 4.5 leaf stage) (on the 21st day after application) Measured value | Calculated value |
|---|---|---|---|
| No. 55 | 15 | 73 | — |
|  | 7.5 | 73 | — |
| Atrazine | 250 | 10 | — |
|  | 125 | 10 | — |
| No. 55 + atrazine | 15 + 250 | 100 | 75.7 |
|  | 7.5 + 125 | 95 | 75.7 |

TABLE 5-10

| Compound | Active ingredient amount (g/ha) | Growth inhibition rate (%) of velvetleaf (3.0 to 3.5 leaf stage) (on the 21st day after application) | |
|---|---|---|---|
| | | Measured value | Calculated value |
| No. 55 | 15 | 89 | — |
| | 7.5 | 75 | — |
| Atrazine | 250 | 20 | — |
| | 125 | 10 | — |
| No. 55 + atrazine | 15 + 250 | 95 | 91.2 |
| | 7.5 + 125 | 88 | 77.5 |

TABLE 5-11

| Compound | Active ingredient amount (g/ha) | Growth inhibition rate (%) of crabgrass (3.5 to 4.0 leaf stage) (on the 21st day after application) | |
|---|---|---|---|
| | | Measured value | Calculated value |
| No. 55 | 7 | 95 | — |
| Terbuthylazine | 125 | 0 | — |
| No. 55 + terbuthylazine | 7 + 125 | 100 | 95 |

TABLE 5-12

| Compound | Active ingredient amount (g/ha) | Growth inhibition rate (%) of velvetleaf (2.0 to 2.5 leaf stage) (on the 21st day after application) | |
|---|---|---|---|
| | | Measured value | Calculated value |
| No. 55 | 7 | 65 | — |
| Terbuthylazine | 125 | 0 | — |
| No. 55 + terbuthylazine | 7 + 125 | 100 | 65 |

TABLE 5-13

| Compound | Active ingredient amount (g/ha) | Growth inhibition rate (%) of crabgrass (4.0 to 4.5 leaf stage) (on the 21st day after application) | |
|---|---|---|---|
| | | Measured value | Calculated value |
| No. 55 | 15 | 85 | — |
| S-Metolachlor | 300 | 8 | — |
| No. 55 + S-metolachlor | 15 + 300 | 93 | 86.2 |

TABLE 5-14

| Compound | Active ingredient amount (g/ha) | Growth inhibition rate (%) of velvetleaf (3.0 to 3.5 leaf stage) (on the 21st day after application) | |
|---|---|---|---|
| | | Measured value | Calculated value |
| No. 55 | 15 | 75 | — |
| | 7.5 | 78 | — |
| S-Metolachlor | 300 | 0 | — |
| | 150 | 0 | — |
| No. 55 + S-metolachlor | 15 + 300 | 97 | 75 |
| | 7.5 + 150 | 83 | 78 |

TABLE 5-15

| Compound | Active ingredient amount (g/ha) | Growth inhibition rate (%) of crabgrass (3.5 to 4.0 leaf stage) (on the 21st day after application) | |
|---|---|---|---|
| | | Measured value | Calculated value |
| No. 55 | 7 | 95 | — |
| Bromoxynil-octanoate | 63 | 0 | — |
| No. 55 + bromoxynil-octanoate | 7 + 63 | 98 | 95 |

TABLE 5-16

| Compound | Active ingredient amount (g/ha) | Growth inhibition rate (%) of velvetleaf (2.0 to 2.5 leaf stage) (on the 21st day after application) | |
|---|---|---|---|
| | | Measured value | Calculated value |
| No. 55 | 7 | 65 | — |
| Bromoxynil-octanoate | 63 | 25 | — |
| No. 55 + bromoxynil-octanoate | 7 + 63 | 100 | 73.8 |

TABLE 5-17

| Compound | Active ingredient amount (g/ha) | Growth inhibition rate (%) of velvetleaf (2.0 to 2.5 leaf stage) (on the 21st day after application) | |
|---|---|---|---|
| | | Measured value | Calculated value |
| No. 55 | 7 | 65 | — |
| Dimethenamid | 125 | 0 | — |
| No. 55 + dimethenamid | 7 + 125 | 73 | 65 |

TABLE 5-18

| Compound | Active ingredient amount (g/ha) | Growth inhibition rate (%) of velvetleaf (2.0 to 2.5 leaf stage) (on the 21st day after application) | |
|---|---|---|---|
| | | Measured value | Calculated value |
| No. 55 | 7 | 65 | — |
| Acetochlor | 150 | 0 | — |
| No. 55 + acetochlor | 7 + 150 | 73 | 65 |

TABLE 5-19

| Compound | Active ingredient amount (g/ha) | Growth inhibition rate (%) of velvetleaf (2.0 to 2.5 leaf stage) (on the 21st day after application) | |
|---|---|---|---|
| | | Measured value | Calculated value |
| No. 55 | 7 | 65 | — |
| Bentazone-sodium | 150 | 95 | — |
| No. 55 + bentazone-sodium | 7 + 150 | 100 | 98.3 |

TABLE 5-20

| Compound | Active ingredient amount (g/ha) | Growth inhibition rate (%) of velvetleaf (2.0 to 2.5 leaf stage) (on the 21st day after application) Measured value | Calculated value |
| --- | --- | --- | --- |
| No. 55 | 7 | 65 | — |
| Carfentrazone-ethyl | 5 | 98 | — |
| No. 55 + carfentrazone-ethyl | 7 + 5 | 100 | 99.3 |

TABLE 5-21

| Compound | Active ingredient amount (g/ha) | Growth inhibition rate (%) of crabgrass (3.0 to 4.3 leaf stage) (on the 21st day after application) Measured value | Calculated value |
| --- | --- | --- | --- |
| No. 55 | 15 | 95 | — |
|  | 7 | 83 | — |
| Flufenacet | 300 | 5 | — |
|  | 150 | 0 | — |
| No. 55 + flufenacet | 15 + 300 | 99 | 95.3 |
|  | 7 + 150 | 92 | 83 |

TABLE 5-22

| Compound | Active ingredient amount (g/ha) | Growth inhibition rate (%) of crabgrass (3.0 to 4.3 leaf stage) (on the 21st day after application) Measured value | Calculated value |
| --- | --- | --- | --- |
| No. 55 | 15 | 95 | — |
|  | 7 | 83 | — |
| Dicamba-dimethylammonium | 200 | 0 | — |
|  | 100 | 0 | — |
| No. 55 + dicamba-dimethylammonium | 15 + 200 | 98 | 95 |
|  | 7 + 100 | 90 | 83 |

TABLE 5-23

| Compound | Active ingredient amount (g/ha) | Growth inhibition rate (%) of velvetleaf (2.0 to 2.8 leaf stage) (on the 21st day after application) Measured value | Calculated value |
| --- | --- | --- | --- |
| No. 55 | 15 | 90 | — |
|  | 7 | 70 | — |
| Dicamba-dimethylammonium | 200 | 55 | — |
|  | 100 | 50 | — |
| No. 55 + dicamba-dimethylammonium | 15 + 200 | 98 | 95.5 |
|  | 7 + 100 | 98 | 85 |

TABLE 5-24

| Compound | Active ingredient amount (g/ha) | Growth inhibition rate (%) of crabgrass (3.0 to 4.3 leaf stage) (on the 21st day after application) Measured value | Calculated value |
| --- | --- | --- | --- |
| No. 55 | 7 | 83 | — |
| Clopyralid-olamine | 100 | 0 | — |
| No. 55 + clopyralid-olamine | 7 + 100 | 93 | 83 |

TABLE 5-25

| Compound | Active ingredient amount (g/ha) | Growth inhibition rate (%) of crabgrass (3.0 to 4.3 leaf stage) (on the 21st day after application) Measured value | Calculated value |
| --- | --- | --- | --- |
| No. 55 | 15 | 95 | — |
|  | 7 | 83 | — |
| Pyridate | 200 | 0 | — |
|  | 100 | 0 | — |
| No. 55 + pyridate | 15 + 200 | 99 | 95 |
|  | 7 + 100 | 95 | 83 |

TABLE 5-26

| Compound | Active ingredient amount (g/ha) | Growth inhibition rate (%) of crabgrass (3.2 to 4.2 leaf stage) (on the 21st day after application) Measured value | Calculated value |
| --- | --- | --- | --- |
| No. 55 | 15 | 98 | — |
|  | 7 | 80 | — |
| Metribuzin | 250 | 20 | — |
|  | 125 | 15 | — |
| No. 55 + metribuzin | 15 + 250 | 100 | 98.4 |
|  | 7 + 125 | 100 | 83 |

TABLE 5-27

| Compound | Active ingredient amount (g/ha) | Growth inhibition rate (%) of crabgrass (3.2 to 4.2 leaf stage) (on the 21st day after application) Measured value | Calculated value |
| --- | --- | --- | --- |
| No. 55 | 15 | 98 | — |
|  | 7 | 80 | — |
| Sulcotrione | 31 | 65 | — |
|  | 15.6 | 50 | — |
| No. 55 + sulcotrione | 15 + 31 | 100 | 99.3 |
|  | 7 + 15.6 | 99 | 90 |

TABLE 5-28

| Compound | Active ingredient amount (g/ha) | Growth inhibition rate (%) of velvetleaf (2.0 to 2.8 leaf stage) (on the 21st day after application) Measured value | Calculated value |
| --- | --- | --- | --- |
| No. 55 | 15 | 90 | — |
|  | 7 | 70 | — |
| Foramsulfuron | 30 | 25 | — |
|  | 15 | 0 | — |
| No. 55 + foramsulfuron | 15 + 30 | 94 | 92.5 |
|  | 7 + 15 | 75 | 70 |

TABLE 5-29

| Compound | Active ingredient amount (g/ha) | Growth inhibition rate (%) of crabgrass (3.0 to 4.3 leaf stage) (on the 21st day after application) Measured value | Calculated value |
| --- | --- | --- | --- |
| No. 55 | 15 | 95 | — |
|  | 7 | 83 | — |
| Prosulfuron | 30 | 0 | — |
|  | 15 | 0 | — |

TABLE 5-29-continued

| | Active ingredient | Growth inhibition rate (%) of crabgrass (3.0 to 4.3 leaf stage) (on the 21st day after application) | |
|---|---|---|---|
| Compound | amount (g/ha) | Measured value | Calculated value |
| No. 55 + | 15 + 30 | 97 | 95 |
| prosulfuron | 7 + 15 | 95 | 83 |

TABLE 5-30

| | Active ingredient | Growth inhibition rate (%) of crabgrass (3.2 to 4.2 leaf stage) (on the 21st day after application) | |
|---|---|---|---|
| Compound | amount (g/ha) | Measured value | Calculated value |
| No. 55 | 7 | 80 | — |
| Iodosulfuron-methyl-sodium | 7.5 | 5 | — |
| No. 55 + iodosulfuron-methyl-sodium | 7 + 7.5 | 94 | 81 |

TABLE 5-31

| | Active ingredient | Growth inhibition rate (%) of crabgrass (3.2 to 4.2 leaf stage) (on the 21st day after application) | |
|---|---|---|---|
| Compound | amount (g/ha) | Measured value | Calculated value |
| No. 55 | 15 | 98 | — |
| | 7 | 80 | — |
| Tritosulfuron | 15 | 0 | — |
| | 7.8 | 0 | — |
| No. 55 + | 15 + 15 | 100 | 98 |
| tritosulfuron | 7 + 7.8 | 97 | 80 |

TABLE 5-32

| | Active ingredient | Growth inhibition rate (%) of crabgrass (2.7 to 3.6 leaf stage) (on the 21st day after application) | |
|---|---|---|---|
| Compound | amount (g/ha) | Measured value | Calculated value |
| No. 208 | 15.5 | 83 | — |
| | 7.75 | 83 | — |
| Atrazine | 375 | 20 | — |
| | 175 | 0 | — |
| No. 208 + | 15.5 + 375 | 99 | 86.4 |
| atrazine | 7.75 + 175 | 88 | 83 |

TABLE 5-33

| | Active ingredient | Growth inhibition rate (%) of velvetleaf (3.2 to 4.1 leaf stage) (on the 21st day after application) | |
|---|---|---|---|
| Compound | amount (g/ha) | Measured value | Calculated value |
| No. 208 | 15.5 | 73 | — |
| | 7.75 | 73 | — |
| Atrazine | 375 | 5 | — |
| | 175 | 3 | — |
| No. 208 + | 15.5 + 375 | 95 | 74.4 |
| atrazine | 7.75 + 175 | 90 | 73.8 |

TABLE 5-34

| | Active ingredient | Growth inhibition rate (%) of crabgrass (2.7 to 3.6 leaf stage) (on the 21st day after application) | |
|---|---|---|---|
| Compound | amount (g/ha) | Measured value | Calculated value |
| No. 208 | 15.5 | 83 | — |
| Bromoxynil | 165 | 0 | — |
| No. 208 + bromoxynil | 15.5 + 165 | 98 | 83 |

TABLE 5-35

| | Active ingredient | Growth inhibition rate (%) of velvetleaf (3.2 to 4.1 leaf stage) (on the 21st day after application) | |
|---|---|---|---|
| Compound | amount (g/ha) | Measured value | Calculated value |
| No. 208 | 15.5 | 73 | — |
| | 7.75 | 73 | — |
| Bromoxynil | 165 | 30 | — |
| | 77 | 0 | — |
| No. 208 + | 15.5 + 165 | 100 | 81.1 |
| bromoxynil | 7.75 + 77 | 88 | 73 |

TABLE 5-36

| | Active ingredient | Growth inhibition rate (%) of crabgrass (3.1 to 4.0 leaf stage) (on the 22nd day after application) | |
|---|---|---|---|
| Compound | amount (g/ha) | Measured value | Calculated value |
| No. 241 | 15 | 90 | — |
| Atrazine | 375 | 0 | — |
| No. 241 + atrazine | 15 + 375 | 100 | 90 |

TABLE 5-37

| | Active ingredient | Growth inhibition rate (%) of velvetleaf (4.0 to 4.4 leaf stage) (on the 22nd day after application) | |
|---|---|---|---|
| Compound | amount (g/ha) | Measured value | Calculated value |
| No. 241 | 15 | 97 | — |
| | 7.5 | 80 | — |
| Atrazine | 375 | 25 | — |
| | 175 | 20 | — |
| No. 241 + | 15 + 375 | 100 | 97.8 |
| atrazine | 7.5 + 175 | 100 | 84 |

TABLE 5-38

| | Active ingredient | Growth inhibition rate (%) of crabgrass (3.1 to 4.0 leaf stage) (on the 22nd day after application) | |
|---|---|---|---|
| Compound | amount (g/ha) | Measured value | Calculated value |
| No. 241 | 15 | 90 | — |
| | 7.5 | 78 | — |
| Terbuthylazine | 375 | 0 | — |
| | 175 | 0 | — |
| No. 241 + | 15 + 375 | 99 | 90 |
| terbuthylazine | 7.5 + 175 | 83 | 78 |

TABLE 5-39

| Compound | Active ingredient amount (g/ha) | Growth inhibition rate (%) of velvetleaf (4.0 to 4.4 leaf stage) (on the 22nd day after application) Measured value | Calculated value |
|---|---|---|---|
| No. 241 | 15 | 97 | — |
|  | 7.5 | 80 | — |
| Terbuthylazine | 375 | 25 | — |
|  | 175 | 15 | — |
| No. 241 + terbuthylazine | 15 + 375 | 100 | 97.8 |
|  | 7.5 + 175 | 88 | 83 |

TABLE 5-40

| Compound | Active ingredient amount (g/ha) | Growth inhibition rate (%) of velvetleaf (4.0 to 4.4 leaf stage) (on the 22nd day after application) Measured value | Calculated value |
|---|---|---|---|
| No. 241 | 15 | 97 | — |
| Bromoxynil | 165 | 50 | — |
| No. 241 + bromoxynil | 15 + 165 | 100 | 98.5 |

TABLE 5-41

| Compound | Active ingredient amount (g/ha) | Growth inhibition rate (%) of crabgrass (4.3 to 4.5 leaf stage) (on the 20th day after application) Measured value | Calculated value |
|---|---|---|---|
| No. 2-28 | 15 | 80 | — |
| Nicosulfuron | 15 | 88 | — |
| No. 2-28 + nicosulfuron | 15 + 15 | 99 | 97.6 |

TABLE 5-42

| Compound | Active ingredient amount (g/ha) | Growth inhibition rate (%) of crabgrass (4.3 to 4.5 leaf stage) (on the 20th day after application) Measured value | Calculated value |
|---|---|---|---|
| No. 2-28 | 15 | 80 | — |
|  | 7.5 | 75 | — |
| Atrazine | 250 | 0 | — |
|  | 125 | 0 | — |
| No. 2-28 atrazine | 15 + 250 | 100 | 80 |
|  | 7.5 + 125 | 95 | 75 |

TABLE 5-43

| Compound | Active ingredient amount (g/ha) | Growth inhibition rate (%) of velvetleaf (3.0 to 3.5 leaf stage) (on the 20th day after application) Measured value | Calculated value |
|---|---|---|---|
| No. 2-28 | 7.5 | 85 | — |
| Atrazine | 125 | 0 | — |
| No. 2-28 + atrazine | 7.5 + 125 | 100 | 85 |

TABLE 5-44

| Compound | Active ingredient amount (g/ha) | Growth inhibition rate (%) of crabgrass (4.3 to 4.5 leaf stage) (on the 20th day after application) Measured value | Calculated value |
|---|---|---|---|
| No. 2-28 | 15 | 80 | — |
|  | 7.5 | 75 | — |
| Terbuthylazine | 250 | 0 | — |
|  | 125 | 0 | — |
| No. 2-28 + terbuthylazine | 15 + 250 | 99 | 80 |
|  | 7.5 + 125 | 100 | 75 |

TABLE 5-45

| Compound | Active ingredient amount (g/ha) | Growth inhibition rate (%) of velvetleaf (3.0 to 3.5 leaf stage) (on the 20th day after application) Measured value | Calculated value |
|---|---|---|---|
| No. 2-28 | 7.5 | 85 | — |
| Terbuthylazine | 125 | 0 | — |
| No. 2-28 + terbuthylazine | 7.5 + 125 | 100 | 85 |

TABLE 5-46

| Compound | Active ingredient amount (g/ha) | Growth inhibition rate (%) of velvetleaf (3.0 to 3.5 leaf stage) (on the 20th day after application) Measured value | Calculated value |
|---|---|---|---|
| No. 2-28 | 7.5 | 85 | — |
| S-Metolachlor | 150 | 0 | — |
| No. 2-28 + S-metolachlor | 7.5 + 150 | 100 | 85 |

TABLE 5-47

| Compound | Active ingredient amount (g/ha) | Growth inhibition rate (%) of crabgrass (4.0 to 5.0 leaf stage) (on the 21st day after application) Measured value | Calculated value |
|---|---|---|---|
| No. 241 | 7 | 60 | — |
| Bromoxynil | 165 | 0 | — |
|  | 77 | 0 | — |
| No. 241 + bromoxynil | 7 + 165 | 70 | 60 |
|  | 7 + 77 | 65 | 60 |

TABLE 5-48

| Compound | Active ingredient amount (g/ha) | Growth inhibition rate (%) of velvetleaf (2.5 to 3.3 leaf stage) (on the 21st day after application) Measured value | Calculated value |
|---|---|---|---|
| No. 241 | 15 | 80 | — |
|  | 7 | 65 | — |
| Bromoxynil | 165 | 40 | — |
|  | 77 | 30 | — |
| No. 241 + bromoxynil | 15 + 165 | 100 | 88 |
|  | 15 + 77 | 100 | 86 |
|  | 7 + 165 | 89 | 79 |
|  | 7 + 77 | 95 | 75.5 |

TABLE 5-49

| Compound | Active ingredient amount (g/ha) | Growth inhibition rate (%) of crabgrass (4.0 to 5.0 leaf stage) (on the 21st day after application) Measured value | Calculated value |
| --- | --- | --- | --- |
| No. 241 | 15 | 80 | — |
|  | 7 | 60 | — |
| S-Metolachlor | 150 | 0 | — |
| No. 241 + | 15 + 150 | 83 | 80 |
| S-metolachlor | 7 + 150 | 65 | 60 |

TABLE 5-50

| Compound | Active ingredient amount (g/ha) | Growth inhibition rate (%) of velvetleaf (2.5 to 3.3 leaf stage) (on the 21st day after application) Measured value | Calculated value |
| --- | --- | --- | --- |
| No. 241 | 15 | 80 | — |
|  | 7 | 65 | — |
| S-Metolachlor | 300 | 0 | — |
|  | 150 | 0 | — |
| No. 241 + | 15 + 300 | 90 | 80 |
| S-metolachlor | 15 + 150 | 90 | 80 |
|  | 7 + 300 | 70 | 65 |

TABLE 5-51

| Compound | Active ingredient amount (g/ha) | Growth inhibition rate (%) of crabgrass (3.7 to 4.6 leaf stage) (on the 21st day after application) Measured value | Calculated value |
| --- | --- | --- | --- |
| No. 241 | 15 | 94 | — |
|  | 7 | 80 | — |
| Dicamba-dimethylammonium | 200 | 15 | — |
|  | 100 | 0 | — |
| No. 241 + | 15 + 200 | 97 | 94.9 |
| dicamba-dimethylammonium | 7 + 100 | 85 | 80 |

TABLE 5-52

| Compound | Active ingredient amount (g/ha) | Growth inhibition rate (%) of crabgrass (3.7 to 4.6 leaf stage) (on the 21st day after application) Measured value | Calculated value |
| --- | --- | --- | --- |
| No. 241 | 7 | 80 | — |
| Carfentrazone-ethyl | 5 | 0 | — |
| No. 241 + carfentrazone-ethyl | 7 + 5 | 85 | 80 |

TABLE 5-53

| Compound | Active ingredient amount (g/ha) | Growth inhibition rate (%) of crabgrass (3.2 to 4.3 leaf stage) (on the 21st day after application) Measured value | Calculated value |
| --- | --- | --- | --- |
| No. 241 | 15 | 88 | — |
| Carfentrazone-ethyl | 2.5 | 0 | — |
| No. 241 + carfentrazone-ethyl | 15 + 2.5 | 93 | 88 |

TABLE 5-54

| Compound | Active ingredient amount (g/ha) | Growth inhibition rate (%) of velvetleaf (3.3 to 4.3 leaf stage) (on the 20th day after application) Measured value | Calculated value |
| --- | --- | --- | --- |
| No. 241 | 15 | 80 | — |
| Carfentrazone-ethyl | 5 | 80 | — |
| No. 241 + carfentrazone-ethyl | 15 + 5 | 98 | 96 |

TABLE 5-55

| Compound | Active ingredient amount (g/ha) | Growth inhibition rate (%) of velvetleaf (3.2 to 4.3 leaf stage) (on the 21st day after application) Measured value | Calculated value |
| --- | --- | --- | --- |
| No. 241 | 15 | 85 | — |
|  | 7.5 | 60 | — |
| Carfentrazone-ethyl | 2.5 | 65 | — |
| No. 241 + | 15 + 2.5 | 100 | 94.8 |
| carfentrazone-ethyl | 7.5 + 2.5 | 94 | 86 |

TABLE 5-56

| Compound | Active ingredient amount (g/ha) | Growth inhibition rate (%) of velvetleaf (2.6 to 3.3 leaf stage) (on the 20th day after application) Measured value | Calculated value |
| --- | --- | --- | --- |
| No. 241 | 7 | 70 | — |
| Glyphosate-ammonium | 63 | 0 | — |
| No. 241 + glyphosate-ammonium | 7 + 63 | 85 | 70 |

TABLE 5-57

| Compound | Active ingredient amount (g/ha) | Growth inhibition rate (%) of velvetleaf (3.0 to 4.0 leaf stage) (on the 21st day after application) Measured value | Calculated value |
| --- | --- | --- | --- |
| No. 241 | 15 | 80 | — |
|  | 7 | 60 | — |
| Glyphosate-ammonium | 200 | 0 | — |
| No. 241 + | 15 + 200 | 85 | 80 |
| glyphosate-ammonium | 7 + 200 | 63 | 60 |

TABLE 5-58

| Compound | Active ingredient amount (g/ha) | Growth inhibition rate (%) of crabgrass (3.2 to 4.1 leaf stage) (on the 14th day after application) Measured value | Calculated value |
| --- | --- | --- | --- |
| No. 241 | 15 | 94 | — |
| Prosulfuron | 30 | 10 | — |
|  | 15 | 0 | — |
| No. 241 + | 15 + 30 | 97 | 94.6 |
| prosulfuron | 15 + 15 | 97 | 94 |

TABLE 5-59

Growth inhibition rate (%) of crabgrass (3.2 to 4.1 leaf stage) (on the 21st day after application)

| Compound | Active ingredient amount (g/ha) | Measured value | Calculated value |
|---|---|---|---|
| No. 241 | 7 | 80 | — |
| Prosulfuron | 15 | 0 | — |
| No. 241 + prosulfuron | 7 + 15 | 85 | 80 |

TABLE 5-60

Growth inhibition rate (%) of crabgrass (3.2 to 4.3 leaf stage) (on the 14th day after application)

| Compound | Active ingredient amount (g/ha) | Measured value | Calculated value |
|---|---|---|---|
| No. 241 | 15 | 93 | — |
|  | 7.5 | 80 | — |
| Prosulfuron | 10 | 0 | — |
|  | 5 | 0 | — |
| No. 241 + prosulfuron | 15 + 10 | 97 | 93 |
|  | 15 + 5 | 98 | 93 |
|  | 7.5 + 10 | 83 | 80 |
|  | 7.5 + 5 | 90 | 80 |

TABLE 5-61

Growth inhibition rate (%) of velvetleaf (3.0 to 4.0 leaf stage) (on the 21st day after application)

| Compound | Active ingredient amount (g/ha) | Measured value | Calculated value |
|---|---|---|---|
| No. 241 | 15 | 80 | — |
| Prosulfuron | 30 | 95 | — |
| No. 241 + prosulfuron | 15 + 30 | 100 | 99 |

TABLE 5-62

Growth inhibition rate (%) of velvetleaf (3.0 to 4.0 leaf stage) (on the 21st day after application)

| Compound | Active ingredient amount (g/ha) | Measured value | Calculated value |
|---|---|---|---|
| No. 241 | 15 | 80 | — |
|  | 7 | 60 | — |
| Rimsulfuron | 20 | 95 | — |
|  | 10 | 75 | — |
| No. 241 + rimsulfuron | 15 + 20 | 100 | 99 |
|  | 15 + 10 | 97 | 95 |
|  | 7 + 10 | 93 | 90 |

TABLE 5-63

Growth inhibition rate (%) of velvetleaf (3.2 to 4.3 leaf stage) (on the 21st day after application)

| Compound | Active ingredient amount (g/ha) | Measured value | Calculated value |
|---|---|---|---|
| No. 241 | 15 | 85 | — |
| Rimsulfuron | 7 | 50 | — |
| No. 241 + rimsulfuron | 15 + 7 | 97 | 92.5 |

TABLE 5-64

Growth inhibition rate (%) of crabgrass (3.2 to 4.1 leaf stage) (on the 21st day after application)

| Compound | Active ingredient amount (g/ha) | Measured value | Calculated value |
|---|---|---|---|
| No. 241 | 15 | 93 | — |
| Bentazone-sodium | 200 | 0 | — |
| No. 241 + bentazone-sodium | 15 + 200 | 95 | 93 |

TABLE 5-65

Growth inhibition rate (%) of velvetleaf (3.0 to 4.0 leaf stage) (on the 21st day after application)

| Compound | Active ingredient amount (g/ha) | Measured value | Calculated value |
|---|---|---|---|
| No. 241 | 15 | 80 | — |
|  | 7 | 60 | — |
| Bentazone-sodium | 200 | 20 | — |
|  | 100 | 0 | — |
| No. 241 + bentazone-sodium | 15 + 200 | 95 | 84 |
|  | 15 + 100 | 88 | 80 |
|  | 7 + 200 | 70 | 68 |
|  | 7 + 100 | 63 | 60 |

TABLE 5-66

Growth inhibition rate (%) of velvetleaf (3.3 to 4.3 leaf stage) (on the 20th day after application)

| Compound | Active ingredient amount (g/ha) | Measured value | Calculated value |
|---|---|---|---|
| No. 241 | 15 | 80 | — |
|  | 7.5 | 55 | — |
| Glufosinate-ammonium | 200 | 10 | — |
|  | 100 | 0 | — |
| No. 241 + glufosinate-ammonium | 15 + 200 | 83 | 82 |
|  | 7.5 + 200 | 65 | 59.5 |
|  | 7.5 + 100 | 70 | 55 |

TABLE 5-67

Growth inhibition rate (%) of crabgrass (3.5 to 4.2 leaf stage) (on the 14th day after application)

| Compound | Active ingredient amount (g/ha) | Measured value | Calculated value |
|---|---|---|---|
| No. 241 | 15 | 90 | — |
|  | 7.5 | 75 | — |
| Linuron | 500 | 35 | — |
|  | 250 | 20 | — |
| No. 241 + linuron | 15 + 500 | 100 | 93.5 |
|  | 15 + 250 | 97 | 92 |
|  | 7.5 + 500 | 92 | 83.8 |

TABLE 5-68

Growth inhibition rate (%) of velvetleaf (3.3 to 4.3 leaf stage) (on the 20th day after application)

| Compound | Active ingredient amount (g/ha) | Measured value | Calculated value |
|---|---|---|---|
| No. 241 | 15 | 80 | — |
|  | 7.5 | 55 | — |
| Linuron | 500 | 93 | — |

TABLE 5-68-continued

| Compound | Active ingredient amount (g/ha) | Growth inhibition rate (%) of velvetleaf (3.3 to 4.3 leaf stage) (on the 20th day after application) Measured value | Calculated value |
|---|---|---|---|
|  | 250 | 55 | — |
| No. 241 + | 15 + 500 | 100 | 98.6 |
| linuron | 15 + 250 | 100 | 91 |
|  | 7.5 + 500 | 100 | 96.9 |
|  | 7.5 + 250 | 98 | 79.8 |

TABLE 5-69

| Compound | Active ingredient amount (g/ha) | Growth inhibition rate (%) of velvetleaf (3.3 to 4.3 leaf stage) (on the 20th day after application) Measured value | Calculated value |
|---|---|---|---|
| No. 241 | 15 | 80 | — |
|  | 7.5 | 55 | — |
| Clopyralid-olamine | 300 | 10 | — |
|  | 150 | 5 | — |
| No. 241 + | 15 + 300 | 83 | 82 |
| clopyralid-olamine | 7.5 + 300 | 70 | 59.5 |
|  | 7.5 + 150 | 63 | 57.3 |

TABLE 5-70

| Compound | Active ingredient amount (g/ha) | Growth inhibition rate (%) of crabgrass (3.2 to 4.3 leaf stage) (on the 21st day after application) Measured value | Calculated value |
|---|---|---|---|
| No. 241 | 15 | 88 | — |
|  | 7.5 | 70 | — |
| 2,4-D-ethyl | 125 | 0 | — |
| No. 241 + | 15 + 125 | 97 | 88 |
| 2,4-D-ethyl | 7.5 + 125 | 93 | 70 |

TABLE 5-71

| Compound | Active ingredient amount (g/ha) | Growth inhibition rate (%) of velvetleaf (3.2 to 4.3 leaf stage) (on the 21st day after application) Measured value | Calculated value |
|---|---|---|---|
| No. 241 | 15 | 85 | — |
|  | 7.5 | 60 | — |
| 2,4-D-ethyl | 125 | 50 | — |
| No. 241 + | 15 + 125 | 100 | 92.5 |
| 2,4-D-ethyl | 7.5 + 125 | 100 | 80 |

TABLE 5-72

| Compound | Active ingredient amount (g/ha) | Growth inhibition rate (%) of crabgrass (3.2 to 4.3 leaf stage) (on the 21st day after application) Measured value | Calculated value |
|---|---|---|---|
| No. 241 | 15 | 88 | — |
|  | 7.5 | 70 | — |
| Pyridate | 200 | 0 | — |
| No. 241 + | 15 + 200 | 98 | 88 |
| pyridate | 7.5 + 200 | 83 | 70 |

TABLE 5-73

| Compound | Active ingredient amount (g/ha) | Growth inhibition rate (%) of velvetleaf (3.2 to 4.3 leaf stage) (on the 21st day after application) Measured value | Calculated value |
|---|---|---|---|
| No. 241 | 15 | 85 | — |
| Pyridate | 200 | 0 | — |
| No. 241 + | 15 + 200 | 95 | 85 |
| pyridate |  |  |  |

TABLE 5-74

| Compound | Active ingredient amount (g/ha) | Growth inhibition rate (%) of crabgrass (3.2 to 4.3 leaf stage) (on the 21st day after application) Measured value | Calculated value |
|---|---|---|---|
| No. 241 | 15 | 88 | — |
|  | 7.5 | 70 | — |
| Sulcotrione | 15 | 10 | — |
| No. 241 + | 15 + 15 | 95 | 89.2 |
| sulcotrione | 7.5 + 15 | 88 | 73 |

TABLE 5-75

| Compound | Active ingredient amount (g/ha) | Growth inhibition rate (%) of velvetleaf (3.2 to 4.3 leaf stage) (on the 21st day after application) Measured value | Calculated value |
|---|---|---|---|
| No. 241 | 15 | 85 | — |
| Sulcotrione | 15 | 25 | — |
| No. 241 + | 15 + 15 | 90 | 88.8 |
| sulcotrione |  |  |  |

TABLE 5-76

| Compound | Active ingredient amount (g/ha) | Growth inhibition rate (%) of crabgrass (3.2 to 4.3 leaf stage) (on the 21st day after application) Measured value | Calculated value |
|---|---|---|---|
| No. 241 | 7.5 | 70 | — |
| Flufenacet | 300 | 10 | — |
| No. 241 + | 7.5 + 300 | 80 | 73 |
| flufenacet |  |  |  |

TABLE 5-77

| Compound | Active ingredient amount (g/ha) | Growth inhibition rate (%) of velvetleaf (3.2 to 4.3 leaf stage) (on the 21st day after application) Measured value | Calculated value |
|---|---|---|---|
| No. 241 | 15 | 85 | — |
|  | 7.5 | 60 | — |
| Flufenacet | 300 | 0 | — |
| No. 241 + | 15 + 300 | 94 | 85 |
| flufenacet | 7.5 + 300 | 70 | 60 |

TABLE 5-78

| Compound | Active ingredient amount (g/ha) | Growth inhibition rate (%) of prickly sida (2.1 to 3.1 leaf stage) (on the 20th day after application) Measured value | Calculated value |
|---|---|---|---|
| No. 241 | 100 | 60 | — |
|  | 50 | 60 | — |
| Nicosulfuron | 60 | 55 | — |
|  | 30 | 10 | — |
|  | 20 | 0 | — |
|  | 7 | 0 | — |
| No. 241 + nicosulfuron | 100 + 60 | 97 | 82 |
|  | 100 + 30 | 95 | 64 |
|  | 100 + 20 | 90 | 60 |
|  | 100 + 7 | 78 | 60 |
|  | 50 + 30 | 93 | 64 |
|  | 50 + 20 | 88 | 60 |
|  | 50 + 7 | 70 | 60 |

TABLE 5-79

| Compound | Active ingredient amount (g/ha) | Growth inhibition rate (%) of velvetleaf (2.5 to 3.3 leaf stage) (on the 21st day after application) Measured value | Calculated value |
|---|---|---|---|
| No. 241 | 15 | 80 | — |
|  | 7 | 65 | — |
| Nicosulfuron | 30 | 20 | — |
|  | 20 | 20 | — |
|  | 10 | 10 | — |
| No. 241 + nicosulfuron | 15 + 30 | 95 | 84 |
|  | 15 + 20 | 95 | 84 |
|  | 15 + 10 | 90 | 82 |
|  | 7 + 30 | 90 | 72 |
|  | 7 + 20 | 80 | 72 |
|  | 7 + 10 | 78 | 68.5 |

TABLE 5-80

| Compound | Active ingredient amount (g/ha) | Growth inhibition rate (%) of velvetleaf (2.8 to 3.6 leaf stage) (on the 24th day after application) Measured value | Calculated value |
|---|---|---|---|
| No. 241 | 3.75 | 45 | — |
| Nicosulfuron | 80 | 60 | — |
| No. 241 + nicosulfuron | 3.75 + 80 | 80 | 78 |

TABLE 5-81

| Compound | Active ingredient amount (g/ha) | Growth inhibition rate (%) of velvetleaf (3.3 to 4.3 leaf stage) (on the 20th day after application) Measured value | Calculated value |
|---|---|---|---|
| No. 241 | 3.75 | 45 | — |
| Nicosulfuron | 50 | 50 | — |
| No. 241 + nicosulfuron | 3.75 + 50 | 75 | 72.5 |

TABLE 5-82

| Compound | Active ingredient amount (g/ha) | Growth inhibition rate (%) of crabgrass (3.5 to 4.2 leaf stage) (on the 20th day after application) Measured value | Calculated value |
|---|---|---|---|
| No. 241 | 3.75 | 68 | — |
|  | 1.875 | 30 | — |
| Nicosulfuron | 30 | 92 | — |
| No. 241 + nicosulfuron | 3.75 + 30 | 99 | 97.4 |
|  | 1.875 + 30 | 100 | 94.4 |

TABLE 5-83

| Compound | Active ingredient amount (g/ha) | Growth inhibition rate (%) of prickly sida (2.1 to 3.1 leaf stage) (on the 20th day after application) Measured value | Calculated value |
|---|---|---|---|
| No. 241 | 100 | 60 | — |
| Terbuthylazine | 500 | 55 | — |
|  | 250 | 15 | — |
|  | 125 | 0 | — |
|  | 63 | 0 | — |
|  | 45 | 0 | — |
| No. 241 + terbuthylazine | 100 + 500 | 98 | 82 |
|  | 100 + 250 | 95 | 66 |
|  | 100 + 125 | 89 | 60 |
|  | 100 + 63 | 94 | 60 |
|  | 100 + 45 | 80 | 60 |

TABLE 5-84

| Compound | Active ingredient amount (g/ha) | Growth inhibition rate (%) of velvetleaf (2.8 to 3.6 leaf stage) (on the 24th day after application) Measured value | Calculated value |
|---|---|---|---|
| No. 241 | 7.5 | 60 | — |
|  | 3.75 | 45 | — |
| Terbuthylazine | 2000 | 20 | — |
| No. 241 + terbuthylazine | 7.5 + 2000 | 100 | 68 |
|  | 3.75 + 2000 | 98 | 56 |

TABLE 5-85

| Compound | Active ingredient amount (g/ha) | Growth inhibition rate (%) of velvetleaf (3.3 to 4.3 leaf stage) (on the 20th day after application) Measured value | Calculated value |
|---|---|---|---|
| No. 241 | 7.5 | 55 | — |
|  | 3.75 | 45 | — |
| Terbuthylazine | 750 | 30 | — |
|  | 375 | 20 | — |
| No. 241 + terbuthylazine | 7.5 + 750 | 100 | 68.5 |
|  | 7.5 + 375 | 95 | 64 |
|  | 3.75 + 750 | 98 | 61.5 |
|  | 3.75 + 375 | 94 | 56 |

TABLE 5-86

| Compound | Active ingredient amount (g/ha) | Growth inhibition rate (%) of ivyleaf morningglory (1.5 to 2.1 leaf stage) (on the 23rd day after application) Measured value | Calculated value |
| --- | --- | --- | --- |
| No. 241 | 100 | 85 | — |
| Atrazine | 500 | 83 | — |
|  | 180 | 0 | — |
|  | 90 | 0 | — |
|  | 31 | 0 | — |
| No. 241 + atrazine | 100 + 500 | 99 | 97.5 |
|  | 100 + 180 | 90 | 85 |
|  | 100 + 90 | 93 | 85 |
|  | 100 + 31 | 90 | 85 |

TABLE 5-87

| Compound | Active ingredient amount (g/ha) | Growth inhibition rate (%) of velvetleaf (2.8 to 3.6 leaf stage) (on the 24th day after application) Measured value | Calculated value |
| --- | --- | --- | --- |
| No. 241 | 7.5 | 60 | — |
|  | 3.75 | 45 | — |
| Atrazine | 2000 | 25 | — |
|  | 1500 | 15 | — |
|  | 1000 | 15 | — |
| No. 241 + atrazine | 7.5 + 2000 | 95 | 70 |
|  | 7.5 + 1500 | 100 | 66 |
|  | 7.5 + 1000 | 93 | 66 |
|  | 3.75 + 2000 | 85 | 58.8 |
|  | 3.75 + 1500 | 88 | 53.3 |
|  | 3.75 + 1000 | 93 | 53.3 |

TABLE 5-88

| Compound | Active ingredient amount (g/ha) | Growth inhibition rate (%) of ivyleaf morningglory (1.5 to 2.1 leaf stage) (on the 14th day after application) Measured value | Calculated value |
| --- | --- | --- | --- |
| No. 241 | 75 | 88 | — |
| Acetochlor | 200 | 0 | — |
|  | 150 | 0 | — |
|  | 100 | 0 | — |
| No. 241 + acetochlor | 75 + 200 | 95 | 88 |
|  | 75 + 150 | 95 | 88 |
|  | 75 + 100 | 94 | 88 |

TABLE 5-89

| Compound | Active ingredient amount (g/ha) | Growth inhibition rate (%) of crabgrass (3.3 to 4.2 leaf stage) (on the 24th day after application) Measured value | Calculated value |
| --- | --- | --- | --- |
| No. 241 | 15 | 75 | — |
|  | 7.5 | 68 | — |
| Acetochlor | 1600 | 0 | — |
|  | 800 | 0 | — |
|  | 600 | 0 | — |
|  | 400 | 0 | — |
| No. 241 + acetochlor | 15 + 1600 | 99 | 75 |
|  | 15 + 800 | 94 | 75 |
|  | 15 + 600 | 99 | 75 |

TABLE 5-89-continued

| Compound | Active ingredient amount (g/ha) | Growth inhibition rate (%) of crabgrass (3.3 to 4.2 leaf stage) (on the 24th day after application) Measured value | Calculated value |
| --- | --- | --- | --- |
|  | 15 + 400 | 85 | 75 |
|  | 7.5 + 1600 | 75 | 68 |
|  | 7.5 + 800 | 70 | 68 |
|  | 7.5 + 600 | 80 | 68 |
|  | 7.5 + 400 | 73 | 68 |

TABLE 5-90

| Compound | Active ingredient amount (g/ha) | Growth inhibition rate (%) of velvetleaf (3.3 to 4.2 leaf stage) (on the 22nd day after application) Measured value | Calculated value |
| --- | --- | --- | --- |
| No. 2-28 | 15 | 97 | — |
|  | 7 | 93 | — |
| Bromoxynil-octanoate | 125 | 50 | — |
|  | 63 | 45 | — |
| No. 2-28 + bromoxynil-octanoate | 15 + 125 | 100 | 99 |
|  | 15 + 63 | 100 | 98 |
|  | 7 + 125 | 100 | 97 |
|  | 7 + 63 | 100 | 96 |

TABLE 5-91

| Compound | Active ingredient amount (g/ha) | Growth inhibition rate (%) of velvetleaf (3.3 to 4.2 leaf stage) (on the 22nd day after application) Measured value | Calculated value |
| --- | --- | --- | --- |
| No. 2-28 | 15 | 97 | — |
|  | 7 | 93 | — |
| Acetochlor | 300 | 0 | — |
|  | 150 | 0 | — |
| No. 2-28 + acetochlor | 15 + 300 | 99 | 97 |
|  | 15 + 150 | 100 | 97 |
|  | 7 + 300 | 93 | 93 |
|  | 7 + 150 | 97 | 93 |

TABLE 5-92

| Compound | Active ingredient amount (g/ha) | Growth inhibition rate (%) of velvetleaf (3.3 to 4.2 leaf stage) (on the 14th day after application) Measured value | Calculated value |
| --- | --- | --- | --- |
| No. 2-28 | 15 | 97 | — |
|  | 7 | 93 | — |
| S-Metolachlor | 300 | 0 | — |
|  | 150 | 0 | — |
| No. 2-28 + S-metolachlor | 15 + 300 | 98 | 97 |
|  | 15 + 150 | 99 | 97 |
|  | 7 + 300 | 97 | 93 |
|  | 7 + 150 | 95 | 93 |

TABLE 5-93

| Compound | Active ingredient amount (g/ha) | Growth inhibition rate (%) of crabgrass (3.6 to 4.5 leaf stage) (on the 14th day after application) | |
|---|---|---|---|
| | | Measured value | Calculated value |
| No. 2-28 | 15 | 97 | — |
| | 7 | 90 | — |
| 2,4-D-ethyl | 100 | 0 | — |
| No. 2-28 + 2,4-D-ethyl | 15 + 100 | 98 | 97 |
| | 7 + 100 | 99 | 90 |

TABLE 5-94

| Compound | Active ingredient amount (g/ha) | Growth inhibition rate (%) of crabgrass (3.6 to 4.5 leaf stage) (on the 22nd day after application) | |
|---|---|---|---|
| | | Measured value | Calculated value |
| No. 2-28 | 7 | 93 | — |
| 2,4-D-ethyl | 200 | 25 | — |
| No. 2-28 + 2,4-D-ethyl | 7 + 200 | 95 | 94.8 |

TABLE 5-95

| Compound | Active ingredient amount (g/ha) | Growth inhibition rate (%) of crabgrass (3.6 to 4.5 leaf stage) (on the 14th day after application) | |
|---|---|---|---|
| | | Measured value | Calculated value |
| No. 2-28 | 15 | 97 | — |
| | 7 | 90 | — |
| Carfentrazone-ethyl | 2.5 | 0 | — |
| No. 2-28 + carfentrazone-ethyl | 15 + 2.5 | 99 | 97 |
| | 7 + 2.5 | 93 | 90 |

TABLE 5-96

| Compound | Active ingredient amount (g/ha) | Growth inhibition rate (%) of crabgrass (3.5 to 5.0 leaf stage) (on the 22nd day after application) | |
|---|---|---|---|
| | | Measured value | Calculated value |
| No. 2-28 | 15 | 93 | — |
| | 7 | 88 | — |
| Pethoxamid | 100 | 0 | — |
| No. 2-28 + pethoxamid | 15 + 100 | 95 | 93 |
| | 7 + 100 | 90 | 88 |

TABLE 5-97

| Compound | Active ingredient amount (g/ha) | Growth inhibition rate (%) of velvetleaf (3.5 to 4.0 leaf stage) (on the 14th day after application) | |
|---|---|---|---|
| | | Measured value | Calculated value |
| No. 2-28 | 15 | 95 | — |
| | 7 | 83 | — |
| Pethoxamid | 200 | 60 | — |
| No. 2-28 + pethoxamid | 15 + 200 | 98 | 98 |
| | 7 + 200 | 98 | 93 |

TABLE 5-98

| Compound | Active ingredient amount (g/ha) | Growth inhibition rate (%) of crabgrass (3.5 to 5.0 leaf stage) (on the 22nd day after application) | |
|---|---|---|---|
| | | Measured value | Calculated value |
| No. 2-28 | 15 | 93 | — |
| | 7 | 88 | — |
| Pendimethalin | 100 | 30 | — |
| No. 2-28 + pendimethalin | 15 + 100 | 97 | 95 |
| | 7 + 100 | 93 | 92 |

TABLE 5-99

| Compound | Active ingredient amount (g/ha) | Growth inhibition rate (%) of velvetleaf (3.5 to 4.0 leaf stage) (on the 22nd day after application) | |
|---|---|---|---|
| | | Measured value | Calculated value |
| No. 2-28 | 7 | 90 | — |
| Pendimethalin | 200 | 45 | — |
| No. 2-28 + pendimethalin | 7 + 200 | 99 | 95 |

TABLE 5-100

| Compound | Active ingredient amount (g/ha) | Growth inhibition rate (%) of velvetleaf (3.5 to 4.0 leaf stage) (on the 14th day after application) | |
|---|---|---|---|
| | | Measured value | Calculated value |
| No. 2-28 | 15 | 95 | — |
| | 7 | 83 | — |
| Pyroxasulfone | 100 | 50 | — |
| | 50 | 40 | — |
| No. 2-28 + pyroxasulfone | 15 + 100 | 99 | 98 |
| | 15 + 50 | 99 | 97 |
| | 7 + 100 | 99 | 92 |
| | 7 + 50 | 98 | 90 |

TABLE 5-101

| Compound | Active ingredient amount (g/ha) | Growth inhibition rate (%) of crabgrass (3.5 to 5.0 leaf stage) (on the 22nd day after application) | |
|---|---|---|---|
| | | Measured value | Calculated value |
| No. 2-28 | 15 | 93 | — |
| | 7 | 88 | — |
| Dicamba-dimethyl-ammonium | 200 | 0 | — |
| | 100 | 0 | — |
| No. 2-28 + dicamba-dimethyl-ammonium | 15 + 200 | 97 | 93 |
| | 15 + 100 | 95 | 93 |
| | 7 + 200 | 90 | 88 |
| | 7 + 100 | 90 | 88 |

TABLE 5-102

| Compound | Active ingredient amount (g/ha) | Growth inhibition rate (%) of velvetleaf (3.5 to 4.1 leaf stage) (on the 20th day after application) | |
|---|---|---|---|
| | | Measured value | Calculated value |
| No. 2-28 | 15 | 88 | — |
| | 7 | 75 | — |
| Glyphosate- | 150 | 0 | — |

TABLE 5-102-continued

| Compound | Active ingredient amount (g/ha) | Growth inhibition rate (%) of velvetleaf (3.5 to 4.1 leaf stage) (on the 20th day after application) Measured value | Calculated value |
|---|---|---|---|
| ammonium | 75 | 0 | — |
| No. 2-28 + glyphosate-ammonium | 15 + 150 | 98 | 88 |
| | 15 + 75 | 95 | 88 |
| | 7 + 150 | 85 | 75 |
| | 7 + 75 | 78 | 75 |

TABLE 5-103

| Compound | Active ingredient amount (g/ha) | Growth inhibition rate (%) of velvetleaf (3.5 to 4.1 leaf stage) (on the 14th day after application) Measured value | Calculated value |
|---|---|---|---|
| No. 2-28 | 15 | 85 | — |
| | 7 | 75 | — |
| Glyphosate-ammonium | 200 | 50 | — |
| | 100 | 25 | — |
| No. 2-28 + glyphosate-ammonium | 15 + 200 | 99 | 93 |
| | 15 + 100 | 93 | 89 |
| | 7 + 200 | 99 | 88 |
| | 7 + 100 | 97 | 81 |

TABLE 5-104

| Compound | Active ingredient amount (g/ha) | Growth inhibition rate (%) of crabgrass (4.1 to 5.3 leaf stage) (on the 14th day after application) Measured value | Calculated value |
|---|---|---|---|
| No. 2-28 | 15 | 85 | — |
| Bentazone-sodium | 200 | 0 | — |
| No. 2-28 + bentazone-sodium | 15 + 200 | 88 | 85 |

TABLE 5-105

| Compound | Active ingredient amount (g/ha) | Growth inhibition rate (%) of velvetleaf (3.5 to 4.1 leaf stage) (on the 14th day after application) Measured value | Calculated value |
|---|---|---|---|
| No. 2-28 | 15 | 85 | — |
| | 7 | 75 | — |
| Clopyralid-olamine | 300 | 20 | — |
| | 150 | 20 | — |
| No. 2-28 + clopyralid-olamine | 15 + 300 | 95 | 88 |
| | 15 + 150 | 88 | 88 |
| | 7 + 300 | 90 | 80 |
| | 7 + 150 | 88 | 80 |

TABLE 5-106

| Compound | Active ingredient amount (g/ha) | Growth inhibition rate (%) of crabgrass (4.1 to 5.3 leaf stage) (on the 20th day after application) Measured value | Calculated value |
|---|---|---|---|
| No. 2-28 | 15 | 97 | — |
| | 7 | 85 | — |

TABLE 5-106-continued

| Compound | Active ingredient amount (g/ha) | Growth inhibition rate (%) of crabgrass (4.1 to 5.3 leaf stage) (on the 20th day after application) Measured value | Calculated value |
|---|---|---|---|
| Pyridate | 200 | 5 | — |
| No. 2-28 + pyridate | 15 + 200 | 99 | 97 |
| | 7 + 200 | 99 | 86 |

TABLE 5-107

| Compound | Active ingredient amount (g/ha) | Growth inhibition rate (%) of crabgrass (3.8 to 4.4 leaf stage) (on the 21st day after application) Measured value | Calculated value |
|---|---|---|---|
| No. 2-1 | 3.5 | 45 | — |
| Nicosulfuron | 15 | 45 | — |
| | 7.5 | 0 | — |
| No. 2-1 + nicosulfuron | 3.5 + 15 | 80 | 70 |
| | 3.5 + 7.5 | 73 | 45 |

TABLE 5-108

| Compound | Active ingredient amount (g/ha) | Growth inhibition rate (%) of velvetleaf (3.5 to 4.3 leaf stage) (on the 21st day after application) Measured value | Calculated value |
|---|---|---|---|
| No. 2-1 | 3.5 | 30 | — |
| Atrazine | 150 | 0 | — |
| No. 2-1 + atrazine | 3.5 + 150 | 75 | 30 |

TABLE 5-109

| Compound | Active ingredient amount (g/ha) | Growth inhibition rate (%) of velvetleaf (3.5 to 4.3 leaf stage) (on the 21st day after application) Measured value | Calculated value |
|---|---|---|---|
| No. 2-1 | 3.5 | 30 | — |
| S-Metolachlor | 150 | 0 | — |
| No. 2-1 + S-metolachlor | 3.5 + 150 | 65 | 30 |

TABLE 5-110

| Compound | Active ingredient amount (g/ha) | Growth inhibition rate (%) of velvetleaf (3.5 to 4.3 leaf stage) (on the 21st day after application) Measured value | Calculated value |
|---|---|---|---|
| No. 2-1 | 3.5 | 30 | — |
| Bromoxynil-octanoate | 50 | 0 | — |
| No. 2-1 + bromoxynil-octanoate | 3.5 + 50 | 60 | 30 |

TABLE 5-111

Growth inhibition rate (%) of velvetleaf (3.5 to 4.3 leaf stage) (on the 21st day after application)

| Compound | Active ingredient amount (g/ha) | Measured value | Calculated value |
|---|---|---|---|
| No. 2-1 | 3.5 | 30 | — |
| Dicamba-dimethylammonium | 100 | 50 | — |
| No. 2-1 + dicamba-dimethylammonium | 3.5 + 100 | 75 | 65 |

TABLE 5-112

Growth inhibition rate (%) of velvetleaf (3.5 to 4.3 leaf stage) (on the 21st day after application)

| Compound | Active ingredient amount (g/ha) | Measured value | Calculated value |
|---|---|---|---|
| No. 2-1 | 3.5 | 30 | — |
| Glyphosate-ammonium | 75 | 0 | — |
| No. 2-1 + glyphosate-ammonium | 3.5 + 75 | 70 | 30 |

TABLE 5-113

Growth inhibition rate (%) of crabgrass (3.8 to 5.2 leaf stage) (on the 21st day after application)

| Compound | Active ingredient amount (g/ha) | Measured value | Calculated value |
|---|---|---|---|
| No. 2-19 | 7 | 30 | — |
| Nicosulfuron | 15 | 40 | — |
|  | 7.5 | 5 | — |
| No. 2-19 + nicosulfuron | 7 + 15 | 98 | 58 |
|  | 7 + 7.5 | 70 | 34 |

TABLE 5-114

Growth inhibition rate (%) of velvetleaf (3.2 to 5.0 leaf stage) (on the 21st day after application)

| Compound | Active ingredient amount (g/ha) | Measured value | Calculated value |
|---|---|---|---|
| No. 2-19 | 7 | 50 | — |
| Atrazine | 150 | 60 | — |
| No. 2-19 + atrazine | 7 + 150 | 93 | 80 |

TABLE 5-115

Growth inhibition rate (%) of velvetleaf (3.2 to 5.0 leaf stage) (on the 14th day after application)

| Compound | Active ingredient amount (g/ha) | Measured value | Calculated value |
|---|---|---|---|
| No. 2-19 | 7 | 60 | — |
| S-Metolachlor | 150 | 0 | — |
| No. 2-19 + S-metolachlor | 7 + 150 | 73 | 60 |

TABLE 5-116

Growth inhibition rate (%) of velvetleaf (3.2 to 5.0 leaf stage) (on the 14th day after application)

| Compound | Active ingredient amount (g/ha) | Measured value | Calculated value |
|---|---|---|---|
| No. 2-19 | 7 | 60 | — |
| Bromoxynil-octanoate | 50 | 20 | — |
| No. 2-19 + bromoxynil-octanoate | 7 + 50 | 78 | 68 |

TABLE 5-117

Growth inhibition rate (%) of velvetleaf (3.2 to 5.0 leaf stage) (on the 14th day after application)

| Compound | Active ingredient amount (g/ha) | Measured value | Calculated value |
|---|---|---|---|
| No. 2-19 | 7 | 60 | — |
| Dicamba-dimethylammonium | 100 | 50 | — |
| No. 2-19 + dicamba-dimethylammonium | 7 + 100 | 85 | 80 |

TABLE 5-118

Growth inhibition rate (%) of velvetleaf (3.2 to 5.0 leaf stage) (on the 14th day after application)

| Compound | Active ingredient amount (g/ha) | Measured value | Calculated value |
|---|---|---|---|
| No. 2-19 | 7 | 60 | — |
| Glyphosate-ammonium | 75 | 0 | — |
| No. 2-19 + glyphosate-ammonium | 7 + 75 | 80 | 60 |

TABLE 5-119

Growth inhibition rate (%) of crabgrass (3.8 to 5.2 leaf stage) (on the 21st day after application)

| Compound | Active ingredient amount (g/ha) | Measured value | Calculated value |
|---|---|---|---|
| No. 2-41 | 3.5 | 35 | — |
| Nicosulfuron | 15 | 40 | — |
|  | 7.5 | 5 | — |
| No. 2-41 + nicosulfuron | 3.5 + 15 | 99 | 61 |
|  | 3.5 + 7.5 | 73 | 38 |

TABLE 5-120

Growth inhibition rate (%) of velvetleaf (3.2 to 5.0 leaf stage) (on the 21st day after application)

| Compound | Active ingredient amount (g/ha) | Measured value | Calculated value |
|---|---|---|---|
| No. 2-41 | 3.5 | 60 | — |
| Atrazine | 150 | 60 | — |
| No. 2-41 + atrazine | 3.5 + 150 | 85 | 84 |

TABLE 5-121

| Compound | Active ingredient amount (g/ha) | Growth inhibition rate (%) of velvetleaf (3.2 to 5.0 leaf stage) (on the 14th day after application) | |
|---|---|---|---|
| | | Measured value | Calculated value |
| No. 2-41 | 3.5 | 70 | — |
| S-Metolachlor | 150 | 0 | — |
| No. 2-41 + S-metolachlor | 3.5 + 150 | 78 | 70 |

TABLE 5-122

| Compound | Active ingredient amount (g/ha) | Growth inhibition rate (%) of velvetleaf (3.2 to 5.0 leaf stage) (on the 21st day after application) | |
|---|---|---|---|
| | | Measured value | Calculated value |
| No. 2-41 | 3.5 | 60 | — |
| Bromoxynil-octanoate | 50 | 10 | — |
| No. 2-41 + bromoxynil-octanoate | 3.5 + 50 | 90 | 64 |

TABLE 5-123

| Compound | Active ingredient amount (g/ha) | Growth inhibition rate (%) of velvetleaf (3.2 to 5.0 leaf stage) (on the 14th day after application) | |
|---|---|---|---|
| | | Measured value | Calculated value |
| No. 2-41 | 3.5 | 70 | — |
| Glyphosate-ammonium | 75 | 0 | — |
| No. 2-41 + glyphosate-ammonium | 3.5 + 75 | 80 | 70 |

TABLE 5-124

| Compound | Active ingredient amount (g/ha) | Growth inhibition rate (%) of velvetleaf (3.0 to 3.8 leaf stage) (on the 28th day after application) | |
|---|---|---|---|
| | | Measured value | Calculated value |
| No. 2-161 | 7 | 65 | — |
| | 3.5 | 45 | — |
| Nicosulfuron | 15 | 10 | — |
| | 7.5 | 0 | — |
| No. 2-161 + nicosulfuron | 7 + 15 | 70 | 68.5 |
| | 7 + 7.5 | 78 | 65 |
| | 3.5 + 15 | 60 | 51 |

TABLE 5-125

| Compound | Active ingredient amount (g/ha) | Growth inhibition rate (%) of velvetleaf (3.0 to 3.8 leaf stage) (on the 15th day after application) | |
|---|---|---|---|
| | | Measured value | Calculated value |
| No. 2-161 | 7 | 60 | — |
| | 3.5 | 60 | — |
| Atrazine | 150 | 0 | — |

TABLE 5-125-continued

| Compound | Active ingredient amount (g/ha) | Growth inhibition rate (%) of velvetleaf (3.0 to 3.8 leaf stage) (on the 15th day after application) | |
|---|---|---|---|
| | | Measured value | Calculated value |
| No. 2-161 + atrazine | 7 + 150 | 80 | 60 |
| | 3.5 + 150 | 80 | 60 |

TABLE 5-126

| Compound | Active ingredient amount (g/ha) | Growth inhibition rate (%) of velvetleaf (3.0 to 3.8 leaf stage) (on the 15th day after application) | |
|---|---|---|---|
| | | Measured value | Calculated value |
| No. 2-161 | 7 | 60 | — |
| S-Metolachlor | 15 | 0 | — |
| No. 2-161 + S-metolachlor | 7 + 15 | 65 | 60 |

TABLE 5-127

| Compound | Active ingredient amount (g/ha) | Growth inhibition rate (%) of velvetleaf (3.0 to 3.8 leaf stage) (on the 15th day after application) | |
|---|---|---|---|
| | | Measured value | Calculated value |
| No. 2-161 | 7 | 60 | — |
| | 3.5 | 60 | — |
| Bromoxynil-octanoate | 50 | 0 | — |
| No. 2-161 + bromoxynil-octanoate | 7 + 50 | 85 | 60 |
| | 3.5 + 50 | 90 | 60 |

TABLE 5-128

| Compound | Active ingredient amount (g/ha) | Growth inhibition rate (%) of velvetleaf (3.0 to 3.8 leaf stage) (on the 28th day after application) | |
|---|---|---|---|
| | | Measured value | Calculated value |
| No. 2-161 | 7 | 65 | — |
| | 3.5 | 45 | — |
| Dicamba-dimethylammonium | 100 | 50 | — |
| No. 2-161 + dicamba-dimethylammonium | 7 + 100 | 93 | 83 |
| | 3.5 + 100 | 93 | 73 |

TABLE 5-129

| Compound | Active ingredient amount (g/ha) | Growth inhibition rate (%) of crabgrass (3.3 to 4.2 leaf stage) (on the 28th day after application) | |
|---|---|---|---|
| | | Measured value | Calculated value |
| No. 2-161 | 7 | 83 | — |
| | 3.5 | 70 | — |
| Glyphosate-potassium | 75 | 0 | — |

TABLE 5-129-continued

| Compound | Active ingredient amount (g/ha) | Growth inhibition rate (%) of crabgrass (3.3 to 4.2 leaf stage) (on the 28th day after application) Measured value | Calculated value |
| --- | --- | --- | --- |
| No. 2-161 + glyphosate-potassium | 7 + 75 | 95 | 83 |
| | 3.5 + 75 | 73 | 70 |

TABLE 5-130

| Compound | Active ingredient amount (g/ha) | Growth inhibition rate (%) of crabgrass (3.8 to 4.4 leaf stage) (on the 21st day after application) Measured value | Calculated value |
| --- | --- | --- | --- |
| No. 2-191 | 3.5 | 45 | — |
| Nicosulfuron | 15 | 45 | — |
| No. 2-191 + nicosulfuron | 3.5 + 15 | 88 | 70 |

TABLE 5-131

| Compound | Active ingredient amount (g/ha) | Growth inhibition rate (%) of velvetleaf (3.5 to 4.3 leaf stage) (on the 21st day after application) Measured value | Calculated value |
| --- | --- | --- | --- |
| No. 2-191 | 3.5 | 40 | — |
| Nicosulfuron | 7.5 | 0 | — |
| No. 2-191 + nicosulfuron | 3.5 + 7.5 | 70 | 40 |

TABLE 5-132

| Compound | Active ingredient amount (g/ha) | Growth inhibition rate (%) of crabgrass (3.8 to 4.4 leaf stage) (on the 21st day after application) Measured value | Calculated value |
| --- | --- | --- | --- |
| No. 2-191 | 3.5 | 45 | — |
| Atrazine | 150 | 0 | — |
| No. 2-191 + atrazine | 3.5 + 150 | 60 | 45 |

TABLE 5-133

| Compound | Active ingredient amount (g/ha) | Growth inhibition rate (%) of velvetleaf (3.5 to 4.3 leaf stage) (on the 21st day after application) Measured value | Calculated value |
| --- | --- | --- | --- |
| No. 2-191 | 3.5 | 40 | — |
| S-Metolachlor | 150 | 0 | — |
| No. 2-191 + S-metolachlor | 3.5 + 150 | 60 | 40 |

TABLE 5-134

| Compound | Active ingredient amount (g/ha) | Growth inhibition rate (%) of velvetleaf (3.5 to 4.3 leaf stage) (on the 21st day after application) Measured value | Calculated value |
| --- | --- | --- | --- |
| No. 2-191 | 3.5 | 40 | — |
| Bromoxynil-octanoate | 50 | 0 | — |
| No. 2-191 + bromoxynil-octanoate | 3.5 + 50 | 55 | 40 |

TABLE 5-135

| Compound | Active ingredient amount (g/ha) | Growth inhibition rate (%) of velvetleaf (3.5 to 4.3 leaf stage) (on the 21st day after application) Measured value | Calculated value |
| --- | --- | --- | --- |
| No. 2-191 | 3.5 | 40 | — |
| Dicamba-dimethylammonium | 100 | 50 | — |
| No. 2-191 + dicamba-dimethylammonium | 3.5 + 100 | 75 | 70 |

TABLE 5-136

| Compound | Active ingredient amount (g/ha) | Growth inhibition rate (%) of velvetleaf (3.5 to 4.3 leaf stage) (on the 21st day after application) Measured value | Calculated value |
| --- | --- | --- | --- |
| No. 2-191 | 3.5 | 40 | — |
| Glyphosate-ammonium | 75 | 0 | — |
| No. 2-191 + glyphosate-ammonium | 3.5 + 75 | 65 | 40 |

TABLE 5-137

| Compound | Active ingredient amount (g/ha) | Growth inhibition rate (%) of velvetleaf (3.2 to 5.0 leaf stage) (on the 21st day after application) Measured value | Calculated value |
| --- | --- | --- | --- |
| No. 2-41 | 3.5 | 60 | — |
| Dicamba-dimethylammonium | 100 | 50 | — |
| No. 2-41 + dicamba-dimethylammonium | 3.5 + 100 | 85 | 80 |

Example 2

Upland field soil is put into a 1/1,000,000 hectare pot, and seeds of various plants are sown. When the respective plants reach predetermined leaf stage, herbicidal compositions in predetermined amounts are diluted with water in an amount corresponding to 300 L/ha and applied for foliar treatment by a small sprayer.

On the 14th to 28th day after application, the state of growth of the respective plants is visually observed to determine the growth inhibition rate (measured value) in accordance with the evaluation standards in Example 1. Further, in accordance with the above Colby's formula, the growth inhibition rate (calculated value) is calculated.

When the compound A and other herbicidal compound are used in the following active ingredient amount in the following mixing ratio, a synergistic herbicidal effect is shown. With respect to the compound A, Compound Nos. in Table 1 or 3 are described, and with respect to other herbicidal compounds, common names are described.

Using as the compound A the Compound No. 2-1, No. 2-19, No. 2-41, No. 2-161 or No. 2-191 and terbuthylazine as said other herbicidal compound, (a) the compound A in an amount of from 1 to 100 g/ha and (b) terbuthylazine in an amount of from 40 to 2,000 g/ha are used as mixed in a weight ratio of from 3:1 to 1:550.

Using as the compound A the Compound No. 2-1, No. 2-19, No. 2-28, No. 2-41, No. 2-161 or No. 2-191 and alachlor as said other herbicidal compound, (a) the compound A in an amount of from 1 to 100 g/ha and (b) alachlor in an amount of from 100 to 1,600 g/ha are used as mixed in a weight ratio of from 1:1 to 1:220.

Using as the compound A the Compound No. 2-1, No. 2-19, No. 2-41, No. 2-161 or No. 2-191 and acetochlor as said other herbicidal compound, (a) the compound A in an amount of from 1 to 100 g/ha and (b) acetochlor in an amount of from 100 to 1,600 g/ha are used as mixed in a weight ratio of from 1:1 to 1:220.

Using as the compound A the Compound No. 2-1, No. 2-19, No. 2-41, No. 2-161 or No. 2-191 and pethoxamid as said other herbicidal compound, (a) the compound A in an amount of from 1 to 100 g/ha and (b) pethoxamid in an amount of from 100 to 1,600 g/ha are used as mixed in a weight ratio of from 1:1 to 1:220.

Using as the compound A the Compound No. 2-1, No. 2-19, No. 2-41, No. 2-161 or No. 2-191 and pyroxasulfone as said other herbicidal compound, (a) the compound A in an amount of from 1 to 100 g/ha and (b) pyroxasulfone in an amount of from 50 to 1,000 g/ha are used as mixed in a weight ratio of from 1:1 to 1:100.

INDUSTRIAL APPLICABILITY

The herbicidal composition of the present invention is very highly industrially applicable since a wide variety of undesired plants can be controlled at a low dose either in agricultural fields or in non-agricultural fields, and its herbicidal effect lasts for a long period of time.

The entire disclosures of Japanese Patent Application No. 2007-024866 filed on Feb. 2, 2007, and Japanese Patent Application No. 2007-152676 filed on Jun. 8, 2007 including specifications, claims, drawings and summaries are incorporated herein by reference in their entireties.

The invention claimed is:
1. A herbicidal composition comprising active ingredients, comprising:
(a) a herbicidal benzoylpyrazole compound of formula (I) or its salt:

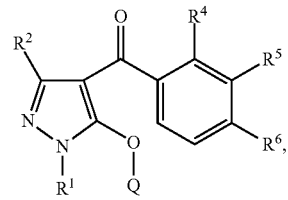

wherein
Q is a hydrogen atom,
$R^1$ is ethyl,
$R^2$ is a hydrogen atom,
$R^4$ is methyl,
$R^5$ is —OCH$_2$CH$_2$OCH$_3$,
$R^6$ is —SO$_2$CH$_3$, and
(b) a further herbicidal compound.

2. The composition of claim 1, wherein the further herbicidal compound (b) is at least one compound selected from the group consisting of a phenoxy compound, an aromatic carboxylic acid compound, a urea compound, a triazine compound, a uracil compound, an anilide compound, a carbamate compound, a hydroxybenzonitrile compound, a quaternary ammonium salt compound, a diphenylether compound, a cyclic imide compound, a pyridazinone compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, an amide compound, an organic phosphorus compound, a phenyl carbamate compound, a cumylamine compound, a chloroacetamide compound, a thiocarbamate compound, those which are believed to exhibit herbicidal effects by being parasitic on plants, naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, chlorflurenol-methyl, pyridate, bentazone, bentazone-sodium, amicarbazone, methazole, pentanochlor, oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone, amitrole, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachlortole, benzobicyclon, picolinafen, beflubutamid, flamprop-M, flamprop-M-methyl, flamprop-M-isopropyl, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, cinmethylin, asulam, asulam-sodium, dithiopyr, thiazopyr, chlorthal, chlorthal-dimethyl, diphenamid, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium, trichloroacetic acid, MSMA, DSMA, CMA, endothall, endothall-dipotassium, endothall-sodium, endothall-mono(N,N-dimethylalkylammonium), ethofumesate, sodium chlorate, pelargonic acid, fosamine, fosamine-ammonium, pinoxaden, HOK-201, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, and urea sulfate.

3. The composition of claim 1, wherein the further herbicidal compound (b) is
   (b-1) a compound selectively controlling undesired plants in a corn field,
   (b-2) a compound selectively controlling undesired plants in a wheat, a barley or a rye field,
   (b-3) a compound selectively controlling undesired plants in a rice field, or
   (b-4) a compound nonselectively controlling undesired plants.

4. The composition of claim 3, wherein the further herbicidal compound (b) is at least one compound selected from the group consisting of a phenoxy compound, an aromatic carboxylic acid compound, a urea compound, a triazine compound, a uracil compound, an anilide compound, a carbamate compound, a hydroxybenzonitrile compound, a quaternary ammonium salt compound, a diphenylether compound, a cyclic imide compound, a pyrazole compound, an aryloxyphenoxypropionic acid compound, a cyclohexanedione compound, a sulfonylurea compound, a triazolopyrimidine-sulfonamide compound, an imidazolinone compound, a pyrimidinylsalicylic acid compound, a sulfonylaminocarbonyl-triazolinone compound, a dinitroaniline compound, an organic phosphorus compound, a phenyl carbamate compound, a cumylamine compound, a chloroacetamide compound, a thiocarbamate compound, those which are believed to exhibit herbicidal effects by being parasitic on plants, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, chlorflurenol-methyl, pyridate, bentazone, bentazone-sodium, amicarbazone, pentanochlor, oxadiargyl, oxadiazon, carfentrazone-ethyl, thidiazimin, pentoxazone, pyraflufen-ethyl, butafenacil, saflufenacil, flupoxam, fluazolate, pyraclonil, flufenpyr-ethyl, bencarbazone, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachlortole, benzobicyclon, picolinafen, beflubutamid, flamprop-M, flamprop-M-methyl, flamprop-M-isopropyl, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, cinmethylin, asulam, asulam-sodium, dithiopyr, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium, trichloroacetic acid, CMA, fosamine, fosamine-ammonium, pinoxaden, HOK-201, ammonium sulfamate, borax, chloroacetic acid, sodium chloroacete, methylarsonic acid, dimethylarsinic acid, sodium dimethylarsinate, dinoterb, dinoterb-ammonium, dinoterb-diolamine, dinoterb-acetate, DNOC, flupropanate, flupropanate-sodium, isoxaben, mefluidide, mefluidide-diolamine, pentachlorophenol, sodium pentachlorophenoxide, pentachlorophenol laurate, and quinoclamine.

5. The composition of claim 2 or 4, wherein the further herbicidal compound (b) is at least one compound selected from the group consisting of a phenoxy compound, an aromatic carboxylic acid compound, a urea compound, a triazine compound, a hydroxybenzonitrile compound, a diphenylether compound, a cyclic imide compound, a sulfonylurea compound, a dinitroaniline compound, a chloroacetamide compound, fluoroxypyr, pyridate, bentazone, bentazone-sodium, carfentrazone-ethyl, sulcotrione, mesotrione, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, and flufenacet.

6. The composition of claim 5, wherein
   the phenoxy compound is at least one compound selected from the group consisting of 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide, and clomeprop;
   the aromatic carboxylic acid compound is at least one compound selected from the group consisting of 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium, and aminopyralid;
   the urea compound is at least one compound selected from the group consisting of chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, and trietazine;
   the triazine compound is at least one compound selected from the group consisting of simazine, atrazine, atratone, simetryn, prometryn, dimethametryn, hexazinone, metribuzin, terbuthylazine, cyanazine, ametryn, cybutryne, triaziflam, terbutryn, propazine, metamitron, and prometon;
   the hydroxybenzonitrile compound is at least one compound selected from the group consisting of bromoxynil, bromoxynil-octanoate, bromoxynil-heptanoate, ioxynil, ioxynil-octanoate, ioxynil-potassium, and ioxynil-sodium;
   the diphenylether compound is at least one compound selected from the group consisting of nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl, and fluoroglycofen;

the cyclic imide compound is at least one compound selected from the group consisting of chlorphthalim, flumioxazin, flumiclorac, flumiclorac-pentyl, cinidon-ethyl, and fluthiacet-methyl;

the sulfonylurea compound is at least one compound selected from the group consisting of chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, and TH-547;

the dinitroaniline compound is at least one compound selected from the group consisting of trifluralin, oryzalin, nitralin, pendimethalin, ethalfluralin, benfluralin, prodiamine, butralin, and dinitramine; and the chloroacetamide compound is at least one compound selected from the group consisting of alachlor, metazachlor, butachlor, pretilachlor, metolachlor, S-metolachlor, thenylchlor, pethoxamid, acetochlor, propachlor, dimethenamid, dimethenamid-P, propisochlor, and dimethachlor.

7. The composition of claim 6, wherein the further herbicidal compound (b) is at least one compound selected from the group consisting of 2,4-D, 2,4-D-ethyl, dicamba, dicamba-dimethylammonium, clopyralid, clopyralid-olamine, fluoroxypyr, linuron, atrazine, metribuzin, terbuthylazine, terbutryn, bromoxynil, bromoxynil-octanoate, pyridate, bentazone, bentazone-sodium, aclonifen, cinidon-ethyl, carfentrazone-ethyl, sulcotrione, mesotrione, rimsulfuron, nicosulfuron, prosulfuron, halosulfuron-methyl, thifensulfuron-methyl, iodosulfuron, iodosulfuron-methyl-sodium, tritosulfuron, foramsulfuron, flumetsulam, metosulam, florasulam, imazamox, imazamox-ammonium, glyphosate, glyphosate-sodium, glyphosate-potassium, glyphosate-ammonium, glyphosate-isopropylammonium, glufosinate, glufosinate-ammonium, pendimethalin, alachlor, metolachlor, S-metolachlor, pethoxamid, acetochlor, flufenacet, dimethenamid, and pyroxasulfone.

8. The composition of claim 3, wherein the further herbicidal compound (b) is (b-1) a compound selectively controlling undesired plants in a corn field.

9. The composition of claim 8, wherein the further herbicidal compound (b) is at least one compound selected from the group consisting of a phenoxy compound, an aromatic carboxylic acid compound, a urea compound, a triazine compound, a hydroxybenzonitrile compound, a diphenylether compound, a cyclic imide compound, a pyrazole compound, a sulfonylurea compound, a triazolopyrimidinesulfonamide compound, an imidazolinone compound, a dinitroaniline compound, a chloroacetamide compound, a thiocarbamate compound, benazolin, benazolin-ethyl, diflufenzopyr, diflufenzopyr-sodium, fluoroxypyr, fluoroxypyr-2-butoxy-1-methylethyl, fluoroxypyr-meptyl, pyridate, bentazone, bentazone-sodium, amicarbazone, carfentrazone-ethyl, saflufenacil, flufenpyr-ethyl, bencarbazone, fluridone, clomazone, sulcotrione, mesotrione, tembotrione, isoxaflutole, difenzoquat, difenzoquat-metilsulfate, isoxachlortole, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, flufenacet, tridiphane, benfuresate, pyroxasulfone, dalapon, dalapon-sodium, dinoterb, dinoterb-ammonium, dinoterb-diolamine, dinoterb-acetate, and DNOC.

10. The composition of claim 3, wherein the further herbicidal compound (b) is (b-2) a compound selectively controlling undesired plants in a wheat, a barley, or a rye field.

11. The composition of claim 10, wherein the further herbicidal compound (b) is at least one compound selected from the group consisting of a phenoxy compound, an aromatic carboxylic acid compound, a urea compound, a triazine compound, an anilide compound, a hydroxybenzonitrile compound, a diphenylether compound, a cyclic imide compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, a phenyl carbamate compound, a chloroacetamide compound, a thiocarbamate compound, benazolin, benazolin-ethyl, quinclorac, quinmerac, fluoroxypyr, fluoroxypyr-2-butoxy-1-methylethyl, fluoroxypyr-meptyl, pyridate, bentazone, bentazone-sodium, carfentrazone-ethyl, thidiazimin, pyraflufen-ethyl, saflufenacil, flupoxam, fluazolate, bencarbazone, flurtamone, diflufenican, sulcotrione, difenzoquat, difenzoquat-metilsulfate, picolinafen, beflubutamid, flamprop-M, flamprop-M-methyl, flamprop-M-isopropyl, flufenacet, indanofan, pinoxaden, dinoterb, dinoterb-ammonium, dinoterb-diolamine, dinoterb-acetate, DNOC, and isoxaben.

12. The composition of claim 3, wherein the further herbicidal compound (b) is (b-3) a compound selectively controlling undesired plants in a rice field.

13. The composition of claim 12, wherein the further herbicidal compound (b) is at least one compound selected from the group consisting of a phenoxy compound, an aromatic carboxylic acid compound, a urea compound, a triazine compound, an anilide compound, a carbamate compound, a diphenylether compound, a pyrazole compound, an aryloxyphenoxypropionic acid compound, a cyclohexanedione compound, a sulfonylurea compound, a triazolopyrimidinesulfonamide compound, a pyrimidinylsalicylic acid compound, a dinitroaniline compound, an organic phosphorus compound, a cumylamine compound, a chloroacetamide compound, a thiocarbamate compound, those which are believed to exhibit herbicidal effects by being parasitic on plants, quinclorac, quinmerac, pyridate, bentazone, bentazone-sodium, oxadiargyl, oxadiazon, carfentrazone-ethyl, pentoxazone, pyraclonil, fluridone, diflufenican, methoxyphenone, clomazone, mesotrione, tefuryltrione, benzobicyclon, cinmethylin, dithiopyr, etobenzanid, mefenacet, flufenacet, cafenstrole, fentrazamide, oxaziclomefone, indanofan, benfuresate, TCA-sodium, trichloroacetic acid, HOK-201, and quinoclamine.

14. The composition of claim 3, wherein the further herbicidal compound (b) is (b-4) a compound nonselectively controlling undesired plants.

15. The composition of claim 14, wherein the further herbicidal compound (b) is at least one compound selected from the group consisting of a phenoxy compound, an aromatic carboxylic acid compound, a urea compound, a triazine compound, a uracil compound, a hydroxybenzonitrile compound, a quaternary ammonium salt compound, a sulfonylurea compound, an imidazolinone compound, a pyrimidinylsalicylic acid compound, a dinitroaniline compound, benazolin, benazolin-ethyl, diflufenzopyr, diflufenzopyr-sodium, chlorflurenol, chlorflurenol-methyl, pentanochlor, butafenacil, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, asulam, asulam-sodium, dalapon, dalapon-sodium, TCA-sodium, trichloroacetic acid, CMA, fosamine, fosamine-ammonium, ammonium sulfamate, borax, chloroacetic acid, sodium chloroacete, methylarsonic acid, dimethylarsinic acid, sodium dimethylarsinate, flupropanate, flupropanate-sodium, isoxaben, mefluidide, mefluidide-diolamine, pentachlorophenol, sodium pentachlorophenoxide, and pentachlorophenol laurate.

16. The composition of claim 1, wherein the further herbicidal compound (b) is a compound which inhibits photosynthesis of plants.

17. The composition of claim 16, wherein the further herbicidal compound (b) is at least one compound selected from the group consisting of a urea compound, a triazine compound, a uracil compound, an anilide compound, a carbamate compound, a hydroxybenzonitrile compound, pyridate, bentazone, bentazone-sodium, amicarbazone, methazole, and pentanochlor.

18. The composition of claim 1, wherein the further herbicidal compound (b) is a compound which inhibits amino acid biosynthesis of plants.

19. The composition of claim 18, wherein the further herbicidal compound (b) is at least one compound selected from the group consisting of a sulfonylurea compound, a triazolopyrimidinesulfonamide compound, an imidazolinone compound, a pyrimidinylsalicylic acid compound, a sulfonylaminocarbonyltriazolinone compound, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium, and cinmethylin.

20. The composition of claim 1, wherein the further herbicidal compound (b) is a compound which exhibits herbicidal effects by disturbing hormone activities of plants.

21. The composition of claim 20, wherein the further herbicidal compound (b) is at least one compound selected from the group consisting of a phenoxy compound, an aromatic carboxylic acid compound, naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, and chlorflurenol-methyl.

22. The composition of claim 1, wherein the further herbicidal compound (b) is a compound which exhibits herbicidal effects characterized by bleaching activities by inhibiting chromogenesis of plants such as carotenoids.

23. The composition of claim 22, wherein the further herbicidal compound (b) is at least one compound selected from the group consisting of a pyridazinone compound, a pyrazole compound, amitrole, fluridone, flurtamone, diflufenican, methoxyphenone, clomazone, sulcotrione, mesotrione, tembotrione, tefuryltrione, isoxaflutole, difenzoquat, difenzoquat-metilsulfate, isoxachlortole, benzobicyclon, picolinafen, and beflubutamid.

24. The composition of claim 1, wherein the further herbicidal compound (b) is a compound which exhibits herbicidal effects by inhibiting protein biosynthesis or lipid biosynthesis of plants.

25. The composition of claim 24, wherein the further herbicidal compound (b) is at least one compound selected from the group consisting of a chloroacetamide compound, a thiocarbamate compound, etobenzanid, mefenacet, flufenacet, tridiphane, cafenstrole, fentrazamide, oxaziclomefone, indanofan, benfuresate, pyroxasulfone, dalapon, dalapon-sodium, TCA-sodium, and trichloroacetic acid.

26. The composition of claim 1, wherein the mixing ratio of the herbicidal benzoylpyrazole compound of the formula (I) or its salt (a) to the further herbicidal compound (b) is from 1:1,000 to 1,000:1 by the weight ratio.

27. A method for controlling an undesired plant, the method comprising:
applying a herbicidally effective amount of the herbicidal composition of claim 1 to the undesired plant or
to a place where the undesired plant grows.

28. The method of claim 27, wherein the undesired plant is controlled in a corn field.

29. The method of claim 28, wherein the corn is a genetically-modified corn.

30. The method of claim 27, wherein the undesired plant is controlled in a wheat, a barley, or a rye field.

31. The method of claim 27, wherein the undesired plant is controlled in a rice field.

32. The method of claim 27, wherein the undesired plant is nonselectively controlled.

* * * * *